US009068003B2

(12) United States Patent
Siegel et al.

(10) Patent No.: US 9,068,003 B2
(45) Date of Patent: Jun. 30, 2015

(54) ANTIBODIES THAT BIND TO TL1A AND METHODS OF TREATING INFLAMMATORY OR AUTOIMMUNE DISEASE COMPRISING ADMINISTERING SUCH ANTIBODIES

(75) Inventors: Richard M Siegel, Bethesda, MD (US); Francoise Meylan, Bethesda, MD (US); Yun-Jeong Song, Rockville, MD (US)

(73) Assignee: The United States of America, as represented by the Secretary, Dept. of Health and Human Services, Washington, DC (US)

( * ) Notice: Subject to any disclaimer, the term of this patent is extended or adjusted under 35 U.S.C. 154(b) by 0 days.

(21) Appl. No.: 13/419,203

(22) Filed: Mar. 13, 2012

(65) Prior Publication Data

US 2012/0263718 A1 Oct. 18, 2012

Related U.S. Application Data

(63) Continuation-in-part of application No. 11/972,395, filed on Jan. 10, 2008, now abandoned.

(60) Provisional application No. 60/879,668, filed on Jan. 10, 2007, provisional application No. 61/488,671, filed on May 20, 2011.

(51) Int. Cl.
*A61K 39/395* (2006.01)
*C07K 16/18* (2006.01)
*C07K 16/28* (2006.01)

(52) U.S. Cl.
CPC ........ *C07K 16/2875* (2013.01); *G01N 2500/02* (2013.01); *G01N 2800/7095* (2013.01); *C07K 2317/76* (2013.01)

(58) Field of Classification Search
None
See application file for complete search history.

(56) References Cited

U.S. PATENT DOCUMENTS

| 4,676,980 | A | 6/1987 | Segal et al. |
| 4,873,191 | A | 10/1989 | Wagner et al. |
| 4,897,355 | A | 1/1990 | Eppstein et al. |
| 4,946,778 | A | 8/1990 | Ladner et al. |
| 5,162,215 | A | 11/1992 | Bosselmann et al. |
| 5,708,607 | A | 1/1998 | Lee et al. |
| 5,955,590 | A | 9/1999 | Levina et al. |
| 6,096,551 | A | 8/2000 | Barbas et al. |
| 6,759,513 | B2 | 7/2004 | Yu et al. |
| 7,148,061 | B2 | 12/2006 | Lenardo et al. |
| 8,263,743 | B2 | 9/2012 | Smith et al. |
| 2002/0150534 | A1* | 10/2002 | Yu et al. ......................... 424/1.49 |
| 2009/0317388 | A1 | 12/2009 | Burkly et al. |
| 2011/0217310 | A1 | 9/2011 | Siegel et al. |

FOREIGN PATENT DOCUMENTS

| WO | WO 89/07136 | 8/1989 |
| WO | WO 90/02806 | 3/1990 |
| WO | WO 92/03566 | 3/1992 |
| WO | WO 93/22434 | 11/1993 |
| WO | WO 94/04679 | 3/1994 |
| WO | WO 94/29348 | 12/1994 |
| WO | WO 95/24489 | 9/1995 |
| WO | WO 97/18312 | 5/1997 |
| WO | WO 98/58057 | 12/1998 |
| WO | WO 98/58058 | 12/1998 |
| WO | WO 02/44321 | 6/2002 |
| WO | WO 2005/018571 | 3/2005 |
| WO | WO 2006/127900 | 11/2006 |
| WO | WO 2009/064854 | 5/2009 |

OTHER PUBLICATIONS

Zimmerman et al. (2005). biology of Blood and Marrow Transplantation. 11:576-586.*
Adams DJ, Biggs PJ, Cox T, et al. Mutagenic insertion and chromosome engineering resource (MICER). Nat Genet 2004;36(8):867-71.
Adler B, Ashkar S, Cantor H, Weber GF. Costimulation by extracellular matrix proteins determines the response to TCR ligation. Cell Immunol 2001;210(1):30-40.
Adriani M, Aoki J, Horai R, et al. Impaired in vitro regulatory T cell function associated with Wiskott-Aldrich syndrome. Clin Immunol 2007;124(1):41-8.
Arestides, R.S., He, H., Westlake, R.M., Chen, A.I., Sharpe, A.H., Perkins, D.L., and Finn, P.W. (2002). Costimulatory molecule OX40L is critical for both Th1 and Th2 responses in allergic inflammation. Eur J Immunol 32, 2874-2880.
Badour K, Zhang J, Shi F, Leng Y, Collins M, Siminovitch KA. Fyn and PTP-PEST-mediated regulation of Wiskott-Aldrich syndrome protein (WASp) tyrosine phosphorylation is required for coupling T cell antigen receptor engagement to WASp effector function and T cell activation. J Exp Med 2004;199(1):99-112.
Bamias, G., Martin, C., 3rd, Marini, M., Hoang, S., Mishina, M., Ross, W.G., Sachedina, M.A., Friel, C.M., Mize, J., Bickston, S.J., et al. (2003). Expression, localization, and functional activity of TL1A, a novel Th1-polarizing cytokine in inflammatory bowel disease. J Immunol 171, 4868-4874.

(Continued)

*Primary Examiner* — Christine J Saoud
*Assistant Examiner* — Jon M Lockard
(74) *Attorney, Agent, or Firm* — Sheridan Ross P.C.

(57) ABSTRACT

Provided are methods and compositions for treating inflammatory or autoimmune diseases in a subject comprising blocking the interaction between DR3 and TL1A. The interaction between DR3 and TL1A can be blocked by reducing expression of TL1A. The interaction between DR3 and TL1A can be blocked by administration of anti-DR3 antibodies. The interaction between DR3 and TL1A can be blocked by administration of anti-TL1A antibodies. In the methods of treating inflammatory or autoimmune disease, the inflammatory or autoimmune disease can be an autoimmune disease with a T cell component. In the methods of treating inflammatory or autoimmune disease, the inflammatory or autoimmune disease can be asthma, multiple sclerosis, rheumatoid arthritis, type 1 diabetes, graft versus host disease or inflammatory bowel disease (IBD).

13 Claims, 61 Drawing Sheets

(56) References Cited

OTHER PUBLICATIONS

Bamias, G., Mishina, M., Nyce, M., Ross, W.G., Kollias, G., Rivera-Nieves, J., Pizarro, T.T., and Cominelli, F. (2006). Role of TL1A and its receptor DR3 in two models of chronic murine ileitis. Proc Natl Acad Sci U S A. May 30, 2006;103(22):8441-6.

Baum W, Kirkin V, Fernandez SB, et al. Binding of the intracellular Fas ligand (FasL) domain to the adaptor protein PSTPIP results in a cytoplasmic localization of FasL. J Biol Chem 2005;280(48):40012-24.

Blott EJ, Bossi G, Clark R, Zvelebil M, Griffiths GM. Fas ligand is targeted to secretory lysosomes via a proline-rich domain in its cytoplasmic tail. J Cell Sci 2001;114(Pt 13):2405-16.

Brocker T, Riedinger M, Karjalainen K. Targeted expression of major histocompatibility complex (MHC) class II molecules demonstrates that dendritic cells can induce negative but not positive selection of thymocytes in vivo. J Exp Med 1997;185(3):541-50.

Bruijn LI, Becher MW, Lee MK, et al. ALS-linked SOD1 mutant G85R mediates damage to astrocytes and promotes rapidly progressive disease with SOD1-containing inclusions. Neuron 1997;18(2):327-38.

Cassatella, M.A., da Silva, G.P., Tinazzi, I., Facchetti, F., Scapini, P., Calzetti, F., Tamassia, N., Wei, P., Nardelli, B., Roschke, V., et al. (2007). Soluble TNF-like cytokine (TL1A) production by immune complexes stimulated monocytes in rheumatoid arthritis. J Immunol 178, 7325-7333.

Chakrabandhu K, Herincs Z, Huault S, et al. Palmitoylation is required for efficient Fas cell death signaling. Embo J 2007;26(1):209-20.

Chinnaiyan, A.M., O'Rourke, K., Yu, G.L., Lyons, R.H., Garg, M., Duan, D.R., Xing, L., Gentz, R., Ni, J., and Dixit, V.M. (1996). Signal transduction by DR3, a death domaincontaining receptor related to TNFR-1 and CD95. Science 274, 990-994.

Croft, M. (2003). Co-stimulatory members of the TNFR family: keys to effective T-cell immunity? Nat Rev Immunol 3, 609-620.

Dagnaes-Hansen, F., Hoist, H.U., Sondergaard, M., Vorup-Jensen, T., Flyvbjerg, A., Jensen, U.B., and Jensen, T.G. (2002). Physiological effects of human growth hormone produced after hydrodynamic gene transfer of a plasmid vector containing the human ubiquitin promotor. Journal of molecular medicine (Berlin, Germany) 80, 665-670.

Derry JM, Ochs HD, Francke U. Isolation of a novel gene mutated in Wiskott-Aldrich syndrome. Cell 1994;79(5):following 922.

Deshpande P, King IL, Segal BM. IL-12 driven upregulation of P-selectin ligand on myelin-specific T cells is a critical step in an animal model of autoimmune demyelination. Journal of neuroimmunology 2006;173(1-2):35-44.

Deshpande SS, Angkeow P, Huang J, Ozaki M, Irani K. Rac1 inhibits TNF-alpha-induced endothelial cell apoptosis: dual regulation by reactive oxygen species. Faseb J 2000;14(12):1705-14.

Devadas S, Das J, Liu C, et al. Granzyme B is critical for T cell receptor-induced cell death of type 2 helper T cells. Immunity 2006;25(2):237-47.

Di Prospero NA, Baker A, Jeffries N, Fischbeck KH. Neurological effects of high-dose idebenone in patients with Friedreich's ataxia: a randomised, placebo-controlled trial. Lancet neurology 2007;6(10):878-86.

Dupuis-Girod S, Medioni J, Haddad E, et al. Autoimmunity in Wiskott-Aldrich syndrome: risk factors, clinical features, and outcome in a single-center cohort of 55 patients. Pediatrics 2003;111(5 Pt 1):e622-7.

Faure S, Salazar-Fontana LI, Semichon M, et al. ERM proteins regulate cytoskeleton relaxation promoting T cell-APC conjugation. Nat Immunol 2004;5(3):272-9.

Feig C, Tchikov V, Schutze S, Peter ME. Palmitoylation of CD95 facilitates formation of SDS-stable receptor aggregates that initiate apoptosis signaling. Embo J 2007;26{1):221-31.

Fritsch RD, Shen X, Illei GG, et al. Abnormal differentiation of memory T cells in systemic lupus erythematosus. Arthritis Rheum 2006;54(7):2184-97.

Fritzsching B, Oberle N, Eberhardt N, et al. In contrast to effector T cells, CD4+CD25+FoxP3+ regulatory T cells are highly susceptible to CD95 ligand- but not to TCR-mediated cell death. J Immunol 2005;175(1):32-6.

Fuss IJ, Becker C, Yang Z, et al. Both IL-12p70 and IL-23 are synthesized during active Crohn's disease and are down-regulated by treatment with anti-IL-12 p40 monoclonal antibody. Inflammatory bowel diseases 2006;12(1):9-15.

Gaudet S, Janes KA, Albeck JG, Pace EA, Lauffenburger DA, Sorger PK. A compendium of signals and responses triggered by prodeath and prosurvival cytokines. Mol Cell Proteomics 2005;4(10):1569-90.

Gavett, S.H., Chen, X., Finkelman, F., and Wills-Karp, M. (1994). Depletion of murine CD4+ T lymphocytes prevents antigen-induced airway hyperreactivity and pulmonary eosinophilia. American journal of respiratory cell and molecular biology 10, 587-593.

Gout S, Morin C, Houle F, Huot J. Death receptor-3, a new E-Selectin counter-receptor that confers migration and survival advantages to colon carcinoma cells by triggering p38 and ERK MAPK activation. Cancer Res 2006;66(18):9117-24.

Grunvald, E., Chiaramonte, M., Hieny, S., Wysocka, M., Trinchieri, G., Vogel, S.N., Gazzinelli, R.T., and Sher, A. (1996). Biochemical characterization and protein kinase C dependency of monokine-inducing activities of *Toxoplasma gondii*. Infect Immun 64, 2010-2018.

Hao, Z., Hampel, B., Yagita, H., and Rajewsky, K. (2004). T cell-specific ablation of Fas leads to Fas ligand-mediated lymphocyte depletion and inflammatory pulmonary fibrosis. J Exp Med 199, 1355-1365.

He L, Wu X, Meylan F, et al. Monitoring caspase activity in living cells using fluorescent proteins and flow cytometry. Am J Pathol 2004;164(6):1901-13.

Hodges, B.L., and Scheule, R.K. (2003). Hydrodynamic delivery of DNA. Expert opinion on biological therapy 3, 911-918.

Hue S, Ahern P, Buonocore S, et al. Interleukin-23 drives innate and T cell-mediated intestinal inflammation. J Exp Med 2006;203(11):2473-83.

Humblet-Baron S, Sather B, Anover S, et al. Wiskott-Aldrich syndrome protein is required for regulatory T cell homeostasis. J Clin Invest 2007;117(2):407-18.

International Search Report dated Sep. 26, 2012 PCTUS2012028926.

Jones RG, Elford AR, Parsons MJ, et al. CD28-dependent activation of protein kinase B/Akt blocks Fas-mediated apoptosis by preventing death-inducing signaling complex assembly. J Exp Med 2002;196(3):335-48.

Kamata H, Honda S, Maeda S, Chang L, Hirata H, Karin M. Reactive oxygen species promote TNFalpha-induced death and sustained JNK activation by inhibiting MAP kinase phosphatases. Cell 2005;120(5):649-61.

Kilpatrick KE, et al. Gene gun delivered DNA-based immunizations mediate rapid production of murine monoclonal antibodies to the Flt-3 receptor. Hybridoma. Dec. 1998;17(6):569-76.

Kilpatrick KE et al. High-affinity monoclonal antibodies to PED/PEA-15 generated using 5 microg of DNA. Hybridoma. Oct. 2000; 19(4):297-302.

Kim YS, Morgan MJ, Choksi S, Liu ZG. TNF-induced activation of the Nox1 NADPH oxidase and its role in the induction of necrotic cell death. Mol Cell 2007;26(5):675-87.

Kim, S., and Zhang, L. (2005). Identification of naturally secreted soluble form of TL1A, a TNF-like cytokine. J Immunol Methods 298, 1-8.

Kimberley FC, Lobito AA, Siegel RM, Screaton GR. Falling into TRAPS—receptor misfolding in the TNF receptor 1-associated periodic fever syndrome. Arthritis research & therapy 2007;9(4):217.

Lambeth JD. NOX enzymes and the biology of reactive oxygen. Nat Rev Immunol 2004;4(3):181-9.

Lecocq, M., Andrianaivo, F., Warnier, M.T., Wattiaux-De Coninck, S., Wattiaux, R., and Jadot, M. (2003). Uptake by mouse liver and intracellular fate of plasmid DNA after a rapid tail vein injection of a small or a large volume. The journal of gene medicine 5, 142-156.

Li QJ, Chau J, Ebert PJ, et al. miR-181a is an intrinsic modulator of T cell sensitivity and selection. Cell 2007;129(1):147-61.

(56) References Cited

OTHER PUBLICATIONS

Lobito AA, Kimberley FC, Muppidi JR, et al. Abnormal disulfide-linked oligomerization results in ER retention and altered signaling by TNFR1 mutants in TNFR1-associated periodic fever syndrome (TRAPS). Blood 2006;108(4}:1320-7.
Maillard MH, Cotta-de-Almeida V, Takeshima F, et al. The Wiskott-Aldrich syndrome protein is required for the function of CD4(+)CD25(+)Foxp3(+) regulatory T cells. J Exp Med 2007;204(2):381-91.
Man S, Ubogu EE, Ransohoff RM. Inflammatory cell migration into the central nervous system: a few new twists on an old tale. Brain Pathol 2007;17(2):243-50.
Marsters SA, Sheridan JP, Donahue CJ, et al. Apo-3, a new member of the tumor necrosis factor receptor family, contains a death domain and activates apoptosis and NF-kappa B. Curr Biol 1996;6(12):1669-76.
Martinez-Lorenzo MJ, Anel A, Gamen S, et al. Activated human T cells release bioactive Fas ligand and APO2 ligand in microvesicles. J Immunol 1999;163(3):1274-81.
McConchie, B.W., Norris, H.H., Bundoc, V.G., Trivedi, S., Boesen, A., Urban, J.F., Jr., and Keane-Myers, A.M. (2006). *Ascaris suum*-derived products suppress mucosal allergic inflammation in an interleukin-10-independent manner via interference with dendritic cell function. Infect Immun 74, 6632-6641.
McDermott MF, Aksentijevich I, Galon J, et al. Germline mutations in the extracellular domains of the 55 kDa TNF receptor, TNFR1, define a family of dominantly inherited autoinflammatory syndromes. Cell1999;97(1):133-44.
McKenzie BS, Kastelein RA, Cua DJ. Understanding the IL-23-IL-17 immune pathway. Trends Immunol 2006;27{1}:17-23.
Meylan F, Davidson TS, Kahle E, Kinder M, Acharya K, Jankovic D, Bundoc V, Hodges M, Shevach EM, Keane-Myers A, Wang EC, Siegel RM. The TNF-Family Receptor DR3 is Essential for Diverse T Cell-Mediated Inflammatory Diseases. Immunity. Jun. 18, 2008.
Micheau O, Tschopp J. Induction of TNF receptor I-mediated apoptosis via two sequential signaling complexes. Cell 2003;114(2):181-90.
Migone, T.S., Zhang, J., Luo, X., Zhuang, L., Chen, C., Hu, B., Hong, J.S., Perry, J.W., Chen, S.F., Zhou, J.X., et al. (2002). TL1A is a TNF-like ligand for DR3 and TR6/DcR3 and functions as a T cell costimulator. Immunity 16, 479-492.
Misulovin Z, Yang XW, Yu W, Heintz N, Meffre E. A rapid method for targeted modification and screening of recombinant bacterial artificial chromosome. Journal of immunological methods 2001;257(1-2}:99-105.
Morales-Tirado V, Johannson S, Hanson E, et al. Cutting edge: selective requirement for the Wiskott-Aldrich syndrome protein in cytokine, but not chemokine, secretion by CD4+ T cells. J Immunol 2004;173(2):726-30.
Muppidi JR, Lobito AA, Ramaswamy M, et al. Homotypic FADD interactions through a conserved RXDLL motif are required for death receptor-induced apoptosis. Cell Death Differ 2006;13(10):1641-50.
Muppidi JR, Siegel RM. Ligand-independent redistribution of Fas (CD95) into lipid rafts mediates clonotypic T cell death. Nat Immunol 2004;5(2):182-9.
Nadkarni S, Mauri C, Ehrenstein MR. Anti-TNF-{alpha} therapy induces a distinct regulatory T cell population in patients with rheumatoid arthritis via TGF-{beta}. J Exp Med 2007.
Nakajima, A., Oshima, H., Nohara, C., Morimoto, S., Yoshino, S., Kobata, T., Yagita, H., and Okumura, K. (2000). Involvement of CD70-CD27 interactions in the induction of experimental autoimmune encephalomyelitis. Journal of neuroimmunology 109, 188-196.
Neurath M, Fuss I, Strober W. TNBS-colitis. International reviews of immunology 2000;19(1):51-62.
Neurath MF, Fuss I, Pasparakis M, et al. Predominant pathogenic role of tumor necrosis factor in experimental colitis in mice. Eur J Immunol 1997;27(7):1743-5O.
New England Biolabs Product Catalog, 1996, p. 164.

Nohara, C., Akiba, H., Nakajima, A., Inoue, A., Koh, C.S., Ohshima, H., Yagita, H., Mizuno, Y., and Okumura, K. (2001 ). Amelioration of experimental autoimmune encephalomyelitis with anti-OX40 ligand monoclonal antibody: a critical role for OX40 ligand in migration, but not development, of pathogenic T cells. J Immunol 166, 2108-2115.
Osawa, K., Takami, N., Shiozawa, K., Hashiramoto, A., and Shiozawa, S. (2004). Death receptor 3 (DR3) gene duplication in a chromosome region 1 p36.3: gene duplication is more prevalent in rheumatoid arthritis. Genes and immunity 5, 439-443.
Papadakis, K.A., Prehn, J.L., Landers, C., Han, Q., Luo, X., Cha, S.C., Wei, P., and Targan, S.R. (2004). TL1A synergizes with IL-12 and IL-18 to enhance IFN-gamma production in human T cells and NK cells. J Immunol 172, 7002-7007.
Papadakis, K.A., Zhu, D., Prehn, J.L., Landers, C., Avanesyan, A., Lafkas, G., and Targan, S.R. (2005). Dominant role for TL1A/DR3 pathway in IL-12 plus IL-18-induced IFN-gamma production by peripheral blood and mucosal CCR9+ T lymphocytes. J Immunol 174, 4985-4990.
Parlato S, Giammarioli AM, Logozzi M, et al. CD95 (APO-1/Fas) linkage to the actin cytoskeleton through ezrin in human T lymphocytes: a novel regulatory mechanism of the CD95 apoptotic pathway. Embo J 2000;19(19):5123-34.
Pivniouk VI, Snapper SB, Kettner A, et al. Impaired signaling via the high-affinity IgE receptor in Wiskott-Aldrich syndrome protein-deficient mast cells. Int Immunol 2003;15(12):1431-40.
Powrie F, Leach MW, Mauze S, Caddie LB, Coffman RL. Phenotypically distinct subsets of CD4+ T cells induce or protect from chronic intestinal inflammation in C. B-17 scid mice. Int Immunol 1993;5(11):1461-71.
Prehn, J.L., Thomas, L.S., Landers, C.J., Yu, Q.T., Michelsen, K.S., and Targan, S.R. (2007). The T cell costimulator TL1A is induced by FcgammaR signaling in human monocytes and dendritic cells. J Immunol 178, 4033-4038.
Ramaswamy M, Dumont C, Cruz AC, et al. Cutting Edge: Rac GTPases Sensitize Activated T Cells to Die via Fas. J Immunol 2007;179(10):6384-8.
Reinhardt RL, Khoruts A, Merica R, Zell T, Jenkins MK. Visualizing the generation of memory CD4 T cells in the whole body. Nature 2001;410(6824):101-5.
Riou C, Yassine-Diab B, Van grevenynghe J, et al. Convergence of TCR and cytokine signaling leads to FOXO3a phosphorylation and drives the survival of CD4+ central memory T cells. J Exp Med 2007;204(1):79-91.
Salek-Ardakani, S., Song, J., Halteman, B.S., Jember, A.G., Akiba, H., Yagita, H., and Croft, M. (2003). OX40 (CD134) controls memory T helper 2 cells that drive lung inflammation. J Exp Med 198, 315-324.
Schwartz M. Rho signalling at a glance. J Cell Sci 2004;117(Pt 23):5457-8.
Screaton, G.R., Xu, X.N., Olsen, A.L., Cowper, A.E., Tan, R., McMichael, A.J., and Bell, J.I. (1997). LARD: a new lymphoid-specific death domain containing receptor regulated by alternative pre-mRNA splicing. Proc Natl Acad Sci U S A 94, 4615-4619.
Shaner NC, Campbell RE, Steinbach PA, Giepmans BN, Palmer AE, Tsien RY. Improved monomeric red, orange and yellow fluorescent proteins derived from *Discosoma* sp. red fluorescent protein. Nat Biotechnol 2004;22(12):1567-72.
Shell S, Park SM, Radjabi AR, et al. Let-7 expression defines two differentiation stages of cancer. Proc Natl Acad Sci U S A 2007;104(27):11400-5.
Siegel RM, Chan FK, Chun HJ, Lenardo MJ. The multifaceted role of Fas signaling in immune cell homeostasis and autoimmunity. Nat Immunol 2000;1(6):469-74.
Siegel RM, Frederiksen JK, Zacharias DA, et al. Fas preassociation required for apoptosis signaling and dominant inhibition by pathogenic mutations. Science 2000;288(5475):2354-7.
Siegel RM, Muppidi JR, Sarker M, et al. SPOTS: signaling protein oligomeric transduction structures are early mediators of death receptor-induced apoptosis at the plasma membrane. J Cell Bioi 2004;167(4):735-44.

(56) References Cited

OTHER PUBLICATIONS

Soroosh, P., Ine, S., Sugamura, K., and Ishii, N. (2006). OX40-OX40 ligand interaction through T cell-T cell contact contributes to CD4 T cell longevity. J Immunol 176, 5975-5987.
Steed, P.M., Tansey, M.G., Zalevsky, J., Zhukovsky, E.A., Desjarlais, J.R., Szymkowski, D.E., Abbott, C., Carmichael, D., Chan, C., Cherry, L., et al. (2003). Inactivation of TNF signaling by rationally designed dominant-negative TNF variants. Science 301, 1895-1898.
Storey H, Stewart A, Vandenabeele P, Luzio JP. The p55 tumour necrosis factor receptor TNFR1 contains a trans-Golgi network localization signal in the C-terminal region of its cytoplasmic tail. The Biochemical journal 2002;366(Pt 1):15-22.
Stranges PB, Watson J, Cooper CJ, et al. Elimination of antigen-presenting cells and autoreactive T cells by fas contributes to prevention of autoimmunity. Immunity 2007;26(5):629-41.
Strober W, Fuss I, Mannon P. The fundamental basis of inflammatory bowel disease. J Clin Invest 2007;117(3):514-21.
Su, A.I., Wiltshire, T., Batalov, S., Lapp, H., Ching, K.A., Block, D., Zhang, J., Soden, R., Hayakawa, M., Kreiman, G., et al. (2004). A gene atlas of the mouse and human protein-encoding transcriptomes. Proc Natl Acad Sci U S A 101, 6062-6067.
Sukits SF, Lin LL, Hsu S, Malakian K, Powers R, Xu GY. Solution structure of the tumor necrosis factor receptor-1 death domain. Journal of molecular biology 2001;310(4):895-906.
Sullivan KE, Mullen CA. Blaese RM, Winkelstein JA. A multiinstitutional survey of the Wiskott-Aldrich syndrome. J Pediatr 1994;125(6 Pt 1):876-85.
Suzuki A, Yamaguchi MT, Ohteki T, et al. T cell-specific loss of Pten leads to defects in central and peripheral tolerance. Immunity 2001;14(5):523-34.
Tang Q, Adams JY, Tooley AJ, et al. Visualizing regulatory T cell control of autoimmune responses in nonobese diabetic mice. Nat Immunol 2006;7(1):83-92.
Tao, X., Constant, S., Jorritsma, P., and Bottomly, K. (1997). Strength of TCR signal determines the costimulatory requirements for Th1 and Th2 CD4+ T cell differentiation. J Immunol 159, 5956-5963.
Touitou I, Lesage S, McDermott M, et al. Infevers: an evolving mutation database for auto-inflammatory syndromes. Human mutation 2004;24(3):194-8.
Valencia X, Stephens G, Goldbach-Mansky R, Wilson M, Shevach EM, Lipsky PE. TNF downmodulates the function of human CD4+CD25hi T-regulatory cells. Blood 2006;108(1):253-61.
von Andrian UH, Mackay CR. T-cell function and migration. Two sides of the same coin. N Engl J Med 2000;343(14):1020-34.
Wang, D., et al., Chem. Mater. 2003 15, 2724.
Wang, E.C., Thern, A., Denzel, A., Kitson, J., Farrow, S.N., and Owen, M.J. (2001). DR3 regulates negative selection during thymocyte development. Mol Cell Biol 21, 3451-3461.
Watts, T.H. (2005). TNF/TNFR family members in costimulation of T cell responses. Annu Rev Immunol 23, 23-68.
Wen, L., Zhuang, L., Luo, X., and Wei, P. (2003). TL1A-induced NF-kappaB activation and c-IAP2 production prevent DR3-mediated apoptosis in TF-1 cells. J Biol Chem 278, 39251-39258.
Wise CA, Gillum JD, Seidman CE, et al. Mutations in CD2BP1 disrupt binding to PTP PEST and are responsible for PAPA syndrome, an autoinflammatory disorder. Human molecular genetics 2002;11(8):961-9.
Xiao, Q., Hsu, C.Y., Chen, H., Ma, X., Xu, J., and Lee, J.M. (2005). Characterization of cis-regulatory elements of the vascular endothelial growth inhibitor gene promoter. Biochem J 388, 913-920.
Yamazaki, K., McGovern, D., Ragoussis, J., Paolucci, M., Butler, H., Jewell, D., Cardon, L., Takazoe, M., Tanaka, T., Ichimori, T., et al. (2005). Single nucleotide polymorphisms in TNFSF15 confer susceptibility to Crohn's disease. Human molecular genetics 14, 3499-3506.
Zhang Z, Zheng M, Bindas J, Schwarzenberger P, Kolls JK. Critical role of IL-17 receptor signaling in acute TNBS-induced colitis. Inflammatory bowel diseases 2006;12(5):382-8.
Zhang, J., Salcedo, T.W., Wan, X., Ullrich, S., Hu, B., Gregorio, T., Feng, P., Qi, S., Chen, H., Cho, Y.H., et al. (2001). Modulation of T-cell responses to alloantigens by TR6/DcR3. J Clin Invest 107, 1459-1468.
Zhumabekov T, Corbella P, Tolaini M, Kioussis D. Improved version of a human CD2 minigene based vector for T cell-specific expression in transgenic mice. Journal of immunological methods 1995;185(1):133-40.
Siegel et al., "TL1A-DR3 interactions drive immunopathology mediated by multiple T-cell subsets," Cytokine, 2008, vol. 43, Abstract No. 41, p. 246.
Song et al., "TL1A-DR3 Interactions are Important in Both Adaptive and Innate Immunity in Inflammatory Arthritis," Clin. Immunol., 2010, vol. 135, Abstract No. F.43, p. S88.
Song et al., "TL1A-DR3 Interactions in T-cell Mediated Autoimmunity; an Attractive Target for Immunotherapy," Clin. Immunol., 2009, vol. 131, Abstract No. T.80, p. S74.
Supplementary European Search Report for European Patent Application No. 12790157.7, dated Jan. 9, 2015, 9 pages.

\* cited by examiner

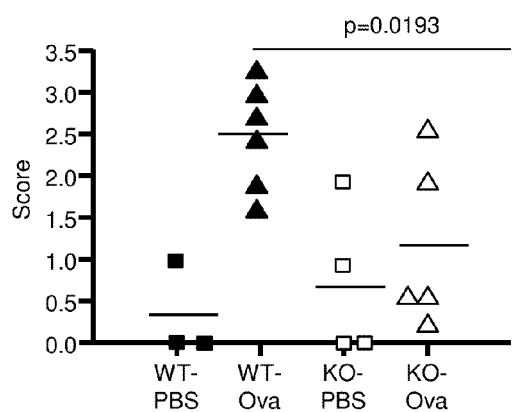
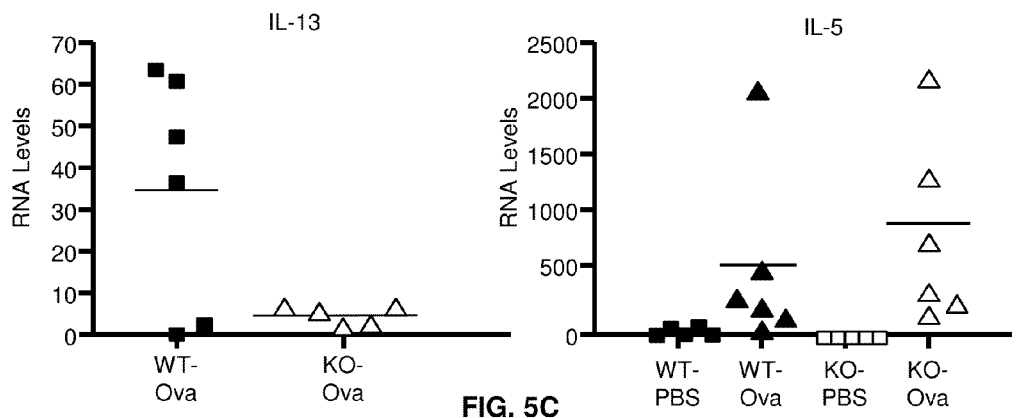
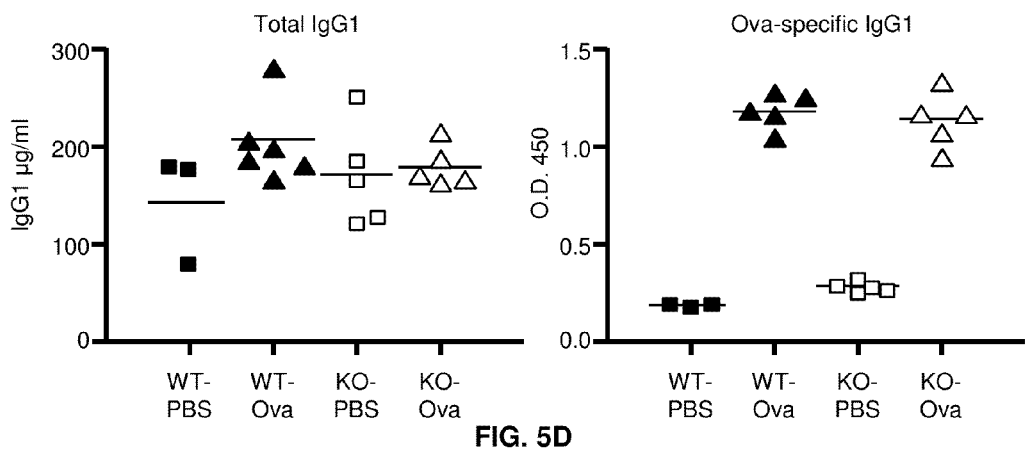
FIG. 5B
FIG. 5C
FIG. 5D

+ CTLA4 Ig

SEQUENCE LISTING

<160> NUMBER OF SEQ ID NOS: 32

<210> SEQ ID NO 1
<211> LENGTH: 1743
<212> TYPE: DNA
<213> ORGANISM: Homo sapiens

<400> SEQUENCE: 1

```
ctgaaggcgg aaccacgacg ggcagagagc acggagccgg gaagcccctg ggcgcccgtc      60
ggagggctat ggagcagcgg ccgcggggct gcgcggcggt ggcggcggcg ctcctcctgg     120
tgctgctggg ggcccgggcc cagggcggca ctcgtagccc caggtgtgac gtgtgccggtg    180
acttccacaa gaagattggt ctgttttgtt gcagaggctg cccagcgggg cactacctga     240
aggccccttg cacggagccc tgcggcaact ccacctgcct tgtgtgtccc caagacacct     300
tcttggcctg ggagaaccac cataattctg aatgtgcccg ctgccaggcc tgtgatgagc     360
aggcctccca ggtggcgctg gagaactgtt cagcagtggc cgacacccgc tgtggctgta     420
agccaggctg gtttgtggag tgccaggtca gccaatgtgt cagcagttca cccttctact     480
gccaaccatg cctagactgc ggggccctgc accgccacac acggctactc tgttcccgca     540
gagatactga ctgtgggacc tgcctgcctg gcttctatga acatggcgat ggctgcgtgt     600
cctgccccac gagcaccctg ggagctgtc cagagcgctg tgccgctgtc tgtggctgga     660
ggcagagtag gtggtgtgct gggaatgcgc gtgggagaac tgggatggac cgaggggagg     720
cgggtgagga gggggcaac cacccaacac ccaccagctg ctttcagtgt tctgggtcca     780
ggtgctcctg gctggccttg tggtcccct cctgcttggg gccaccctga cctacacata     840
ccgccactgc tggcctcaca agccctggt tactgcagat gaagctggga tggaggctct     900
gaccccacca ccggccaccc atctgtcacc cttggacagc gcccacaccc ttctagcacc     960
tcctgacagc agtgagaaga tctgcaccgt ccagttggtg ggtaacagct ggacccctgg    1020
ctaccccgag acccaggagg cgctctgccc gcaggtgaca tggtcctggg accagttgcc    1080
cagcagagct cttggccccg ctcgtgcgcc cacactctcg ccagagtccc cagccggctc    1140
gccagccatg atgctgcagc cgggcccgca gctctacgac gtgatggacg cggtcccagc    1200
gcggcgctgg aaggagttcg tgcgcacgct ggggctgcgc gaggcagaga tcgaagccgt    1260
ggaggtggag atcggtctct tccgagacca gcagtacgag atgctcaagc actggcgcca    1320
gcagcagccc gcgggcctcg gagccgttta cgcggccctg gagcgcatgg ggctggacgg    1380
ctgcgtggaa gacttgcgca gccgcctgca gcgtggccg tgacacgcag cccacttgcc    1440
acctaggcgc tctggtggcc cttgcagaag ccctaagtac ggttacttat gcgtgtagac    1500
attttatgtc acttattaag ccgctggcac ggccctgcgt aggcacacca gccggcccca    1560
ccctgctcg cccctatcgc tccagccaag gcgaagaagc acgaacgaat gtcgagaggg    1620
```

```
ggtgaagaca tttctcaact tctcggccgg agtttggctg agatcgcggt attaaatctg    1680
tgaaagaaat aagaaaaaa acaaacaaa acaaaaaaaa aaaaaaaaaa aaaaaaaaaa     1740
aaa                                                                1743
```

<210> SEQ ID NO 2
<211> LENGTH: 417
<212> TYPE: PRT
<213> ORGANISM: Homo sapiens

<400> SEQUENCE: 2

```
Met Glu Gln Arg Pro Arg Gly Cys Ala Ala Val Ala Ala Ala Leu Leu
1               5                   10                  15

Leu Val Leu Leu Gly Ala Arg Ala Gln Gly Gly Thr Arg Ser Pro Arg
            20                  25                  30

Cys Asp Cys Ala Gly Asp Phe His Lys Lys Ile Gly Leu Phe Cys Cys
        35                  40                  45

Arg Gly Cys Pro Ala Gly His Tyr Leu Lys Ala Pro Cys Thr Glu Pro
    50                  55                  60

Cys Gly Asn Ser Thr Cys Leu Val Cys Pro Gln Asp Thr Phe Leu Ala
65                  70                  75                  80

Trp Glu Asn His His Asn Ser Glu Cys Ala Arg Cys Gln Ala Cys Asp
                85                  90                  95

Glu Gln Ala Ser Gln Val Ala Leu Glu Asn Cys Ser Ala Val Ala Asp
            100                 105                 110

Thr Arg Cys Gly Cys Lys Pro Gly Trp Phe Val Glu Cys Gln Val Ser
        115                 120                 125

Gln Cys Val Ser Ser Ser Pro Phe Tyr Cys Gln Pro Cys Leu Asp Cys
    130                 135                 140

Gly Ala Leu His Arg His Thr Arg Leu Leu Cys Ser Arg Arg Asp Thr
145                 150                 155                 160

Asp Cys Gly Thr Cys Leu Pro Gly Phe Tyr Glu His Gly Asp Gly Cys
                165                 170                 175

Val Ser Cys Pro Thr Ser Thr Leu Gly Ser Cys Pro Glu Arg Cys Ala
            180                 185                 190

Ala Val Cys Gly Trp Arg Gln Met Phe Trp Val Gln Val Leu Leu Ala
        195                 200                 205

Gly Leu Val Val Pro Leu Leu Leu Gly Ala Thr Leu Thr Tyr Thr Tyr
    210                 215                 220

Arg His Cys Trp Pro His Lys Pro Leu Val Thr Ala Asp Glu Ala Gly
225                 230                 235                 240

Met Glu Ala Leu Thr Pro Pro Ala Thr His Leu Ser Pro Leu Asp
                245                 250                 255

Ser Ala His Thr Leu Leu Ala Pro Pro Asp Ser Ser Glu Lys Ile Cys
            260                 265                 270

Thr Val Gln Leu Val Gly Asn Ser Trp Thr Pro Gly Tyr Pro Glu Thr
        275                 280                 285

Gln Glu Ala Leu Cys Pro Gln Val Thr Trp Ser Trp Asp Gln Leu Pro
    290                 295                 300

Ser Arg Ala Leu Gly Pro Ala Ala Ala Pro Thr Leu Ser Pro Glu Ser
305                 310                 315                 320

Pro Ala Gly Ser Pro Ala Met Met Leu Gln Pro Gly Pro Gln Leu Tyr
                325                 330                 335

Asp Val Met Asp Ala Val Pro Ala Arg Arg Trp Lys Glu Phe Val Arg
```

```
                340             345             350
Thr Leu Gly Leu Arg Glu Ala Glu Ile Glu Ala Val Glu Val Glu Ile
            355                 360                 365

Gly Arg Phe Arg Asp Gln Gln Tyr Glu Met Leu Lys Arg Trp Arg Gln
        370                 375                 380

Gln Gln Pro Ala Gly Leu Gly Ala Val Tyr Ala Leu Glu Arg Met
385                 390                 395                 400

Gly Leu Asp Gly Cys Val Glu Asp Leu Arg Ser Arg Leu Gln Arg Gly
                405                 410                 415

Pro

<210> SEQ ID NO 3
<211> LENGTH: 2016
<212> TYPE: DNA
<213> ORGANISM: Homo sapiens

<400> SEQUENCE: 3
```

| | | | | | |
|---|---|---|---|---|---|
| gagagggaaa | agggaaggag | gagactgagt | gattaagtca | cccactgtga | agagctggtc | 60 |
| ttctatttaa | tgggggctct | ctctgcccag | gagtcagagg | tgcctccagg | agcagcagga | 120 |
| gcatggccga | ggatctggga | ctgagctttg | gggaaacagc | cagtgtggaa | atgctgccag | 180 |
| agcacggcag | ctgcaggccc | aaggccagga | gcagcagcgc | acgctgggct | ctcacctgct | 240 |
| gcctggtgtt | gctccccttc | cttgcaggac | tcaccacata | cctgcttgtc | agccagctcc | 300 |
| gggcccaggg | agaggcctgt | gtgcagttcc | aggctctaaa | aggacaggag | tttgcacctt | 360 |
| cacatcagca | agtttatgca | cctcttagag | cagacggaga | taagccaagg | gcacacctga | 420 |
| cagttgtgag | acaaactccc | acacagcact | ttaaaaatca | gttcccagct | ctgcactggg | 480 |
| aacatgaact | aggcctggcc | ttcaccaaga | accgaatgaa | ctataccaac | aaattcctgc | 540 |
| tgatcccaga | gtcgggagac | tacttcattt | actcccaggt | cacattccgt | gggatgacct | 600 |
| ctgagtgcag | tgaaatcaga | caagcaggcc | gaccaaacaa | gccagactcc | atcactgtgg | 660 |
| tcatcaccaa | ggtaacagac | agctaccctg | agccaaccca | gctcctcatg | gggaccaagt | 720 |
| ctgtatgcga | agtaggtagc | aactggttcc | agcccatcta | cctcggagcc | atgttctctc | 780 |
| tgcaagaagg | ggacaagcta | atggtgaacg | tcagtgacat | ctcttttggtg | gattacacaa | 840 |
| aagaagataa | aaccttcttt | ggagccttct | tactatagga | ggagagcaaa | tatcattata | 900 |
| tgaaagtcct | ctgccaccga | gttcctaatt | ttctttgttc | aaatgtaatt | ataaccaggg | 960 |
| gttttcttgg | ggccgggagt | aggggcatt | ccacagggac | aacggtttag | ctatgaaatt | 1020 |
| tggggcccaa | aatttcacac | ttcatgtgcc | ttactgatga | gagtactaac | tggaaaaggc | 1080 |
| tgaagagagc | aaatatatta | ttaagatggg | ttggaggatt | ggcgagtttc | taaatattaa | 1140 |
| gacactgatc | actaaatgaa | tggatgatct | actcgggtca | ggattgaaag | agaaatattt | 1200 |
| caacacctcc | ctgctataca | atggtcacca | gtggtccagt | tattgttcaa | tttgatcata | 1260 |
| aatttgcttc | aattcaggag | ctttgaagga | agtccaagga | aagctctaga | aaacagtata | 1320 |
| aactttcaga | ggcaaaatcc | ttcaccaatt | tttccacata | ctttcatgcc | ttgcctaaaa | 1380 |
| aaaatgaaaa | gagagttggt | atgtctcatg | aatgttcaca | cagaaggagt | tggttttcat | 1440 |
| gtcatctaca | gcatatgaga | aaagctacct | ttcttttgat | tatgtacaca | gatatctaaa | 1500 |
| taaggaagta | tgagtttcac | atgtatatca | aaaatacaac | agttgcttgt | attcagtaga | 1560 |
| gttttcttgc | ccacctattt | tgtgctgggt | tctaccttaa | cccagaagac | actatgaaaa | 1620 |
| acaagacaga | ctccactcaa | aatttatatg | aacaccacta | gatacttcct | gatcaaacat | 1680 |

```
cagtcaacat actctaaaga ataactccaa gtcttggcca ggcgcagtgg ctcacacctg   1740
taatcccaac actttgggag gccaaggtgg gtggatcatc taaggccggg agttcaagac   1800
cagcctgacc aacgtggaga aaccccatct ctactaaaaa tacaaaatta gccgggcgtg   1860
gtagcgcatg gctgtaatcc tggctactca ggaggccgag gcagaagaat tgcttgaact   1920
ggggaggcag aggttgcggt gagcccagat cgcgccattg cactccagcc tgggtaacaa   1980
gagcaaaact ctgtccaaaa aaaaaaaaaa aaaaaa                             2016
```

<210> SEQ ID NO 4
<211> LENGTH: 251
<212> TYPE: PRT
<213> ORGANISM: Homo sapiens

<400> SEQUENCE: 4

```
Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Pro Phe Leu Ala
        35                  40                  45

Gly Leu Thr Thr Tyr Leu Leu Val Ser Gln Leu Arg Ala Gln Gly Glu
    50                  55                  60

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
    130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250
```

<210> SEQ ID NO 5
<211> LENGTH: 141
<212> TYPE: PRT
<213> ORGANISM: Homo sapiens

<400> SEQUENCE: 5

```
Met Glu Gln Arg Pro Arg Gly Cys Ala Ala Val Ala Ala Ala Leu Leu
1               5                   10                  15
```

```
Leu Val Leu Leu Gly Ala Arg Ala Gln Gly Gly Thr Arg Ser Pro Arg
            20                  25                  30

Cys Asp Cys Ala Gly Asp Phe His Lys Lys Ile Gly Leu Phe Cys Cys
            35                  40                  45

Arg Gly Cys Pro Ala Gly His Tyr Leu Lys Ala Pro Cys Thr Glu Pro
    50                  55                  60

Cys Gly Asn Ser Thr Cys Leu Val Cys Pro Gln Asp Thr Phe Leu Ala
65                  70                  75                  80

Trp Glu Asn His His Asn Ser Glu Cys Ala Arg Cys Gln Ala Cys Asp
                85                  90                  95

Glu Gln Ala Ser Gln Val Ala Leu Glu Asn Cys Ser Ala Val Ala Asp
            100                 105                 110

Thr Arg Cys Gly Cys Lys Pro Gly Trp Phe Val Glu Cys Gln Val Ser
            115                 120                 125

Gln Cys Val Ser Ser Ser Pro Phe Tyr Cys Gln Pro Cys
            130                 135                 140

<210> SEQ ID NO 6
<211> LENGTH: 159
<212> TYPE: PRT
<213> ORGANISM: Murine

<400> SEQUENCE: 6

Met Glu Glu Leu Pro Arg Arg Glu Arg Ser Pro Gly Ala Ala Thr
1               5                   10                  15

Pro Gly Ser Thr Ala Arg Val Leu Gln Pro Leu Phe Leu Pro Leu Leu
            20                  25                  30

Leu Leu Leu Leu Leu Leu Leu Gly Gly Gln Gly Gln Gly Gly Met Ser
            35                  40                  45

Gly Arg Cys Asp Cys Ala Ser Glu Ser Gln Lys Arg Tyr Gly Pro Phe
    50                  55                  60

Cys Cys Arg Gly Cys Pro Lys Gly His Tyr Met Lys Ala Pro Cys Ala
65                  70                  75                  80

Glu Pro Cys Gly Asn Ser Thr Cys Leu Pro Cys Pro Ser Asp Thr Phe
                85                  90                  95

Leu Thr Arg Asp Asn His Phe Lys Thr Asp Cys Thr Arg Cys Gln Val
            100                 105                 110

Cys Asp Glu Glu Ala Leu Gln Val Thr Leu Glu Asn Cys Ser Ala Lys
            115                 120                 125

Ser Asp Thr His Cys Gly Cys Gln Ser Gly Trp Cys Val Asp Cys Ser
            130                 135                 140

Thr Glu Pro Cys Gly Lys Ser Ser Pro Phe Ser Cys Val Pro Cys
145                 150                 155

<210> SEQ ID NO 7
<211> LENGTH: 170
<212> TYPE: PRT
<213> ORGANISM: Murine

<400> SEQUENCE: 7

Gln Gln Val Tyr Ala Pro Leu Arg Ala Asp Gly Asp Lys Pro Arg Ala
1               5                   10                  15

His Leu Thr Val Val Arg Gln Thr Pro Thr Gln His Phe Lys Asn Gln
            20                  25                  30

Phe Pro Ala Leu His Trp Glu His Glu Leu Gly Leu Ala Phe Thr Lys
            35                  40                  45
```

```
Asn Arg Met Asn Tyr Thr Asn Lys Phe Leu Leu Ile Pro Glu Ser Gly
             50                  55                  60

Asp Tyr Phe Ile Tyr Ser Gln Val Thr Phe Arg Gly Met Thr Ser Glu
 65                  70                  75                  80

Cys Ser Glu Ile Arg Gln Ala Gly Arg Pro Asn Lys Pro Asp Ser Ile
                 85                  90                  95

Thr Val Val Ile Thr Lys Val Thr Asp Ser Tyr Pro Glu Pro Thr Gln
            100                 105                 110

Leu Leu Met Gly Thr Lys Ser Val Cys Glu Val Gly Ser Asn Trp Phe
            115                 120                 125

Gln Pro Ile Tyr Leu Gly Ala Met Phe Ser Leu Gln Glu Gly Asp Lys
            130                 135                 140

Leu Met Val Asn Val Ser Asp Ile Ser Leu Val Asp Tyr Thr Lys Glu
145                 150                 155                 160

Asp Lys Thr Phe Phe Gly Ala Phe Leu Leu
                165                 170

<210> SEQ ID NO 8
<211> LENGTH: 180
<212> TYPE: PRT
<213> ORGANISM: Homo sapiens

<400> SEQUENCE: 8

Met Leu Arg Ala Ile Thr Glu Glu Arg Ser Glu Pro Ser Pro Gln Gln
 1               5                  10                  15

Val Tyr Ser Pro Pro Arg Gly Lys Pro Arg Ala His Leu Thr Ile Lys
             20                  25                  30

Lys Gln Thr Pro Ala Pro His Leu Lys Asn Gln Leu Ser Ala Leu His
         35                  40                  45

Trp Glu His Asp Leu Gly Met Ala Phe Thr Lys Asn Gly Met Lys Tyr
     50                  55                  60

Ile Asn Lys Ser Leu Val Ile Pro Glu Ser Gly Asp Tyr Phe Ile Tyr
 65                  70                  75                  80

Ser Gln Ile Thr Phe Arg Gly Thr Thr Ser Val Cys Gly Asp Ile Ser
                 85                  90                  95

Arg Gly Arg Arg Pro Asn Lys Pro Asp Ser Ile Thr Val Ile Thr Lys
            100                 105                 110

Val Ala Asp Ser Tyr Pro Glu Pro Ala Arg Leu Leu Thr Gly Ser Lys
            115                 120                 125

Ser Val Cys Glu Ile Ser Asn Asn Trp Phe Gln Ser Leu Tyr Leu Gly
            130                 135                 140

Ala Thr Phe Ser Leu Glu Glu Gly Asp Arg Leu Met Val Asn Val Ser
145                 150                 155                 160

Asp Ile Ser Leu Val Asp Tyr Thr Lys Glu Asp Lys Thr Phe Phe Gly
                165                 170                 175

Ala Phe Leu Leu
            180

<210> SEQ ID NO 9
<211> LENGTH: 60
<212> TYPE: PRT
<213> ORGANISM: Artificial Sequence
<220> FEATURE:
<223> OTHER INFORMATION: PLAD of DR3

<400> SEQUENCE: 9
```

Gly Ala Arg Ala Gln Gly Gly Thr Arg Ser Pro Arg Cys Asp Cys Ala
1               5                   10                  15

Gly Asp Phe His Lys Lys Ile Gly Leu Phe Cys Cys Arg Gly Cys Pro
            20                  25                  30

Ala Gly His Tyr Leu Lys Ala Pro Cys Thr Glu Pro Cys Gly Asn Ser
        35                  40                  45

Thr Cys Leu Val Cys Pro Gln Asp Thr Phe Leu Ala
    50                  55                  60

<210> SEQ ID NO 10
<211> LENGTH: 50
<212> TYPE: PRT
<213> ORGANISM: Artificial Sequence
<220> FEATURE:
<223> OTHER INFORMATION: PLAD of DR3

<400> SEQUENCE: 10

Gly Ala Arg Ala Gln Gly Gly Thr Arg Ser Pro Arg Cys Asp Cys Ala
1               5                   10                  15

Gly Asp Phe His Lys Lys Ile Gly Leu Phe Cys Cys Arg Gly Cys Pro
            20                  25                  30

Ala Gly His Tyr Leu Lys Ala Pro Cys Thr Glu Pro Cys Gly Asn Ser
        35                  40                  45

Thr Cys
    50

<210> SEQ ID NO 11
<211> LENGTH: 40
<212> TYPE: PRT
<213> ORGANISM: Artificial Sequence
<220> FEATURE:
<223> OTHER INFORMATION: PLAD of DR3

<400> SEQUENCE: 11

Gly Ala Arg Ala Gln Gly Gly Thr Arg Ser Pro Arg Cys Asp Cys Ala
1               5                   10                  15

Gly Asp Phe His Lys Lys Ile Gly Leu Phe Cys Cys Arg Gly Cys Pro
            20                  25                  30

Ala Gly His Tyr Leu Lys Ala Pro
        35                  40

<210> SEQ ID NO 12
<211> LENGTH: 38
<212> TYPE: PRT
<213> ORGANISM: Artificial Sequence
<220> FEATURE:
<223> OTHER INFORMATION: PLAD of DR3

<400> SEQUENCE: 12

Gly Ala Arg Ala Gln Gly Gly Thr Arg Ser Pro Arg Cys Asp Cys Ala
1               5                   10                  15

Gly Asp Phe His Lys Lys Ile Gly Leu Phe Cys Cys Arg Gly Cys Pro
            20                  25                  30

Ala Gly His Tyr Leu Lys
        35

<210> SEQ ID NO 13
<211> LENGTH: 50
<212> TYPE: PRT
<213> ORGANISM: Artificial Sequence
<220> FEATURE:
<223> OTHER INFORMATION: PLAD of DR3

<400> SEQUENCE: 13

Pro Arg Cys Asp Cys Ala Gly Asp Phe His Lys Ile Gly Leu Phe
1               5                   10                  15

Cys Cys Arg Gly Cys Pro Ala Gly His Tyr Leu Lys Ala Pro Cys Thr
            20                  25                  30

Glu Pro Cys Gly Asn Ser Thr Cys Leu Val Cys Pro Gln Asp Thr Phe
        35                  40                  45

Leu Ala
    50

<210> SEQ ID NO 14
<211> LENGTH: 40
<212> TYPE: PRT
<213> ORGANISM: Artificial Sequence
<220> FEATURE:
<223> OTHER INFORMATION: PLAD of DR3

<400> SEQUENCE: 14

Lys Lys Ile Gly Leu Phe Cys Cys Arg Gly Cys Pro Ala Gly His Tyr
1               5                   10                  15

Leu Lys Ala Pro Cys Thr Glu Pro Cys Gly Asn Ser Thr Cys Leu Val
            20                  25                  30

Cys Pro Gln Asp Thr Phe Leu Ala
        35                  40

<210> SEQ ID NO 15
<211> LENGTH: 38
<212> TYPE: PRT
<213> ORGANISM: Artificial Sequence
<220> FEATURE:
<223> OTHER INFORMATION: PLAD of DR3

<400> SEQUENCE: 15

Ile Gly Leu Phe Cys Cys Arg Gly Cys Pro Ala Gly His Tyr Leu Lys
1               5                   10                  15

Ala Pro Cys Thr Glu Pro Cys Gly Asn Ser Thr Cys Leu Val Cys Pro
            20                  25                  30

Gln Asp Thr Phe Leu Ala
        35

<210> SEQ ID NO 16
<211> LENGTH: 9
<212> TYPE: PRT
<213> ORGANISM: Artificial Sequence
<220> FEATURE:
<223> OTHER INFORMATION: Polyarginine

<400> SEQUENCE: 16

Arg Arg Arg Arg Arg Arg Arg Arg Arg
1               5

<210> SEQ ID NO 17
<211> LENGTH: 16
<212> TYPE: PRT
<213> ORGANISM: Artificial Sequence
<220> FEATURE:
<223> OTHER INFORMATION: Antp

<400> SEQUENCE: 17

Arg Gln Pro Lys Ile Trp Phe Pro Asn Arg Arg Lys Pro Trp Lys Lys
1               5                   10                  15

<210> SEQ ID NO 18
<211> LENGTH: 11
<212> TYPE: PRT
<213> ORGANISM: Artificial Sequence
<220> FEATURE:
<223> OTHER INFORMATION: HIV-Tat

<400> SEQUENCE: 18

```
Gly Arg Lys Lys Arg Arg Gln Arg Pro Pro Gln
1               5                  10
```

<210> SEQ ID NO 19
<211> LENGTH: 16
<212> TYPE: PRT
<213> ORGANISM: Artificial Sequence
<220> FEATURE:
<223> OTHER INFORMATION: Penetratin

<400> SEQUENCE: 19

```
Arg Gln Ile Lys Ile Trp Phe Gln Asn Arg Arg Met Lys Trp Lys Lys
1               5                   10                  15
```

<210> SEQ ID NO 20
<211> LENGTH: 16
<212> TYPE: PRT
<213> ORGANISM: Artificial Sequence
<220> FEATURE:
<223> OTHER INFORMATION: Antp-3A

<400> SEQUENCE: 20

```
Arg Gln Ile Ala Ile Trp Phe Gln Asn Arg Arg Met Lys Trp Ala Ala
1               5                   10                  15
```

<210> SEQ ID NO 21
<211> LENGTH: 9
<212> TYPE: PRT
<213> ORGANISM: Artificial Sequence
<220> FEATURE:
<223> OTHER INFORMATION: Tat

<400> SEQUENCE: 21

```
Arg Lys Lys Arg Arg Gln Arg Arg Arg
1               5
```

<210> SEQ ID NO 22
<211> LENGTH: 21
<212> TYPE: PRT
<213> ORGANISM: Artificial Sequence
<220> FEATURE:
<223> OTHER INFORMATION: Buforin II

<400> SEQUENCE: 22

```
Thr Arg Ser Ser Arg Ala Gly Leu Gln Phe Pro Val Gly Arg Val His
1               5                   10                  15

Arg Leu Leu Arg Lys
            20
```

<210> SEQ ID NO 23
<211> LENGTH: 26
<212> TYPE: PRT
<213> ORGANISM: Artificial Sequence
<220> FEATURE:
<223> OTHER INFORMATION: Transportan

<400> SEQUENCE: 23

```
Gly Trp Thr Leu Asn Ser Ala Gly Tyr Leu Leu Gly Lys Ile Asn Lys
```

```
1               5                   10                  15
Ala Leu Ala Ala Leu Ala Lys Lys Ile Leu
            20                  25

<210> SEQ ID NO 24
<211> LENGTH: 18
<212> TYPE: PRT
<213> ORGANISM: Artificial Sequence
<220> FEATURE:
<223> OTHER INFORMATION: Model Amphipathic Peptide (MAP)

<400> SEQUENCE: 24

Lys Leu Ala Leu Lys Leu Ala Leu Lys Ala Leu Lys Ala Ala Leu Lys
1               5                   10                  15

Leu Ala

<210> SEQ ID NO 25
<211> LENGTH: 16
<212> TYPE: PRT
<213> ORGANISM: Artificial Sequence
<220> FEATURE:
<223> OTHER INFORMATION: K-FGF

<400> SEQUENCE: 25

Ala Ala Val Ala Leu Leu Pro Ala Val Leu Leu Ala Leu Leu Ala Pro
1               5                   10                  15

<210> SEQ ID NO 26
<211> LENGTH: 10
<212> TYPE: PRT
<213> ORGANISM: Artificial Sequence
<220> FEATURE:
<223> OTHER INFORMATION: Ku70

<400> SEQUENCE: 26

Val Pro Met Leu Lys Pro Met Leu Lys Glu
1               5                   10

<210> SEQ ID NO 27
<211> LENGTH: 28
<212> TYPE: PRT
<213> ORGANISM: Artificial Sequence
<220> FEATURE:
<223> OTHER INFORMATION: Prion

<400> SEQUENCE: 27

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 28
<211> LENGTH: 18
<212> TYPE: PRT
<213> ORGANISM: Artificial Sequence
<220> FEATURE:
<223> OTHER INFORMATION: pVEC

<400> SEQUENCE: 28

Leu Leu Ile Ile Leu Arg Arg Arg Ile Arg Lys Gln Ala His Ala His
1               5                   10                  15

Ser Lys

<210> SEQ ID NO 29
```

```
<211> LENGTH: 21
<212> TYPE: PRT
<213> ORGANISM: Artificial Sequence
<220> FEATURE:
<223> OTHER INFORMATION: Pep-1

<400> SEQUENCE: 29

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 30
<211> LENGTH: 18
<212> TYPE: PRT
<213> ORGANISM: Artificial Sequence
<220> FEATURE:
<223> OTHER INFORMATION: SynB1

<400> SEQUENCE: 30

Arg Gly Gly Arg Leu Ser Tyr Ser Arg Arg Arg Phe Ser Thr Ser Thr
1               5                   10                  15

Gly Arg

<210> SEQ ID NO 31
<211> LENGTH: 15
<212> TYPE: PRT
<213> ORGANISM: Artificial Sequence
<220> FEATURE:
<223> OTHER INFORMATION: Pep-7

<400> SEQUENCE: 31

Ser Asp Leu Trp Glu Met Met Met Val Ser Leu Ala Cys Gln Tyr
1               5                   10                  15

<210> SEQ ID NO 32
<211> LENGTH: 12
<212> TYPE: PRT
<213> ORGANISM: Artificial Sequence
<220> FEATURE:
<223> OTHER INFORMATION: HN-1

<400> SEQUENCE: 32

Thr Ser Pro Leu Asn Ile His Asn Gly Gln Lys Leu
1               5                   10
```

ANTIBODIES THAT BIND TO TL1A AND METHODS OF TREATING INFLAMMATORY OR AUTOIMMUNE DISEASE COMPRISING ADMINISTERING SUCH ANTIBODIES

PRIORITY DATA

This application is a continuation-in-part of U.S. application Ser. No. 11/972,395, entitled "Blockade of TL1A-DR3 Interactions to Ameliorate T Cell Mediated Disease Pathology", filed Jan. 10, 2008; which claims the benefit of U.S. Provisional Application No. 60/879,668, filed Jan. 10, 2007, the entire disclosures of which are hereby incorporated by reference. This application also claims the benefit of U.S. Provisional Application No. 61/488,671 filed May 20, 2011, the entire disclosure of which is hereby incorporated by reference. Any disclaimer that may have occurred during the prosecution of the above-referenced applications is hereby expressly rescinded, and reconsideration of all relevant art is respectfully requested.

STATEMENT OF GOVERNMENT INTEREST

The Government of the United States owns the invention(s) disclosed and claimed herein.

Mouse hybridoma line 1A9 was deposited on Sep. 20, 2012 at American Type Culture Collection (ATCC) Patent Depository at 10801 University Boulevard, Manassas, Va., 20110 USA and assigned Accession No. PTA-13230. Mouse hybridoma line 106 was deposited on Sep. 20, 2012 at American Type Culture Collection (ATCC) Patent Depository at University Boulevard, Manassas, Va., 20110 USA and assigned Accession No. PTA-13231.

SEQUENCE LISTING

The Sequence Listing text file attached hereto, created Mar. 13, 2012, size 25 kilobytes, and filed herewith as file name "6137NIAMS2CIP_SEQ_20120313_ST25.txt" is incorporated herein by reference in its entirety.

FIELD OF THE INVENTION

The present invention relates to methods and compositions for treating disease in a subject comprising blocking the interaction between DR3 and TL1A, and compositions comprising the same.

BACKGROUND

DR3 (TRAMP, LARD, WSL-1, TNFRSF25) is a tumor necrosis receptor family member expressed specifically on T cells that is most similar to TNFR1. The ligand for DR3 is TL1A, a TNF family member protein reported to be expressed by endothelial cells. TL1A can costimulate T cell activation in vitro, but the physiological sources of TL1A and its in vivo role in peripheral T cell biology are not known.

Interactions between numerous TNF family ligands and receptors play an important role in shaping specific features of T cell responses. A subfamily of TNF receptors including CD30, TNFR2, OX40, CD27, GITR, HVEM, and 4-1BB are expressed on T cells and mediate distinct aspects of costimulation in specific T cell subsets (Croft, 2003). For example, OX40 potentiates post-activation survival of activated CD4+ T cells (Croft), TNFR2 costimulates CD8+ T cell activation, and GITR has a unique role in regulatory T cells. DR3 (TNFRSF25/TRAMP/LARD/WSL-1) is a death domain-containing TNF-family receptor that, like its closest homolog TNFR1, recruits TRADD and has the ability to activate NF-kB and MAP-Kinases or, alternatively, trigger caspase activation and programmed cell death on the cellular context. Unlike TNFR1, DR3 is specifically expressed in lymphocytes with the highest levels on T cells. However the function of this receptor in T cell homeostasis is not well understood, particularly since the authentic ligand for this receptor, TL1A, was only recently identified. Initial reports suggested that TL1A was expressed exclusively on endothelial cells, and addition of exogenous TL1A was reported to costimulate IL-2 and IFN-γ production by human T cells stimulated though the TCR (Papadakis et al., 2004; Papadakis et al., 2005). More recently, TL1A has also been found at sites of inflammation such as in inflammatory bowel disease (Bamias et al., 2003; Bamias et al., 2006).

BRIEF SUMMARY

In accordance with the purpose of this invention, as embodied and broadly described herein, this invention relates to compositions and methods for treating an inflammatory or autoimmune disease in a subject comprising blocking the interaction between DR3 and TL1A.

Additional advantages of the disclosed method and compositions will be set forth in part in the description which follows, and, in part, will be understood from the description or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and, together with the description, serve to explain the principles of the disclosed method and compositions.

FIG. 1A shows Bone marrow-derived DCbone marrow-derived DC or CD11c+ DC were cultured and stimulated for the indicated time with or without 100 ng/ml of LPS, SEA, or STAg. FIG. 1B shows TL1A mRNA expression in bone marrow-derived DC from various knock-out (KO, $^{-/-}$) mice in the presence or absence of 100 ng/ml of LPS for 3 h. RNA was prepared from each sample and used in quantitative PCR. Results indicate the amount of TL1A mRNA calculated relative to the resting cells of each population. FIG. 1C shows purified T cells were cultured and stimulated with 5 µg/ml of anti-CD3/CD28 for the indicated time. RNA was prepared from each sample and used in quantitative PCR. Results indicate the amount of TL1A mRNA calculated relative to freshly purified T cells. FIG. 1D shows TL1A mRNA induction in human Peripheral Blood Mononuclear Cells (PBMC) after T cell activation with anti-CD3/CD28. FIG. 1E shows early peak in TL1A induction comes from non-T, non-B cells. The indicated cell types were purified from PBMC and stimulated as described.

FIG. 2A shows purified T cells were activated with anti-CD3 or anti-CD3/CD28 in presence or absence of 10 ng/ml rTL1A for 3 days. $^3$H was added to the culture, incubated overnight, and analyzed for thymidine incorporation. FIG. 2B shows purified T cells were activated with anti-CD3 or anti-CD3/CD28 in the presence or absence of 10 ng/ml rTL1A and 10 μg/ml of 3C7 antibody for 3 days. $^3$H-thymidine was added to the culture, incubated overnight, and analyzed for thymidine incorporation. FIG. 2C shows CFSE-labeled, purified T cells were activated with anti-CD3 or anti-CD3/CD28 in the presence or absence of 10 ng/ml rTL1A. Cells were analyzed by flow cytometry. FIG. 2D shows supernatants from T cells activated by anti-CD3/CD28 were harvested and analyzed for the production of the indicated cytokines after 24 hours.

FIG. 3A shows bone marrow DC were cultured with naïve OT-II or DR3 KO OTT-II T cells in the presence of indicated Ova peptide concentration for 3 days. $^3$H was added to the culture, incubated overnight, and analyzed for thymidine incorporation. FIG. 3B shows bone marrow DC were cultured with naïve OT-II or DR3 KO OTT-II T cells in the presence of indicated Ova peptide concentration. Cells were harvested after 24, 48, and 72 hours and stained for activation marker and analyzed by flow cytometry. Supernatants from co-culture were harvested at 24, 48, and 72 hours and tested for IL-2 production.

FIG. 4A shows purified naïve T cells stimulated with anti-CD3/CD28 were cultured under Th1 (anti-IL-4+IL-12) or under Th2 (anti-IFN-γ+IL-4) conditions for 6 days. Cells were then restimulated with anti-CD3/CD28 for 5-6 h and stained for intracellular cytokines and analyzed by flow cytometry. B-sorted CD11c$^+$ DC were cultured with OT-II or DR3-OT-II T cells in presence of Ova peptide with either SEA, STAg, or IL-12 for 6 days. Cells were then restimulated with PMA/ionomycin for 6 h and stained for intracellular cytokines and analyzed by flow cytometry.

FIGS. 5A-5D show that DR3 KO mice have reduced lung histopathology in an Ova-mediated asthma model. Mice were sensitized with Alum+PBS (control) or Alum+Ova. Mice were then challenge with PBS (control) or Ova. FIG. 5A shows histology of the lungs was performed with PAS staining. FIG. 5B shows histopathology of the lungs was scored. FIG. 5C shows RNA prepared from lungs and used in quantitative PCR. Results indicate the amount of cytokine mRNA calculated relative to the lungs of the control mice treated with PBS (right panel). Spleens of the Ova-mediated asthma model mice were harvested, and splenocytes were cultured in the absence or presence of either 10 μg/ml or 50 μg/ml Ova protein for 3 days. $^3$H was added to the culture, incubated overnight, and analyzed for thymidine incorporation. The supernatant of the splenocytes cultured with 50 μg/ml was harvested after 3 days and analyzed for cytokines (left panel). FIG. 5D shows blood of the Ova-mediated asthma model mice harvested and the serum tested for IgG1 and Ova specific IgG1 level by ELISA.

FIG. 6A shows the clinical score. FIG. 6B shows spleen, non-draining, and draining lymph nodes cultured and restimulated with MOG. $^3$H was added to the culture, incubated overnight, and analyzed for thymidine incorporation, or cells were restimulated for 6 h with PMA/ionomycin and stained for IL-17 and IFNγ (FIG. 6C). FIG. 6D shows cells from spinal cord were restimulated with PMA/ionomycin for 6 h and stained for IL-17 and IFNγ.

FIG. 7A shows increased CD44 expression in T cells isolated from three independent founder lines of CD2-TL1A transgenic mice. FIG. 7B shows representative Gross (top), low power H&E section (middle), and high power H&E section (bottom) images of ileum from CD2-TL1A transgenic mice and littermate controls (WT). Bowel wall thickening, destruction of villi, and infiltration of inflammatory cells into the mucosa can be seen.

FIG. 8A shows purified CD4$^+$ T cells from C57BL/6 or DR3 KODR3 KO mice were activated with anti-CD3 or anti-CD3 and anti-CD28 in the presence or absence of 10 ng/ml mouse rTL1A for 3 days. $^3$H-thymidine was added to the culture, incubated overnight, and analyzed for thymidine incorporation. Error bars represent s.e.m. of triplicate samples. FIG. 8B shows purified T cells from C57BL/6 cultured as above, but also in the presence of 10 μg/ml anti-IL-2Rα antibody or isotype control for 3 days (left panel). Purified T cells from IL-2$^{-/-}$ or IL-2$^{+/+}$ were cultured as above, in the absence or presence 10 U/ml IL-2 for 3 days (middle and right panels). Error bars represent s.e.m. of triplicate samples. FIG. 8C shows supernatants from CD4$^+$ T cells activated and cultured as in FIG. 8A, harvested at the indicated time points, with the indicated cytokines measured with cytokine bead arrays; n.d.=below limit of detection (4 pg/ml).

FIG. 9A shows bone marrow-derived DC or CD11c$^+$ DC from wild-type C57BL/6 mice cultured and stimulated for the indicated time with or without 100 ng/ml LPS, 20 μg/ml SEA, or 10 μg/ml STAg. RNA was prepared from each sample and used in reverse-transcriptase quantitative PCR(RT-qPCR). FIG. 9B shows bone marrow-derived DC from wild-type C57BL/6 or the indicated knock-out (KO) mice cultured and stimulated in the presence or absence of 100 ng/ml LPS for 3 hours. RNA was prepared from each sample and used in RT-qPCR. FIG. 9C shows bone marrow-derived DC from wild-type C57BL/6 cultured and stimulated for the indicated times with or without 100 ng/ml LPS, or Ig cross-linking, and RNA prepared from each sample and used in RT-qPCR. FIG. 9D shows purified T cells from wild-type C57BL/6 or DR3 KO mice cultured and stimulated with 5 μg/ml anti-CD3 and anti-CD28 for the indicated time. RNA was prepared from each sample and used in RT-qPCR. Results indicate the amount of TL1A mRNA calculated relative to the untreated cells of each population (FIG. 9A-C), or relative to unstimulated T cells of each genotype (FIG. 9D). TL1A basal mRNA levels in T cells were approximately 50-fold lower than in DC. Error bars represent s.e.m. of triplicate samples.

FIG. 10A shows bone marrow DC cultured with naïve OT-II or DR3 KO OT-II CD4$^+$ T cells in the presence of the indicated Ova peptide concentration, and in the absence (left panel) or presence (right panel) of CTLA4Ig for 3 days. $^3$H-thymidine was added to the culture, incubated overnight, and analyzed for thymidine incorporation. FIG. 10B shows supernatants from the above cultures harvested after 72 hours and tested for cytokine production. n.d.=below limit of detection (4 pg/ml).

FIG. 11A shows T-depleted APC cultured with C57BL/6 or DR3 KO purified naïve CD4+ T cells in the presence of soluble anti-CD3 and anti-CD28 under Th0, Th1, Th2, or Th17 polarization conditions for 4 days. Cells were then restimulated with PMA and Ionomycin for 5-6 hours, stained for intracellular cytokines, and analyzed by flow cytometry. FIG. 11B shows sorted CD11c+ DC cultured with OT-II or DR3 KO OT-II purified naïve CD4+ T cells in the presence of Ova peptide under Th0, Th1, or Th2 polarization conditions or in the presence of STAg for 6 days. Cells were then restimulated with anti-CD3 and anti-CD28 for 5-6 hours, stained for intracellular cytokines, and analyzed by flow cytometry.

FIG. 12A shows examples of PAS-stained histology with airways (aw) and infiltrating cells (arrowheads). FIG. 12B shows histopathology of the lungs scored (top panel) and cells in the BAL counted (bottom panel). FIG. 12C shows cells extracted from the lungs and analyzed by flow cytometry (FIG. 12D). RNA was prepared from lungs and used in RT-qPCR. Results indicate the amount of cytokine mRNA calculated relative to the lungs of control mice treated with PBS. P values are for unpaired t-tests on mRNA levels of the indicated cytokines between DR3 KO and control mice induced with Ova. FIG. 12E shows splenocytes cultured in the presence of 50 μg/ml Ova protein or media control for 3 days. Supernatants were analyzed for cytokine production by cytometric bead array. FIG. 12F shows serum tested for Ova-specific IgE and Ova-specific IgG1 levels by ELISA. P values obtained by comparing groups with an unpaired two-tailed T test are shown where significant; n.s.=not significant.

FIG. 13A shows DR3 KO mice and C57BL/6 control mice induced for EAE as described below and clinical scores measured daily. FIG. 13B shows draining lymph nodes from the site of MOG injection harvested and cells restimulated with the indicated amounts of MOG peptide. T cell proliferation was assessed by $^3$H-thymidine incorporation after 3 days. FIG. 13C shows cells harvested from spinal cords restimulated for 4 hours with anti-CD3 and anti-CD28 and analyzed by flow cytometry for T cell surface markers, and gated CD4+CD45+ cells were analyzed for intracellular cytokine production. FIG. 13D shows mRNA from spinal cord or spleen from the indicated groups of mice analyzed by RT-qPCR for IL-17 and IFN-γ mRNA. Results are normalized to β2m or CD3-δ. Error bars represent s.e.m of triplicate samples.

FIG. 17A shows purified naïve)(CD62L$^{hi}$TD44$^{lo}$) CD4+ T cells from C57BL/6 or DR3 KO mice activated with anti-CD3 in the presence or absence of 10 ng/ml mouse rTL1A for 3 days. $^3$H-thymidine was added to the culture, incubated overnight, and analyzed for thymidine incorporation. FIG. 17B shows supernatants from naïve CD4+ T cells cultured as above, harvested after 3 days, and analyzed for cytokine production. FIG. 17C shows spleen and lymph nodes (mLN) from C57BL/6 or DR3 KO mice analyzed for memory population by determining CD44 expression in CD4+ T cells.

FIGS. 20A-D show flow cytometric staining of cells transfected with mouse TL1A-GFP fusion protein. FIG. 20A is a negative control mAb. FIGS. 20B and 20C are two positive anti-TL1A clones. FIG. 20D is a positive clone reacted with cells transfected with GFP alone. FIG. 20E shows blockade of TL1A-induced apoptosis in the RPMI 8826 cell line. 100 ng/ml TL1A+Cycloheximide (CHX) was added to RPMI-8826 B lymphoma cells, and cellular viability was measured 24 hours later with an MTT assay. Viability was normalized to 100% for medium alone. Anti-TL1A antiserum was used at 1:1000 dilution.

FIG. 21A shows gross (top row), low (middle row), and high (bottom row) power magnification of sections of ileum from Wild-type (WT), TL1A-CD2 line R6 (R6) and TL1A CD11c line I4 (I4) transgenic mice. FIGS. 21B and 21C show summaries of histopathological IBD scores of the indicated regions of CD2-TL1A and CD11c-TL1A transgenic mice. FIG. 21D shows weight gain in the three weeks following weaning in the indicated groups of mice. FIG. 21E shows relative levels of RNA for the indicated cytokines in ileum from CD2-TL1A transgenic mice measured with quantitative RT-PCR and normalized to an average of 1 in wild-type mice.

DETAILED DESCRIPTION

Figure 1A:
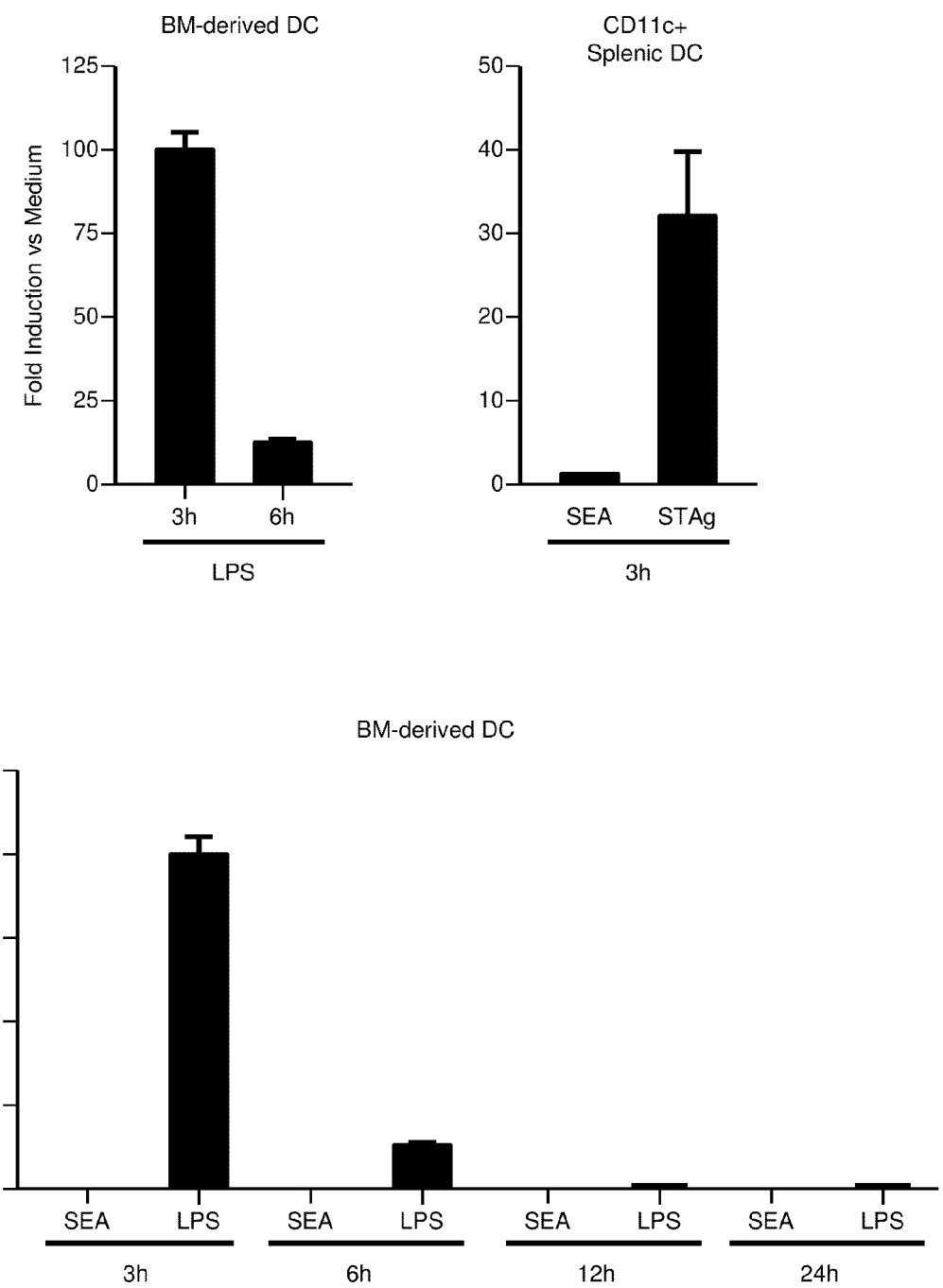
FIGS. 1A-1E show that TL1A mRNA expression is strongly induced in bone marrow-derived dentritic cells (DC) after various innate stimuli and is MyD88-dependent.

The disclosed methods and compositions may be understood more readily by reference to the following detailed description of particular embodiments and the examples included therein and to the Figures and their previous and following description.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed, while specific reference of each of the various individual and collective combinations and permutation of these compounds may not be explicitly disclosed, each is specifically contemplated and described herein. For example, if a peptide is disclosed and discussed, and a number of modifications that can be made to a number of molecules including the peptide are discussed, each and every combination and permutation of peptide and the modifications that are possible are specifically contemplated unless specifically indicated to the contrary. Thus, if a class of molecules A, B, and C are disclosed, as well as a class of molecules D, E, and F and an example of a combination molecule, A-D, is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed, it is understood that each of these additional steps can be performed with any specific embodiment or combination of embodiments of the disclosed methods, and that each such combination is specifically contemplated and should be considered disclosed.

The meanings of abbreviations used are as follows: "BSA" means bovine serum albumin, "ELISA" means enzyme linked immunosorbent assay, "CIH" means collagen-induced arthritis, "SF" means synovial fluid, "microCT" means microtomography, "APC" means antigen-presenting cells, "WT" means wild-type, "KO" means knockout, "DC" means dendritic cells, "RIA" means radioimmunoassay, "RIPA" means radioimmune precipitation assays, "FRET" means fluorescence resonance energy transfer, "FRAP/FLAP"

means fluorescence recovery/localization after photobleaching, "FACS" means fluorescence activated cell sorting, "RT-PCR" means real time polymerase chain reaction, "LPS" means lipopolysaccharide, "FADD" means Fas-Associated protein with Death Domain, "BALF" means bronchoalveolar lavage fluid.

Those skilled in the art will recognize, or be able to ascertain using no more than routine experimentation, many equivalents to the specific embodiments of the method and compositions described herein. Such equivalents are intended to be encompassed by the following claims.

It is understood that the disclosed methods and compositions are not limited to the particular methodology, protocols, and reagents described as these may vary. It is also to be understood that the terminology used herein is for the purpose of describing particular embodiments only and is not intended to limit the scope of the present invention, which will be limited only by the appended claims.

A. METHODS OF TREATMENT

Provided is a method of treating an inflammatory or autoimmune disease in a subject comprising blocking the interaction between DR3 and TL1A.

The interaction between DR3 and TL1A can be blocked by reducing endogenous DR3 levels, activity, or availability. The interaction between DR3 and TL1A can also be blocked by reducing endogenous TL1A levels, activity, or availability. The interaction between DR3 and TL1A can be blocked using agents that directly interfere with the interaction between the two molecules. For example, direct interference can be affected by an agent that binds to DR3 at its binding site for TL1A or an agent that binds to TL1A at its binding site for DR3. Typically, this binding would competitively interfere with the ability of the other molecule to bind at that site.

Protein levels, activity, or availability can be affected by modulating, for example, the transcription, translation, translocation, ubiquitination, phosphorylation, glycosylation, or propeptide cleavage of the peptide.

i. Functional Nucleic Acids

For example, endogenous levels of TL1A can be reduced using functional nucleic acids, such as antisense, RNAi, siRNA, ribozymes, or aptamers.

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, RNAi, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA of TL1A or the genomic DNA of TL1A, or they can interact with the polypeptide TL1A. Alternatively, functional nucleic acids can interact with the mRNA of DR3 or the genomic DNA of TR,3 or they can interact with the DR3 polypeptide. Often, functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule but, rather, is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH-mediated RNA-DNA hybrid degradation. Alternatively, the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$. A representative sample of methods and techniques which aid in the design and use of antisense molecules can be found in U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically, aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $K_d$'s from the target molecule of less than $10^{-12}$ M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule (U.S. Pat. No. 5,543,293). It is preferred that the aptamer have a $K_d$ with the target molecule at least 10, 100, 1000, 10,000, or 100,000 fold lower than the $K_d$ with a background binding molecule. It is preferred when doing the comparison for a polypeptide, for example, that the background molecule be a different polypeptide. Representative examples of how to make and use aptamers to bind a variety of different target molecules can be found in U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698 The term "synthetic aptamer" means an aptamer or aptameric sequence that is not heretofore known to occur in nature and function as a biological recognition site or an aptamer conjugate.

Ribozymes are nucleic acid molecules that are capable of catalyzing a chemical reaction, either intramolecularly or intermolecularly. Ribozymes are, thus, catalytic nucleic acids. It is preferred that the ribozymes catalyze intermolecular reactions. There are a number of different types of ribozymes that catalyze nuclease or nucleic acid polymerase-type reactions, which are based on ribozymes found in natural systems, such as hammerhead ribozymes, (U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203; International Patent Application Nos. WO 9858058 by Ludwig and Sproat, WO 9858057 by Ludwig and Sproat, and WO 9718312 by Ludwig and Sproat) hairpin ribozymes (for example, U.S. Pat. Nos. 5,631,115, 5,646,031, 5,683,902, 5,712,384, 5,856,188, 5,866,701, 5,869,339, and 6,022,962), and tetrahymena ribozymes (for example, U.S. Pat. Nos. 5,595,873 and 5,652,107). There are also a number of ribozymes that are not found in natural systems, but which have been engineered to catalyze specific reactions de novo (for example, U.S. Pat. Nos. 5,580,967, 5,688,670, 5,807, 718, and 5,910,408). Preferred ribozymes cleave RNA or DNA substrates and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target-specific cleavage of nucleic acids, because recognition of the target substrate is based on the target substrates sequence. Representative examples of how to make and use ribozymes to catalyze a variety of different reactions can be found in U.S. Pat. Nos. 5,646,042, 5,693,535, 5,731,295, 5,811,300, 5,837, 855, 5,869,253, 5,877,021, 5,877,022, 5,972,699, 5,972,704, 5,989,906, and 6,017,756.

Triplex-forming functional nucleic acid molecules are molecules that can interact with either double-stranded or single-stranded nucleic acids. When triplex molecules interact with a target region, a structure called a triplex is formed, in which there are three strands of DNA forming a complex dependent on both Watson-Crick and Hoogsteen base-pairing. Triplex molecules are preferred because they can bind target regions with high affinity and specificity. It is preferred that the triplex-forming molecules bind the target molecule with a $K_d$ less than $10^{-6}$, $10^{-8}$, $10^{-10}$, or $10^{-12}$. Representative examples of how to make and use triplex-forming molecules to bind a variety of different target molecules can be found in U.S. Pat. Nos. 5,176,996; 5,645,985; 5,650,316; 5,683,874; 5,693,773; 5,834,185; 5,869,246; 5,874,566 and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, Science 238:407-409 (1990)).

Similarly, eukaryotic EGS/RNAse P-directed cleavage of RNA can be utilized to cleave desired targets within eukarotic cells. (Yuan et al., Proc. Natl. Acad. Sci. USA 89:8006-8010 (1992); WO 93/22434 by Yale; WO 95/24489 by Yale; Yuan and Altman, EMBO J 14:159-168 (1995), and Carrara et al., Proc. Natl. Acad. Sci. (USA) 92:2627-2631 (1995)). Representative examples of how to make and use EGS molecules to facilitate cleavage of a variety of different target molecules be found in U.S. Pat. Nos. 5,168,053, 5,624,824, 5,683,873, 5,728,521, 5,869,248, and 5,877,162.

Gene expression can also be effectively silenced in a highly specific manner through RNA interference (RNAi). This silencing was originally observed with the addition of double-stranded RNA (dsRNA) (Fire, A., et al. (1998) Nature, 391: 806-11; Napoli, C., et al. (1990) Plant Cell 2:279-89; Hannon, G. J. (2002) Nature, 418:244-51). Once dsRNA enters a cell, it is cleaved by an RNase III-like enzyme, Dicer, into double-stranded small interfering RNAs (siRNA) 21-23 nucleotides in length that contain 2 nucleotide overhangs on the 3' ends (Elbashir, S. M., et al. (2001) Genes Dev., 15:188-200; Bernstein, E., et al. (2001) Nature, 409:363-6; Hammond, S. M., et al. (2000) Nature, 404:293-6). In an ATP-dependent step, the siRNAs become integrated into a multi-subunit protein complex, commonly known as the RNAi-induced silencing complex (RISC), which guides the siRNAs to the target RNA sequence (Nykanen, A., et al. (2001) Cell, 107:309-21). At some point, the siRNA duplex unwinds, and it appears that the antisense strand remains bound to RISC and directs degradation of the complementary mRNA sequence by a combination of endo and exonucleases (Martinez, J., et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence-specific gene silencing can be achieved in mammalian cells using synthetic, short double-stranded RNAs that mimic the siRNAs produced by the enzyme Dicer (Elbashir, S. M., et al. (2001) Nature, 411:494 498) (Ui-Tei, K., et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit. In certain examples, siRNAs are directed against certain target genes, such as the TL1A gene or the DR3 gene.

The production of siRNA from a vector is more commonly done through the transcription of short hairpin RNAs (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors. Disclosed herein are any shRNA designed as described above based on the sequences for the herein disclosed inflammatory mediators.

Plasmids include antisense sequences that recognize one or more of the sequences shown in SEQ ID NOS:1 and 3 or a sequence that encodes a protein listed in SEQ ID NOS: 2 and 4. For example, cDNA fragments or variants coding for a host protein involved in viral infection are PCR amplified. The nucleotides are amplified using Pfu DNA polymerase (Stratagene) and cloned in antisense orientation in a vector, such as a pcDNA vector (InVitrogen, Carlsbad, Calif.). The nucleotide sequence and orientation of the insert can be confirmed by sequencing using a Sequenase kit (Amersham Pharmacia Biotech).

ii. Dominant Negative Peptides

The interaction between DR3 and TL1A can also be blocked using dominant negative mutants.

For example, dominant negative mutants can consist of a truncated cytoplasmic domain of DR3 lacking the 'death domain' that recruits FADD, or point mutations in this region that abrogate FADD binding. Dominant negative constructs such as this have successfully blocked signaling by related receptors such as Fas.

Likewise, dominant negative mutants of TL1A can be engineered to bind wild-type subunits of the TL1A trimer, but not bind ligand, as previously described (Steed et al., 2003).

Another strategy for dominating inhibition could employ a pre-ligand assembly domain (PLAD) as described for TNFR1 and Fas in U.S. Pat. No. 7,148,061, which is hereby incorporated herein by reference in its entirety for the teaching of PLADs.

The PLAD for DR3 can comprise as few as 38 amino acids of the N-terminus of the mature DR3 receptor polypeptide. A mature receptor polypeptide does not include a signal sequence. Thus, a polypeptide having the sequence $R^1$-PLAD-$R^2$ is provided. Examples of PLADs of DR3 include:

TABLE 1

Pre-ligand assembly domain (PLAD)

| PLADs of DR3 | SEQ ID NO: |
|---|---|
| GARAQGGTRSPRCDCAGDFHKKIGLFCCRGCPAGHYLKAPCTEPCGNSTCLVCPQDTFLA | 9 |
| GARAQGGTRSPRCDCAGDFHKKIGLFCCRGCPAGHYLKAPCTEPCGNSTC | 10 |
| GARAQGGTRSPRCDCAGDFHKKIGLFCCRGCPAGHYLKAP | 11 |
| GARAQGGTRSPRCDCAGDFHKKIGLFCCRGCPAGHYLK | 12 |
| ..........PRCDCAGDFHKKIGLFCCRGCPAGHYLKAPCTEPCGNSTCLVCPQDTFLA | 13 |
| ..................KKIGLFCCRGCPAGHYLKAPCTEPCGNSTCLVCPQDTFLA | 14 |
| .....................IGLFCCRGCPAGHYLKAPCTEPCGNSTCLVCPQDTFLA | 15 |

Disclosed is a polypeptide comprising $R^1$-DR3 PLAD-$R^2$, wherein $R^1$ and $R^2$ are optional and, when present, can be H, acyl, $NH_2$, an amino acid, or a peptide. The DR3 PLAD can comprise amino acids 43-58 of SEQ ID NO:2.

Thus, the DR3 PLAD can consist of amino acids 21-80, 22-80, 23-80, 24-80, 25-80, 26-80, 27-80, 28-80, 29-80, 30-80, 31-80, 32-80, 33-80, 34-80, 35-80, 36-80, 37-80, 38-80, 39-80, 40-80, 41-80, 42-80, 43-80 of SEQ ID NO:2. The DR3 PLAD can consist of amino acids 21-79, 22-79, 23-79, 24-79, 25-79, 26-79, 27-79, 28-79, 29-79, 30-79, 31-79, 32-79, 33-79, 34-79, 35-79, 36-79, 37-79, 38-79, 39-79, 40-79, 41-79, 42-79, 43-79 of SEQ ID NO:2. The DR3 PLAD can consist of amino acids 21-78, 22-78, 23-78, 24-78, 25-78, 26-78, 27-78, 28-78, 29-78, 30-78, 31-78, 32-78, 33-78, 34-78, 35-78, 36-78, 37-78, 38-78, 39-78, 40-78, 41-78, 42-78, 43-78 of SEQ ID NO:2. The DR3 PLAD can consist of amino acids 21-77, 22-77, 23-77, 24-77, 25-77, 26-77, 27-77, 28-77, 29-77, 30-77, 31-77, 32-77, 33-77, 34-77, 35-77, 36-77, 37-77, 38-77, 39-77, 40-77, 41-77, 42-77, 43-77 of SEQ ID NO:2. The DR3 PLAD can consist of amino acids 21-76, 22-76, 23-76, 24-76, 25-76, 26-76, 27-76, 28-76, 29-76, 30-76, 31-76, 32-76, 33-76, 34-76, 35-76, 36-76, 37-76, 38-76, 39-76, 40-76, 41-76, 42-76, 43-76 of SEQ ID NO:2. The DR3 PLAD can consist of amino acids 21-75, 22-75, 23-75, 24-75, 25-75, 26-75, 27-75, 28-75, 29-75, 30-75, 31-75, 32-75, 33-75, 34-75, 35-75, 36-75, 37-75, 38-75, 39-75, 40-75, 41-75, 42-75, 43-75 of SEQ ID NO:2. The DR3 PLAD can consist of amino acids 21-74, 22-74, 23-74, 24-74, 25-74, 26-74, 27-74, 28-74, 29-74, 30-74, 31-74, 32-74, 33-74, 34-74, 35-74, 36-74, 37-74, 38-74, 39-74, 40-74, 41-74, 42-74, 43-74 of SEQ ID NO:2. The DR3 PLAD can consist of amino acids 21-73, 22-73, 23-73, 24-73, 25-73, 26-73, 27-73, 28-73, 29-73, 30-73, 31-73, 32-73, 33-73, 34-73, 35-73, 36-73, 37-73, 38-73, 39-73, 40-73, 41-73, 42-73, 43-73 of SEQ ID NO:2. The DR3 PLAD can consist of amino acids 21-72, 22-72, 23-72, 24-72, 25-72, 26-72, 27-72, 28-72, 29-72, 30-72, 31-72, 32-72, 33-72, 34-72, 35-72, 36-72, 37-72, 38-72, 39-72, 40-72, 41-72, 42-72, 43-72 of SEQ ID NO:2. The DR3 PLAD can consist of amino acids 21-71, 22-71, 23-71, 24-71, 25-71, 26-71, 27-71, 28-71, 29-71, 30-71, 31-71, 32-71, 33-71, 34-71, 35-71, 36-71, 37-71, 38-71, 39-71, 40-71, 41-71, 42-71, 43-71 of SEQ ID NO:2. The DR3 PLAD can consist of amino acids 21-70, 22-70, 23-70, 24-70, 25-70, 26-70, 27-70, 28-70, 29-70, 30-70, 31-70, 32-70, 33-70, 34-70, 35-70, 36-70, 37-70, 38-70, 39-70, 40-70, 41-70, 42-70, 43-70 of SEQ ID NO:2. The DR3 PLAD can consist of amino acids 21-69, 22-69, 23-69, 24-69, 25-69, 26-69, 27-69, 28-69, 29-69, 30-69, 31-69, 32-69, 33-69, 34-69, 35-69, 36-69, 37-69, 38-69, 39-69, 40-69, 41-69, 42-69, 43-69 of SEQ ID NO:2. The DR3 PLAD can consist of amino acids 21-68, 22-68, 23-68, 24-68, 25-68, 26-68, 27-68, 28-68, 29-68, 30-68, 31-68, 32-68, 33-68, 34-68, 35-68, 36-68, 37-68, 38-68, 39-68, 40-68, 41-68, 42-68, 43-68 of SEQ ID NO:2. The DR3 PLAD can consist of amino acids 21-67, 22-67, 23-67, 24-67, 25-67, 26-67, 27-67, 28-67, 29-67, 30-67, 31-67, 32-67, 33-67, 34-67, 35-67, 36-67, 37-67, 38-67, 39-67, 40-67, 41-67, 42-67, 43-67 of SEQ ID NO:2. The DR3 PLAD can consist of amino acids 21-66, 22-66, 23-66, 24-66, 25-66, 26-66, 27-66, 28-66, 29-66, 30-66, 31-66, 32-66, 33-66, 34-66, 35-66, 36-66, 37-66, 38-66, 39-66, 40-66, 41-66, 42-66, 43-66 of SEQ ID NO:2. The DR3 PLAD can consist of amino acids 21-65, 22-65, 23-65, 24-65, 25-65, 26-65, 27-65, 28-65, 29-65, 30-65, 31-65, 32-65, 33-65, 34-65, 35-65, 36-65, 37-65, 38-65, 39-65, 40-65, 41-65, 42-65, 43-65 of SEQ ID NO:2. The DR3 PLAD can consist of amino acids 21-64, 22-64, 23-64, 24-64, 25-64, 26-64, 27-64, 28-64, 29-64, 30-64, 31-64, 32-64, 33-64, 34-64, 35-64, 36-64, 37-64, 38-64, 39-64, 40-64, 41-64, 42-64, 43-64 of SEQ ID NO:2. The DR3 PLAD can consist of amino acids 21-63, 22-63, 23-63, 24-63, 25-63, 26-63, 27-63, 28-63, 29-63, 30-63, 31-63, 32-63, 33-63, 34-63, 35-63, 36-63, 37-63, 38-63, 39-63, 40-63, 41-63, 42-63, 43-63 of SEQ ID NO:2. The DR3 PLAD can consist of amino acids 21-62, 22-62, 23-62, 24-62, 25-62, 26-62, 27-62, 28-62, 29-62, 30-62, 31-62, 32-62, 33-62, 34-62, 35-62, 36-62, 37-62, 38-62, 39-62, 40-62, 41-62, 42-62, 43-62 of SEQ ID NO:2. The DR3 PLAD can consist of amino acids 21-61, 22-61, 23-61, 24-61, 25-61, 26-61, 27-61, 28-61, 29-61, 30-61, 31-61, 32-61, 33-61, 34-61, 35-61, 36-61, 37-61, 38-61, 39-61, 40-61, 41-61, 42-61, 43-61 of SEQ ID NO:2. The DR3 PLAD can consist of amino acids 21-60, 22-60, 23-60, 24-60, 25-60, 26-60, 27-60, 28-60, 29-60, 30-60, 31-60, 32-60, 33-60, 34-60, 35-60, 36-60, 37-60, 38-60, 39-60, 40-60, 41-60, 42-60, 43-60 of SEQ ID NO:2. The DR3 PLAD can consist of amino acids 21-59, 22-59, 23-59, 24-59, 25-59, 26-59, 27-59, 28-59, 29-59, 30-59, 31-59, 32-59, 33-59, 34-59, 35-59, 36-59, 37-59, 38-59, 39-59, 40-59, 41-59, 42-59, 43-59 of SEQ ID NO:2. The DR3 PLAD can consist of amino acids 21-58, 22-58, 23-58, 24-58, 25-58, 26-58, 27-58, 28-58, 29-58, 30-58, 31-58, 32-58, 33-58, 34-58, 35-58, 36-58, 37-58, 38-58, 39-58, 40-58, 41-58, 42-58, 43-58 of SEQ ID NO:2.

When $R^1$ and/or $R^2$ is a peptide, this peptide can vary in length. For example, $R^1$ and/or $R^2$ can be 1, 2, 3, 4, 5, 6, 7, 8, 9, 10, 11, 12, 13, 14, 15, 16, 17, 18, 19, 20, 21, 22, 23, 24, 25 or more amino acids in length.

The PLAD-containing polypeptide can be from 35-125 amino acids in length. In a further aspect, the entire polypeptide comprising the isolated TNF-like PLAD can be no more than 125 amino acid residues, and can, thus, be 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124 or 125 amino acids in length. $R^1$ and $R^2$ can be sequences that do not normally flank the DR3 PLAD in a naturally occurring DR3 receptor. $R^1$ and $R^2$ can also be sequences of the DR3 receptor that normally flank the DR3 PLAD in a naturally occurring TNF receptor-like receptor, wherein the polypeptide comprising the TNF-like receptor PLAD is not the entire extracellular domain of a TNF receptor-like receptor.

iii. DR3 Fusion Protein

The interaction between DR3 and TL1A can also be blocked using a DR3 Fc fusion protein. Thus, provided is a composition comprising a DR3 Fc fusion protein.

A fusion protein comprising or consisting of the DR3 extracellular domain (about 140-150 aa) fused to a non-Fc receptor binding mutant of human IgG1 (IgG Fc (DR3 (human)-huIg Fusion Protein)) is provided. The fusion protein can be expressed in eukaryotic cells and purified using protein A for use in vitro and in vivo. Alternatively, the cDNA encoding the fusion protein is expressed through hydrodynamic injection into the tail vein of mice. This technique can produce high-level expression of the DR3 Fc protein during or after induction of autoimmune disease models. (Dagnaes-Hansen et al., 2002; Hodges and Scheule, 2003; Lecocq et al., 2003)

The nucleic acids encoding a polypeptide comprising or consisting of a DR3 region can also be functionally linked to other nucleic acids to encode an immunoadhesin. For the purposes of the present disclosure, the term "immunoadhesin" is defined as including any polypeptide encoded by a nucleic acid, where at least a portion of a nucleic acid encoding a non-immunoglobulin molecule such as a DR3 extracellular domain is coupled to at least a portion of a nucleic acid encoding an immunoglobulin heavy chain polypeptide, IgG, for example. The Fc regions of IgG2, IgG3, IgM, IgA, IgE can also be utilized to construct an immunoadhesin. The coupling may be achieved in a manner which provides for a functional transcribing and translating of the nucleic acid segment and message derived therefrom, respectively. These IgG immunoadhesins can be expressed by transient or stable transfection in a variety of mammalian host cells, as well as in baculovirus-infected cells. Similar to antibodies, IgG immunoadhesins can be purified from the culture medium into which they are secreted by single-step protein A or protein G affinity chromatography.

iv. Antibodies

The interaction between DR3 and TL1A can be blocked by administration of anti-DR3 antibodies. To block the interaction, the anti-DR3 antibody must be antagonistic. Additionally, a DR3 Fc fusion protein can inhibit the interaction between DR3 and TL1A.

Figure 20A:
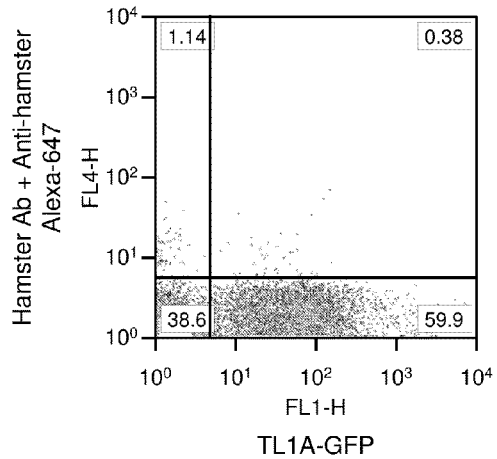
FIGS. 20A-20E show characterization of functional anti-TL1A blocking antibodies.
Figure 20B:
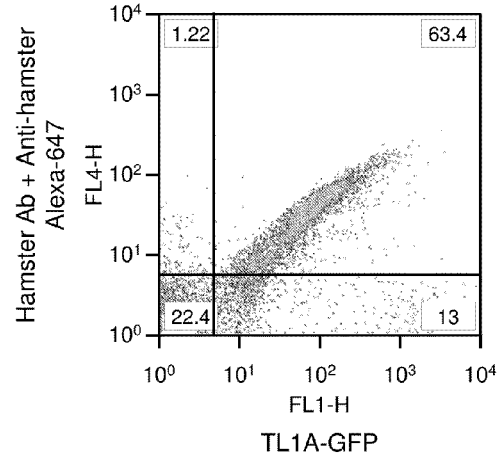
Figure 20C:
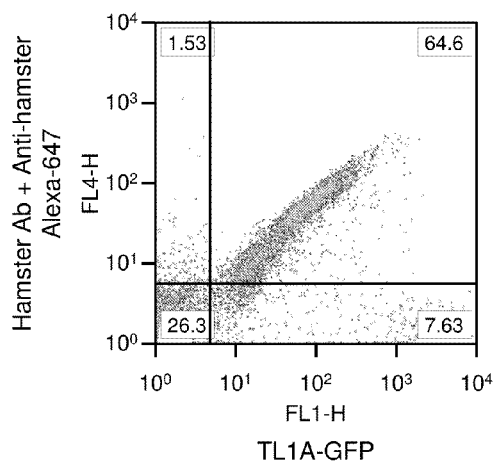
Figure 20D:
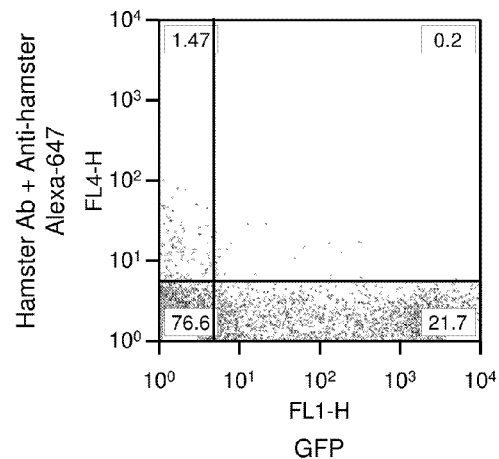
Figure 20E:
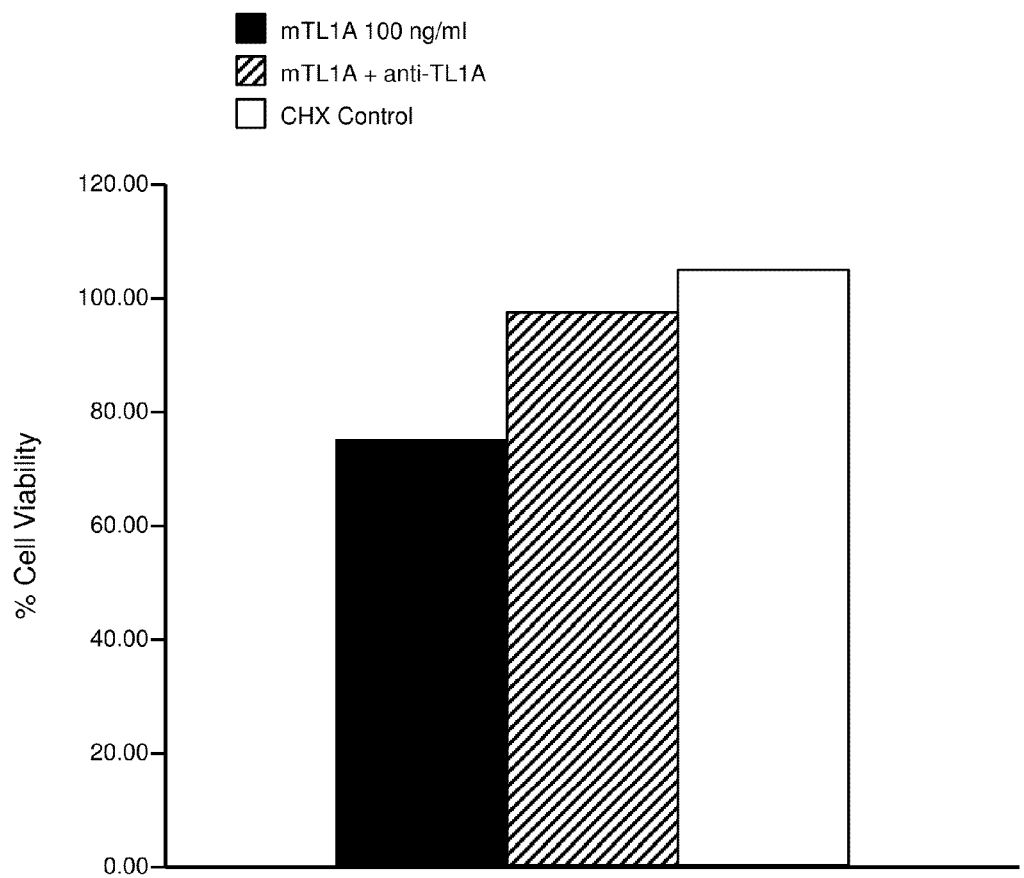

The interaction between DR3 and TL1A can be blocked by administration of anti-TL1A antibodies. Blocking antibodies against TL1A and DR3 are generated by immunizing mice with the fully glycosylated mammalian extracellular domains of these proteins and specifically screening for blocking activity in a bioassay for TL1A-DR3 binding and signal transduction. Thus, provided is an anti-TL1A antibody that specifically binds surface TL1A and interferes with TL1A-induced cell death of an indicator cell line. For example, FIG. 20 shows the characterization of functional anti-TL1A blocking antibodies. These antibodies inhibited TL1A-induced apoptosis (FIG. 20E).

v. Diseases

In the disclosed methods of treating inflammatory or autoimmune disease, the inflammatory or autoimmune disease can be an autoimmune disease with a T cell component.

In the disclosed methods of treating inflammatory or autoimmune disease, the inflammatory or autoimmune disease is asthma. The present data show that DR3 knock-out mice are resistant to an animal model of asthma, suggesting that blockade of TL1A/DR3 interactions would be effective in this model and human asthma.

In the disclosed methods of treating inflammatory or autoimmune disease, the inflammatory or autoimmune disease can be multiple sclerosis. There is abundant evidence to support the role of activated T cells in MS: extravasation of activated T cells into the brain, spinal cord and CSF of MS patients, production of inflammatory cytokines such as IL-17 and interferon gamma by T cells in MS and experimental MS animal model lesions. DR3 is expressed on activated T cells and deficiency of DR3 impairs inflammatory cytokine production by activated T cells as shown herein. Therefore, blockade of DR3-TL1A interactions is expected to impair T cell cytokine production and ameliorate MS.

In the disclosed methods of treating inflammatory or autoimmune disease, the inflammatory or autoimmune disease can be rheumatoid arthritis. Activated T cells can be found in the synovium of patients with rheumatoid arthritis, and agents that block T cell function are efficacious in this disease, for example, costimulatory T cell blockade by CTLA4. DR3 is expressed on activated T cells, and deficiency of DR3 impairs inflammatory cytokine production by activated T cells as shown herein. Therefore, blockade of DR3-TL1A interactions is expected to impair T cell cytokine production and ameliorate RA.

In the disclosed methods of treating inflammatory or autoimmune disease, the inflammatory or autoimmune disease can be type 1 diabetes. Type I diabetes is caused by activated T cells which infiltrate the pancreas and destroy the islets of langerhans. DR3 is expressed on activated T cells, and deficiency of DR3 impairs inflammatory cytokine production by activated T cells. Therefore, blockade of DR3-TL1A interactions is expected to impair T cell cytokine production and ameliorate type I diabetes.

In the disclosed methods of treating inflammatory or autoimmune disease, the inflammatory or autoimmune disease can be graft versus host disease. Allospecific activated T cells which express DR3 secrete cytokines and effector molecules that are critical for graft vs. host disease. Blockade of the TNF family members TL1A, Light, and FasL through administration of a soluble decoy receptor DcR3/TR6 that binds all three ligands did downmodulate graft vs. host disease in a mouse model (Zhang et al., 2001). Because deficiency of DR3 impairs inflammatory cytokine production by activated T cells, blockade of DR3/TL1A interactions by the above-disclosed methods is expected to treat or prevent graft vs. host disease.

In some aspects of the disclosed methods of treating inflammatory or autoimmune disease, the inflammatory or autoimmune disease is inflammatory bowel disease (IBD). Thus, in some aspects, the inflammatory or autoimmune disease of the method is Crohn's disease.

TL1A and DR3 have been found to be expressed in tissue samples from patients with inflammatory bowel disease and mouse models of IBD (Bamias et al., 2003; Bamias et al., 2006). In addition, multiple lines of transgenic mice expressing TL1A constitutively in T cells or dendritic cells develop spontaneous inflammatory bowel disease centered in the duodenum and ileum characterized histologically by destruction of villi, bowel wall thickening, and inflammatory cell infiltrates. Thus, blockade of DR3/TL1A interactions by the above-disclosed methods is expected to treat or prevent IBD.

In other aspects, the inflammatory or autoimmune disease of the method is not inflammatory bowel disease (IBD). Thus, in some aspects, the inflammatory or autoimmune disease of the method is not Crohn's disease.

2. Verification of Efficacy

Also provided are methods for verifying the efficacy of the compositions and methods for treating inflammatory or autoimmune diseases. Animals can be induced to exhibit relevant characteristics of inflammatory bowel disease and colitis. The animal in which the colitis is produced can be any mammal and can include, but is not limited to, mouse, rat, guinea pig, hamster, rabbit, cat, dog, goat, monkey, and chimpanzee. The colitis can be produced in the animal by any method known in the art. For example, the colitis can be produced by introducing into the colon of the animal an effective amount of a hapten reagent. As an example, the hapten reagent can be trinitrobenzene sulfonic acid (TNBS) or oxazolone (4-ethoxymethylene-2-phenyl-2-oxazolin-5-one).

Th1-mediated colitis can be induced in mice using TNBS. Acute TNBS-colitis can be induced in SJL or C57BL10 mice using a single dose of TNBS. Briefly, 2.5 mg of TNBS (pH 1.5-2.0; Sigma Aldrich, St Louis, Mo.) in 50% ethanol is administered intrarectally in a total volume of 150 µl to lightly anesthetized mice. To establish a chronic model of TNBS colitis, Balb/c mice are administered weekly dosages of TNBS per rectum in the following manner. Mice are administered 1.5 mg of TNBS (delivered in a 50% ethanol vehicle in a total volume of 150 µl) for weeks 1-2, 2.0 mg of TNBS for weeks 3-4, and 2.5 mg of TNBS for weeks 5-6.

Th2-mediated colitis can be induced in mice with oxazolone. Briefly, mice are presensitized by painting the skin with 0.2 mL 3% oxazolone in 100% ethanol; 5 days after presensitization, mice are challenged intra-rectally with 150 µl 1% oxazolone in 50% ethanol under general anesthesia with isoflurane (Baxter, Deerfield, Ill.).

These models can be used to test the anti-DR3 and anti-TL1A antibodies and the DR3-Fc fusion protein disclosed herein.

3. Screening Assay

Also provided herein is a method of identifying an agent that can be used to treat an inflammatory disease. The method can comprise providing a sample comprising DR3 and TL1A under conditions that allow the binding of DR3 and TL1A, contacting the sample with a candidate agent, detecting the level of DR3/TL1A binding, comparing the binding level to a control, a decrease in DR3/TL1A binding compared to the control identifying an agent that can be used to treat an inflammatory disease.

The binding of DR3 to TL1A can be detected using routine methods, such as immunodetection methods, that do not disturb protein binding. The methods can be cell-based or cell-free assays. The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods. Immunoassays, in their most simple and direct sense, are binding assays involving binding between antibodies and antigen. Many types and formats of immunoassays are known, and all are suitable for detecting the disclosed biomarkers. Examples of immunoassays are enzyme-linked immunosorbent assays (ELISAs), radioimmunoassays (RIA), radioimmune precipitation assays (RIPA), immunobead capture assays, Western blotting, dot blotting, gel-shift assays, flow cytometry, protein arrays, multiplexed bead arrays, magnetic capture, in vivo imaging, fluorescence resonance energy transfer (FRET), and fluorescence recovery/localization after photobleaching (FRAP/FLAP).

The binding of DR3 to TL1A can be detected using fluorescence activated cell sorting (FACS). For example, disclosed are cell lines transfected with TL1A and DR3 fused to fluorescent proteins. These cell lines can facilitate high-throughput screens for biologically expressed and small molecule binding to TL1A and DR3 in their physiological forms.

In general, candidate agents can be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic-, or animal-based extracts, fermentation broths, and synthetic compounds, as well as modifications of existing compounds. Numerous methods are also available for generating random or directed synthesis (e.g., semi-synthesis or total synthesis) of any number of chemical compounds, including, but not limited to, saccharide-, lipid-, peptide-, polypeptide-, and nucleic acid-based compounds. Synthetic compound libraries are commercially available, e.g., from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods. In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their effect on the activity of reducing inflammation should be employed whenever possible.

When a crude extract is found to have a desired activity, further fractionation of the positive lead extract is necessary to isolate chemical constituents responsible for the observed effect. Thus, the goal of the extraction, fractionation, and purification process is the careful characterization and identification of a chemical entity within the crude extract having an activity that stimulates or inhibits the binding of DR3 and TL1A. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using animal models for diseases or conditions, such as those disclosed herein.

Candidate agents encompass numerous chemical classes, but are most often organic molecules, e.g., small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl, or carboxyl group, for example, at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof. In a further embodiment, candidate agents are peptides.

In some embodiments, the candidate agents are proteins. In some aspects, the candidate agents are naturally occurring proteins or fragments of naturally occurring proteins. Thus, for example, cellular extracts containing proteins, or random or directed digests of proteinaceous cellular extracts, can be used. In this way, libraries of prokaryotic and eukaryotic proteins can be made for screening using the methods herein. The libraries can be bacterial, fungal, viral, vertebrate proteins, and human proteins.

4. Administration

Administration means a method of administering to a subject. Such methods are well known to those skilled in the art and include, but are not limited to: administration topically, parenterally, orally, intravenously, intramuscularly, subcutaneously, or by aerosol. Administration may be effected continuously or intermittently.

For in vivo administration, the pharmaceutical compositions are preferably administered parenterally, i.e., intravenously, intraperitoneally, subcutaneously, intrathecally, injection to the spinal cord, intramuscularly, intraarticularly, portal vein injection, or intratumorally.

The term "parenteral," as used herein, refers to modes of administration, which include intravenous, intramuscular, intraperitoneal, intrasternal, subcutaneous and intraarticular injection, and infusion. Pharmaceutical compositions for parenteral injection comprise pharmaceutically acceptable sterile aqueous or non-aqueous solutions, dispersions, suspensions, or emulsions, as well as sterile powders for reconstitution into sterile injectable solutions or dispersions just prior to use. Examples of suitable aqueous and non-aqueous carriers, diluents, solvents, or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants. These compositions may also contain preservatives, wetting agents, emulsifying agents, and dispersing agents. Prevention of the action of microorganisms may be ensured by the inclusion of various antibacterial and antifungal agents such as paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters), and poly(anhydrides). Depending upon the ratio of drug to polymer and the nature of the particular polymer employed, the rate of drug release can be controlled. Depot injectable formulations are also prepared by entrapping the drug in liposomes or microemulsions, which are compatible with body tissues. The injectable formulations may be sterilized, for example, by filtration through a bacterial-retaining filter or by incorporating sterilizing agents in the form of sterile solid compositions, which can be dissolved or dispersed in sterile water or other sterile injectable media just prior to use.

In other methods, the pharmaceutical preparations may be contacted with the target tissue by direct application of the preparation to the tissue. The application may be made by topical, "open", or "closed" procedures. By "topical", it is meant the direct application of the pharmaceutical preparation to a tissue exposed to the environment, such as the skin, nasopharynx, external auditory canal, eye, inhalation to the lung, genital mucosa, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

Topical administration includes administration to the skin, mucosa, and surfaces of the lung and eye. Compositions for topical administration, including those for inhalation, may be prepared as a dry powder, which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter.

For topical administration to the eye, a compound of the invention is delivered in a pharmaceutically acceptable ophthalmic vehicle, such that the compound is maintained in contact with the ocular surface for a sufficient time period to allow the compound to penetrate the corneal and internal regions of the eye, as, for example, the anterior chamber, posterior chamber, vitreous body, aqueous humor, vitreous humor, cornea, iris/cilary, lens, choroid/retina, and sclera. The pharmaceutically acceptable ophthalmic vehicle may, for example, be an ointment, vegetable oil, or an encapsulating material. Alternatively, a compound of the invention may be injected directly into the vitrious and aqueous humor.

Compositions for rectal or vaginal administration are preferably suppositories, which may be prepared by mixing the compounds of this invention with suitable non-irritating excipients or carriers such as cocoa butter, polyethylene glycol, or a suppository wax, which are solids at room temperature but liquids at body temperature and, therefore, melt in the rectum or vaginal cavity and release the active compound.

Dosage range to have effect on symptoms but to avoid adverse side affects; doses will vary with age, sex, condition, extent of disease. When used in the above or other treatments, a therapeutically effective amount of one of the compounds of the present invention may be employed in pure form or, where such forms exist, in pharmaceutically acceptable salt form and with or without a pharmaceutically acceptable excipient. The specific therapeutically effective dose level for any particular patient will depend upon a variety of factors including the disorder being treated and the severity of the disorder; activity of the specific compound employed; the specific composition employed; the age, body weight, general health, sex, and diet of the patient; the time of administration; the route of administration; the rate of excretion of the specific compound employed; the duration of the treatment; drugs used in combination or coincidential with the specific compound employed and like factors well known in the medical arts. For example, it is well within the skill of the art to start doses of the compound at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose.

The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. Based on experience with other Fc fusion proteins and blocking antibodies against other TNF family members, a typical daily dosage of the FcFusion protein used range from about 0.5 to about 10 mg/kg of body weight or more per day, depending on the factors mentioned above. Monoclonal antibodies are given subcutaneously at about 1 to about 5 mg/kg body weight either as an IV infusion or subcutaneously.

For example, a typical daily dosage of the disclosed composition used alone might range from about 1 mg/kg to up to 100 mg/kg of body weight or more per day, depending on the factors mentioned above.

Following administration of a disclosed composition for treating, inhibiting, or preventing an immunopathology, the efficacy of the therapeutic can be assessed in various ways well known to the skilled practitioner. For instance, one of ordinary skill in the art will understand that a composition disclosed herein is efficacious in treating or inhibiting an immunopathology in a subject by observing that the composition reduces or prevents a further increase in immunopathology. Immunopathology can be measured by methods that are known in the art.

The compositions that inhibit DR3 and TL1A interactions disclosed herein may be administered prophylactically to patients or subjects who are at risk for immunopathology or who have been newly diagnosed with immunopathology.

The disclosed compositions and methods can also be used, for example, as tools to isolate and test new drug candidates for a variety of immunopathology-related diseases.

i. Administration of Proteins

The protein may be formulated for the purpose of administration topically, orally, parenterally, intranasally, intravenously, intramuscularly, subcutaneously, intraocularly, transdermally and the like. Doses of such therapeutic protein agents are well known to those of skill in the art and may be found in pharmaceutical compedia such as the PHYSICIANS DESK REFERENCE, Medical Economics Data Publishers; REMINGTON'S PHARMACEUTICAL SCIENCES, Mack Publishing Co.; GOODMAN & GILMAN, THE PHARMACOLOGICAL BASIS OF THERAPEUTICS, McGraw Hill Publ., THE CHEMOTHERAPY SOURCE BOOK, Williams and Wilkens Publishers, and may, alternatively, routinely be determined using standard techniques well known to those of skill in the art, such as, for example, are described, below, at the end of this Section.

ii. Administration of Antibodies

Administration of the antibodies can be done as disclosed herein. Nucleic acid approaches for antibody delivery also exist. The broadly blocking anti-DR3 or TL1A antibodies and antibody fragments can also be administered to patients or subjects as a nucleic acid preparation (e.g., DNA or RNA) that encodes the antibody or antibody fragment, such that the patient's or subject's own cells take up the nucleic acid and produce and secrete the encoded antibody or antibody fragment.

Antibodies of the invention are preferably administered to a subject in a pharmaceutically acceptable carrier. Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically acceptable salt is used in the formulation to render the formulation isotonic. Examples of the pharmaceutically acceptable carrier include, but are not limited to, saline, Ringer's solution, and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes, or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular) or by other methods such as infusion that ensure its delivery to the bloodstream in an effective form. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used, and other drugs being administered. Guidance in selecting appropriate doses for antibodies is found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

iii. Administration of Nucleic Acids

In the methods described above, which include the administration and uptake of exogenous nucleic acids into the cells of a subject (i.e., gene transduction or transfection), the disclosed nucleic acids can be in the form of naked DNA or RNA, or the nucleic acids can be in a vector for delivering the nucleic acids to the cells, whereby the antibody-encoding DNA fragment is under the transcriptional regulation of a promoter, as would be well understood by one of ordinary skill in the art. The vector can be a commercially available preparation, such as an adenovirus vector (Quantum Biotechnologies, Inc. (Laval, Quebec, Canada)). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.), as well as by means of a SONOPORATION machine (ImaRx Pharmaceutical Corp., Tucson, Ariz.).

As one example, vector delivery can be via a viral system, such as a retroviral vector system, which can package a recombinant retroviral genome (see e.g., Pastan et al., Proc. Natl. Acad. Sci. U.S.A. 85:4486, 1988; Miller et al., Mol. Cell. Biol. 6:2895, 1986). The recombinant retrovirus can then be used to infect and thereby deliver to the infected cells nucleic acid encoding a blocking antibody (or active fragment thereof). The exact method of introducing the altered nucleic acid into mammalian cells is, of course, not limited to the use of retroviral vectors. Other techniques are widely available for this procedure including the use of adenoviral vectors (Mitani et al., Hum. Gene Ther. 5:941-948, 1994), adeno-associated viral (AAV) vectors (Goodman et al., Blood 84:1492-1500, 1994), lentiviral vectors (Naidini et al., Science 272:263-267, 1996), pseudotyped retroviral vectors (Agrawal et al., Exper. Hematol. 24:738-747, 1996). Physical transduction techniques can also be used, such as liposome delivery and receptor-mediated and other endocytosis mechanisms (see, for example, Schwartzenberger et al., Blood 87:472-478, 1996). The disclosed compositions and methods can be used in conjunction with any of these or other commonly used gene transfer methods.

As one example, if the antibody-encoding nucleic acid is delivered to the cells of a subject in an adenovirus vector, the dosage for administration of adenovirus to humans can range from about 107 to 109 plaque-forming units (pfu) per injection but can be as high as 1012 pfu per injection (Crystal, Hum. Gene Ther. 8:985-1001, 1997; Alvarez and Curiel, Hum. Gene Ther. 8:597-613, 1997). A subject can receive a single injection, or, if additional injections are necessary, they can be repeated at six-month intervals (or other appropriate time intervals, as determined by the skilled practitioner) for an indefinite period and/or until the efficacy of the treatment has been established.

B. COMPOSITIONS

1. Antibodies

Provided is an antibody that has the binding characteristics of an antibody that binds the TL1A or DR3 polypeptide and blocks the binding of TL1A to DR3. Thus, provided is an antibody that has the binding characteristics of an antibody that binds the TL1A polypeptide comprising SEQ ID NO:4, or a fragment thereof that binds DR3.

Also provided is an antibody that has the binding characteristics of an antibody that binds the extracellular domain of TL1A polypeptide. Thus, provided is an antibody that has the binding characteristics of an antibody that binds the TL1A polypeptide comprising amino acids 76-252 of SEQ ID NO: 4, or a fragment thereof that binds DR3. Thus, provided is an antibody that has the binding characteristics of an antibody that binds the TL1A polypeptide comprising amino acids 76-252, 77-252, 78-252, 76-252, 79-252, 80 252, 81-252, 82-252, 83-252, 84-252, 85-252, 86-252, 87-252, 88-252, 89-252, 90-252, 91-252, 92-252, 93-252, 94-252, 95-252, 96-252, 97-252, 98-252, 99-252, or 100-252 of SEQ ID NO:4. Thus, provided is an antibody that has the binding characteristics of an antibody that binds the TL1A polypeptide comprising amino acids 76-251, 77-251, 78-251, 76-251, 79-251, 80-251, 81-251, 82-251, 83-251, 84-251, 85-251, 86-251, 87-251, 88-251, 89-251, 90-251, 91-251, 92-251, 93-251, 94-251, 95-251, 96-251, 97-251, 98-251, 99-251, or 100-251 of SEQ ID NO:4. Thus, provided is an antibody that has the binding characteristics of an antibody that binds the TL1A polypeptide comprising amino acids 76-250, 77-250, 78-250, 76-250, 79-250, 80-250, 81-250, 82-250, 83-250, 84-250, 85-250, 86-250, 87-250, 88-250, 89-250, 90-250, 91-250, 92-250, 93-250, 94-250, 95-250, 96-250, 97-250, 98-250, 99-250, or 100-250 of SEQ ID NO:4. Thus, provided is an antibody that has the binding characteristics of an antibody that binds the TL1A polypeptide comprising amino acids 76-249, 77-249, 78-249, 76-249, 79-249, 80-249, 81-249, 82-249, 83-249, 84-249, 85-249, 86-249, 87-249, 88-249, 89-249, 90-249, 91-249, 92-249, 93-249, 94-249, 95-249, 96-249, 97-249, 98-249, 99-249, or 100-249 of SEQ ID NO:4. Thus, provided is an antibody that has the binding characteristics of an antibody that binds the TL1A polypeptide comprising amino acids 76-248, 77-248, 78-248, 76-248, 79-248, 80-248, 81-248, 82-248, 83-248, 84-248, 85-248, 86-248, 87-248, 88-248, 89-248, 90-248, 91-248, 92-248, 93-248, 94-248, 95-248, 96-248, 97-248, 98-248, 99-248, or 100-248 of SEQ ID NO:4. Thus, provided is an antibody that has the binding characteristics of an antibody that binds the TL1A polypeptide comprising amino acids 76-247, 77-247, 78-247, 76-247, 79-247, 80-247, 81-247, 82-247, 83-247, 84-247, 85-247, 86-247, 87-247, 88-247, 89-247, 90-247, 91-247, 92-247, 93-247, 94-247, 95-247, 96-247, 97-247, 98-247, 99-247, or 100-247 of SEQ ID NO:4. Thus, provided is an antibody that has the binding characteristics of an antibody that binds the TL1A polypeptide comprising amino acids 76-246, 77-246, 78-246, 76-246, 79-246, 80-246, 81-246, 82-246, 83-246, 84-246, 85-246, 86-246, 87-246, 88-246, 89-246, 90-246, 91-246, 92-246, 93-246, 94-246, 95-246, 96-246, 97-246, 98-246, 99-246, or 100-246 of SEQ ID NO:4. Thus, provided is an antibody that has the binding characteristics of an antibody that binds the TL1A polypeptide comprising amino acids 76-245, 77-245, 78-245, 76-245, 79-245, 80-245, 81-245, 82-245, 83-245, 84-245, 85-245, 86-245, 87-245, 88-245, 89-245, 90-245, 91-245, 92-245, 93-245, 94-245, 95-245, 96-245, 97-245, 98-245, 99-245, or 100-245 of SEQ ID NO:4. Thus, provided is an antibody that has the binding characteristics of an antibody that binds the TL1A polypeptide comprising amino acids 76-240, 77-240, 78-240, 76-240, 79-240, 80-240, 81-240, 82-240, 83-240, 84-240, 85-240, 86-240, 87-240, 88-240, 89-240, 90-240, 91-240, 92-240, 93-240, 94-240, 95-240, 96-240, 97-240, 98-240, 99-240, or 100-240 of SEQ ID NO:4. Thus, provided is an antibody that has the binding characteristics of an antibody that binds the TL1A polypeptide comprising amino acids 76-230, 77-230, 78-230, 76-230, 79-230, 80-230, 81-230, 82-230, 83-230, 84-230, 85-230, 86-230, 87-230, 88-230, 89-230, 90-230, 91-230, 92-230, 93-230, 94-230, 95-230, 96-230, 97-230, 98-230, 99-230, or 100-230 of SEQ ID NO:4. Thus, provided is an antibody that has the binding characteristics of an antibody that binds the TL1A polypeptide comprising amino acids 76-220, 77-220, 78-220, 76-220, 79-220, 80-220, 81-220, 82-220, 83-220, 84-220, 85-220, 86-220, 87-220, 88-220, 89-220, 90-220, 91-220, 92-220, 93-220, 94-220, 95-220, 96-220, 97-220, 98-220, 99-220, or 100-220 of SEQ ID NO:4. Thus, provided is an antibody that has the binding characteristics of an antibody that binds the TL1A polypeptide comprising amino acids 76-210, 77-210, 78-210, 76-210, 79-210, 80-210, 81-210, 82-210, 83-210, 84-210, 85-210, 86-210, 87-210, 88-210, 89-210, 90-210, 91-210, 92-210, 93-210, 94-210, 95-210, 96-210, 97-210, 98-210, 99-210, or 100-210 of SEQ ID NO:4. Thus, provided is an antibody that has the binding characteristics of an antibody that binds the TL1A polypeptide comprising amino acids 76-200, 77-200, 78-200, 76-200, 79-200, 80-200, 81-200, 82-200, 83-200, 84-200, 85-200, 86-200, 87-200, 88-200, 89-200, 90-200, 91-200, 92-200, 93-200, 94-200, 95-200, 96-200, 97-200, 98-200, 99-200, or 100-200 of SEQ ID NO:4.

Thus, provided is an antibody that has the binding characteristics of an antibody produced by the hybridoma clones designated 1A9 and 106 that bind the human TL1A polypeptide and Hybridoma clones designated 12B12.6 and 5G4.6 that bind the murine TL1A polypeptide.

Binding characteristics of an antibody include its binding specificity. The binding specificity can be specificity for the antigen, or it can be specificity based on the epitope recognized by the antibody. Since both the former and the latter are inherent characteristics of an antibody, the disclosure of the present antibodies provides definition of both epitope and antigen specificity. Reference to the binding specificity of a deposited monoclonal antibody is the equivalent of reference to the specific epitope on DR3 to which that antibody binds. The binding specificity of any individual monoclonal antibody is an inherent property of any other monoclonal antibody of the sub-genus defined by the disclosed, deposited antibody. Methods of identifying the binding specificity of a given antibody are well known in the art. Further methods of measuring avidity and other characteristics of antibody binding are well known.

i. Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with DR3 or TL1A, such that DR3 is inhibited from interacting with TL1A. Antibodies that bind the disclosed regions involved in the interaction between DR3 and TL1A are also disclosed. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies, in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA,* 81:6851-6855 (1984)).

The disclosed monoclonal antibodies can be made using any procedure which produces monoclonal antibodies. For example, disclosed monoclonal antibodies can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

To give the best chance of producing blocking antibodies, the immunizing agents will preferably consist of fully glycosylated native proteins produced by eukaryotic cells. For DR3, the extracellular fragment of the human and mouse receptor expressed as an Fc Fusion protein, and cleaved from the Fc portion by a specific protease will be preferably used:

Human: amino acids 1-141 of the sequences at Accession No. NP_683866.1 (SEQ ID NO:5).

Mouse: amino acids 1-159 of the sequence at Accession No. NP_149031.2 (SEQ ID NO:6).

For TL1A, the extracellular fragment of the human and mouse TL1A expressed as an epitope-tagged fusion protein will be preferably used:

Mouse: Accession No. NP_005109.2 (SEQ ID NO:7).

Human: amino acids 72-251 from the sequence at NP_796345 (SEQ ID NO:8).

If these approaches do not produce blocking antibodies, cells expressing cell surface-localized versions of these proteins will be used to immunize mice, rats, or other species. Traditionally, the generation of monoclonal antibodies has depended on the availability of purified protein or peptides for use as the immunogen. More recently, DNA-based immunizations have shown promise as a way to elicit strong immune responses and generate monoclonal antibodies. In this approach, DNA-based immunization can be used, wherein DNA encoding extracellular fragments of DR3 and TL1A expressed as a fusion protein with human IgG1 or an epitope tag is injected into the host animal according to methods known in the art (e.g., Kilpatrick K E, et al. Gene gun delivered DNA-based immunizations mediate rapid production of murine monoclonal antibodies to the Flt-3 receptor. Hybridoma. 1998 December; 17(6):569-76; Kilpatrick K E et al. High-affinity monoclonal antibodies to PED/PEA-15 generated using 5 microg of DNA. Hybridoma. 2000 August; 19(4):297-302, which are incorporated herein by referenced in full for the methods of antibody production) and as described in the examples.

An alternate approach to immunizations with either purified protein or DNA is to use antigen expressed in baculovirus. The advantages to this system include ease of generation, high levels of expression, and post-translational modifications that are highly similar to those seen in mammalian systems. Use of this system involves expressing the extracellular domain of TL1A or DR3 as fusion proteins with a signal sequence fragment. The antigen is produced by inserting a gene fragment in-frame between the signal sequence and the mature protein domain of the TL1A or DR3 nucleotide sequence. This results in the display of the foreign proteins on the surface of the virion. This method allows immunization with whole virus, eliminating the need for purification of target antigens.

Generally, either peripheral blood lymphocytes ("PBLs") are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, "Monoclonal Antibodies: Principles and Practice" Academic Press, (1986) pp. 59-103). Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, J. Immunol., 133:3001 (1984); Brodeur et al., "Monoclonal Antibody Production Techniques and Applications" Marcel Dekker, Inc., New York, (1987) pp. 51-63). The culture medium in which the hybridoma cells are cultured can then be assayed for the presence of monoclonal antibodies directed against DR3 and/or TL1A. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art and are described further in the Examples below or in Harlow and Lane "Antibodies, A Laboratory Manual" Cold Spring Harbor Publications, New York, (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, protein G, hydroxylapatite chromatography, gel electrophoresis, dialysis, or affinity chromatography.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans and, thus, can give rise to undesirable immune responses when administered to humans. Therefore, the use of human or humanized antibodies in the methods serves to lessen the chance that an antibody administered to a human will evoke an undesirable immune response.

ii. Whole Immunoglobulin

As used herein, the term "antibody" encompasses, but is not limited to, whole immunoglobulin (i.e., an intact antibody) of any class. Native antibodies are usually heterotetrameric glycoproteins composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has, at one end, a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

iii. Antibody Fragments

The term "antibody" as used herein is meant to include intact molecules as well as fragments thereof, such as, for example, Fab and F(ab')$_2$, which are capable of binding the epitopic determinant.

As used herein, the term "antibody or fragments thereof" encompasses chimeric antibodies and hybrid antibodies, with dual or multiple antigen or epitope specificities, and fragments, such as F(ab')2, Fab', Fab, and the like, including hybrid fragments. Thus, fragments of the antibodies that retain the ability to bind their specific antigens are provided. For example, fragments of antibodies which maintain DR3 or TL1A binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

An isolated immunogenically specific paratope or fragment of the antibody is also provided. A specific immunogenic epitope of the antibody can be isolated from the whole antibody by chemical or mechanical disruption of the molecule. The purified fragments thus obtained are tested to determine their immunogenicity and specificity by the methods taught herein. Immunoreactive paratopes of the antibody, optionally, are synthesized directly. An immunoreactive fragment is defined as an amino acid sequence of at least about two to five consecutive amino acids derived from the antibody amino acid sequence.

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains, as well as large amounts of relatively pure proteins with full biological activity (deLisle Milton R C et al., Techniques in Protein Chemistry IV. Academic Press, New York, pp. 257-267 (1992)).

Also disclosed are fragments of antibodies which have bioactivity. The polypeptide fragments can be recombinant proteins obtained by cloning nucleic acids encoding the polypeptide in an expression system capable of producing the polypeptide fragments thereof, such as an adenovirus or baculovirus expression system. For example, one can determine the active domain of an antibody from a specific hybridoma that can cause a biological effect associated with the interaction of the antibody with TL1A or DR3. For example, amino acids found to not contribute to either the activity or the binding specificity or affinity of the antibody can be deleted without a loss in the respective activity. For example, in various embodiments, amino- or carboxy-terminal amino acids are sequentially removed from either the native or the modified non-immunoglobulin molecule or the immunoglobulin molecule and the respective activity assayed in one of many available assays. In another example, a fragment of an antibody comprises a modified antibody wherein at least one amino acid has been substituted for the naturally occurring amino acid at a specific position, and a portion of either amino-terminal or carboxy-terminal amino acids, or even an internal region of the antibody, has been replaced with a polypeptide fragment or other moiety, such as biotin, which can facilitate in the purification of the modified antibody. For example, a modified antibody can be fused to a maltose binding protein, through either peptide chemistry or cloning the respective nucleic acids encoding the two polypeptide fragments into an expression vector, such that the expression of the coding region results in a hybrid polypeptide. The hybrid polypeptide can be affinity purified by passing it over an amylose affinity column, and the modified antibody receptor can then be separated from the maltose binding region by cleaving the hybrid polypeptide with the specific protease factor Xa. (See, for example, New England Biolabs Product Catalog, 1996, pg. 164.). Similar purification procedures are available for isolating hybrid proteins from eukaryotic cells as well.

The fragments, whether attached to other sequences or not, include insertions, deletions, substitutions, or other selected modifications of particular regions or specific amino acid residues, provided the activity of the fragment is not significantly altered or impaired compared to the non-modified antibody or antibody fragment. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller M J et al. Nucl. Acids Res. 10:6487-500 (1982).

Techniques can also be adapted for the production of single-chain antibodies specific to an antigenic protein of the present disclosure (see e.g., U.S. Pat. No. 4,946,778). In addition, methods can be adapted for the construction of F (ab) expression libraries (see e.g., Huse, et al., 1989 Science 246: 1275-1281) to allow rapid and effective identification of monoclonal F (ab) fragments with the desired specificity for a protein or derivatives, fragments, analogs, or homologs thereof. Antibody fragments that contain the idiotypes to a protein antigen may be produced by techniques known in the art including, but not limited to: (i) an F((ab'))(2) fragment produced by pepsin digestion of an antibody molecule; (ii) an Fab fragment generated by reducing the disulfide bridges of an F((ab'))(2) fragment; (iii) an F (ab) fragment generated by the treatment of the antibody molecule with papain and a reducing agent and (iv) F (v) fragments.

Methods for the production of single-chain antibodies are well known to those of skill in the art. The skilled artisan is referred to U.S. Pat. No. 5,359,046, (incorporated herein by reference) for such methods. A single chain antibody is created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15- to 25-amino acid peptide or linker have been developed without significantly disrupting antigen binding or specificity of the binding (Bedzyk et al., 1990; Chaudhary et al., 1990). The linker is chosen to permit the heavy chain and light chain to bind together in their proper conformational orientation. See, for example, Huston, J. S., et al., Methods in Enzym. 203:46-121 (1991), which is incorporated herein by reference. These Fvs lack the constant regions (Fc) present in the heavy and light chains of the native antibody.

iv. Monovalent Antibodies

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

v. Chimeric/Hybrid

In hybrid antibodies, one heavy and light chain pair is homologous to that found in an antibody raised against one antigen recognition feature, e.g., epitope, while the other heavy and light chain pair is homologous to a pair found in an antibody raised against another epitope. This results in the property of multi-functional valency, i.e., ability to bind at least two different epitopes simultaneously. As used herein, the term "hybrid antibody" refers to an antibody wherein each chain is separately homologous with reference to a mammalian antibody chain, but the combination represents a novel assembly, so that two different antigens are recognized by the antibody. Such hybrids can be formed by fusion of hybridomas producing the respective component antibodies or by recombinant techniques. Such hybrids may, of course, also be formed using chimeric chains.

vi. Anti-Idiotypic

The encoded antibodies can be anti-idiotypic antibodies (antibodies that bind other antibodies) as described, for example, in U.S. Pat. No. 4,699,880. Such anti-idiotypic antibodies could bind endogenous or foreign antibodies in a treated individual, thereby to ameliorate or prevent pathological conditions associated with an immune response, e.g., in the context of an autoimmune disease.

vii. Conjugates or Fusions of Antibody Fragments

The targeting function of the antibody can be used therapeutically by coupling the antibody or a fragment thereof with a therapeutic agent. Such coupling of the antibody or fragment (e.g., at least a portion of an immunoglobulin constant region (Fc)) with the therapeutic agent can be achieved by making an immunoconjugate or by making a fusion protein comprising the antibody or antibody fragment and the therapeutic agent. For example, provided is a DR3 Fc fusion protein, e.g., DR3 extracellular domain (150 aa) fused to mouse IgG Fc (DR3 (human)-muIg Fusion Protein).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

An antibody (or fragment thereof) may be conjugated to a therapeutic moiety such as a cytotoxin, a therapeutic agent, or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates disclosed can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, [agr]-interferon, [bgr]-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982). Alternatively, an antibody can be conjugated to a second antibody to form an antibody heteroconjugate as described by Segal in U.S. Pat. No. 4,676,980.

viii. Method of Making Antibodies Using Protein Chemistry

One method of producing proteins comprising the antibodies is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the antibody, for example, can be synthesized by standard chemical reactions. For example, a peptide or polypeptide can be synthesized and not cleaved from its synthesis resin, whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY. Alternatively, the peptide or polypeptide is independently synthesized in vivo as described above. Once isolated, these independent peptides or polypeptides may be linked to form an antibody or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two-step chemical reaction (Dawson et al. Synthesis of Proteins by Native Chemical Ligation. Science, 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

ix. Human and Humanized

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA, 90:2551-255 (1993); Jakobovits et al., Nature, 362:255-258 (1993); Bruggemann et al., Year in Immuno., 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cote et al. and Boerner et al. are also available for the preparation of human monoclonal antibodies (Cole et al., Monoclonal Antibodies and Cancer Therapy, Alan R. Liss, p. 77 (1985); Boerner et al., J. Immunol., 147(1):86-95 (1991)).

Optionally, the antibodies are generated in other species and "humanized" for administration in humans. Humanized forms of non-human (e.g., murine) antibodies are chimeric immunoglobulins, immunoglobulin chains, or fragments thereof (such as Fv, Fab, Fab', F(ab')2, or other antigen-binding subsequences of antibodies), which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992))

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed following the method of Winter and co-workers (Jones et al., Nature, 321: 522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, a humanized form of a non-human antibody (or a fragment thereof) is a chimeric antibody or fragment (U.S. Pat. No. 4,816,567), wherein substantially less than an intact human variable domain has been substituted with the corresponding sequence from a non-human species. In practice, humanized antibodies are typically human antibodies in which some CDR residues and, possibly, some FR residues are substituted with residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody (Sims et al., J. Immunol., 151:2296 (1993) and Chothia et al., J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see, WO 94/04679, published 3 Mar. 1994).

Disclosed are antigen-binding polypeptide molecules that bind specifically to the TNF family cytokine TL1A. The polypeptides include a humanized heavy chain variable region and a humanized light chain variable region. For example, the polypeptides may include the framework (FR) regions of the light and heavy chain variable regions of a human antibody, while retaining substantially the antigen-binding specificity of a parental monoclonal antibody. The humanized heavy chain variable region and/or the humanized light chain variable region are at least about 87% humanized, at least about 90% humanized, at least about 95% humanized, at least about 98% humanized, or at least about 100% humanized, excluding the complementary-determining regions (CDRs). The antigen-binding polypeptide molecules may be derived from monoclonal antibody donors (e.g., mouse monoclonal antibody donors; human monoclonal antibody donors), and may include CDRs from the monoclonal antibodies (e.g., mouse monoclonal CDRs; human monoclonal CDRs). The polypeptides may function as antagonists for the cytokine, TL1A.

As used herein, the term "epitope" is meant to include any determinant capable of specific interaction with the anti-DR3 or anti-TL1A antibodies disclosed. Epitopic determinants usually consist of chemically active surface groupings of molecules such as amino acids or sugar side chains and usually have specific three-dimensional structural characteristics, as well as specific charge characteristics.

An "epitope tag" denotes a short peptide sequence unrelated to the function of the antibody or molecule that can be used for purification or crosslinking of the molecule with anti-epitope tag antibodies or other reagents.

By "specifically binds" is meant that an antibody recognizes and physically interacts with its cognate antigen (e.g., a DR3 receptor polypeptide or a TL1A polypeptide) and does not significantly recognize and interact with other antigens; such an antibody may be a polyclonal antibody or a monoclonal antibody, which are generated by techniques that are well known in the art.

The antibody can be bound to a substrate or labeled with a detectable moiety or both bound and labeled. The detectable moieties contemplated with the present compositions include fluorescent, enzymatic, and radioactive markers.

2. Nucleic Acids i. Sequences

There are a variety of sequences related to the protein molecules involved in the signaling pathways disclosed herein, for example DR3 and TL1A, all of which are encoded by nucleic acids or are nucleic acids. The sequences for the human analogs of these genes, as well as other analogs, and alleles of these genes, and splice variants and other types of variants, are available in a variety of protein and gene databases, including GENBANK® GENBANK®. Those sequences available at the time of filing this application at GENBANK® are herein incorporated by reference in their entireties, as well as for individual subsequences contained therein. GENBANK® can be accessed at www.ncbi.nih.gov/entrez/query.fcgi.

Those of skill in the art understand how to resolve sequence discrepancies and differences and to adjust the compositions and methods relating to a particular sequence to other related sequences. Primers and/or probes can be designed for any given sequence given the information disclosed herein and known in the art. Nucleic acid sequences for DR3 can be accessed via GENBANK® Accession No. NM_001039664.1 (human) or at Accession No. Q93038 (human; SEQ ID NO:1) and NM_033042.3 (mouse). Nucleic acid sequences for TL1A can be accessed at via GENBANK® Accession No. NM_177371 (mouse) and Accession No. NM_005118.2 (human) or at Accession No. Q8NFE9 (SEQ ID NO:3). All of the information, including any nucleic acid and amino acid sequences provided for DR3 under GENBANK® Accession No. NM_001039664.1 (human) and NM_033042.3 (mouse), or for TL1A under GENBANK® Accession No NM_177371 (mouse) and NM_005118.2 (human), is hereby incorporated in its entirety by this reference.

ii. Nucleotides and Related Molecules

A nucleotide is a molecule that contains a base moiety, a sugar moiety, and a phosphate moiety. Nucleotides can be linked together through their phosphate moieties and sugar moieties, creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate). There are many varieties of these types of molecules available in the art and available herein. The term "nucleotide" includes nucleotides and nucleotide analogs, preferably groups of nucleotides comprising oligonucleotides, and refers to any compound containing a heterocyclic compound bound to a phosphorylated sugar by an N-glycosyl link or any monomer capable of complementary base pairing or any polymer capable of hybridizing to an oligonucleotide.

The term "nucleotide analog" refers to molecules that can be used in place of naturally occurring bases in nucleic acid synthesis and processing, preferably enzymatic, as well as chemical synthesis and processing, particularly modified nucleotides capable of base pairing. A nucleotide analog is a nucleotide which contains some type of modification to one of the base, sugar, or phosphate moieties. Modifications to nucleotides are well known in the art and would include, for example, 5-methylcytosine (5 me C), 5-hydroxymethyl cytosine, xanthine, hypoxanthine, and 2-aminoadenine, as well as modifications at the sugar or phosphate moieties.

This term includes, but is not limited to, modified purines and pyrimidines, minor bases, convertible nucleosides, structural analogs of purines and pyrimidines, labeled, derivatized, and modified nucleosides and nucleotides, conjugated nucleosides and nucleotides, sequence modifiers, terminus modifiers, spacer modifiers, and nucleotides with backbone modifications, including, but not limited to, ribose-modified nucleotides, phosphoramidates, phosphorothioates, phosphonamidites, methyl phosphonates, methyl phosphoramidites, methyl phosphonamidites, 5'-β-cyanoethyl phosphoramidites, methylenephosphonates, phosphorodithioates, peptide nucleic acids, achiral and neutral internucleotidic linkages and normucleotide bridges, such as polyethylene glycol, aromatic polyamides and lipids. Optionally, a nucleotide analog is a synthetic base that does not comprise adenine, guanine, cytosine, thymidine, uracil, or minor bases. These and other nucleotide and nucleoside derivatives, analogs, and backbone modifications are known in the art (e.g., Piccirilli J. A. et al. (1990) Nature 343:33-37; Sanghvi et al (1993) In: Nucleosides and Nucleotides as Antitumor and Antiviral Agents (Eds. C. K. Chu and D. C. Baker) Plenum, New York, pp. 311-323; Goodchild J. (1990)); Bioconjugate Chemistry 1:165-187, Beaucage et al. (1993); Tetrahedron 49:1925-1963). Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix-type structure when interacting with the appropriate target nucleic acid. There are many varieties of these types of molecules available in the art and available herein.

It is also possible to link other types of molecules (conjugates) to nucleotides or nucleotide analogs to enhance, for example, cellular uptake. Conjugates can be chemically linked to the nucleotide or nucleotide analogs. Such conjugates include, but are not limited to, lipid moieties such as a cholesterol moiety. (Letsinger et al., Proc. Natl. Acad. Sci. USA, 1989, 86, 6553-6556). There are many varieties of these types of molecules available in the art and available herein.

There are a variety of molecules disclosed herein that are nucleic acid-based, including, for example, the nucleic acids that encode, for example, TL1A and DR3, as well as any other proteins disclosed herein, as well as various functional nucleic acids. The disclosed nucleic acids are made up of, for example, nucleotides, nucleotide analogs, or nucleotide substitutes. Non-limiting examples of these and other molecules are discussed herein. It is understood that, for example, when a vector is expressed in a cell, the expressed mRNA will typically be made up of A, C, G, and U. Likewise, it is understood that if, for example, an antisense molecule is introduced into a cell or cell environment through, for example, exogenous delivery, it is advantageous that the antisense molecule be made up of nucleotide analogs that reduce the degradation of the antisense molecule in the cellular environment.

By "isolated nucleic acid" or "purified nucleic acid" is meant DNA that is free of the genes that, in the naturally-occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (e.g., a cDNA or a genomic or cDNA fragment produced by PCR, restriction endonuclease digestion, or chemical or in vitro synthesis). It also includes a recombinant DNA, which is part of a hybrid gene encoding additional polypeptide sequence. The term "isolated nucleic acid" also refers to RNA, e.g., an mRNA molecule that is encoded by an isolated DNA molecule, or that is chemically synthesized, or that is separated or substantially free from at least some cellular components, e.g., other types of RNA molecules or polypeptide molecules.

iii. Nucleotide Interactions

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine-based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups ($NH_2$ or O) at the C6 position of purine nucleotides.

iv. Oligo- and Polynucleotides

The term "oligonucleotide" means a naturally occurring or synthetic polymer of nucleotides, preferably a polymer comprising at least three nucleotides and more preferably a polymer capable of hybridization. Oligonucleotides may be single-stranded, double-stranded, partially single-stranded, or partially double-stranded ribonucleic or deoxyribonucleic acids, including selected nucleic acid sequences, heteroduplexes, chimeric and hybridized nucleotides, and oligonucleotides conjugated to one or more non-oligonucleotide molecules.

The term "polynucleotide" is used broadly herein to mean a sequence of two or more deoxyribonucleotides or ribonucleotides that are linked together by a phosphodiester bond. As such, the term "polynucleotide" includes RNA and DNA, which can be a gene or a portion thereof, a cDNA, a synthetic polydeoxyribonucleic acid sequence, or the like, and can be single-stranded or double-stranded, as well as a DNA/RNA hybrid. Furthermore, the term "polynucleotide" as used herein includes naturally occurring nucleic acid molecules, which can be isolated from a cell, as well as synthetic molecules, which can be prepared, for example, by methods of chemical synthesis or by enzymatic methods such as by the polymerase chain reaction (PCR). In various embodiments, a polynucleotide of the invention can contain nucleoside or nucleotide analogs or a backbone bond other than a phosphodiester bond. In general, the nucleotides comprising a polynucleotide are naturally occurring deoxyribonucleotides, such as adenine, cytosine, guanine, or thymine linked to 2'-deoxyribose or ribonucleotides such as adenine, cytosine, guanine, or uracil linked to ribose. However, a polynucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., Nucl. Acids Res. 22:5220-5234 (1994); Jellinek et al., Biochemistry 34:11363-11372 (1995); Pagratis et al., Nature Biotechnol. 15:68-73 (1997), each of which is incorporated herein by reference).

The covalent bond linking the nucleotides of a polynucleotide generally is a phosphodiester bond. However, the covalent bond also can be any of numerous other bonds, including a thiodiester bond, a phosphorothioate bond, a peptide-like bond, or any other bond known to those in the art as useful for linking nucleotides to produce synthetic polynucleotides (see, for example, Tam et al., Nucl. Acids Res. 22:977-986 (1994); Ecker and Crooke, BioTechnology 13:351360 (1995), each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

Functional analogs of naturally occurring polynucleotides can bind to RNA or DNA and include peptide nucleic acid (PNA) molecules.

A fragment of a reference nucleic acid contains only contiguous nucleic acids of the reference nucleic acid and is at least one nucleotide shorter than the reference sequence.

v. Primers and Probes

Disclosed are compositions including primers and probes, which are capable of interacting with the disclosed nucleic acids, such as the DR3 or TL1A as disclosed herein. In certain embodiments, the primers are used to support DNA amplification reactions. Typically, the primers will be capable of being extended in a sequence-specific manner. Extension of a primer in a sequence-specific manner includes any methods wherein the sequence and/or composition of the nucleic acid molecule to which the primer is hybridized or otherwise associated directs or influences the composition or sequence of the product produced by the extension of the primer. Extension of the primer in a sequence-specific manner therefore includes, but is not limited to, PCR, DNA sequencing, DNA extension, DNA polymerization, RNA transcription, or reverse transcription. Techniques and conditions that amplify the primer in a sequence-specific manner are preferred. In certain embodiments, the primers are used for the DNA amplification reactions, such as PCR or direct sequencing. It is understood that, in certain embodiments, the primers can also be extended using non-enzymatic techniques where, for example, the nucleotides or oligonucleotides used to extend the primer are modified such that they will chemically react to extend the primer in a sequence-specific manner. Typically, the disclosed primers hybridize with the disclosed nucleic acids or region of the nucleic acids, or they hybridize with the complement of the nucleic acids or complement of a region of the nucleic acids.

The size of the primers or probes for interaction with the nucleic acids in certain embodiments can be any size that supports the desired enzymatic manipulation of the primer, such as DNA amplification or the simple hybridization of the probe or primer. A typical primer or probe would be at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments, a primer or probe can be less than or equal to 6, 7, 8, 9, 10, 11, 12 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

The primers for the DR3 or TL1A gene typically will be used to produce an amplified DNA product that contains a region of the DR3 or TL1A gene or the complete gene. Typically, the size of the product will be such that the size can be accurately determined to within 3, 2, or 1 nucleotides.

In certain embodiments, this product is at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments, the product is less than or equal to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

3. Peptides i. Protein Variants

As discussed herein, there are numerous variants of the DR3 protein and TL1A protein that are known and herein contemplated. In addition to the known functional strain variants, there are derivatives of the DR3 or TL1A proteins which also function in the disclosed methods and compositions. Protein variants and derivatives are well understood to those of skill in the art and can involve amino acid sequence modifications. For example, amino acid sequence modifications typically fall into one or more of three classes: substitutional, insertional, or deletional variants. Insertions include amino- and/or carboxyl-terminal fusions, as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site-specific mutagenesis of nucleotides in the DNA encoding the protein, thereby producing DNA encoding the variant and, thereafter, expressing the DNA in recombinant cell culture. Techniques for making substitution mutations at predetermined sites in DNA having a known sequence are well known, for example, M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions, or any combination thereof may be combined to arrive at a final construct. The mutations must not place the sequence out of reading frame and, preferably, will not create complementary regions that could produce secondary mRNA structure. Substitutional variants are those in which at least one residue has been removed, and a different residue inserted in its place. Such substitutions generally are made in accordance with the following Tables 1 and 2 and are referred to as conservative substitutions.

TABLE 2

Amino Acid Abbreviations

| Amino Acid | Abbreviations | |
|---|---|---|
| Alanine | Ala | A |
| allosoleucine | AIle | |
| Arginine | Arg | R |
| asparagine | Asn | N |
| aspartic acid | Asp | D |
| Cysteine | Cys | C |
| glutamic acid | Glu | E |
| Glutamine | Gln | Q |
| Glycine | Gly | G |
| Histidine | His | H |
| Isolelucine | Ile | I |
| Leucine | Leu | L |
| Lysine | Lys | K |
| phenylalanine | Phe | F |
| proline | Pro | P |
| pyroglutamic acid | pGlu | |
| Serine | Ser | S |
| Threonine | Thr | T |
| Tyrosine | Tyr | Y |
| Tryptophan | Trp | W |
| Valine | Val | V |

TABLE 3

Amino Acid Substitutions

| Original Residue | Exemplary Conservative Substitutions, others are known in the art. |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 3, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which, in general, are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; (d) a residue having a bulky side chain, e.g., phenylalanine, is substituted for (or by) one not having a side chain, e.g., glycine, in this case; or (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, are accomplished, for example, by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO:2 sets forth a particular sequence of DR3, and SEQ ID NO:4 sets forth a particular sequence of TL1A protein. Specifically disclosed are variants of these and other proteins herein disclosed which have at least 70% or 75% or 80% or 85% or 90% or 95% homology to the stated sequence. Those of skill in the art readily understand how to determine the homology of two proteins. For example, the homology can be calculated after aligning the two sequences, so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by, for example, the algorithms disclosed in Zuker, M. Science 244:48-52, 1989, Jaeger et al. *Proc. Natl. Acad. Sci. USA* 86:7706-7710, 1989, Jaeger et al. *Methods Enzymol.* 183:281-306, 1989, which are herein incorporated by reference for at least material related to nucleic acid alignment.

It is understood that the description of conservative mutations and homology can be combined together in any combination, such as embodiments that have at least 70% homology to a particular sequence, wherein the variants are conservative mutations.

As this specification discusses various proteins and protein sequences, it is understood that the nucleic acids that can encode those protein sequences are also disclosed. This would include all degenerate sequences related to a specific protein sequence, i.e. all nucleic acids having a sequence that encodes one particular protein sequence, as well as all nucleic acids, including degenerate nucleic acids, encoding the disclosed variants and derivatives of the protein sequences. Thus, while each particular nucleic acid sequence may not be written out herein, it is understood that each and every sequence is, in fact, disclosed and described herein through the disclosed protein sequence. It is also understood that while no amino acid sequence indicates what particular DNA sequence encodes that protein within an organism, where particular variants of a disclosed protein are disclosed herein, the known nucleic acid sequence that encodes that protein is also known and herein disclosed and described.

It is understood that there are numerous amino acid and peptide analogs which can be incorporated into the disclosed compositions. For example, there are numerous D amino acids or amino acids which have a different functional substituent than the amino acids shown in Table 2 and Table 3. The opposite stereoisomers of naturally occurring peptides are disclosed, as well as the stereoisomers of peptide analogs. These amino acids can readily be incorporated into polypeptide chains by charging tRNA molecules with the amino acid of choice and engineering genetic constructs that utilize, for example, amber codons to insert the analog amino acid into a peptide chain in a site-specific way (Thorson et al., Methods in Molec. Biol. 77:43-73 (1991), Zoller, Current Opinion in Biotechnology, 3:348-354 (1992); Ibba, Biotechnology & Genetic Enginerring Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994), all of which are herein incorporated by reference at least for material related to amino acid analogs).

Molecules can be produced that resemble peptides, but which are not connected via a natural peptide linkage. For example, linkages for amino acids or amino acid analogs can include $-CH_2NH-$, $-CH_2S-$, $-CH_2-CH_2-$, $-CH=CH-$ (cis and trans), $-COCH_2-$, $-CH(OH)CH_2-$, and $-CHH_2SO-$ (these and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) ($-CH_2NH-$, $CH_2CH_2-$); Spatola et al. Life Sci 38:1243-1249 (1986) ($-CHH_2-S$); Hann J. Chem. Soc Perkin Trans. 1307-314 (1982) ($-CH-CH-$, cis and trans); Almquist et al. J. Med. Chem. 23:1392-1398 (1980) ($-COCH_2-$); Jennings-White et al. Tetrahedron Lett 23:2533 (1982) ($-COCH_2-$); Szelke et al. EuropeanAppin, EP 45665 CA (1982): 97:39405 (1982) ($-CH(OH)CH_2-$); Holladay et al. Tetrahedron. Lett 24:4401-4404 (1983) ($-C(OH)CH_2-$); and Hruby Life Sci 31:189-199 (1982) ($-CH_2-S-$); each of which is incorporated herein by reference. A particularly preferred non-peptide linkage is $-CH_2NH-$. It is understood that peptide analogs can have more than one atom between the bond atoms, such as b-alanine, g-aminobutyric acid, and the like.

Amino acid analogs and analogs and peptide analogs often have enhanced or desirable properties, such as more economical production, greater chemical stability, enhanced pharmacological properties (half-life, absorption, potency, efficacy, etc.), altered specificity (e.g., a broad spectrum of biological activities), reduced antigenicity, and others.

D-amino acids can be used to generate more stable peptides, because D-amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

4. Sequence Similarities

It is understood that, as discussed herein, the use of the terms homology and identity mean the same thing as similarity. Thus, for example, if the use of the word homology is used between two non-natural sequences, it is understood that this is not necessarily indicating an evolutionary relationship between these two sequences but, rather, is looking at the similarity or relatedness between their nucleic acid sequences. Many of the methods for determining homology between two evolutionarily related molecules are routinely applied to any two or more nucleic acids or proteins for the purpose of measuring sequence similarity, regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by, for example, the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989, which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method, even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method, even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

5. Hybridization/Selective Hybridization

The term hybridization typically means a sequence-driven interaction between at least two nucleic acid molecules, such as a primer or a probe and a gene. Sequence-driven interaction means an interaction that occurs between two nucleotides or nucleotide analogs or nucleotide derivatives in a nucleotide-specific manner. For example, G interacting with C or A interacting with T are sequence-driven interactions. Typically, sequence-driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments, selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987, which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments, selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in, for example, 10- or 100- or 1000-fold excess. This type of assay can be performed under conditions where both the limiting and non-limiting primer are, for example, 10-fold or 100-fold or 1000-fold below their $k_d$, or where only one of the nucleic acid molecules is 10-fold or 100-fold or 1000-fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments, selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example, if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules but, unless otherwise indicated, meeting the parameters of any of the methods would be sufficient. For example, if 80% hybridization was required, and as long as hybridization occurs within the required parameters in any one of these methods, it is considered disclosed herein.

It is understood that those of skill in the art understand that if a composition or method meets any one of these criteria for determining hybridization either collectively or singly, it is a composition or method that is disclosed herein.

6. Cell Delivery Systems

There are a number of compositions and methods which can be used to deliver nucleic acids to cells, either in vitro or in vivo. These methods and compositions can largely be broken down into two classes: viral-based delivery systems and non-viral-based delivery systems. For example, the nucleic acids can be delivered through a number of direct delivery systems, such as electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

i. Nucleic Acid-Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as DR3 or TL1A, into the cell without degradation and include a promoter yielding expression of the gene in the cells into which it is delivered. In some embodiments, the vectors are derived from either a virus or a retrovirus. Viral vectors are, for example, Adenovirus, Adeno-associated virus, Herpes virus, Vaccinia virus, Polio virus, AIDS virus, neuronal trophic virus, Sindbis, and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors and, for this reason, are a commonly used vector. However, they are not as useful in non-proliferating cells. Adenovirus vectors are relatively stable and easy to work with, have high titers, can be delivered in aerosol formulation, and can transfect non-dividing cells. Pox viral vectors are large and have several sites for inserting genes; they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain non-structural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed, and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

a. Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)), the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis for the replication and packaging of the replicated virus. Typically, a retroviral genome contains the gag, pol, and env genes, which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine-rich sequence 5' to the 3' LTR that serves as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed and, upon replication, be packaged into a new retroviral particle. This amount of nucleic acid is sufficient for the delivery of one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles by the machinery provided in cis by the helper cell. The genomes for the machinery are not packaged because they lack the necessary signals.

b. Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma, and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild-type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed, and these virons are generated in a cell line such as the human 293 cell line. In another preferred embodiment, both the E1 and E3 genes are removed from the adenovirus genome.

c. Adeno-Associated Viral Vectors

Another type of viral vector is based on an adeno-associated virus (AAV). This defective parvovirus is a preferred vector because it can infect many cell types and is non-pathogenic to humans. AAV type vectors can transport about 4 to 5 kb, and wild-type AAV is known to stably insert into chromosome 19. Vectors which contain this site-specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically, the AAV and B19 coding regions have been deleted, resulting in a safe, non-cytotoxic vector. The AAV ITRs or modifications thereof confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral vectors usually contain promoters and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

d. Large Payload Viral Vectors

Molecular genetic experiments with large human herpesviruses have provided a means whereby large heterologous DNA fragments can be cloned, propagated, and established in cells permissive for infection with herpesviruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV)), have the potential to deliver fragments of human heterologous DNA >150 kb to specific cells. EBV recombinants can maintain large pieces of DNA in the infected B-cells as episomal DNA. Individual clones carrying human genomic inserts up to 330 kb appeared genetically stable. The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA >220 kb and to infect cells that can stably maintain DNA as episomes.

Other useful systems include, for example, replicating and host-restricted non-replicating vaccinia virus vectors.

Nucleic acids that are delivered to cells which are to be integrated into the host cell genome typically contain integration sequences. These sequences are often viral-related sequences, particularly when viral-based systems are used. These viral intergration systems can also be incorporated into nucleic acids which are to be delivered using a non-nucleic acid-based system of delivery, such as a liposome, so that the nucleic acid contained in the delivery system can become integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

ii. Non-Nucleic Acid-Based Systems

The disclosed compositions can be delivered to the target cells in a variety of ways. For example, the compositions can be delivered through electroporation, through lipofection, or through calcium phosphate precipitation. The delivery mechanism chosen will depend, in part, on the type of cell targeted, and whether the delivery is occurring, for example, in vivo or in vitro.

Thus, the compositions can comprise, in addition to the disclosed nucleic acids, peptides or vectors, for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci USA* 84:7413-7417 (1987); U.S. Pat. No. 4,897, 355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above, which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany), and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.), as well as by means of a SONOPORATION machine (ImaRx Pharmaceutical Corp., Tucson, Ariz.).

The materials may be in solution or in suspension (for example, incorporated into microparticles, liposomes, or cells). These may be targeted to a particular cell type via antibodies, receptors, or receptor ligands. The following references are examples of the use of this technology to target specific proteins to tumor tissue, the principles of which can be applied to targeting of other cells (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129:57-80, (1992); and Roffler, et al., Biochem. Pharmacol, 42:2062-2065, (1991)). These techniques can be used for a variety of other specific cell types. Vehicles such as "stealth" and other antibody-conjugated liposomes (including lipid-mediated drug targeting to colonic carcinoma), receptor-mediated targeting of DNA through cell-specific ligands, lymphocyte-directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104: 179-187, (1992)). In general, receptors are involved in pathways of endocytosis, either constitutive or ligand-induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

Nucleic acids that are delivered to cells which are to be integrated into the host cell genome typically contain integration sequences. These sequences are often viral-related sequences, particularly when viral-based systems are used. These viral intergration systems can also be incorporated into nucleic acids which are to be delivered using a non-nucleic acid-based system of delivery, such as a liposome, so that the nucleic acid contained in the delivery system can become integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

7. Expression Systems

The nucleic acids that are delivered to cells typically contain expression-controlling systems. For example, the inserted genes in viral and retroviral systems usually contain promoters and/or enhancers to help control the expression of the desired gene product. A promoter is generally a sequence or sequences of DNA that function(s) when in a relatively fixed location in regard to the transcription start site. A promoter contains core elements required for basic interaction of RNA polymerase and transcription factors, and may contain upstream elements and response elements.

i. Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and, most preferably, cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell. Bio. 3: 1108 (1983)) to the transcription unit. Furthermore, enhancers can be within an intron (Banerji, J. L. et al., Cell 33: 729 (1983)), as well as within the coding sequence itself (Osborne, T. F., et al., Mol. Cell. Bio. 4: 1293 (1984)). They are usually between 10 and 300 by in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein, and insulin), typically, one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments, the promoter and/or enhancer region can act as a constitutive promoter and/or enhancer to maximize expression of the region of the transcription unit to be transcribed. In certain constructs, the promoter and/or enhancer region is active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types, such as melanoma cells. The glial fibrillary acetic protein (GFAP) promoter has been used to selectively express genes in cells of glial origin.

Expression vectors used in eukaryotic host cells (yeast, fungi, insect, plant, animal, human, or nucleated cells) may also contain sequences necessary for the termination of transcription, which may affect mRNA expression. These regions are transcribed as polyadenylated segments in the untranslated portion of the mRNA-encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences to improve expression from, or stability of, the construct.

ii. Markers

The viral vectors can include nucleic acid sequence encoding a marker product. This marker product is used to determine if the gene has been delivered to the cell and, once delivered, is being expressed. Preferred marker genes are the *E. coli* lacZ gene, which encodes β-galactosidase, and green fluorescent protein.

In some embodiments, the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of supplemented media. Two examples are: CHO DHF$^{R-}$ cells and mouse LTK$^-$ cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection, which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)), or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

8. Internalization Sequences

The provided polypeptide can further constitute a fusion protein or otherwise have additional N-terminal, C-terminal, or intermediate amino acid sequences, e.g., linkers or tags. "Linker", as used herein, is an amino acid sequence or insertion that can be used to connect or separate two distinct polypeptides or polypeptide fragments, wherein the linker does not otherwise contribute to the essential function of the composition. A polypeptide provided herein can have an amino acid linker comprising, for example, the amino acids GLS, ALS, or LLA. A "tag", as used herein, refers to a distinct amino acid sequence that can be used to detect or purify the provided polypeptide, wherein the tag does not otherwise contribute to the essential function of the composition. The provided polypeptide can further have deleted N-terminal, C-terminal, or intermediate amino acids that do not contribute to the essential activity of the polypeptide.

The disclosed composition can be linked to an internalization sequence or a protein transduction domain to effectively enter the cell. Recent studies have identified several cell-penetrating peptides, including the TAT transactivation domain of the HIV virus, antennapedia, and transportan that can readily transport molecules and small peptides across the plasma membrane (Schwarze et al., 1999; Derossi et al., 1996; Yuan et al., 2002). More recently, polyarginine has shown an even greater efficiency of transporting peptides and proteins across the plasma membrane, making it an attractive tool for peptide-mediated transport (Fuchs and Raines, 2004). Nonaarginine ($R_9$, SEQ ID NO:18) has been described as one of the most efficient polyarginine-based protein transduction domains, with maximal uptake of significantly greater than TAT or antennapeadia. Peptide-mediated cytotoxicity has also been shown to be less with polyarginine-based internalization sequences. $R_9$-mediated membrane transport is facilitated through heparan sulfate proteoglycan binding and endocytic packaging. Once internalized, heparan is degraded by heparanases, releasing $R_9$ which leaks into the cytoplasm (Deshayes et al., 2005). Studies have recently shown that derivatives of polyarginine can deliver a full length p53 protein to oral cancer cells, suppressing their growth and metastasis, defining polyarginine as a potent cell penetrating peptide (Takenobu et al., 2002).

Thus, the provided polypeptide can comprise a cellular internalization transporter or sequence. The cellular internalization sequence can be any internalization sequence known or newly discovered in the art or conservative variants thereof. Non-limiting examples of cellular internalization transporters and sequences include Polyarginine (e.g., $R_9$), Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol) (see Table 4).

TABLE 4

Cell Internalization Transporters

| Name | Sequence | SEQ ID NO |
|---|---|---|
| Polyarginine | RRRRRRRRR | SEQ ID NO: 16 |
| Antp | RQPKIWFPNRRKPWKK | SEQ ID NO: 17 |
| HIV-Tat | GRKKRRQRPPQ | SEQ ID NO: 18 |
| Penetratin | RQIKIWFQNRRMKWKK | SEQ ID NO: 19 |
| Antp-3A | RQIAIWFQNRRMKWAA | SEQ ID NO: 20 |
| Tat | RKKRRQRRR | SEQ ID NO: 21 |
| Buforin II | TRSSRAGLQFPVGRVHRLLRK | SEQ ID NO: 22 |
| Transportan | GWTLNSAGYLLGKINKALAALAKKIL | SEQ ID NO: 23 |
| model amphipathic peptide (MAP) | KLALKLALKALKAALKLA | SEQ ID NO: 24 |
| K-FGF | AAVALLPAVLLALLAP | SEQ ID NO: 25 |
| Ku70 | VPMLK-PMLKE | SEQ ID NO: 26 |
| Prion | MANLGYWLLALFVTMWTDVGLCKKRPKP | SEQ ID NO: 27 |
| pVEC | LLIILRRRIRKQAHAHSK | SEQ ID NO: 28 |
| Pep-1 | KETWWETWWTEWSQPKKKRKV | SEQ ID NO: 29 |
| SynB1 | RGGRLSYSRRRFSTSTGR | SEQ ID NO: 30 |
| Pep-7 | SDLWEMMMVSLACQY | SEQ ID NO: 31 |
| HN-1 | TSPLNIHNGQKL | SEQ ID NO: 32 |

BGSC (Bis-Guanidinium-Spermidine-Cholesterol)

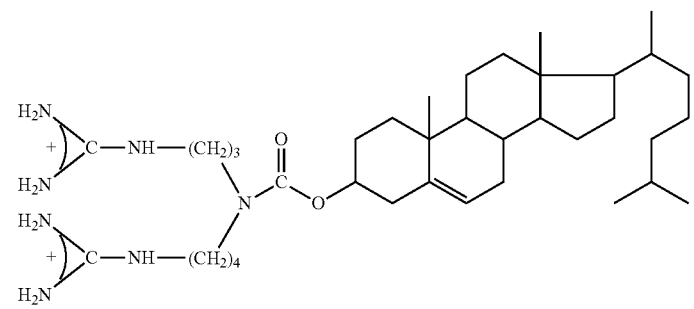

BGSC

TABLE 4-continued

Cell Internalization Transporters

| Name | Sequence | SEQ ID NO |
|---|---|---|
| BGTC (Bis-Guanidinium-Tren-Cholesterol) | 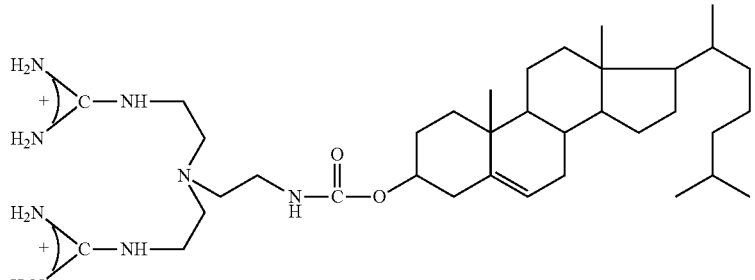<br>BGTC | |

Any other internalization sequences now known or later identified can be combined with a peptide of the invention.

9. Effectors

The herein provided compositions can further comprise an effector molecule. By "effector molecule" is meant a substance that acts upon the target cell(s) or tissue to bring about a desired effect. The effect can, for example, be the labeling, activating, repressing, or killing of the target cell(s) or tissue. Thus, the effector molecule can, for example, be a small molecule, pharmaceutical drug, toxin, fatty acid, detectable marker, conjugating tag, nanoparticle, or enzyme.

Examples of small molecules and pharmaceutical drugs that can be conjugated to a targeting peptide are known in the art. The effector can be a cytotoxic small molecule or drug that kills the target cell. The small molecule or drug can be designed to act on any critical cellular function or pathway. For example, the small molecule or drug can inhibit the cell cycle, activate protein degradation, induce apoptosis, modulate kinase activity, or modify cytoskeletal proteins. Any known or newly discovered cytotoxic small molecule or drugs is contemplated for use with the targeting peptides.

The effector can be a toxin that kills the targeted cell. Non-limiting examples of toxins include abrin, modeccin, ricin, and diphtheria toxin. Other known or newly discovered toxins are contemplated for use with the provided compositions.

Fatty acids (i.e., lipids) that can be conjugated to the provided compositions include those that allow the efficient incorporation of the peptide into liposomes. Generally, the fatty acid is a polar lipid. Thus, the fatty acid can be a phospholipid. The provided compositions can comprise either natural or synthetic phospholipid. The phospholipids can be selected from phospholipids containing saturated or unsaturated mono- or disubstituted fatty acids and combinations thereof. These phospholipids can be dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, palmiticlinoleoylphosphatidic acid. These phospholipids may also be the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol), and phosphatidic acid (lysophosphatidic acid). The monoacyl chain in these lysophosphatidyl derivatives may be palimtoyl, oleoyl, palmitoleoyl, linoleoyl myristoyl or myristoleoyl. The phospholipids can also be synthetic. Synthetic phospholipids are readily available commercially from various sources, such as AVANTI Polar Lipids (Albaster, Ala.); Sigma Chemical Company (St. Louis, Mo.). These synthetic compounds may be varied and may have variations in their fatty acid side chains not found in naturally occurring phospholipids. The fatty acid can have unsaturated fatty acid side chains with C14, C16, C18, or C20 chains length in either or both the PS or PC. Synthetic phospholipids can have dioleoyl (18:1)-PS; palmitoyl (16:0)-oleoyl (18:1)-PS, dimyristoyl (14:0)-PS; dipalmitoleoyl (16:1)-PC, dipalmitoyl (16:0)-PC, dioleoyl (18:1)-PC, palmitoyl (16:0)-oleoyl (18:1)-PC, and myristoyl (14:0)-oleoyl (18:1)-PC as constituents. Thus, as an example, the provided compositions can comprise palmitoyl 16:0.

Detectable markers include any substance that can be used to label or stain a target tissue or cell(s). Non-limiting examples of detectable markers include radioactive isotopes, enzymes, fluorochromes, and quantum dots (Qdot®). Other known or newly discovered detectable markers are contemplated for use with the provided compositions.

The effector molecule can be a nanoparticle, such as a heat-generating nanoshell. As used herein, "nanoshell" is a nanoparticle having a discrete dielectric or semi-conducting core section surrounded by one or more conducting shell layers. U.S. Pat. No. 6,530,944 is hereby incorporated by reference herein in its entirety for its teaching of the methods of making and using metal nanoshells. Nanoshells can be formed with a core of a dielectric or inert material, such as silicon coated with a material such as a highly conductive metal, which can be excited using radiation such as near infrared light (approximately 800 to 1300 nm). Upon excitation, the nanoshells emit heat. The resulting hyperthermia can kill the surrounding cell(s) or tissue. The combined diameter of the shell and core of the nanoshells ranges from the tens to the hundreds of nanometers. Near infrared light is advantageous for its ability to penetrate tissue. Other types of radiation can also be used, depending on the selection of the nanoparticle coating and targeted cells. Examples include x-rays, magnetic fields, electric fields, and ultrasound. The problems with the existing methods for hyperthermia, especially for use in cancer therapy, such as the use of heated probes, microwaves, ultrasound, lasers, perfusion, radiofrequency energy, and radiant heating are avoided, since the levels of radiation used as described herein are insufficient to induce hyperthermia, except at the surface of the nanoparticles where the energy is more effectively concentrated by the metal surface on the dielectric. The particles can also be used to enhance imaging, especially using infrared diffuse photon imaging methods. Targeting molecules can be antibodies or fragments thereof, ligands for specific receptors, or other proteins specifically binding to the surface of the cells to be targeted.

The effector molecule can be covalently linked to the disclosed peptide. The effector molecule can be linked to the amino-terminal end of the disclosed peptide. The effector molecule can be linked to the carboxy-terminal end of the disclosed peptide. The effector molecule can be linked to an amino acid within the disclosed peptide. The herein-provided compositions can further comprise a linker connecting the effector molecule and disclosed peptide. The disclosed peptide can also be conjugated to a coating molecule such as bovine serum albumin (BSA) (see Tkachenko et al., (2003) J Am Chem Soc, 125, 4700-4701) that can be used to coat the Nanoshells with the peptide.

Protein crosslinkers that can be used to crosslink the effector molecule to the disclosed peptide are known in the art and are defined based on utility and structure and include DSS (Disuccinimidylsuberate), DSP (Dithiobis(succinimidylpropionate)), DTSSP (3,3'-Dithiobis (sulfosuccinimidylpropionate)), SULFO BSOCOES (Bis[2-(sulfosuccinimdooxy-carbonyloxy)ethyl]sulfone), BSOCOES (Bis[2-(succinimdooxycarbonyloxy)ethyl]sulfone), SULFO DST (Disulfosuccinimdyltartrate), DST (Disuccinimdyltartrate), SULFO EGS (Ethylene glycolbis(sulfosuccinimidylsuccinate)), EGS (Ethylene glycolbis(sulfosuccinimidylsuccinate)), DPDPB (1,2-Di[3'-(2'-pyridyldithio) propionamido]butane), BSSS (Bis(sulfosuccinimdyl) suberate), SMPB (Succinimdyl-4-(p-maleimidophenyl) butyrate), SULFO SMPB (Sulfosuccinimdyl-4-(p-maleimidophenyl) butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl)aminobenzoate), SULFO SIAB (N-Sulfosuccinimidyl(4-iodoacetyl)aminobenzoate), SMCC (Succinimidyl-4-(N-maleimidomethyl)cyclohexane-1-carboxylate), SULFO SMCC (Sulfosuccinimidyl-4-(N-maleimidomethyl)cyclohexane-1-carboxylate), NHS LC SPDP (Succinimidyl-6-[3-(2-pyridyldithio) propionamido) hexanoate), SULFO NHS LC SPDP (Sulfosuccinimidyl-6-[3-(2-pyridyldithio) propionamido) hexanoate), SPDP (N-Succinimdyl-3-(2-pyridyldithio) propionate), NHS BROMOACETATE (N-Hydroxysuccinimidylbromoacetate), NHS IODOACETATE (N-Hydroxysuccinimidyliodoacetate), MPBH (4-(N-Maleimidophenyl) butyric acid hydrazide hydrochloride), MCCH (4-(N-Maleimidomethyl)cyclohexane-1-carboxylic acid hydrazide hydrochloride), MBH (m-Maleimidobenzoic acid hydrazidehydrochloride), SULFO EMCS (N-(epsilon-Maleimidocaproyloxy) sulfosuccinimide), EMCS(N-(epsilon-Maleimidocaproyloxy) succinimide), PMPI (N-(p-Maleimidophenyl) isocyanate), KMUH (N-(kappa-Maleimidoundecanoic acid) hydrazide), LC SMCC (Succinimidyl-4-(N-maleimidomethyl)-cyclohexane-1-carboxy(6-amidocaproate)), SULFO GMBS (N-(gamma-Maleimidobutryloxy) sulfosuccinimide ester), SMPH (Succinimidyl-6-(beta-maleimidopropionamidohexanoate)), SULFO KMUS (N-(kappa-Maleimidoundecanoyloxy) sulfosuccinimide ester), GMBS (N-(gamma-Maleimidobutyrloxy) succinimide), DMP (Dimethylpimelimidate hydrochloride), DMS (Dimethylsuberimidate hydrochloride), MHBH (Wood's Reagent) (Methyl-p-hydroxybenzimidate hydrochloride, 98%), DMA (Dimethyladipimidate hydrochloride).

10. Computer Readable Mediums

It is understood that the disclosed nucleic acids and proteins can be represented as a sequence consisting of the nucleotides of amino acids. There are a variety of ways to display these sequences; for example, the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved are disclosed herein.

Disclosed are computer readable mediums comprising the sequences and information regarding the sequences set forth herein.

11. Compositions Identified by Screening with Disclosed Compositions/Combinatorial Chemistry The disclosed compositions can be used as targets for any combinatorial technique to identify molecules or macromolecular molecules that interact with the disclosed compositions in a desired way. The DR3 and/or TL1A nucleic acids, peptides, and related molecules disclosed herein can be used as targets for the combinatorial approaches. Also disclosed are the compositions that are identified through combinatorial techniques or screening techniques, in which the compositions disclosed in SEQ ID NOS:1, 2, 3, or 4 or portions thereof are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed compositions, such as in SEQ ID NOS:1, 2, 3, or 4 or portions thereof, are also disclosed. Thus, the products produced using the combinatorial or screening approaches that involve the disclosed compositions, such as in SEQ ID NOS:1, 2, 3, or 4 or portions thereof, are also considered herein disclosed.

It is understood that the disclosed methods for identifying molecules that inhibit the interactions between, for example, DR3 and TL1A can be performed using high throughput means. For example, putative inhibitors can be identified using Fluorescence Resonance Energy Transfer (FRET) to quickly identify interactions. The underlying theory of the techniques is that when two molecules are close in space, i.e., interacting at a level beyond background, a signal is produced, or a signal can be quenched. Then, a variety of experiments can be performed, including, for example, adding in a putative inhibitor. If the inhibitor competes with the interaction between the two signaling molecules, the signals will be removed from each other in space, and this will cause a decrease or an increase in the signal, depending on the type of signal used. This decreasing or increasing signal can be correlated to the presence or absence of the putative inhibitor. Any signaling means can be used. For example, disclosed are methods of identifying an inhibitor of the interaction between any two of the disclosed molecules comprising contacting a first molecule and a second molecule together in the presence of a putative inhibitor, wherein the first molecule or second molecule comprises a fluorescence donor, wherein the first or second molecule, typically the molecule not comprising the donor, comprises a fluorescence acceptor; and measuring Fluorescence Resonance Energy Transfer (FRET) in the presence of the putative inhibitor and the in absence of the putative inhibitor, wherein a decrease in FRET in the presence of the putative inhibitor as compared to FRET measurement in its absence indicates the putative inhibitor inhibits binding between the two molecules. This type of method can be performed with a cell system, as well.

Combinatorial chemistry includes, but is not limited to, all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, *TIBS* 19:89, 1992). One synthesizes a large pool of molecules bearing random and defined sequences and subjects that complex mixture, for example, approximately $10^{15}$ individual sequences in 100 µg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dye. DNA molecules with such ligand-binding behavior have been isolated as well (Ellington and Szostak, 1992; Bock et al., 1992). Techniques aimed at similar goals exist for small organic molecules, proteins, antibodies, and other macromolecules known to those of skill in the art. Screening sets of molecules for a desired activity, whether based on small organic libraries, oligonucleotides, or antibodies, is broadly referred to as combinatorial chemistry. Combinatorial techniques are particularly suited for defining binding interactions between molecules and for isolating molecules that have a specific binding activity, often called aptamers when the macromolecules are nucleic acids.

12. Carriers

The disclosed compositions can be combined, conjugated, or coupled with or to carriers and other compositions to aid administration, delivery, or other aspects of the inhibitors and their use. For convenience, such composition will be referred to herein as carriers. Carriers can, for example, be a small molecule, pharmaceutical drug, fatty acid, detectable marker, conjugating tag, nanoparticle, or enzyme.

The disclosed compositions can be used therapeutically in combination with a pharmaceutically acceptable carrier. By "pharmaceutically acceptable" is meant a material that is not biologically or otherwise undesirable, i.e., the material can be administered to a subject, along with the composition, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically acceptable salt is used in the formulation to render the formulation isotonic. Examples of the pharmaceutically acceptable carrier include, but are not limited to, saline, Ringer's solution, and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds can be administered according to standard procedures used by those skilled in the art.

Pharmaceutical compositions can include carriers, thickeners, diluents, buffers, preservatives, surface active agents, and the like, in addition to the molecule of choice. Pharmaceutical compositions can also include one or more active ingredients, such as antimicrobial agents, antiinflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions, or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable.

Some of the compositions can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines, and substituted ethanolamines.

The materials may be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129: 57-80, (1992); and Roffler, et al., Biochem. Pharmacol, 42:2062-2065, (1991)). Vehicles such as "stealth" and other antibody-conjugated liposomes (including lipid-mediated drug targeting to colonic carcinoma), receptor-mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand-induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

The carrier molecule can be covalently linked to the disclosed inhibitors. The carrier molecule can be linked to the amino-terminal end of the disclosed peptides. The carrier molecule can be linked to the carboxy-terminal end of the disclosed peptides. The carrier molecule can be linked to an amino acid within the disclosed peptides. The herein provided compositions can further comprise a linker connecting the carrier molecule and disclosed inhibitors. The disclosed inhibitors can also be conjugated to a coating molecule such as bovine serum albumin (BSA) (see Tkachenko et al., (2003) J Am Chem Soc, 125, 4700-4701) that can be used to coat microparticles, nanoparticles of nanoshells with the inhibitors.

Protein crosslinkers that can be used to crosslink the carrier molecule to the inhibitors, such as the disclosed peptides, are known in the art and are defined based on utility and structure and include DSS (Disuccinimidylsuberate), DSP (Dithiobis (succinimidylpropionate)), DTSSP (3,3'-Dithiobis (sulfosuccinimidylpropionate)), SULFO BSOCOES (Bis[2-(sulfosuccinimdooxycarbonyloxy)ethyl]sulfone), BSOCOES (Bis[2-(succinimdooxycarbonyloxy)ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis(sulfosuccinimidylsuccinate)), DPDPB (1,2-Di[3'-(2'-pyridyldithio)propionamido]butane), BSSS (Bis(sulfosuccinimdyl)suberate), SMPB (Succinimdyl-4-(p-maleimidophenyl)butyrate), SULFO SMPB (Sulfo-succinimdyl-4-(p-maleimidophenyl)butyrate), MBS (3-Maleimidobenzoyl-N-hydroxysuccinimide ester), SULFO MBS (3-Maleimidobenzoyl-N-hydroxysulfosuccinimide ester), SLAB (N-Succinimidyl(4-iodoacetyl)aminobenzoate), SULFO SIAB (N-Sulfosuccinimidyl(4-iodoacetyl)aminobenzoate), SMCC (Succinimidyl-4-(N-maleimidomethyl) cyclohexane-1-carboxylate), SULFO SMCC (Sulfosuccinimidyl-4-(N-maleimidomethyl)cyclohexane-1-carboxylate), NHS LC SPDP (Succinimidyl-6-[3-(2-pyridyldithio)propionamido) hexanoate), SULFO NHS LC SPDP (Sulfosuccinimidyl-6-[3-(2-pyridyldithio)propionamido) hexanoate), SPDP (N-Succinimidyl-3-(2-pyridyldithio)propionate), NHS BROMOACETATE (N-Hydroxysuccinimidylbromoacetate), NHS IODOACETATE (N-Hydroxysuccinimidyliodoacetate), MPBH (4-(N-Maleimidophenyl)butyric acid hydrazide hydrochloride), MCCH (4-(N-Maleimidomethyl)cyclohexane-1-carboxylic acid hydrazide hydrochloride), MBH (m-Maleimidobenzoic acid hydrazidehydrochloride), SULFO EMCS(N-(epsilon-Maleimidocaproyloxy) sulfosuccinimide), EMCS(N-(epsilon-Maleimidocaproyloxy)succinimide), PMPI (N-(p-Maleimidophenyl)isocyanate), KMUH(N-(kappa-Maleimidoundecanoic acid) hydrazide), LC SMCC (Succinimidyl-4-(N-maleimidomethyl)-cyclohexane-1-carboxy(6-amidocaproate)), SULFO GMBS (N-(gamma-Maleimidobutryloxy)sulfosuccinimide ester), SMPH (Succinimidyl-6-(beta-maleimidopropionamidohexanoate)), SULFO KMUS (N-(kappa-Maleimidoundecanoyloxy)sulfosuccinimide ester), GMBS (N-(gamma-Maleimidobutyrloxy)succinimide), DMP (Dimethylpimelimidate hydrochloride), DMS (Dimethylsuberimidate hydrochloride), MHBH (Wood's Reagent) (Methyl-p-hydroxybenzimidate hydrochloride, 98%), DMA (Dimethyladipimidate hydrochloride).

i. Nanoparticles, Microparticles, and Microbubbles

The term "nanoparticle" refers to a nanoscale particle with a size that is measured in nanometers, for example, a nanoscopic particle that has at least one dimension of less than about 100 nm. Examples of nanoparticles include paramagnetic nanoparticles, superparamagnetic nanoparticles, metal nanoparticles, fullerene-like materials, inorganic nanotubes, dendrimers (such as with covalently attached metal chelates), nanofibers, nanohoms, nano-onions, nanorods, nanoropes, and quantum dots. A nanoparticle can produce a detectable signal, for example, through absorption and/or emission of photons (including radio frequency and visible photons) and plasmon resonance.

Microspheres (or microbubbles) can also be used with the methods disclosed herein. Microspheres containing chromophores have been utilized in an extensive variety of applications, including photonic crystals, biological labeling, and flow visualization in microfluidic channels. See, for example, Y. Lin, et al., Appl. Phys Lett. 2002, 81, 3134; D. Wang, et al., Chem. Mater. 2003, 15, 2724; X. Gao, et al., J. Biomed. Opt. 2002, 7, 532; M. Han, et al., Nature Biotechnology. 2001, 19, 631; V. M. Pai, et al., Mag. & Magnetic Mater. 1999, 194, 262, each of which is incorporated by reference in its entirety. Both the photostability of the chromophores and the monodispersity of the microspheres can be important.

Nanoparticles such as, for example, silica nanoparticles, metal nanoparticles, metal oxide nanoparticles, or semiconductor nanocrystals can be incorporated into microspheres. The optical, magnetic, and electronic properties of the nanoparticles can allow them to be observed while associated with the microspheres and can allow the microspheres to be identified and spatially monitored. For example, the high photostability, good fluorescence efficiency, and wide emission tunability of colloidally synthesized semiconductor nanocrystals can make them an excellent choice of chromophore. Unlike organic dyes, nanocrystals that emit different colors (i.e. different wavelengths) can be excited simultaneously with a single light source. Colloidally synthesized semiconductor nanocrystals (such as, for example, core-shell CdSe/ZnS and CdS/ZnS nanocrystals) can be incorporated into microspheres. The microspheres can be monodisperse silica microspheres.

The nanoparticle can be a metal nanoparticle, a metal oxide nanoparticle, or a semiconductor nanocrystal. The metal of the metal nanoparticle or the metal oxide nanoparticle can include titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, zinc, cadmium, scandium, yttrium, lanthanum, a lanthanide series or actinide series element (e.g., cerium, praseodymium, neodymium, promethium, samarium, europium, gadolinium, terbium, dysprosium, holmium, erbium, thulium, ytterbium, lutetium, thorium, protactinium, and uranium), boron, aluminum, gallium, indium, thallium, silicon, germanium, tin, lead, antimony, bismuth, polonium, magnesium, calcium, strontium, and barium. In certain embodiments, the metal can be iron, ruthenium, cobalt, rhodium, nickel, palladium, platinum, silver, gold, cerium or samarium. The metal oxide can be an oxide of any of these materials or combination of materials. For example, the metal can be gold, or the metal oxide can be an iron oxide, a cobalt oxide, a zinc oxide, a cerium oxide, or a titanium oxide. Preparation of metal and metal oxide nanoparticles is described, for example, in U.S. Pat. Nos. 5,897,945 and 6,759,199, each of which is incorporated by reference in its entirety.

For example, the disclosed compositions can be immobilized on silica nanoparticles (SNPs). SNPs have been widely used for biosensing and catalytic applications owing to their favorable surface area-to-volume ratio, straightforward manufacture and the possibility of attaching fluorescent labels, magnetic nanoparticles (Yang, H. H. et al. 2005) and semiconducting nanocrystals (Lin, Y. W., et al. 2006).

The nanoparticle can also be, for example, a heat-generating nanoshell. As used herein, "nanoshell" is a nanoparticle having a discrete dielectric or semi-conducting core section surrounded by one or more conducting shell layers. U.S. Pat. No. 6,530,944 is hereby incorporated by reference herein in its entirety for its teaching of the methods of making and using metal nanoshells.

Targeting molecules can be attached to the disclosed compositions and/or carriers. For example, the targeting molecules can be antibodies or fragments thereof, ligands for specific receptors, or other proteins specifically binding to the surface of the cells to be targeted.

ii. Liposomes

"Liposome", as the term is used herein, refers to a structure comprising an outer lipid bi- or multi-layer membrane surrounding an internal aqueous space. Liposomes can be used to package any biologically active agent for delivery to cells.

Materials and procedures for forming liposomes are well-known to those skilled in the art. Upon dispersion in an appropriate medium, a wide variety of phospholipids swell, hydrate, and form multilamellar concentric bilayer vesicles with layers of aqueous media separating the lipid bilayers. These systems are referred to as multilamellar liposomes or multilamellar lipid vesicles ("MLVs") and have diameters within the range of 10 nm to 100 µm. These MLVs were first described by Bangham, et al., J. Mol. Biol. 13:238-252 (1965). In general, lipids or lipophilic substances are dissolved in an organic solvent. When the solvent is removed, such as under vacuum by rotary evaporation, the lipid residue forms a film on the wall of the container. An aqueous solution that typically contains electrolytes or hydrophilic biologically active materials is then added to the film. Large MLVs are produced upon agitation. When smaller MLVs are desired, the larger vesicles are subjected to sonication, sequential filtration through filters with decreasing pore size, or reduced by other forms of mechanical shearing. There are also techniques by which MLVs can be reduced both in size and in number of lamellae, for example, by pressurized extrusion (Barenholz, et al., FEBS Lett. 99:210-214 (1979)).

Liposomes can also take the form of unilammelar vesicles, which are prepared by more extensive sonication of MLVs, and consist of a single spherical lipid bilayer surrounding an aqueous solution. Unilamellar vesicles ("ULVs") can be small, having diameters within the range of 20 to 200 nm, while larger ULVs can have diameters within the range of 200 nm to 2 µm. There are several well-known techniques for making unilamellar vesicles. In Papahadjopoulos, et al., Biochim et Biophys Acta 135:624-238 (1968), sonication of an aqueous dispersion of phospholipids produces small ULVs having a lipid bilayer surrounding an aqueous solution. Schneider, U.S. Pat. No. 4,089,801 describes the formation of liposome precursors by ultrasonication, followed by the addition of an aqueous medium containing amphiphilic compounds and centrifugation to form a biomolecular lipid layer system.

Small ULVs can also be prepared by the ethanol injection technique described by Batzri, et al., Biochim et Biophys Acta 298:1015-1019 (1973) and the ether injection technique of Deamer, et al., Biochim et Biophys Acta 443:629-634 (1976). These methods involve the rapid injection of an organic solution of lipids into a buffer solution, which results in the rapid formation of unilamellar liposomes. Another technique for making ULVs is taught by Weder, et al. in "Liposome Technology", ed. G. Gregoriadis, CRC Press Inc., Boca Raton, Fla., Vol. I, Chapter 7, pg. 79-107 (1984). This detergent removal method involves solubilizing the lipids and additives with detergents by agitation or sonication to produce the desired vesicles.

Papahadjopoulos, et al., U.S. Pat. No. 4,235,871, describes the preparation of large ULVs by a reverse phase evaporation technique that involves the formation of a water-in-oil emulsion of lipids in an organic solvent and the drug to be encapsulated in an aqueous buffer solution. The organic solvent is removed under pressure to yield a mixture which, upon agitation or dispersion in an aqueous media, is converted to large ULVs. Suzuki et al., U.S. Pat. No. 4,016,100, describes another method of encapsulating agents in unilamellar vesicles by freezing/thawing an aqueous phospholipid dispersion of the agent and lipids.

In addition to the MLVs and ULVs, liposomes can also be multivesicular. Described in Kim, et al., Biochim et Biophys Acta 728:339-348 (1983), these multivesicular liposomes are spherical and contain internal granular structures. The outer membrane is a lipid bilayer, and the internal region contains small compartments separated by bilayer septum. Still yet another type of liposomes are oligolamellar vesicles ("OLVs"), which have a large center compartment surrounded by several peripheral lipid layers. These vesicles, having a diameter of 2-15 µm, are described in Callo, et al., Cryobiology 22(3):251-267 (1985).

Mezei, et al., U.S. Pat. Nos. 4,485,054 and 4,761,288, also describe methods of preparing lipid vesicles. More recently, Hsu, U.S. Pat. No. 5,653,996, describes a method of preparing liposomes utilizing aerosolization, and Yiournas, et al., U.S. Pat. No. 5,013,497, describes a method for preparing liposomes utilizing a high velocity-shear mixing chamber. Methods are also described that use specific starting materials to produce ULVs (Wallach, et al., U.S. Pat. No. 4,853,228) or OLVs (Wallach, U.S. Pat. Nos. 5,474,848 and 5,628,936).

A comprehensive review of all of the aforementioned lipid vesicles and methods for their preparation are described in "Liposome Technology", ed. G. Gregoriadis, CRC Press Inc., Boca Raton, Fla., Vol. I, II & III (1984). This and the aforementioned references describing various lipid vesicles suitable for use in the invention are incorporated herein by reference.

Fatty acids (i.e., lipids) that can be conjugated to the provided compositions include those that allow the efficient incorporation of the proprotein convertase inhibitors into liposomes. Generally, the fatty acid is a polar lipid. Thus, the fatty acid can be a phospholipid. The provided compositions can comprise either natural or synthetic phospholipid. The phospholipids can be selected from phospholipids containing saturated or unsaturated mono- or di-substituted fatty acids and combinations thereof. These phospholipids can be dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, palmiticlinoleoylphosphatidic acid. These phospholipids may also be the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol), and phosphatidic acid (lysophosphatidic acid). The monoacyl chain in these lysophosphatidyl derivatives may be palimtoyl, oleoyl, palmitoleoyl, linoleoyl myristoyl, or myristoleoyl. The phospholipids can also be synthetic. Synthetic phospholipids are readily available commercially from various sources, such as AVANTI Polar Lipids (Albaster, Ala.); Sigma Chemical Company (St. Louis, Mo.). These synthetic compounds may be varied and may have variations in their fatty acid side chains not found in naturally occurring phospholipids. The fatty acid can have unsaturated fatty acid side chains with C14, C16, C18, or C20 chains length in either or both the PS or PC. Synthetic phospholipids can have dioleoyl (18:1)-PS; palmitoyl (16:0)-oleoyl (18:1)-PS, dimyristoyl (14:0)-PS; dipalmitoleoyl (16:1)-PC, dipalmitoyl (16:0)-PC, dioleoyl (18:1)-PC, palmitoyl (16:0)-oleoyl (18:1)-PC, and myristoyl (14:0)-oleoyl (18:1)-PC as constituents. Thus, as an example, the provided compositions can comprise palmitoyl 16:0.

iii. In Vivo/Ex Vivo

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis, and the like).

If ex vivo methods are employed, cells or tissues can be removed and maintained outside the body according to standard protocols well known in the art. The compositions can be introduced into the cells via any gene transfer mechanism, such as, for example, calcium phosphate-mediated gene delivery, electroporation, microinjection, or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

C. METHODS OF MAKING THE COMPOSITIONS

The compositions disclosed herein and the compositions necessary to perform the disclosed methods can be made using any method known to those of skill in the art for that particular reagent or compound unless otherwise specifically noted.

1. Nucleic Acid Synthesis

A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., Biochemistry 34:11363-11372 (1995)).

For example, the nucleic acids, such as the oligonucleotides to be used as primers, can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

2. Peptide Synthesis

One method of producing the disclosed proteins, such as SEQ ID NO:23, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin, whereas the other fragment of a peptide or protein can be synthesized and subsequently cleaved from the resin, thereby exposing a terminal group, which is functionally blocked on the other fragment. By peptide condensation reactions, these two fragments can be covalently joined via a peptide bond at their carboxyl and amino termini, respectively, to form an antibody or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY, which is herein incorporated by reference at least for material related to peptide synthesis. Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allows relatively short peptide fragments to be joined to produce larger peptide fragments, polypeptides, or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two-step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269: 16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains, as well as large amounts of relatively pure proteins with full biological activity (deLisle Milton R C et al., Techniques in Protein Chemistry IV. Academic Press, New York, pp. 257-267 (1992)).

D. KITS

The materials described above, as well as other materials, can be packaged together in any suitable combination as a kit useful for performing, or aiding in the performance of, the disclosed method. It is useful if the kit components in a given kit are designed and adapted for use together in the disclosed method. For example, disclosed are kits comprising peptides or antibodies that bind DR3 or TL1A.

E. USES

The disclosed compositions can be used in a variety of ways as research tools. For example, the disclosed compositions, such as an isolated polypeptide comprising SEQ ID NOs:2 or 4, can be used to study the interactions between DR3 or TL1A by, for example, acting as inhibitors of binding. Other uses are disclosed, apparent from the disclosure, and/or will be understood by those in the art. Other uses are disclosed, apparent from the disclosure, and/or will be understood by those in the art.

F. DEFINITIONS

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents.

It must be noted that, as used herein and in the appended claims, the singular forms "a," "an," and "the" include plural reference unless the context clearly dictates otherwise. Thus, for example, reference to "a pharmaceutical carrier" includes a plurality of such pharmaceutical carriers, reference to "the pharmaceutical carrier" is a reference to one or more pharmaceutical carriers and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, "less than or equal to" the value, "greater than or equal to the value" and possible ranges between values are also disclosed, as appropriately understood by the skilled artisan. For example, if the value "10" is disclosed, "less than or equal to 10," as well as "greater than or equal to 10," are also disclosed. It is also understood that throughout the application, data is provided in a number of different formats, and that this data represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed, as well as between 10 and 15. It is also understood that each unit between two particular units is also disclosed. For example, if 10 and 15 are disclosed, then 11, 12, 13, and 14 are also disclosed.

Throughout the description and claims of this specification, the word "comprise" and variations of the word, such as "comprising" and "comprises," means "including but not limited to," and is not intended to exclude, for example, other additives, components, integers, or steps.

"Probes" are molecules capable of interacting with a target nucleic acid, typically in a sequence-specific manner, for example through hybridization. The hybridization of nucleic acids is well understood in the art and discussed herein. Typically, a probe can be made from any combination of nucleotides or nucleotide derivatives or analogs available in the art.

"Primers" are a subset of probes which are capable of supporting some type of enzymatic manipulation, and which can hybridize with a target nucleic acid such that the enzymatic manipulation can occur. A primer can be made from any combination of nucleotides or nucleotide derivatives or analogs available in the art which do not interfere with the enzymatic manipulation. Typically, a primer supports extension of a polynucleotide sequence.

"Subject" includes, but is not limited to, animals, plants, bacteria, viruses, parasites and any other organism or entity that has nucleic acid. The subject may be a vertebrate, more specifically a mammal (e.g., a human, horse, pig, rabbit, dog, sheep, goat, non-human primate, cow, cat, guinea pig, or rodent), a fish, a bird, a reptile, or an amphibian. The subject may be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As defined herein, "sample" refers to any sample obtained from an organism. Examples of biological samples include body fluids and tissue specimens. The source of the sample may be physiological media as blood, serum, plasma, breast milk, pus, tissue scrapings, washings, urine, feces, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid, and tissues, such as lymph nodes, spleen or the like.

As used herein, "blocked" can mean complete or partial inhibition of an interaction, for example, the interaction (e.g., binding) between a ligand and its receptor. Inhibited binding can be detected through measurement of the normal downstream effect of normal binding.

As used herein, "treatment" or "treating" means to administer a composition to a subject with a condition, wherein the condition can be any pathologic disease, cancer, or inflammatory condition. The effect of the administration to the subject can be, but is not limited to, reducing the symptoms of the condition, a reduction in the severity of the condition, or the complete cessation of the condition.

By "prevent" is meant to minimize the chance that a subject who has a predisposition for developing a disease or condition involving the interaction of TL1A with DR3 (e.g., an autoimmune disease with a T cell component) will develop the disease or condition.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

G. EXAMPLES

The following examples are put forth so as to provide those of ordinary skill in the art with a complete disclosure and description of how the compounds, compositions, articles, devices, and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

In addition to endothelial cells, TL1A is rapidly upregulated and secreted from dendritic cells after stimulation through TLR4 or TRL11 in a myd88-dependent manner, and is also inducible by activated T cells in part through CD40L-CD40 interactions. T cells themselves upregulate TL1A after activation with delayed kinetics. Exogenous and endogenous TL1A can costimulate naïve T cell proliferation and cytokine production through DR3. Cytokine production by differentiated effector cells is inefficient in DR3-deficient T cells but can be largely overcome by strong stimuli or the presence of dendritic cells. In vivo, DR3-deficient mice display defects in T cell-dependent immunopathology in EAE and asthma models, but systemic T cell polarization and effector function are preserved. DR3 thus functions as a specific potentiator of cytokine production and immunopathology in inflamed tissues and, as such, presents a target for therapy of T-cell mediated autoimmune disease Myeloid DC produce soluble TL1A rapidly following both innate immune stimuli in a TLR- and Myd88-dependent fashion, whereas T cells produce lower amounts of TL1A more slowly, and T cell-derived TL1A is not shed into the supernatant. It was determined that TL1A added exogenously or produced by DC, but not T cells alone, can costimulate naïve T cell proliferation and cytokine production. Differentiation into Th1 and Th2 effector cells is not dependent on DR3, although the efficiency of cytokine production under suboptimal conditions is affected. In vivo, DR3-deficient T cells differentiate into effector cells, which can produce cytokines in the spleen and lymph nodes. However, DR3-deficient mice are resistant to two distinct models of T cell-dependent autoimmunity, with reduced production of effector cytokines at the site of inflammation. TL1A-DR3 interactions, thus, potentiate effector T cell function in target tissues, contributing to T-cell mediated immunopathology.

a. Differential Induction of TL1A in T Cells and Dendritic Cells

Figure 1B:
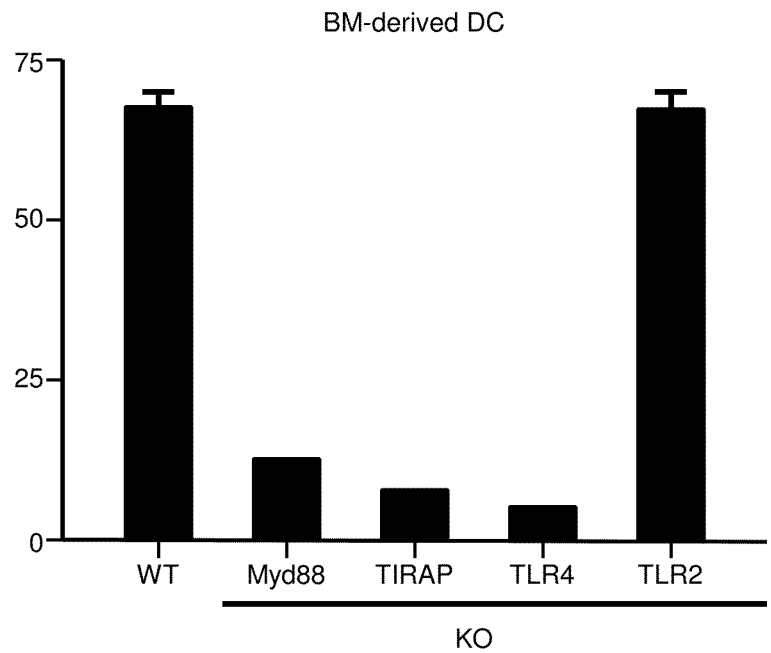
Figure 1C:
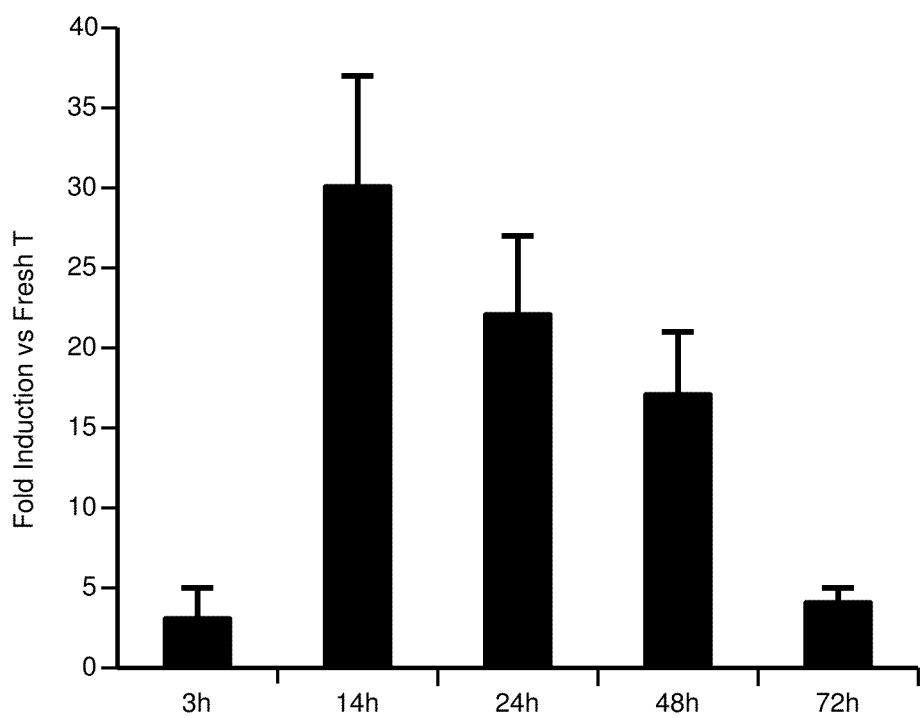
Figure 1D:
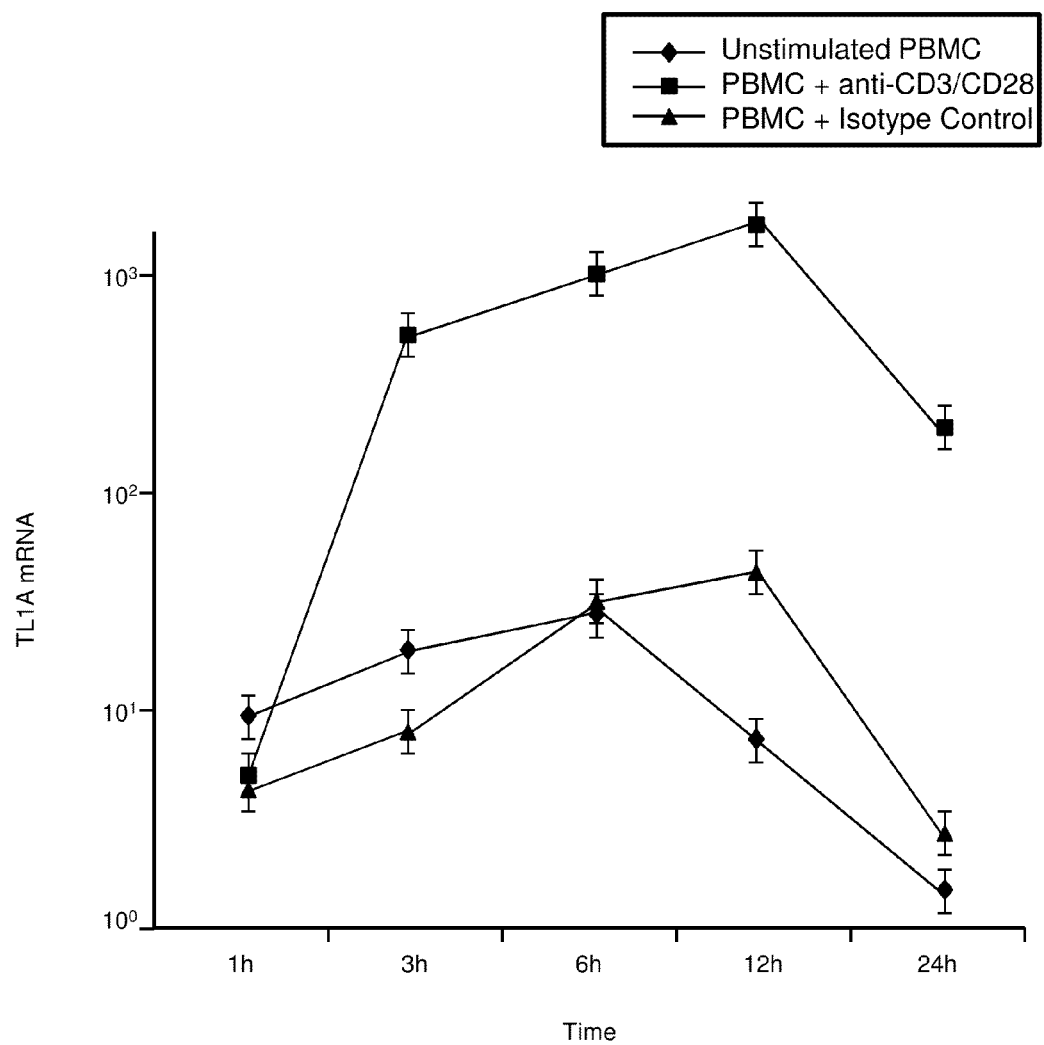
Figure 1E:
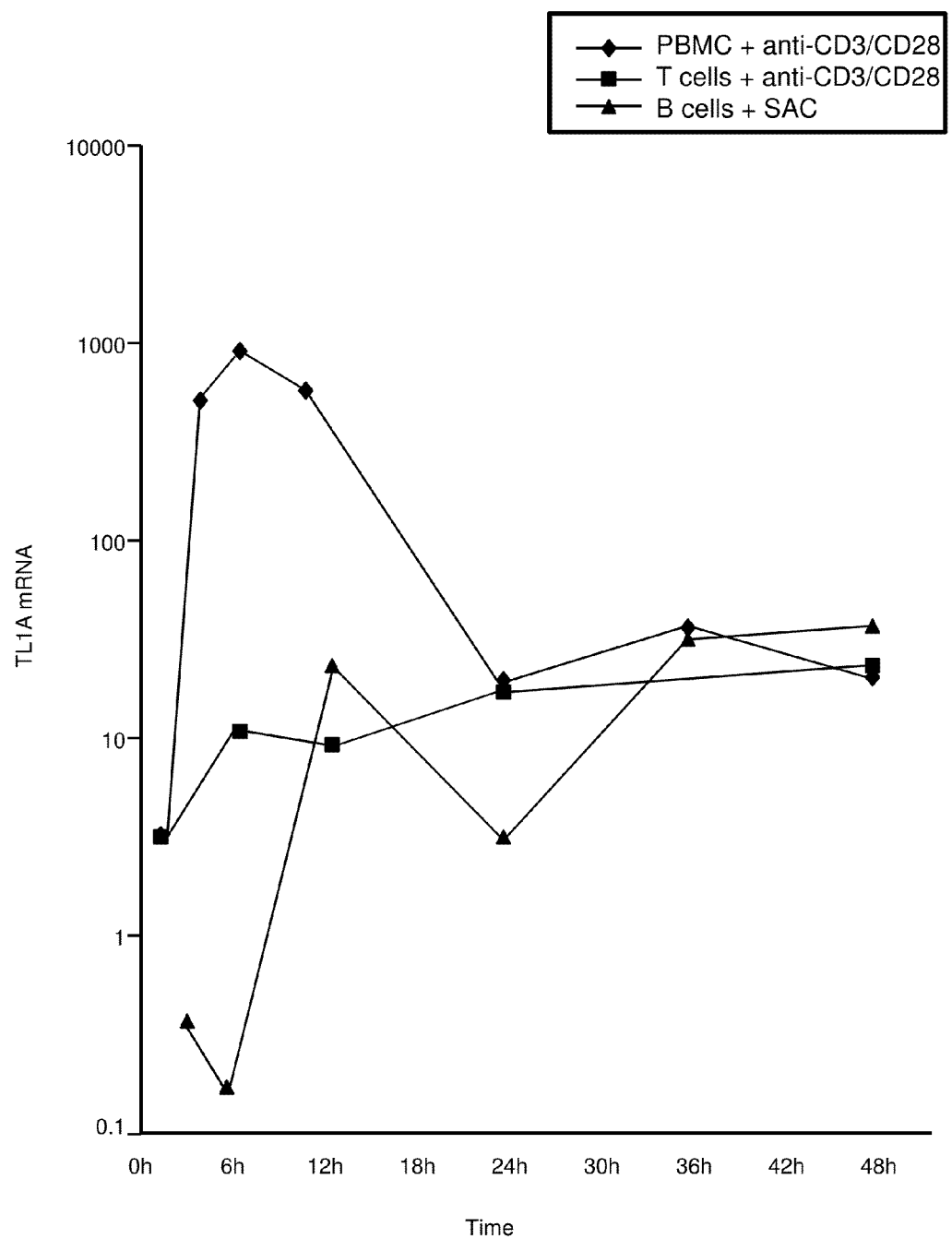

When human peripheral blood mononuclear cells (PBMC) were activated with antibodies against the T cell receptor, a rapid and dramatic upregulation of TL1A mRNA occurred, peaking at 6 hours with ~1000-fold induction (FIG. 1D). However, when T and B cells were purified from peripheral blood and activated in isolation, TL1A upregulation was much slower, peaking at 48 hours with less than 100-fold induction. This indicates that non-lymphocyte antigen-presenting cells may be the major source of TL1A for T cells during initial activation. In purified murine splenic and bone marrow-derived CD11c+ DC, TL1A mRNA was rapidly upregulated by LPS, peaking at 3 hours and returning to baseline by 12 hours (FIG. 1A). To explore the stimuli that induce TL1A in more detail, the parasite-derived immunostimulatory molecules tachyzoite Antigen from *Toxoplasma gondii* (STAg) and *Schistosoma* Egg Antigen from *Schistosoma mansoni* (SEA) were used, which led to differential DC activation programs that prime T cells for Th1 and Th2 responses, respectively. Dendritic cells stimulated with STAg but not with SEA strongly upregulated TL1A mRNA with similar kinetics to LPS (FIG. 1A, right panel). Even after up to 24 hours, SEA did not induce TL1A (lower panel). Experiments with DC from various knockout mice showed that TL1A induction was dependent on Myd88 and TIRAP, and LPS induction of TL1A was TLR4-dependent (FIG. 1B). When highly purified mouse T cells were activated through the TCR, similar TL1A upregulation was observed with delayed kinetics seen in human T cells (FIG. 1C). These data show that, like other TNF-family members, TL1A can be acutely upregulated in DC through TLRs and the Myd88/TIRAP-dependent signaling pathway. DC-derived TL1A would be available to modulate the initial phases of T cell activation, whereas T cells upregulate TL1A more slowly, where it may influence later steps in T cell expansion and differentiation.

b. TL1A Costimulates Proliferation and Cytokine Production in CD4+ T Cells Through DR3.

Figure 2A:
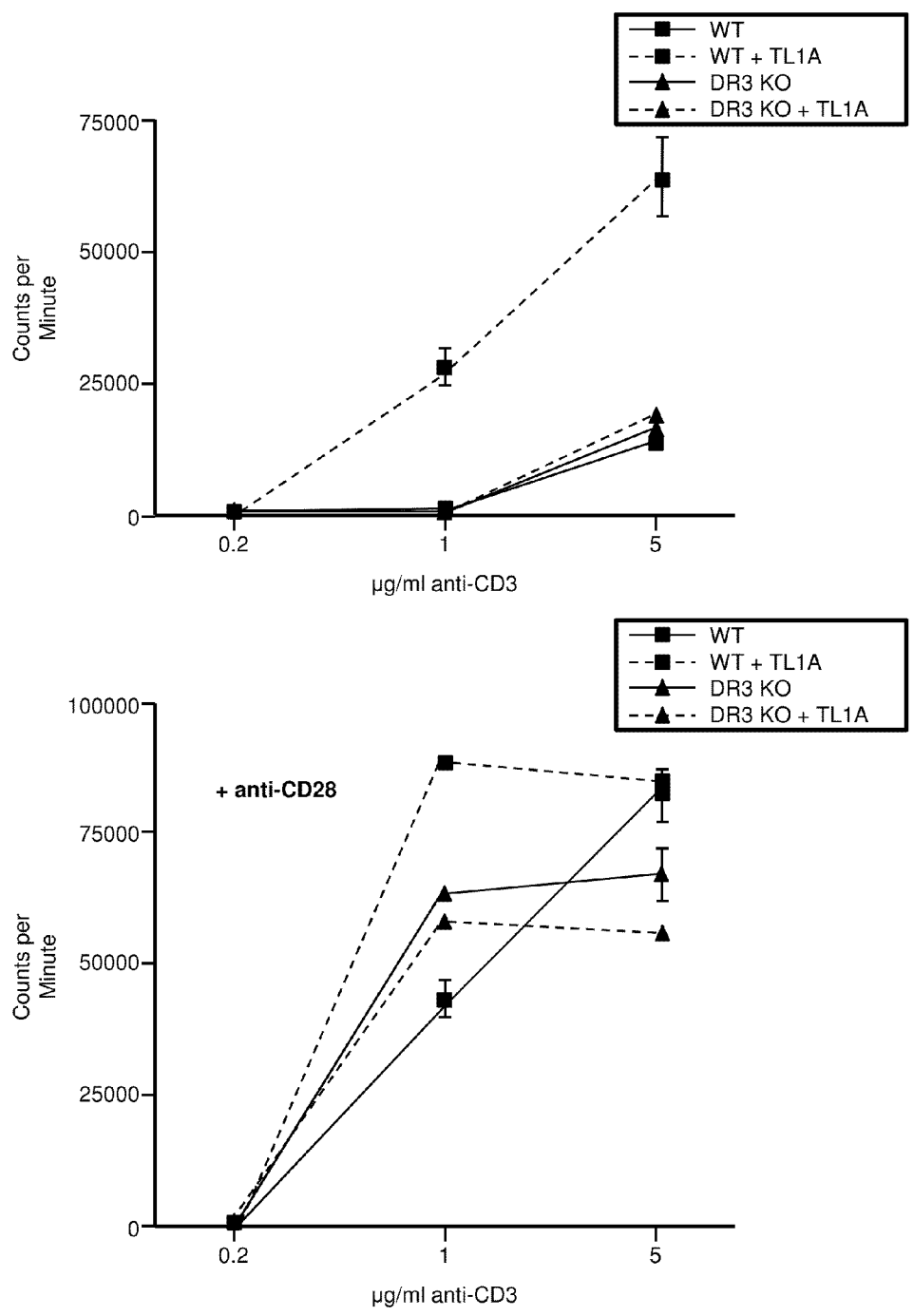
FIGS. 2A-2D show that purified T cells from DR3 KO mice have reduced proliferation, activation marker expression, and altered cytokine production in DC-T co-culture.
Figure 2B:
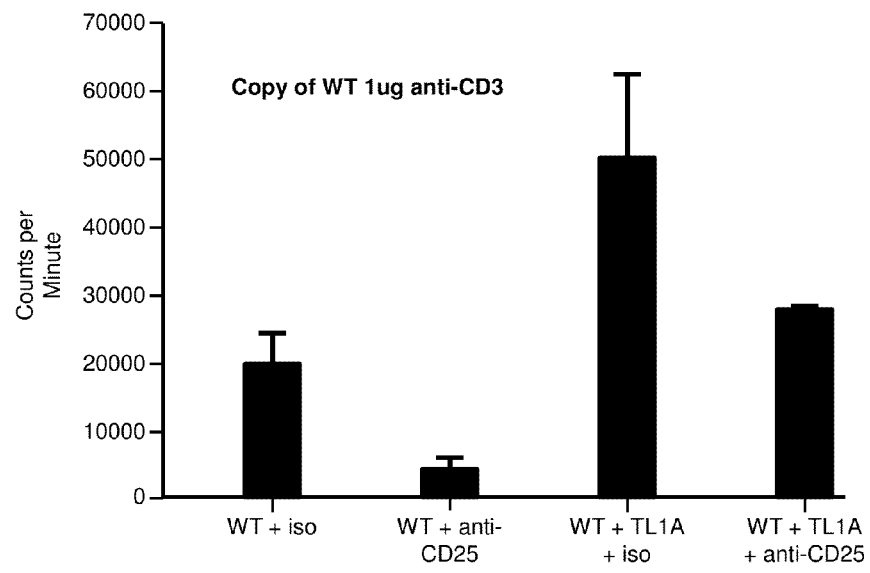
Figure 2C:
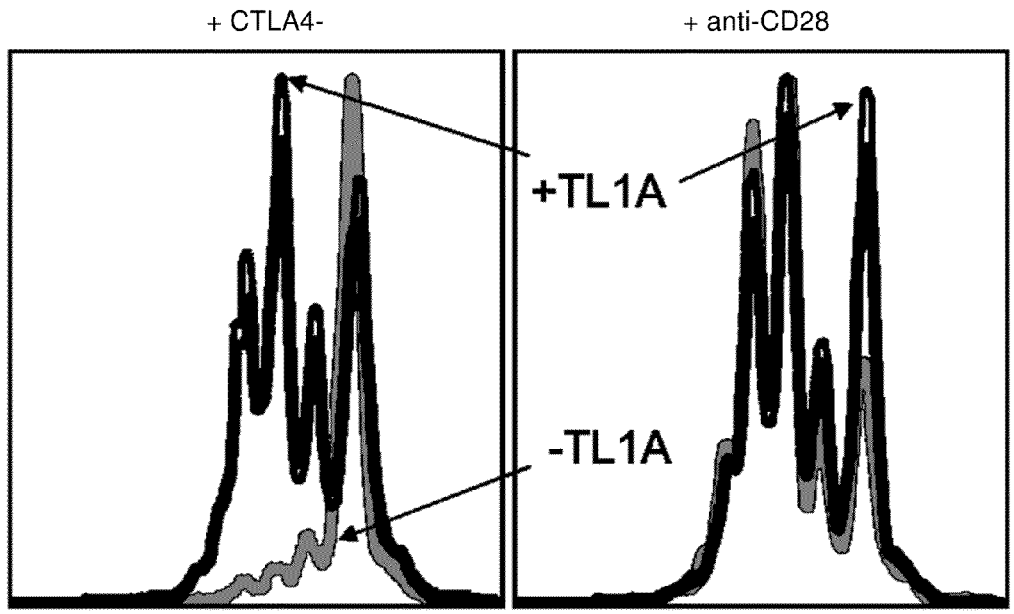

Exogenous TL1A has previously been shown to costimulate T cells, but whether this is dependent on DR3, and what role endogenously produced TL1A plays in mature T cell activation, has not been investigated. To investigate this, CD4+ T cells were purified from spleens and lymph nodes of wild-type (WT) C567Bl/6 or isogenic DR3 knockout (KO) mice and activated in the presence or absence of recombinant murine TL1A. Costimulation by other TNF family members has been shown to be maximal when CD28-mediated costimulation is blocked (Croft, 2003). Exogenously added TL1A consistently increased T cell proliferation, and this effect was more apparent in the absence of CD28-mediated costimulation (FIG. 2A). With dual CD3/CD28 crosslinking, TL1A only costimulated proliferation at lower doses of anti-CD3. Importantly, DR3 KO cells were completely unresponsive to TL1A, indicating that DR3 is the major receptor that mediates costimulation by TL1A. Also, similar to their previously reported normal proliferation in response to ConA (Wang et al., 2001), purified T cells from WT and DR3 KO mice proliferated similarly in response to anti-CD3 with or without costimulation (FIG. 2A). To determine if the increased thymidine incorporation triggered by TL1A was due to increased cell cycling versus effects on cell survival, CFSE dilution experiments were performed under similar conditions. In accordance with the thymidine incorporation data, exogenous TL1A significantly increased CFSE dilution, reflecting increased cell cycling, especially in the absence of CD28 signaling (FIG. 2B). No changes in cell viability in response to TL1A were detected in these experiments.

Figure 2D:
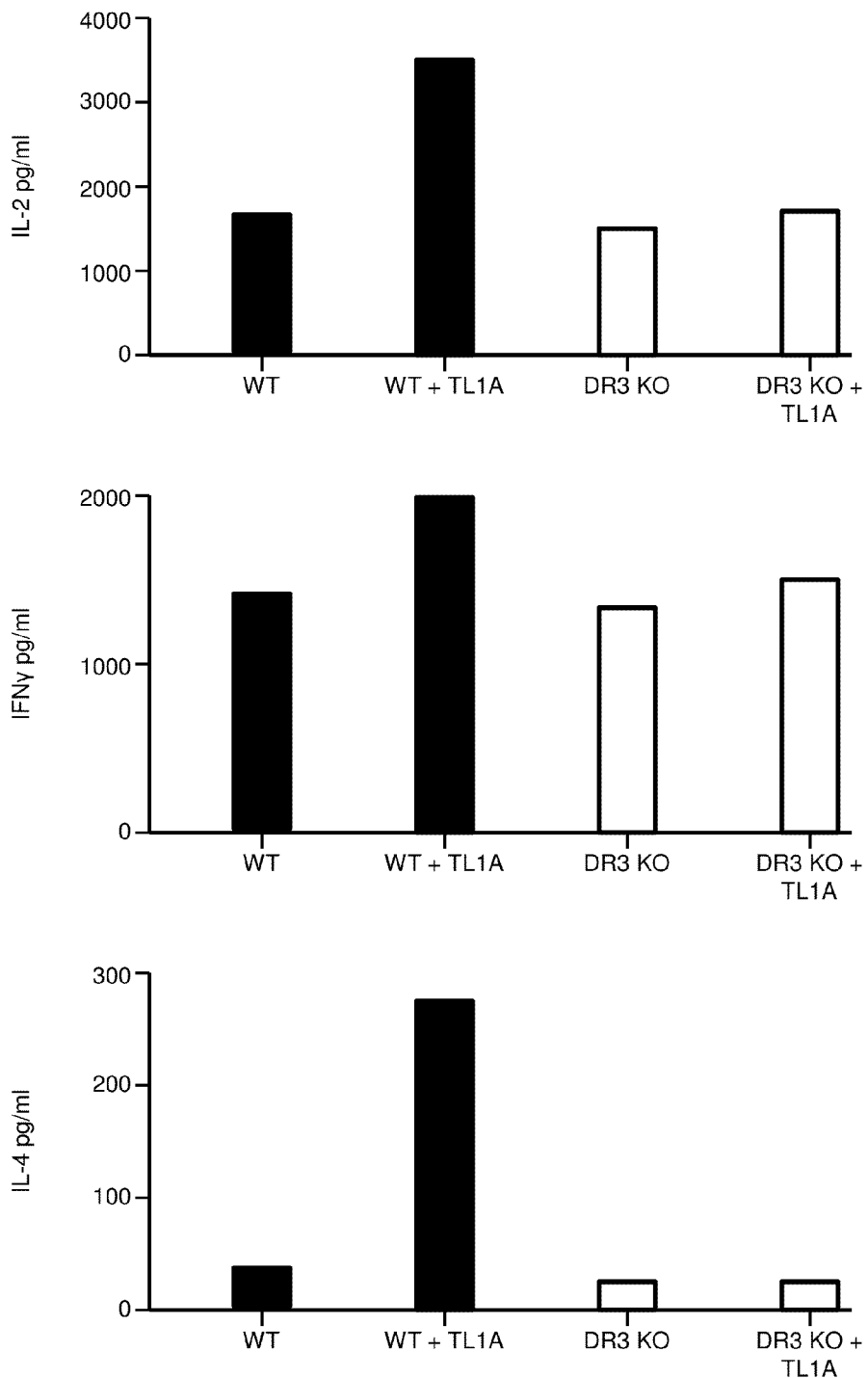

To investigate the spectrum of cytokines that can be costimulated by TL1A and the dependence of cytokine production on DR3, IL-2, interferon-γ (IFN-γ), and IL-4 production were measured in WT or DR3 KO T cells activated in the presence or absence of recombinant TL1A. TL1A increased IL-2 production, interferon-γ production, and IL-4 production by WT, but not DR3 KO, cells activated with or without CD28. IL-4 was the cytokine most prominently induced by TL1A, increasing by approximately 10-fold, whereas IL-2 and interferon-γ increased less than two-fold (FIG. 2D). DR3-deficient T cells were unresponsive to TL1A, but had no defect in cytokine production. Thus, as with proliferative responses, DR3 is the major mediator of TL1A signaling, and endogenously produced T cell-derived TL1A is not necessary for cytokine production by activated T cells under these conditions. To determine if TL1A-driven proliferation is due to increased IL-2 production, an anti-CD25 blocking antibody was added during T cell activation in the presence or absence of TL1A. CD25 blockade blocked most of the increased proliferation induced by TL1A, but some IL-2-independent proliferation could still be seen, indicating that TL1A-driven costimulation is at least partly dependent on increased production of IL-2 (FIG. 2B).

Figure 3A:
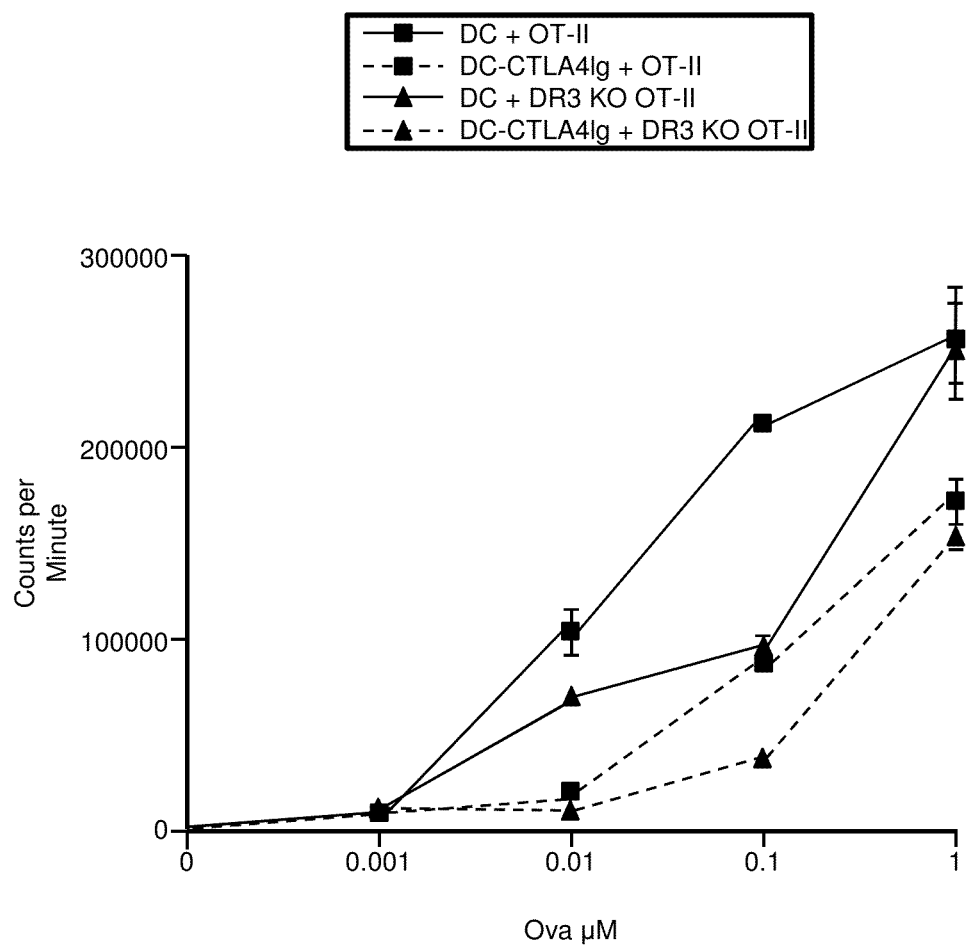
FIGS. 3A-3B show that DR3 KO T cells have reduced proliferation, activation marker expression, and altered cytokine production in DC-T co-culture.
Figure 3B:
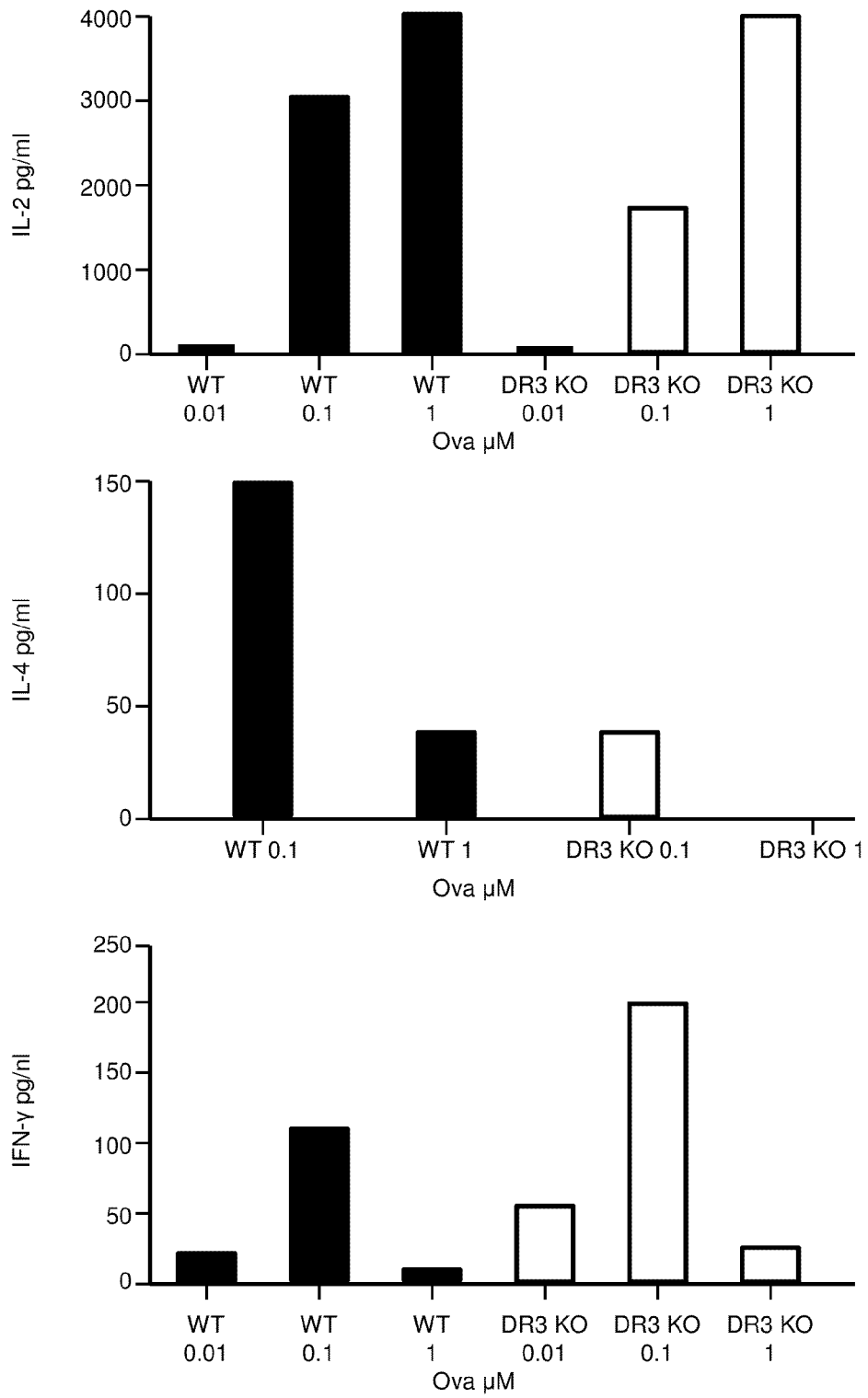

Since purified DR3-deficient T cells did not have major defects in proliferative responses or cytokine production, the TL1A produced by T cells did not seem to be essential for these functions. Thus, the TL1A produced by dendritic cells during cognate DC-T cell interactions may be the more relevant source of TL1A for T cell costimulation. To test this, experiments with DR3 WT or KO mice crossed to the Ovalbumin (Ova)-specific TCR transgenic line OT-II were performed. Purified DR-3-deficient cells were co-cultured with C57Bl/6 bone marrow-derived DC and the cognate Ova peptide. Under these conditions, proliferation of DR3 KO cells was diminished especially in the presence of low concentration of Ova peptide (FIG. 3A) with or without CTLA4-Ig blockade. Cytokine production by OT-II T cells is characteristically dependent on the dose of antigen, with higher doses favoring IFN-γ production and lower doses favoring IL-4 production. DR3 KO OT-II cells produced approximately 50% lower IL-2 at lower doses of Ova and lower amounts of IL-4 at all doses of Ova tested (FIG. 3B). Thus, endogenous TL1A produced by dendritic cells is likely to be a physiologically important source of this costimulatory TNF family member.

c. DR3 KO T Cells have a Reduced Th2 Differentiation when Polarized In Vitro.

Figure 4A:
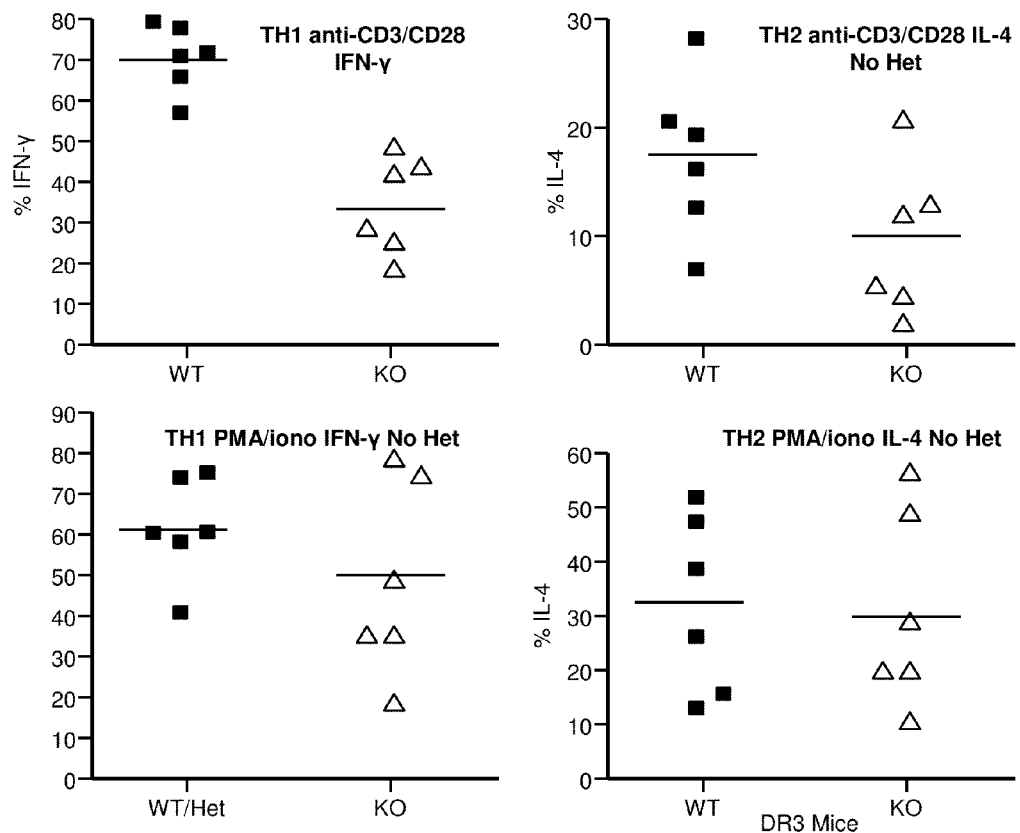
FIGS. 4A-4D show that TL1A can play a role in T cell differentiation.
Figure 4B:
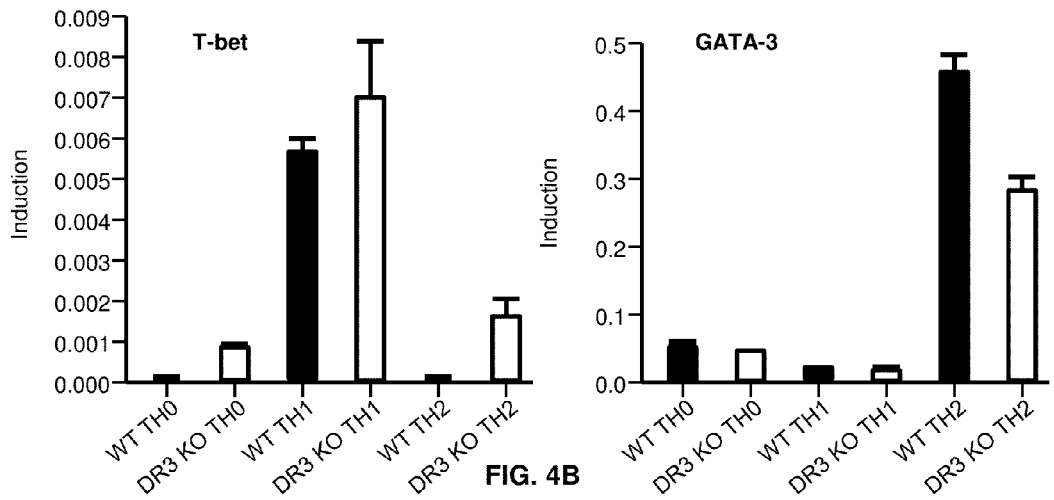
Figure 4C:
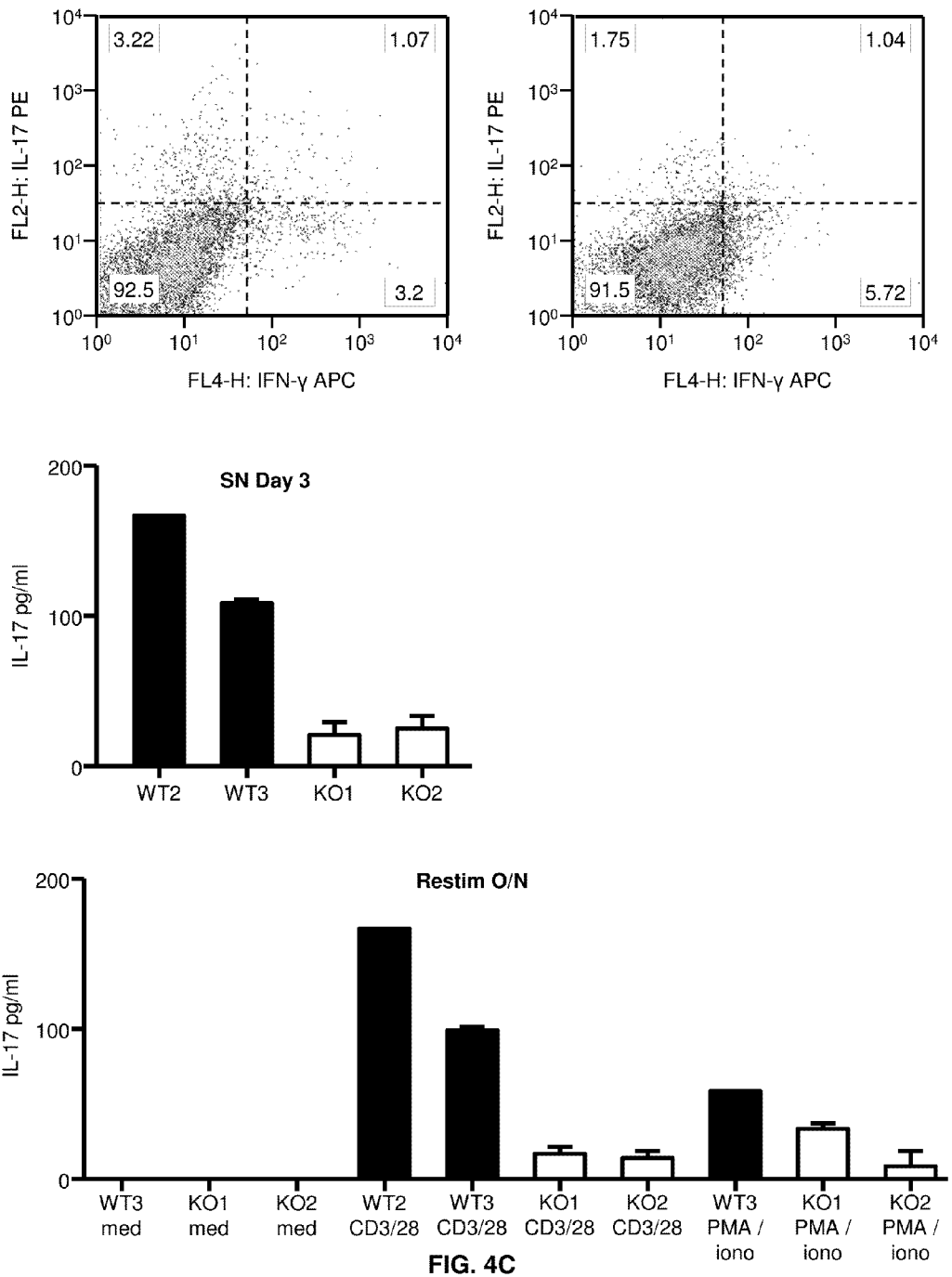
Figure 4C:
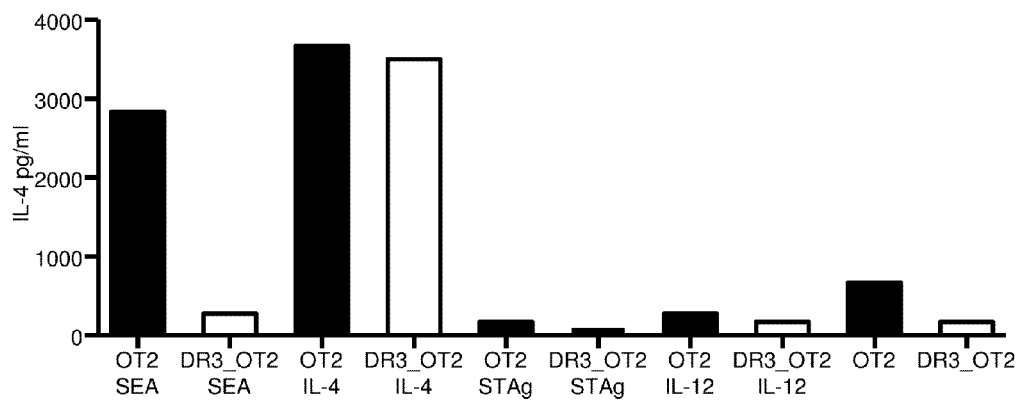
Figure 4C:
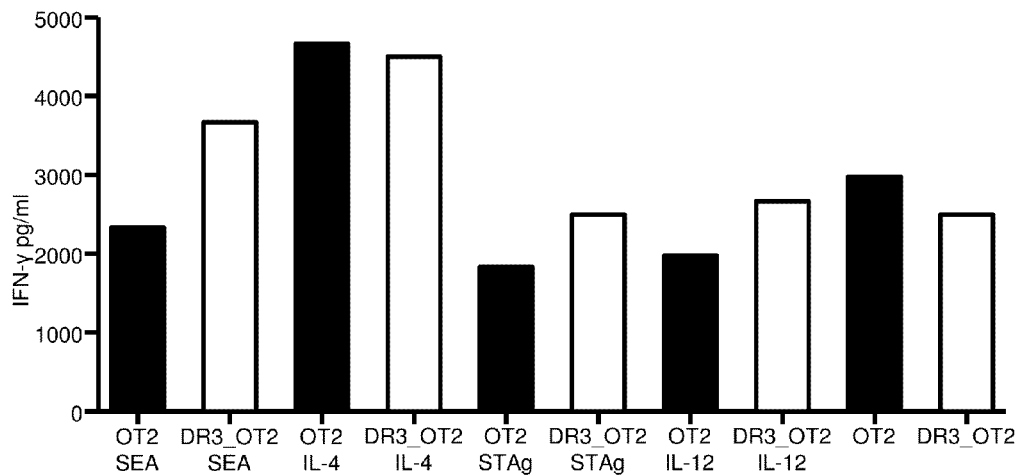

To investigate the consequences of TL1A-DR3 interactions for later steps in T cell differentiation, DR3-deficient T cells were tested for effector cytokine production in two types of T cell polarization assays. Purified T cells from WT or DR3 KO mice were activated with either IL-4 and anti-IFN-γ for Th2 polarization or IL-12 and anti-IL-4 for Th1 polarization. When purified T cells were re-stimulated after 5-6 days of activation and polarization, there were significant defects in the percentages of cells producing IFN-γ and IL-4, when T cells were re-stimulated through the TCR. However, the combination of PMA/ionomycin allowed normal production of these cytokines (FIG. 4A). Interestingly, IL-17 production by polarized T cells polarized to this effector type by a combination of TGF beta, IL-1, IL-6, TNF, and blockade of IL-4 and IL-12 was defective in supernatants 72 hours after primary activation and after re-stimulation with CD3/CD28. Since PMA/ionomycin stimulation appeared to bypass the cytokine secretion defect, the defect in DR3 KO cells may be more in TCR-induced cytokine secretion rather than T cell differentiation itself. To determine whether T cell differentiation was intact in the absence of DR3, the levels of T-bet and GATA-3, the canonical transcription factors that program Th1 and Th2 T cell differentiation, respectively, were measured. As shown in FIG. 4B, induction of T-bet in DR3 KO T cells polarized to differentiate into Th1 cells was normal, and GATA-3 induction under Th2 conditions was only slightly impaired. Thus, it appeared that DR3 is more important in cytokine production than in programming T cells for differentiation into a particular T cell subset. To determine if this was also the case when TL1A was provided by dendritic cells, T cells from DR3

Figure 4D:
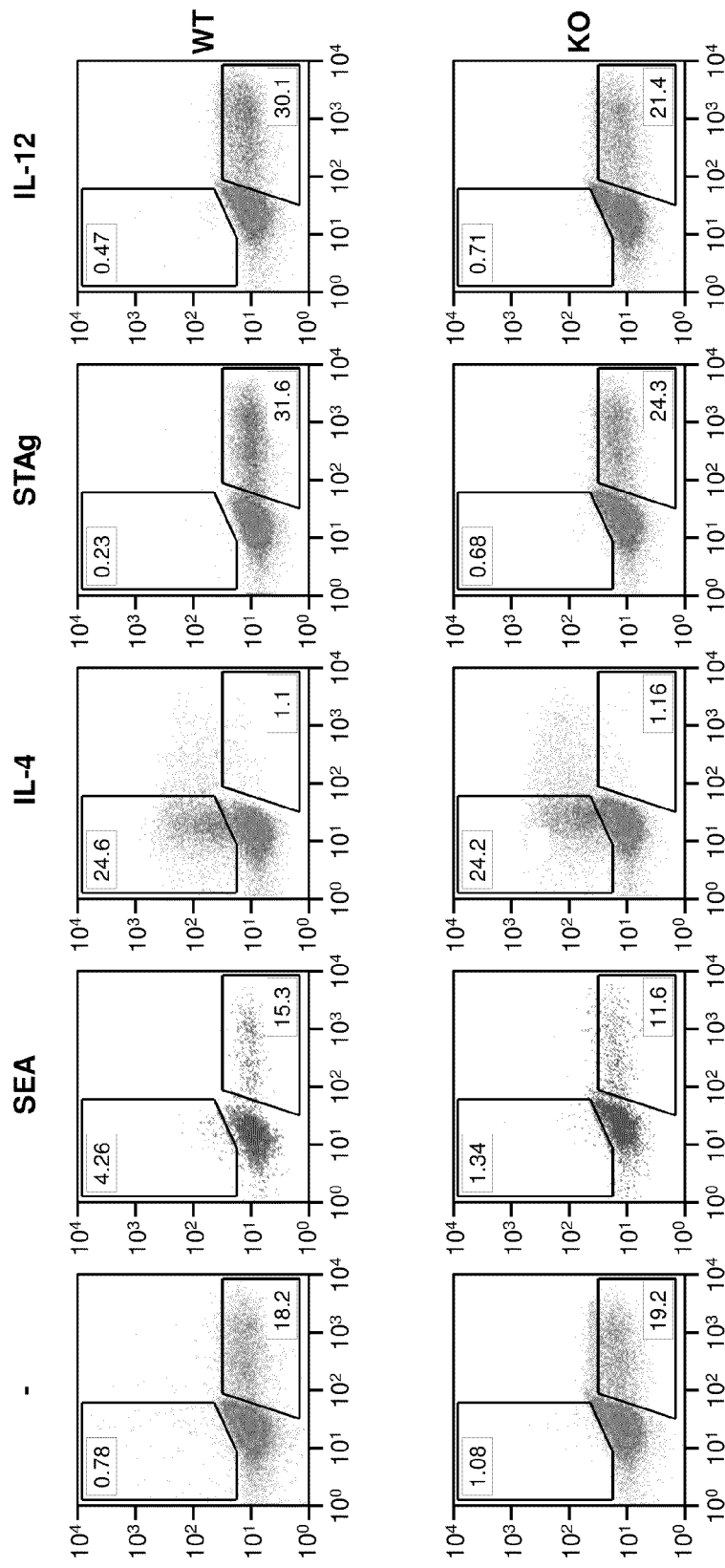

KOxOT-II mice or OT-II controls were cultured with antigen and DC under conditions in which polarization is driven by exogenous cytokines or endogenous factors produced under the influence of the parasite-derived antigens SEA or STag. No defects in IFN-γ were found when DR3 KO T cells were polarized with Stag or exogenous IL-12 and anti-IL4 (FIG. 4D). However, a significant defect in IL-4 production was seen in T cells activated in the presence of SEA. This was overcome by addition of exogenous IL-4. Unlike STAg-induced Th1 polarization that does not require T cell-derived IFN-γ, Th2 polarization by SEA is known to be dependent on T cell-derived IL-4. Thus, the defect in IL-4 production by DR3 KO T cells that was observed (FIG. 3B) may account for the Th2 polarization defect in the absence of exogenous IL-4.

d. DR3 KO Mice have Reduced Lung Inflammation in an Ova-Induced Asthma Model

Figure 5A:
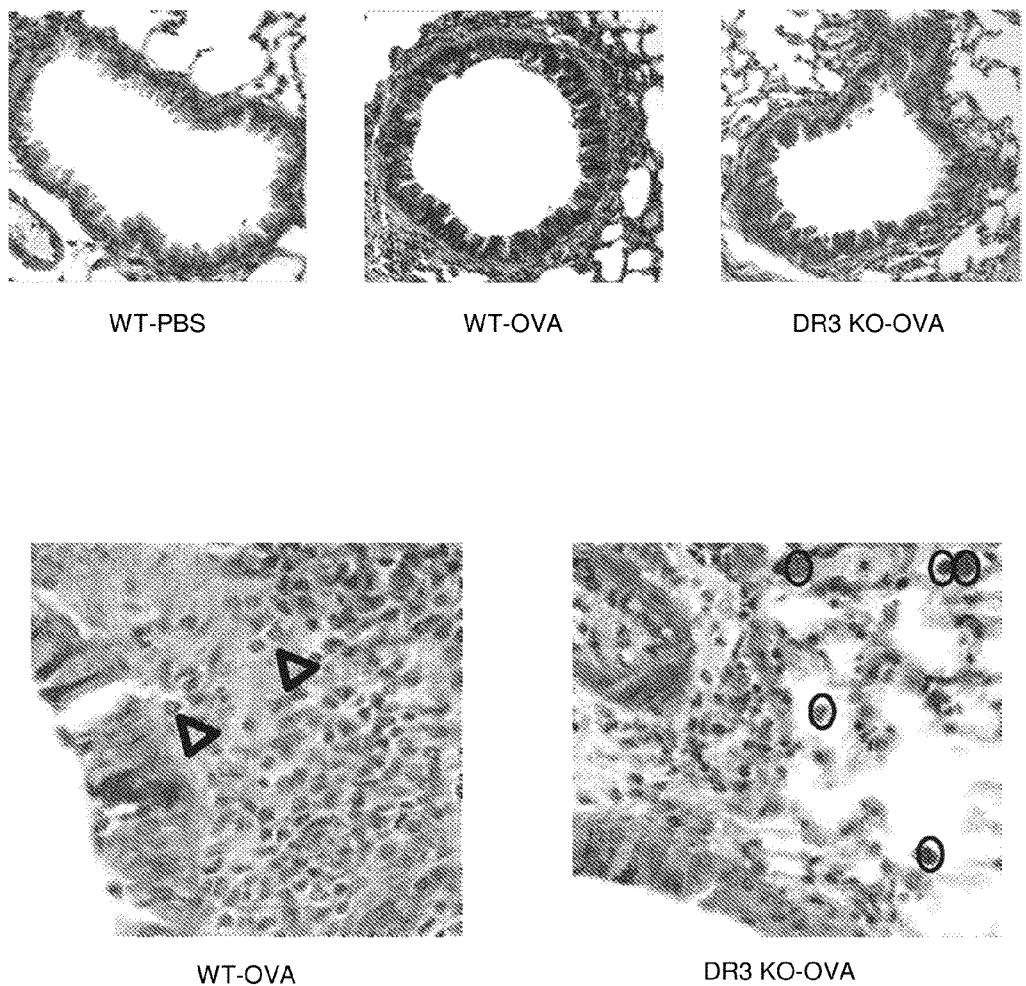

To determine whether the Th2 polarization defect in vitro was significant in an animal model of a Th2-mediated disease, how DR3 KO mice would respond in an Ova-dependent asthma model was investigated. Mice were sensitized with Alum and Ova protein or Alum and PBS as a control and then challenged intratracheally and intranasally with either Ova protein or PBS. The mice were sacrificed two days after the last challenge. The histology showed that the DR3 KO mice lungs had less mucin production than the WT mice, and also less peribroncheal cuffing (FIG. 5A). The histopathology score for the DR3 KO lungs was also reduced compare to the WT lungs (FIG. 5B). In addition, the inflammation in the DR3 KO lungs was predominantly lymphocytic in the DR3 KO versus the typical eosinophilic infiltrates in the WT lungs. Next, the mRNA levels of different cytokines in the lung were determined. DR3 KO lungs have reduced IL-13, a reflection of the mucus production, and IL-5 in the lungs compared to the WT lungs (FIG. 5C). In addition, whether the Ova-specific restimulation of the spleen was affected was determined. Interestingly, in contrast to the cytokine mRNA level observed in the lung, there were no differences in cytokine production, suggesting a more local effect. In addition, there was no difference between the WT and DR3 KO mice T cell proliferation. The level of IgG1 present in the serum was also determined. There was no difference in IgG1, IgG2 sera level between WT and DR3 KO mice, especially in the Ova-specific IgG1 (FIG. 5D) level, suggesting a more local effect of the differences in the pathology. The fact that the IgG1 production was elevated after the Ova challenge in the DR3 KO mice compared to PBS-treated mice indicates that the T cells were able to respond and differentiate, even if it is to a lesser extent (data from in vitro polarization). Thus, the decrease in local inflammation may be due to a defect in a late stage of the immune response.

e. DR3 KO Mice are Less Susceptible to EAE.

Figure 6A:
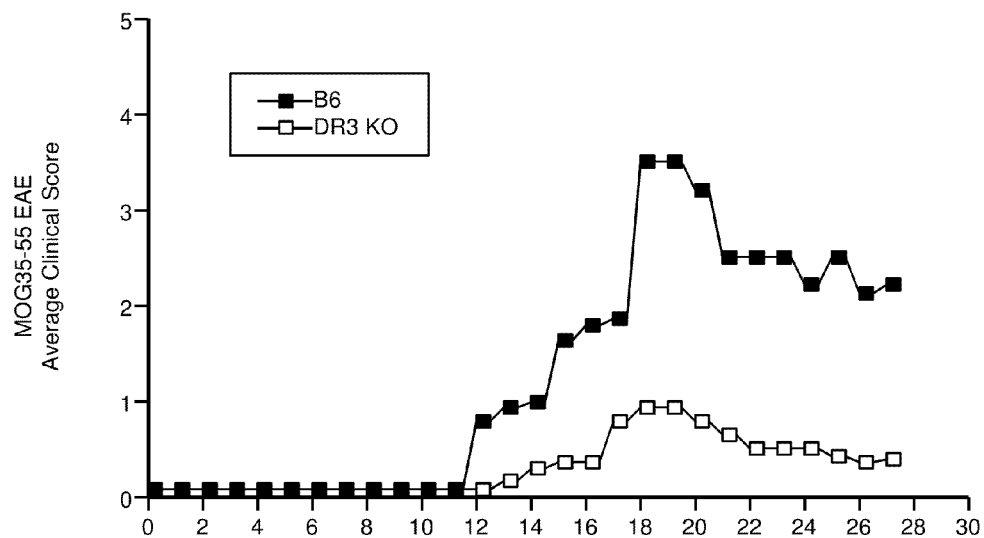
FIGS. 6A-6D show that DR3 KO mice have reduced EAE in a MOG-EAE model.
Figure 6B:
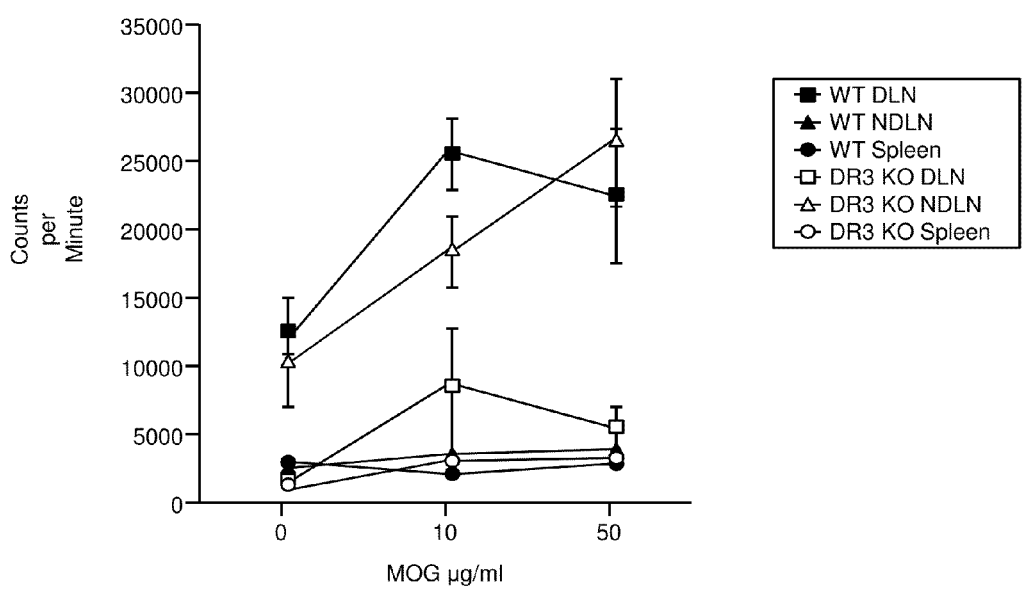
Figure 6C:
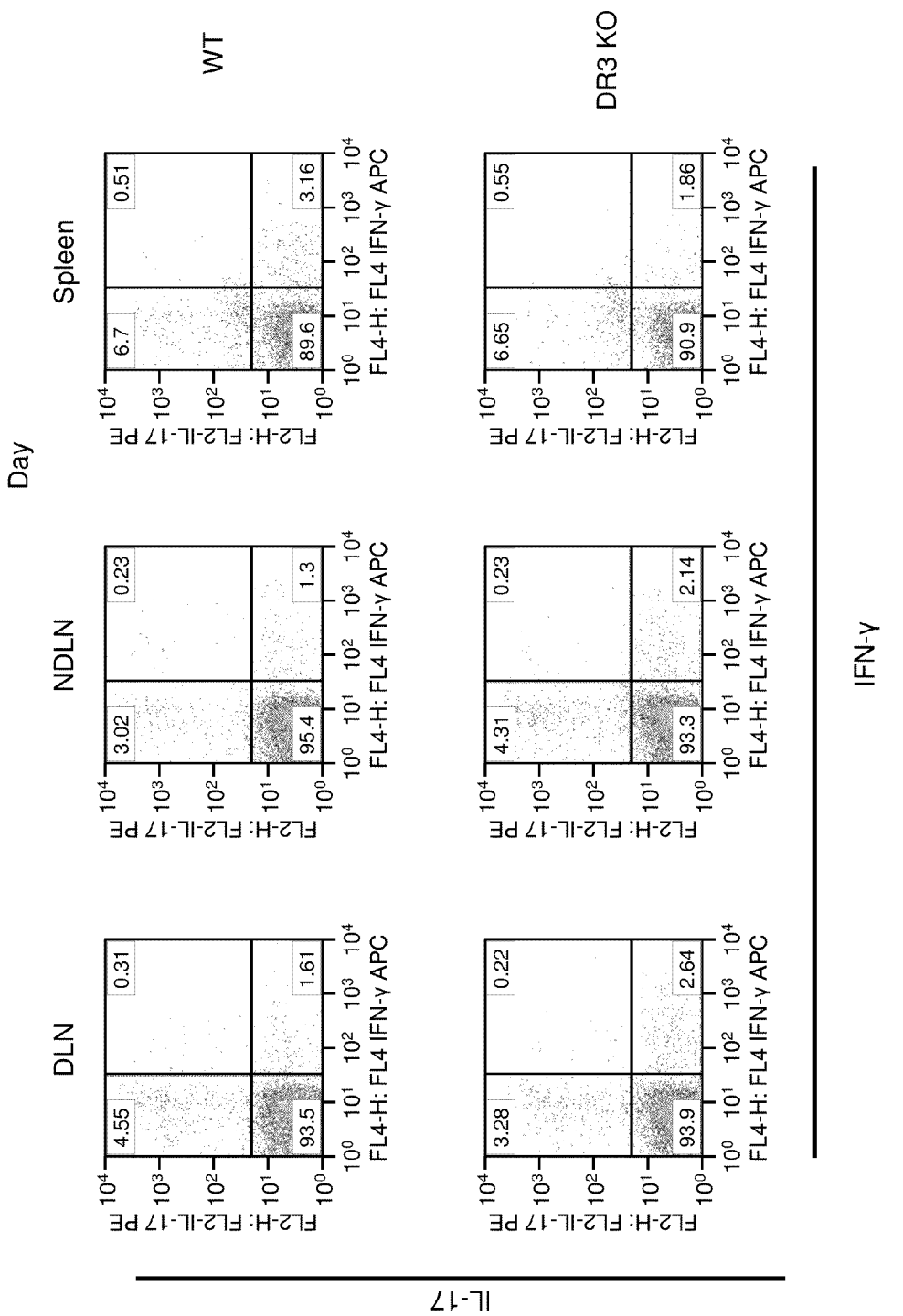
Figure 6D:
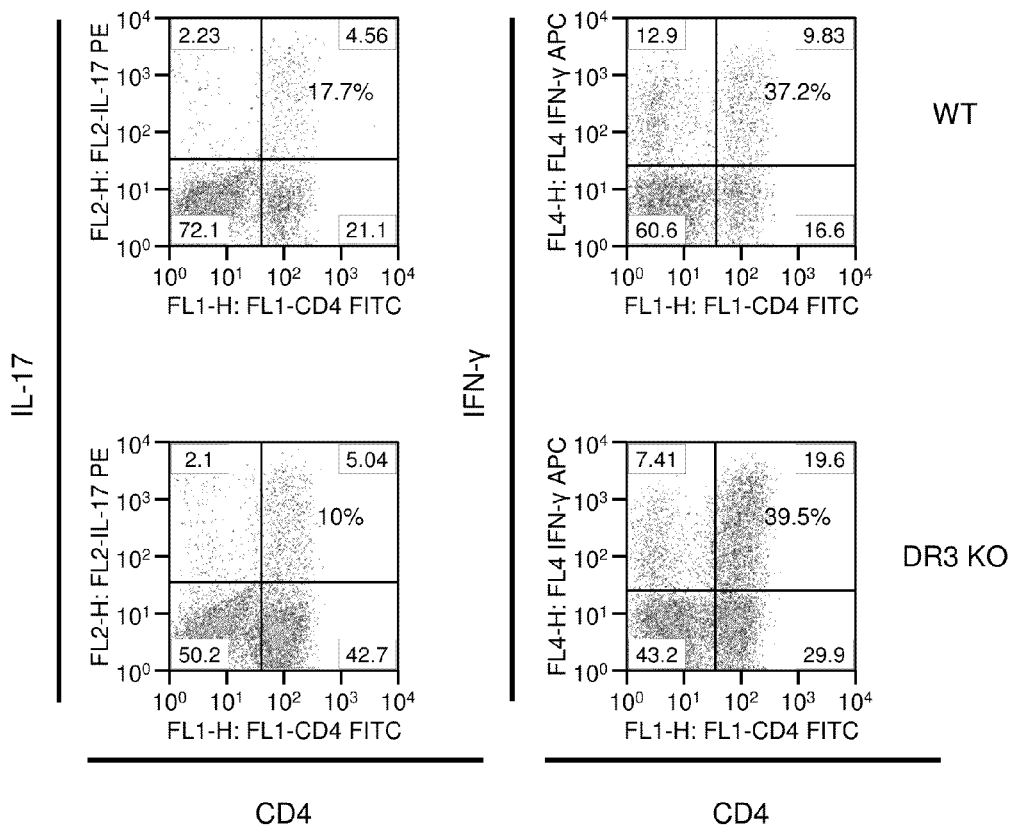
Figure 7A:
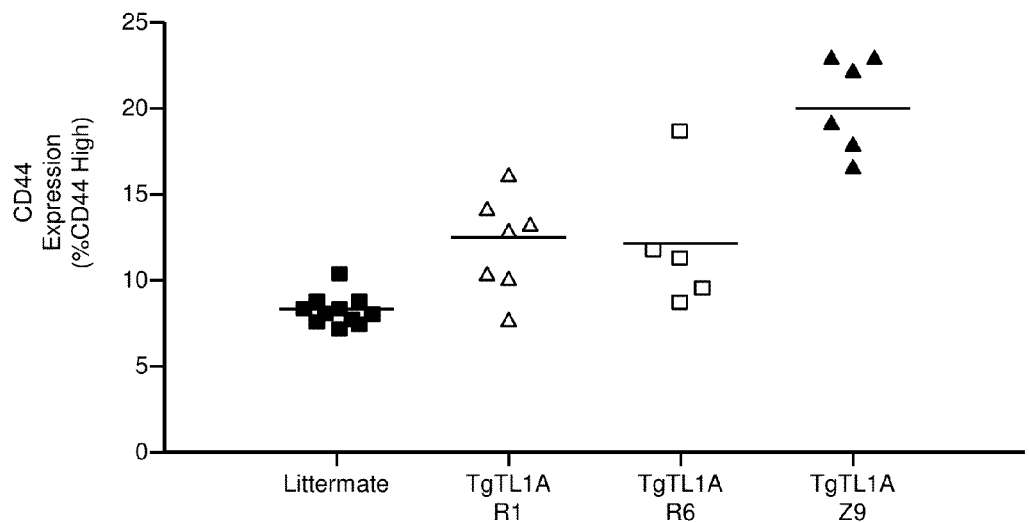
FIGS. 7A-7B show increased T cell activation and spontaneous inflammatory bowel disease in CD2-TL1A transgenic mice in which mouse TL1A has been placed under the control of the human CD2 T cell-specific regulatory element.
Figure 7B:
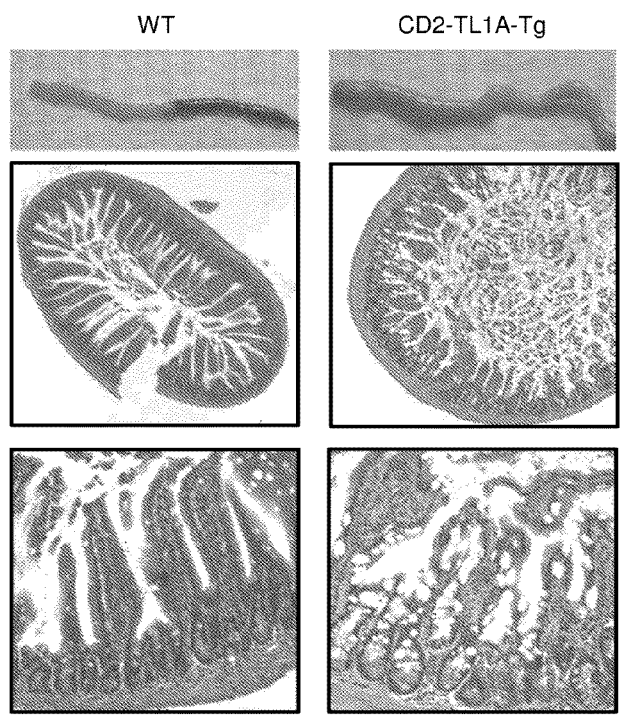

As the DR3 KO mice have a decrease in Th2Th2 T cell-mediated pathology in the asthma model, correlating with a decrease in in vitro Th2 differentiation, how DR3 KO mice would respond to a Th1/Th17-mediated disease was investigated. To this end, a MOG (myelin oligodendrocyte glycoprotein)-induced EAE mouse model was used. DR3 KO mice have a delayed and reduced EAE pathology compared to WT mice that develop clinical pathology about one week after MOG injection (FIG. 6A). This indicates that DR3 KO mice have reduced pathology in disease models that are dependent on entirely different cytokines. In addition, similar to the Ova-asthma model, the MOG-restimulation of the T cells from the spleen and the lymph nodes was not impaired (FIG. 6B). This again indicates that the overall effect of the DR3/TL1A defect seemed to be more local than systemic. Several recent reports indicate that additional subsets of effector T cells such as IL-17 producing cells are produced during immune responses. This population of IL-17 producing cells was thought to be responsible for the pathogenicity in Th1-mediated diseases rather than effector cells producing Th1 cytokines. Thus, to determine to what extent the IL-17 producing cells were present in the brain, spleen, and lymph nodes, hematopoietic cells were taken from the spinal cord and stimulated for 6 hours with PMA/ionomycin before intracellular staining for IL-17 and IFN-γ. Decreased IL-17 producing cells were present in the CNS from DR3 KO mice compared to WT mice. In addition, DR3 KO mice have twice as many T cells in the CNS as WT mice. However, there was no difference in the spleen or in the lymph nodes.

2. Example 2 i. Results a. TL1A Costimulates Proliferation and Cytokine Production in CD4+ T Cells Through DR3

Figure 8A:
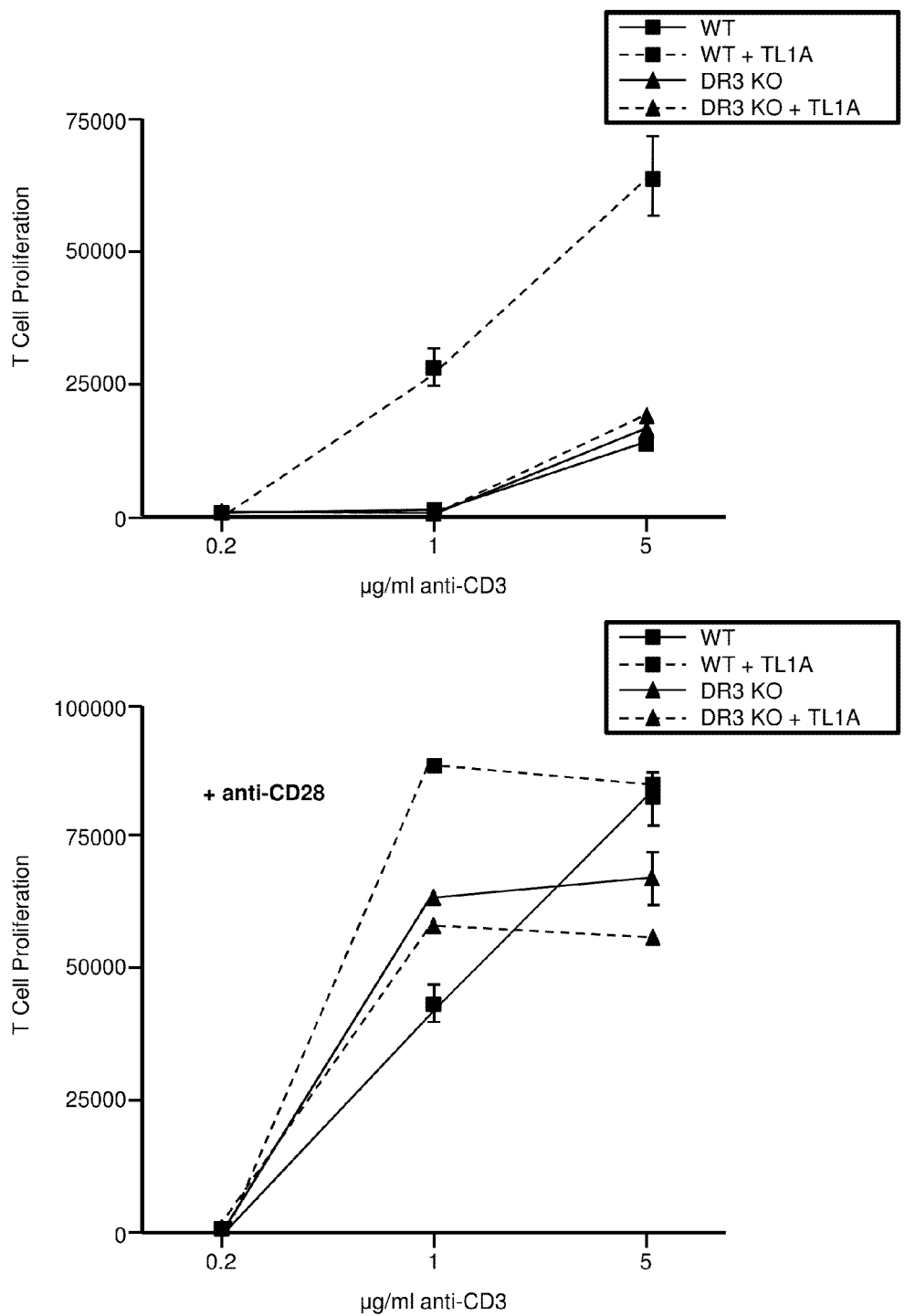
FIGS. 8A-8C show TL1A co-stimulates proliferation and cytokine production in CD4$^+$ T Cells through DR3.
Figure 8B:
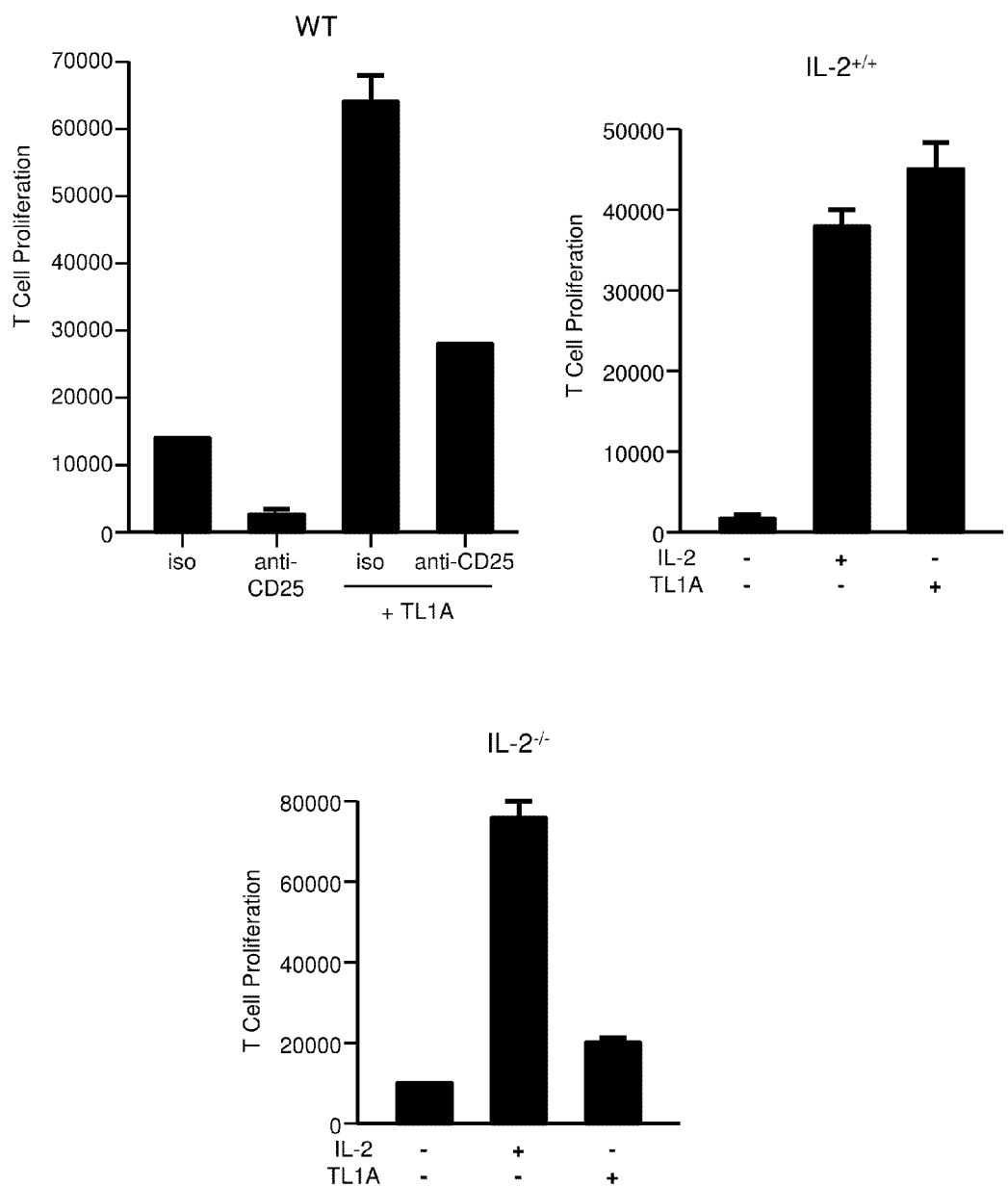

Exogenous TL1A can costimulate human and mouse T cells, but whether DR3 is the sole costimulatory receptor for TL1A and what role endogenously produced TL1A plays in mature T cell activation is not known. To investigate this, CD4$^+$ T cells were purified from spleens and lymph nodes of wild-type (WT) or age- and sex-matched DR3 knockout (DR3 KO) mice (Wang et al., 2001) on a C57BL/6 background and activated through the TCR in the presence or absence of recombinant murine TL1A. Costimulation by other TNF family members has been shown to be maximal when CD28-mediated costimulation is blocked (Croft, 2003). TL1A also increased T cell proliferation most dramatically in the absence of CD28-mediated costimulation (FIG. 8A). When CD28-mediated costimulation was present, TL1A only costimulated proliferation at lower doses of anti-CD3 (FIG. 8A). The increased thymidine incorporation was due to increased cell division and not enhanced survival, as increased CFSE dilution and no significant changes in cellular viability induced by TL1A were observed. Importantly, DR3 KO cells were unresponsive to TL1A, indicating that DR3 is the major receptor that mediates costimulation by TL1A (FIG. 8A). However, stimulation of DR3 through endogenous T cell-derived TL1A was apparently dispensable for T cell proliferation, since there were no deficits in proliferation in cultures of purified DR3 KO T cells (FIG. 8A). TL1A costimulation was largely dependent on increased IL-2 production, as TL1A-induced proliferation was greatly reduced in IL-2-deficient T cells or after the addition of an antagonistic anti-IL-2Rα antibody (FIG. 8B).

Figure 8C:
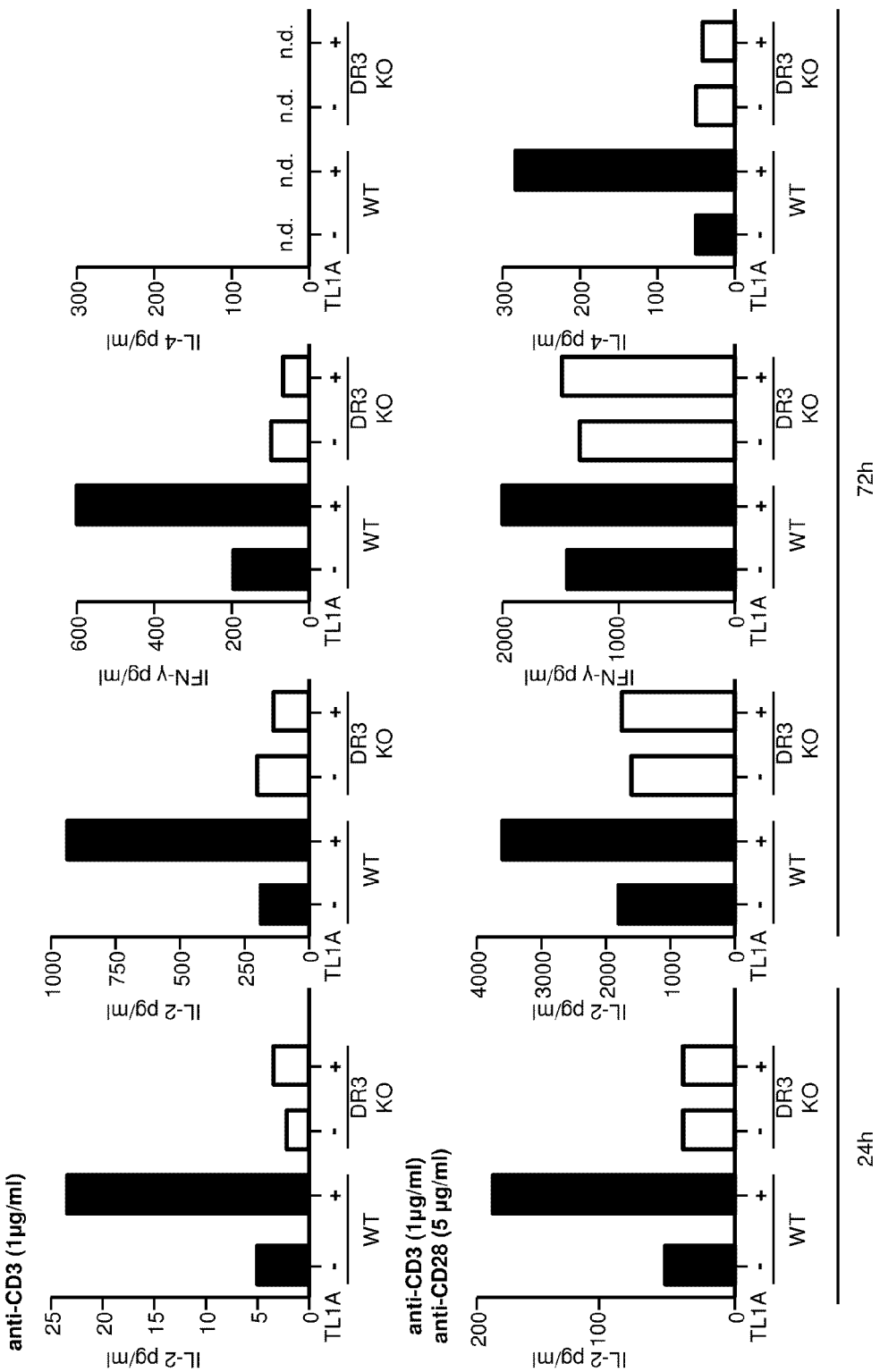
Figure 16:
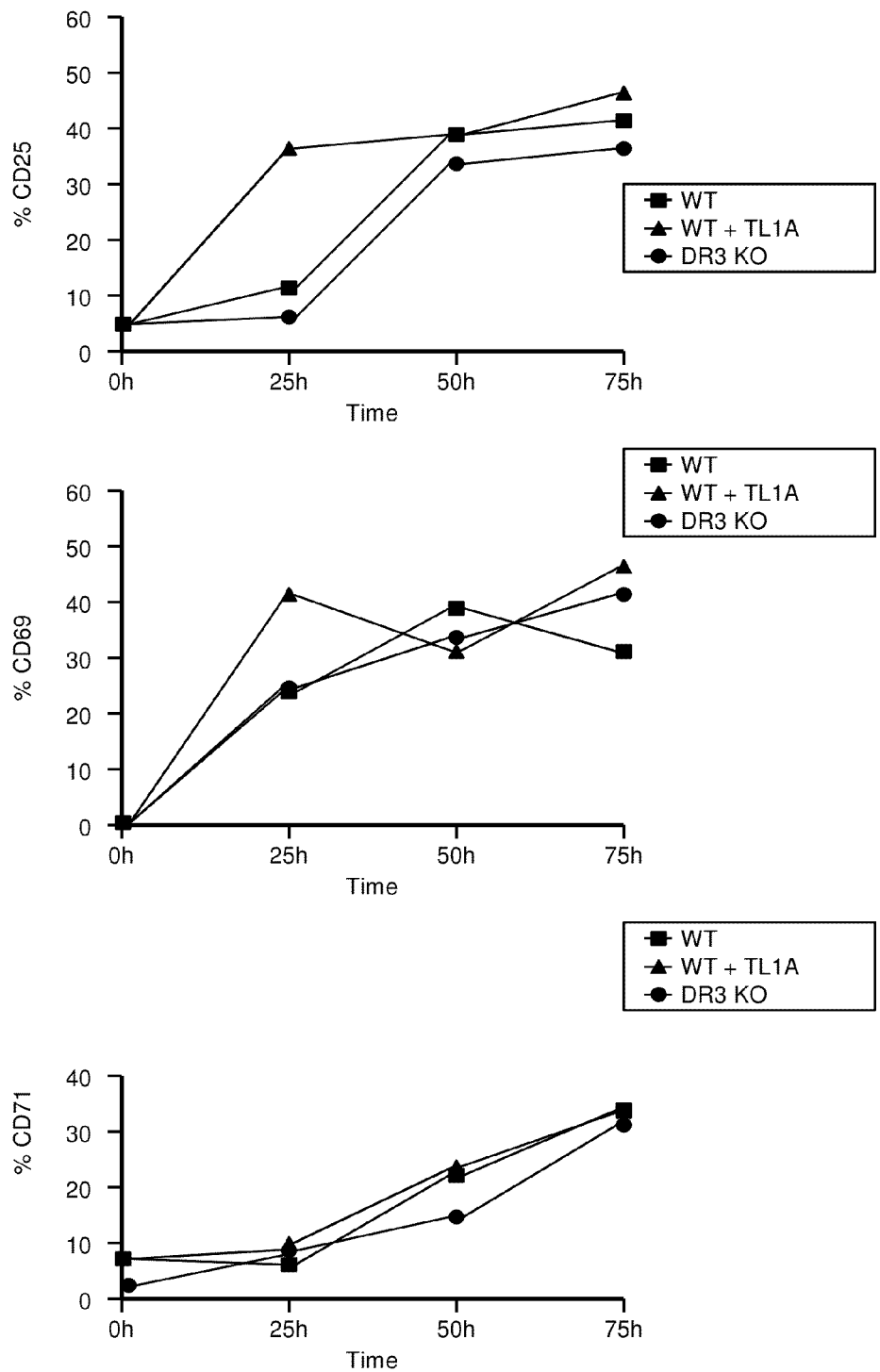
FIG. 16 shows kinetics of surface marker expression after activation of DR3 KO and WT T Cells. Purified CD4+ T cells from C57BL/6 or DR3 KO mice were activated with 1 μg/ml anti-CD3 in the presence or absence of 10 ng/ml mouse rTL1A. Cells were stained for the indicated activation markers before stimulation and after 24, 48, and 72 hours and measured by flow cytometry.
Figure 17A:
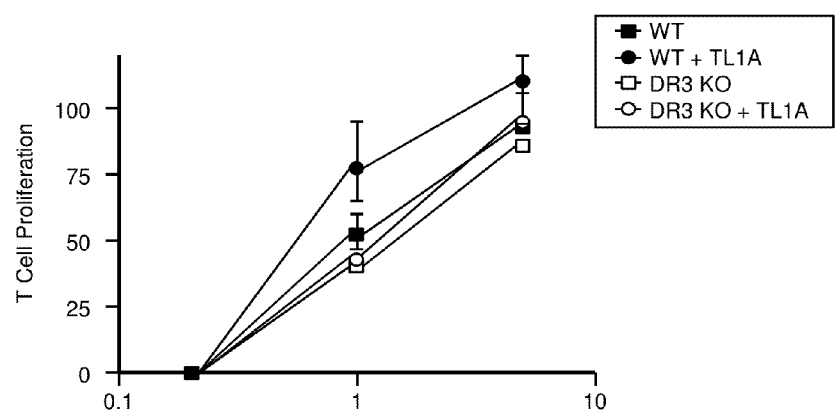
FIGS. 17A-17C show the effects of TL1A on Naïve T Cells.
Figure 17B:
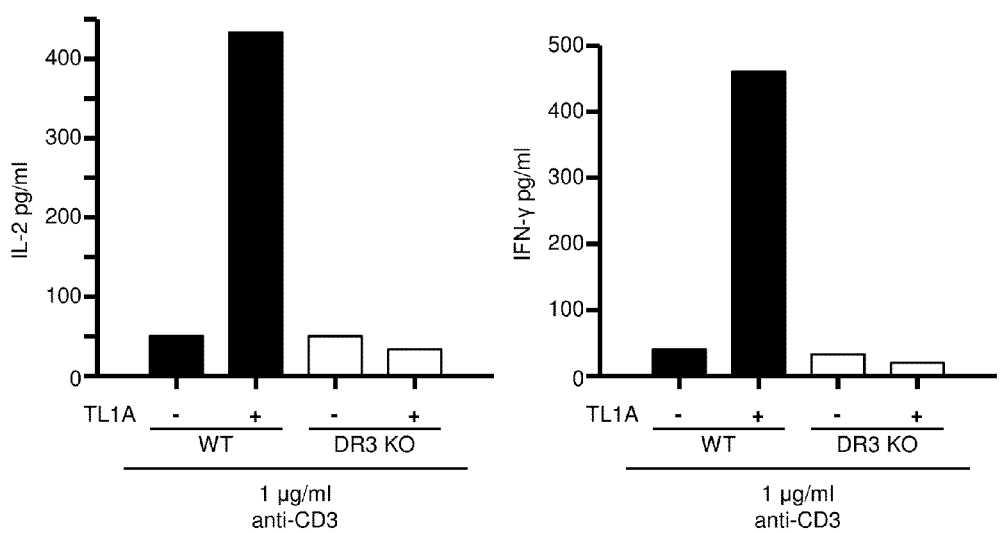
Figure 17C:
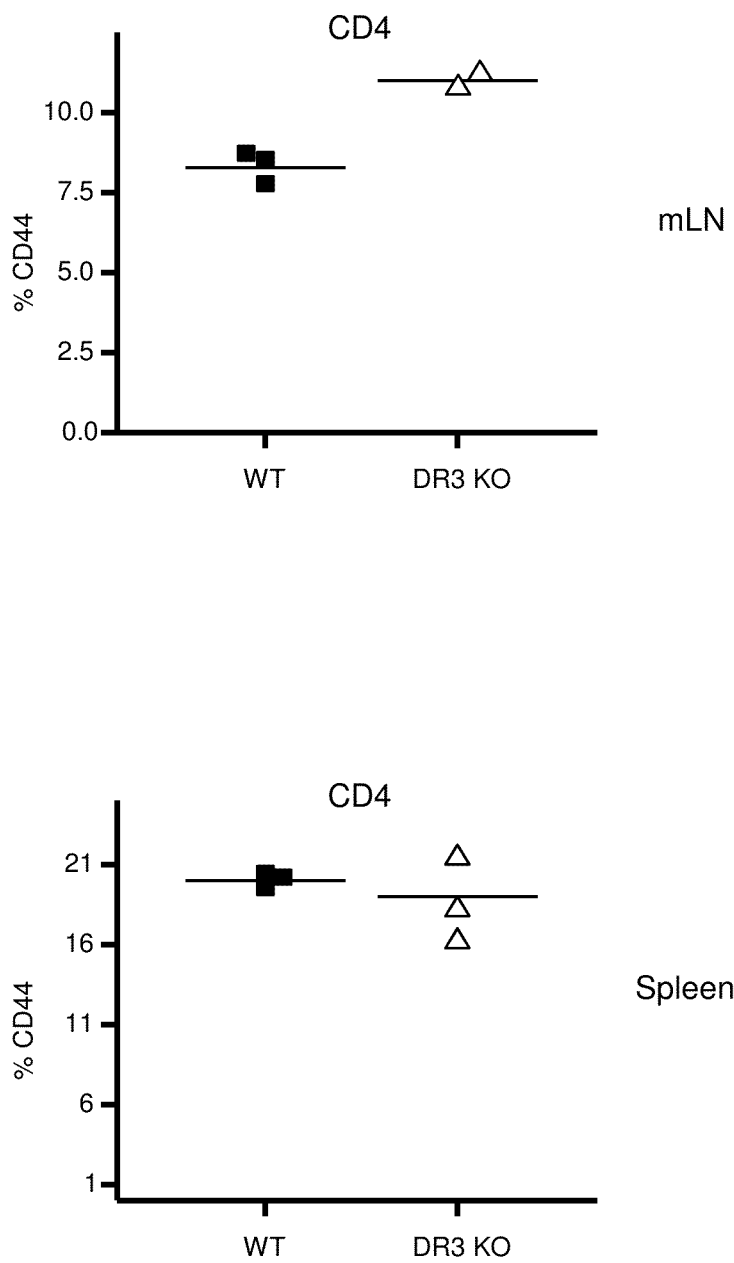

To investigate the spectrum of cytokines that can be costimulated by TL1A and the dependence of cytokine production on DR3, IL-2, IFN-γ and IL-4 production were measured in WT or DR3 KO T cells activated in the presence or absence of recombinant TL1A. TL1A increased IL-2, IFN-γ, and IL-4 production by WT but not by DR3 KO T cells, with IL-4 being most prominently induced by TL1A in the presence of CD28 costimulation (FIG. 8C). DR3-deficient T cells were unresponsive to TL1A, but had no defects in cytokine production compared to wild-type T cells. Thus, as with proliferative responses, DR3 is required for TL1A induced costimulation, but endogenously produced T cell-derived TL1A is not necessary for cytokine production by activated T cells under these conditions. Upregulation of the activation markers CD25 (IL-2Rα) and CD69 was enhanced by TL1A, especially at 24 hours after activation, but no defects in activation marker expression were observed in DR3-deficient T cells compared with wild-type controls (FIG. 16). TL1A has been reported to costimulate memory, but not naïve T cells (Bamias et al., 2006). To address this issue, CD62Lhi/CD4410 naïve CD4+ T cells were purified from WT and DR3-deficient mice and activated with or without exogenous TL1A. TL1A mildly enhanced proliferation with or without CD28 costimulation, and also strongly increased IL-2 and IFN-γ production in a DR3-dependent manner (FIG. 17A, 17B), showing that DR3 can function in naïve T cells. Percentages of memory phenotype CD44hi CD4$^+$ T cells were also identical in age-matched DR3 KO and control mice (FIG. 17C), indicating that TL1A costimulation of unseparated T cells is unlikely to be due to differences in the percentages of memory and naïve cells.

b. Dendritic Cells Produce TL1A in Response to TLR and FcγR Stimuli and can Costimulate T Cells Through DR3

Figure 9A:
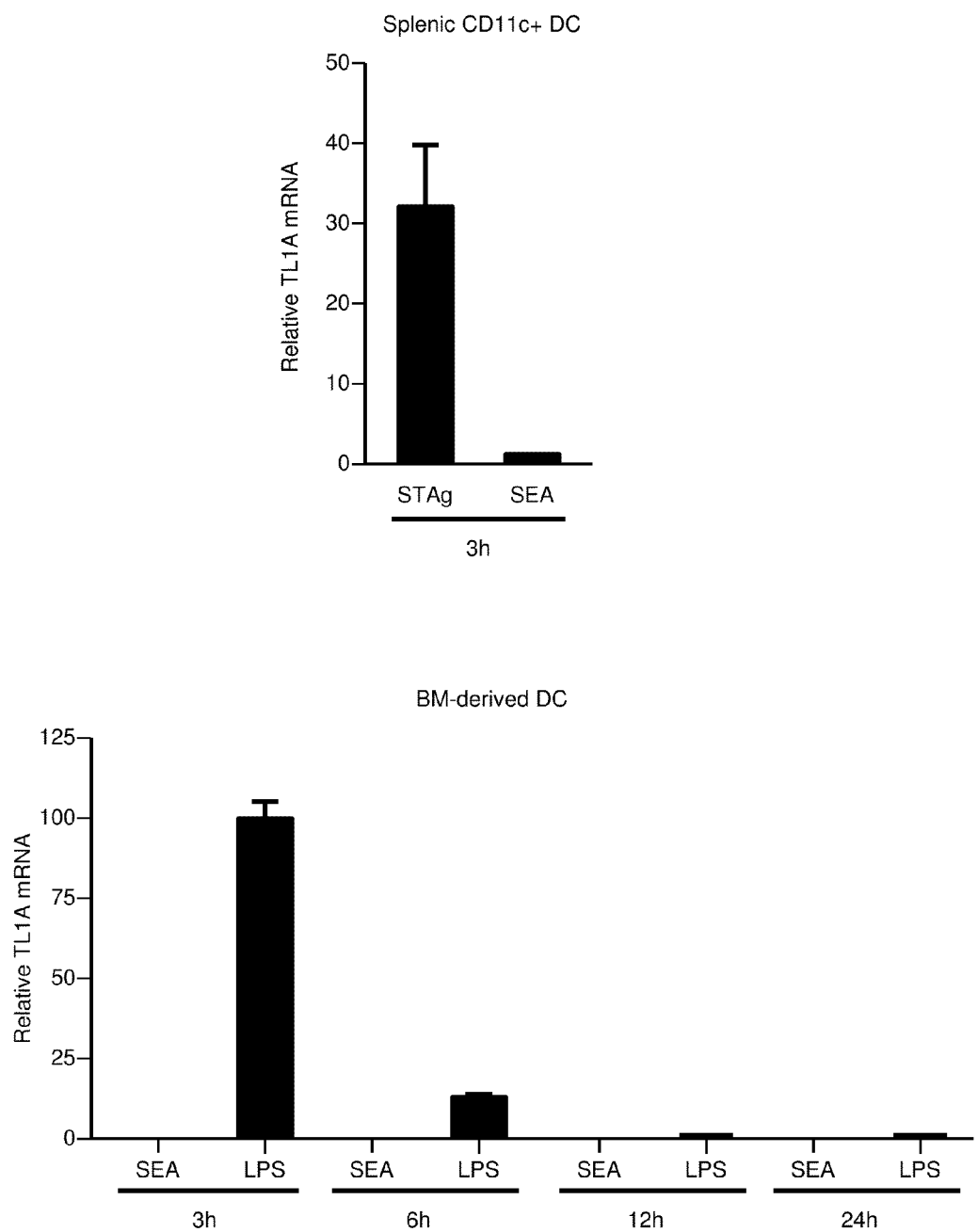
FIGS. 9A-9D show differential induction of TL1A expression in dendritic cells and T cells.
Figure 9B:
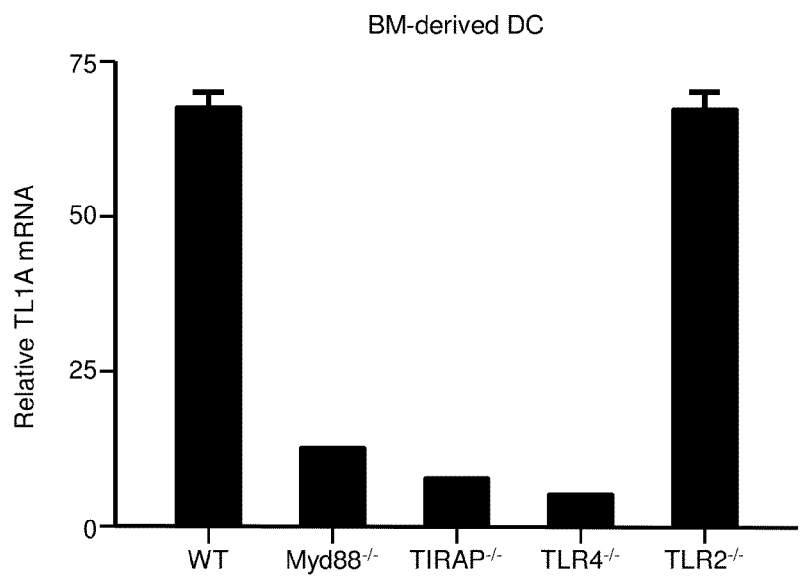
Figure 9C:
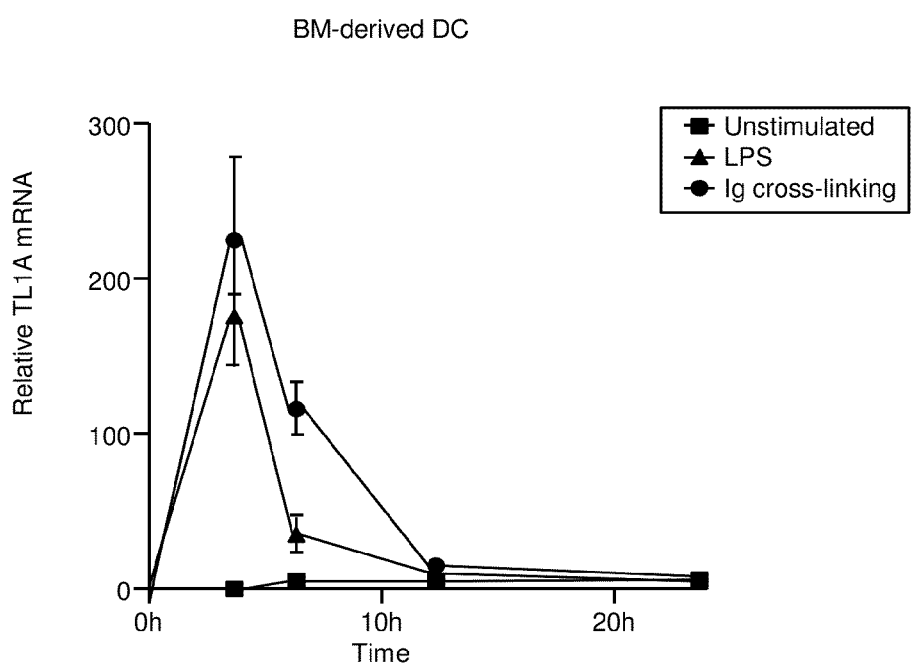
Figure 9D:
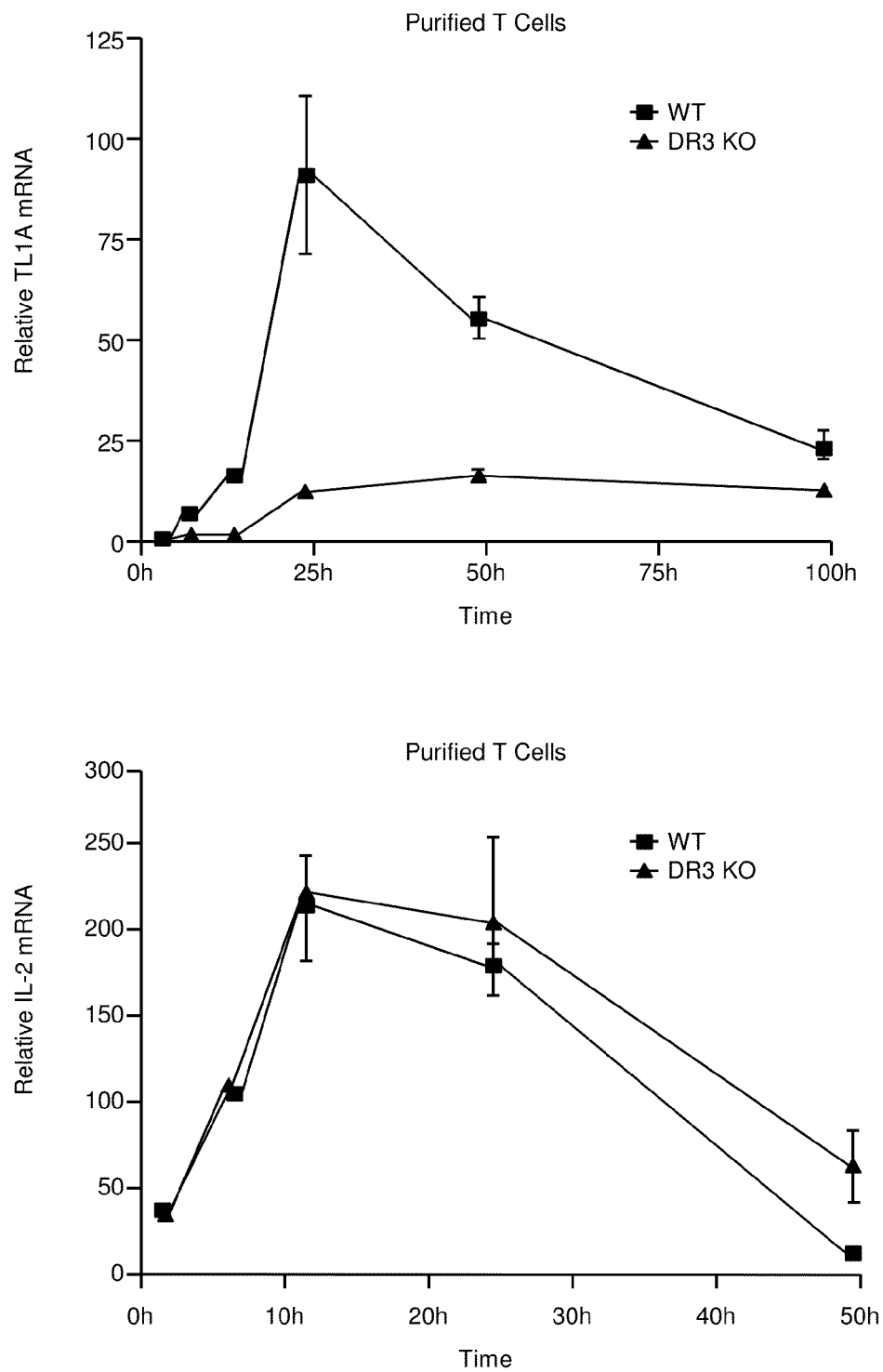

The lack of proliferative or cytokine production defects in purified DR3-deficient T cells suggested that other cell types may be the physiological source of TL1A. TL1A has been reported to be produced by human DC and monocytes after a variety of stimuli, and DCs would be a source of TL1A produced at the appropriate time and place for T cell costimulation. To test this, upregulation of TL1A gene expression was measured by Reverse Transcriptase Quantitative PCR(RT-qPCR) in purified splenic CD11c$^+$ dendritic cells and bone marrow-derived DC stimulated with a variety of agents. LPS and Soluble Tachyzoite Antigen from *Toxoplasma gondii* (STAg), stimuli that act through Toll-Like receptors (TLR's) and that can induce expression of other TNF family members, induced rapid upregulatation of TL1A, with expression peaking at up to 100-fold above baseline at 3 hours, and rapidly declining after that (FIG. 9A). Interestingly, *Schistosoma* Egg Antigen (SEA) from *Schistosoma mansoni*, which triggers alternative activation of DC to program T cells for Th2 differentiation, did not appreciably induce TL1A mRNA (FIG. 9A, left panel). Stimulation of dendritic cells deficient in TLR signaling components showed that LPS induction of TL1A is mediated by TLR4 in a manner dependent on MyD88 and TIRAP (FIG. 9B). Immune complexes acting through low-affinity Fc receptors have recently been shown to be a potent stimulus for TL1A production (Cassatella et al., 2007; Prehn et al., 2007). Stimulation of murine DC with plate-bound crosslinked mouse Ig (IC) also stimulated TL1A gene expression comparably to LPS (FIG. 9C). Thus like other TNF family members, TL1A can be rapidly induced in DC through TLR and immune complexes. To test whether T cells could serve as an autocrine source of TL1A, purified T cells were stimulated through the TCR, and TL1A mRNA levels were measured by RT-qPCR. TL1A mRNA was upregulated after TCR stimulation, but with delayed kinetics compared with DC. Interestingly, TL1A upregulation was specifically dependent on DR3 expression, as DR3-deficient T cells showed dramatically reduced TL1A induction, but normal upregulation of IL-2 mRNA after activation (FIG. 9D). Taken together, these data show that T cells can produce TL1A that acts in an autocrine manner to sustain its own expression, but T cell-derived TL1A is not necessary for proliferation or cytokine production by isolated T cells.

Figure 10A:
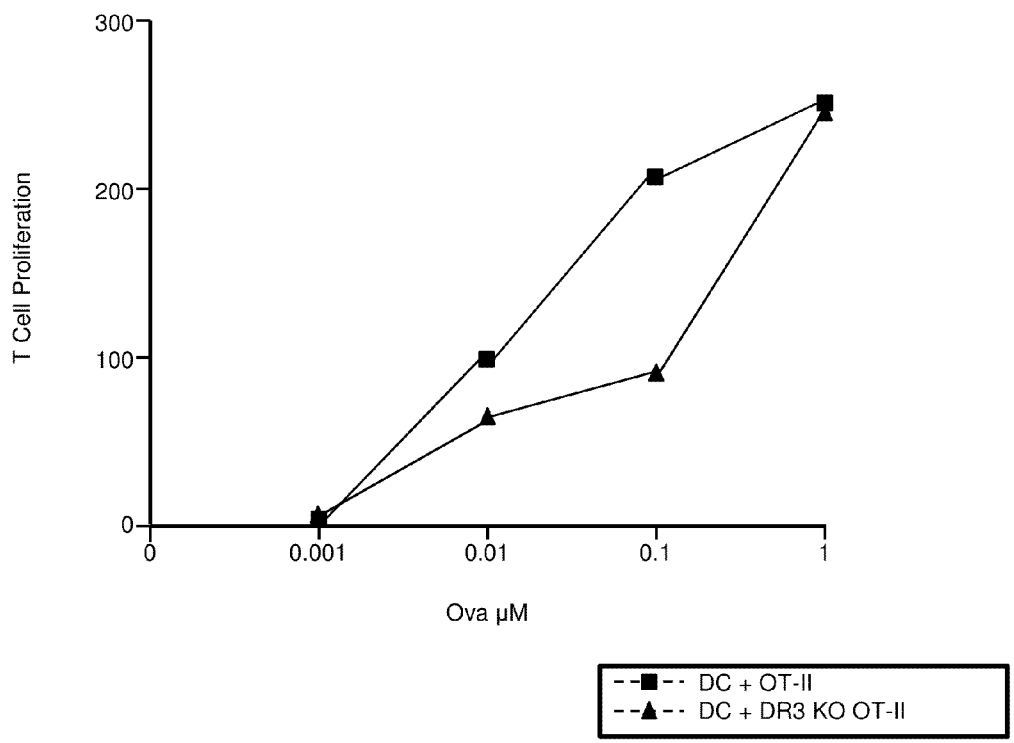
FIGS. 10A-10B show that DR3 KO T cells have reduced proliferation and altered cytokine production when cultured in the presence of dendritic cells.
Figure 10A:
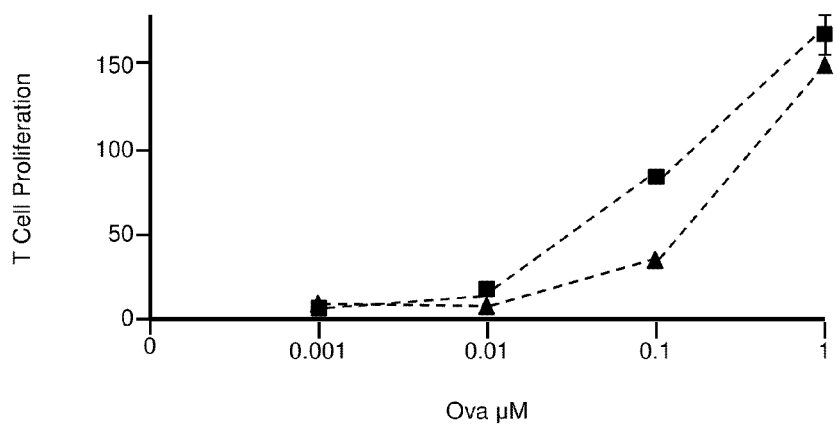
Figure 10B:
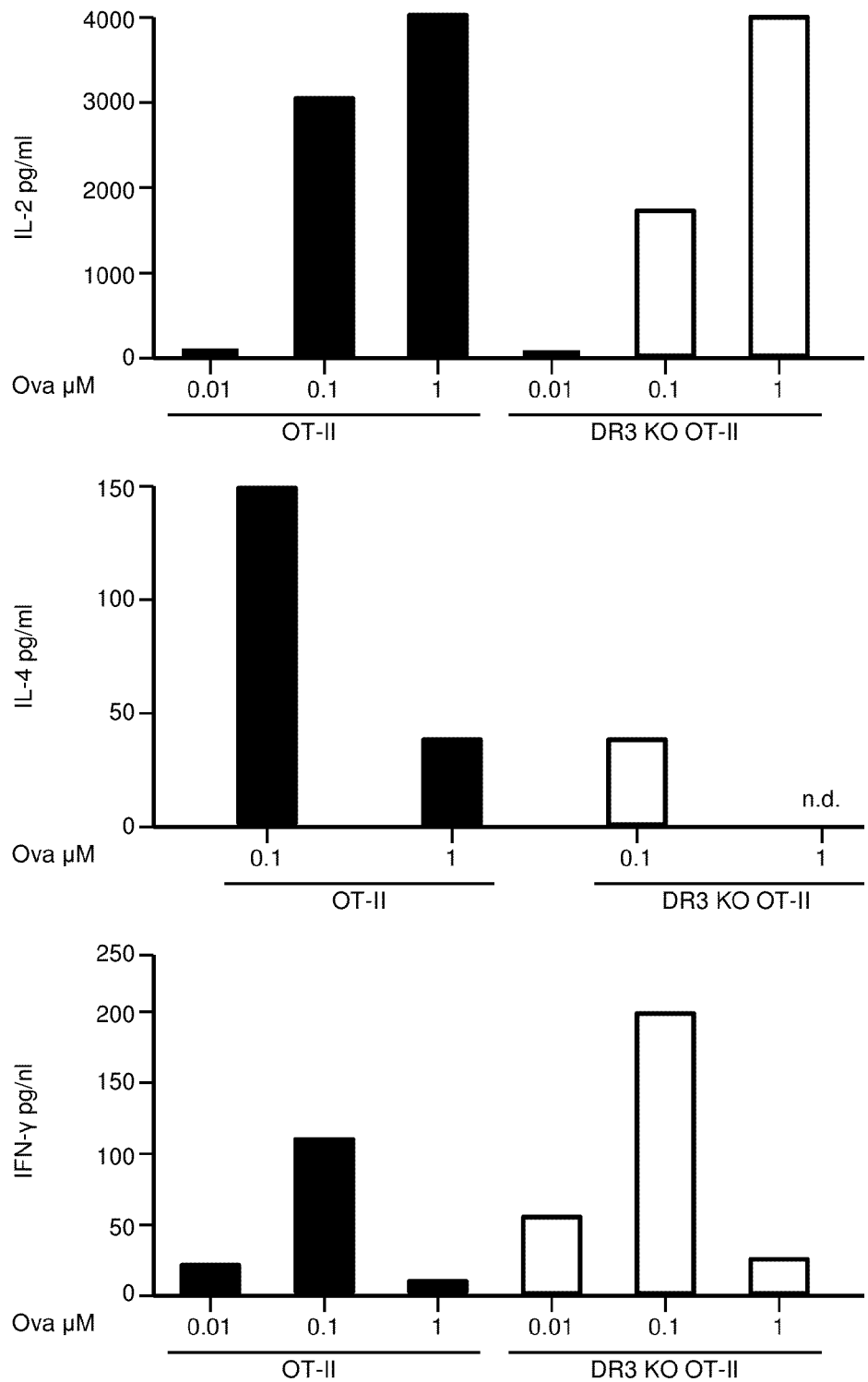
Figure 11A:
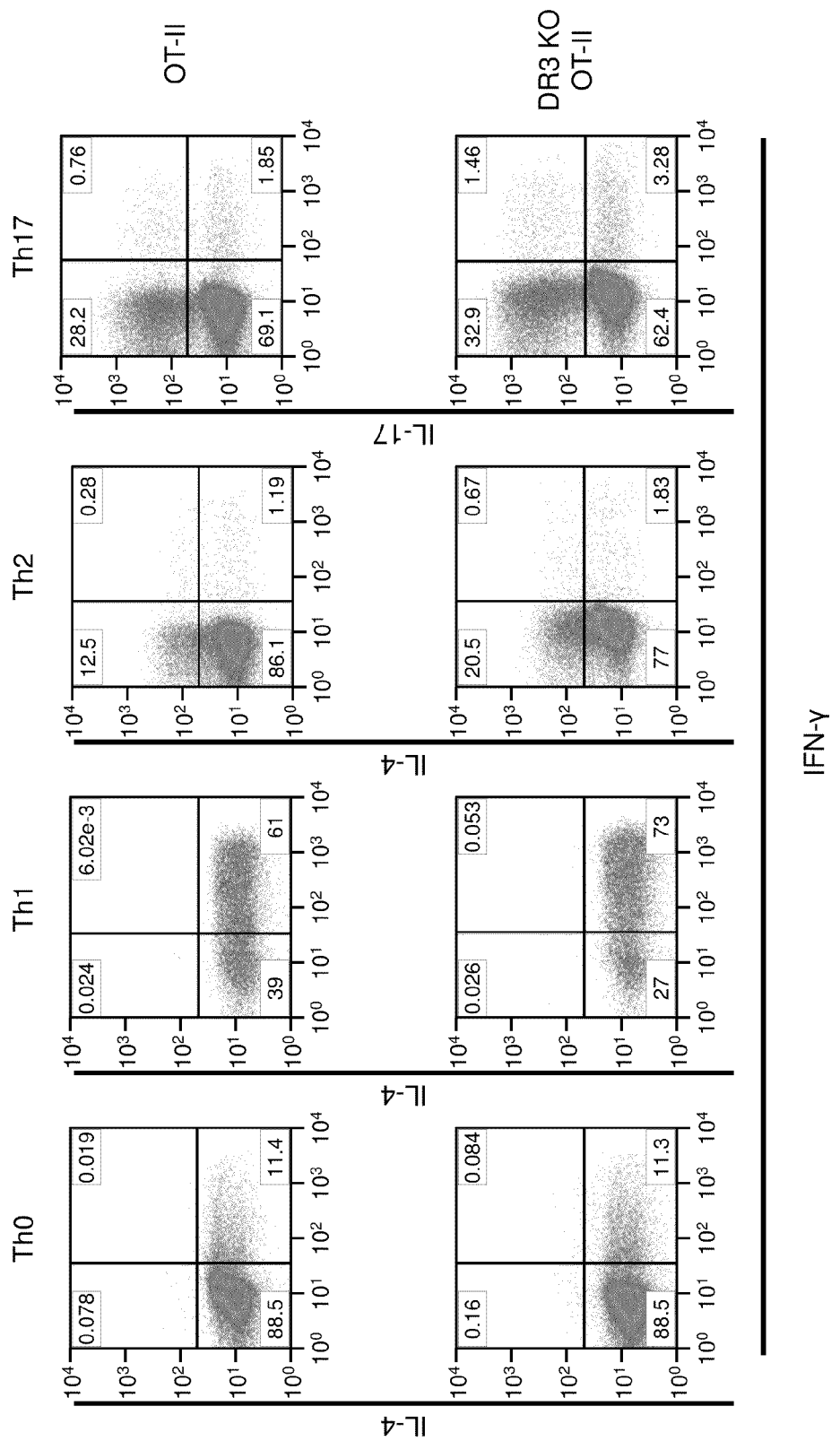
FIGS. 11A-11B show that DR3 is not required for Th1, Th2, or Th17 differentiation of naïve T cells.
Figure 11B:
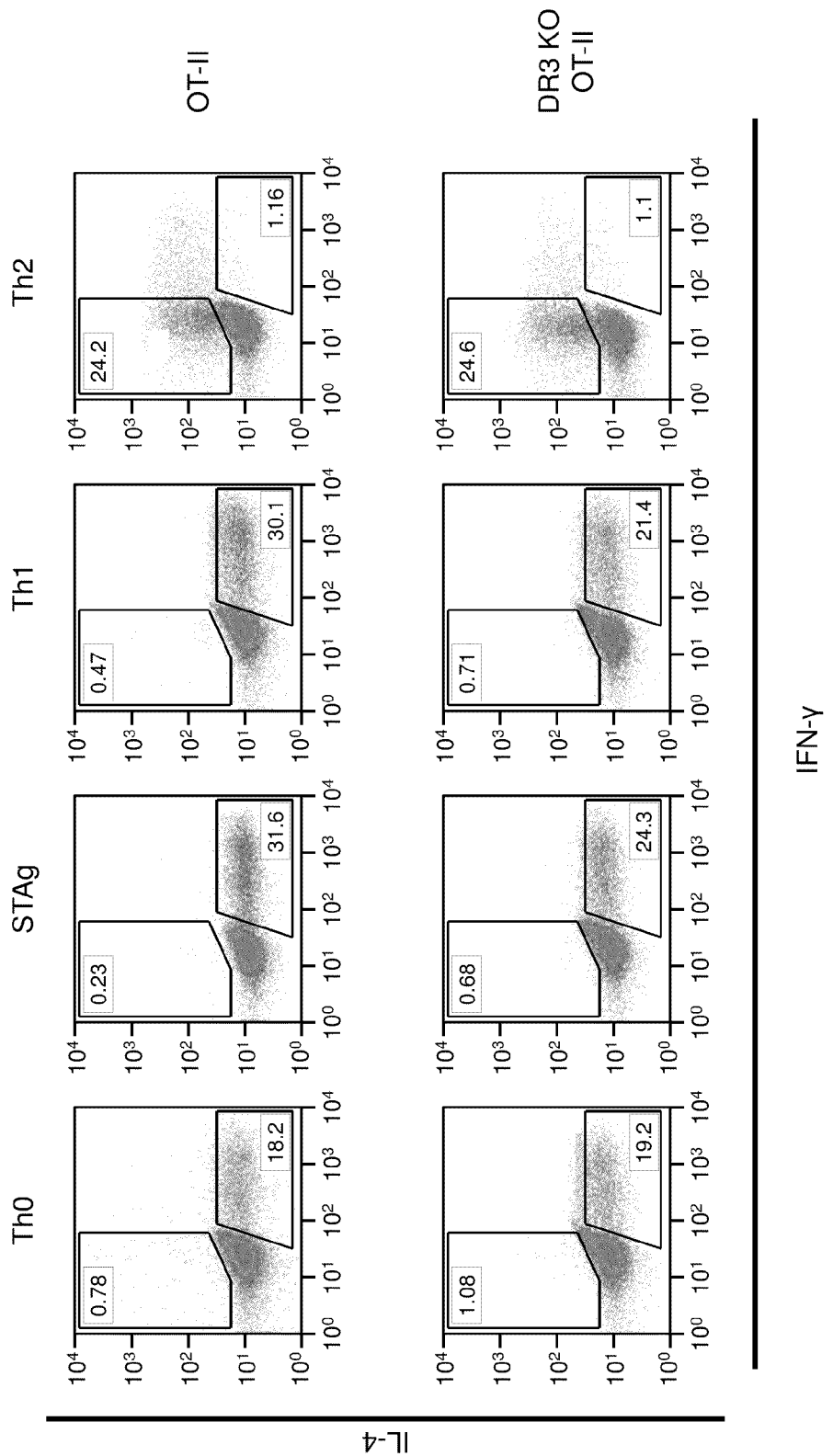
Figure 12A:
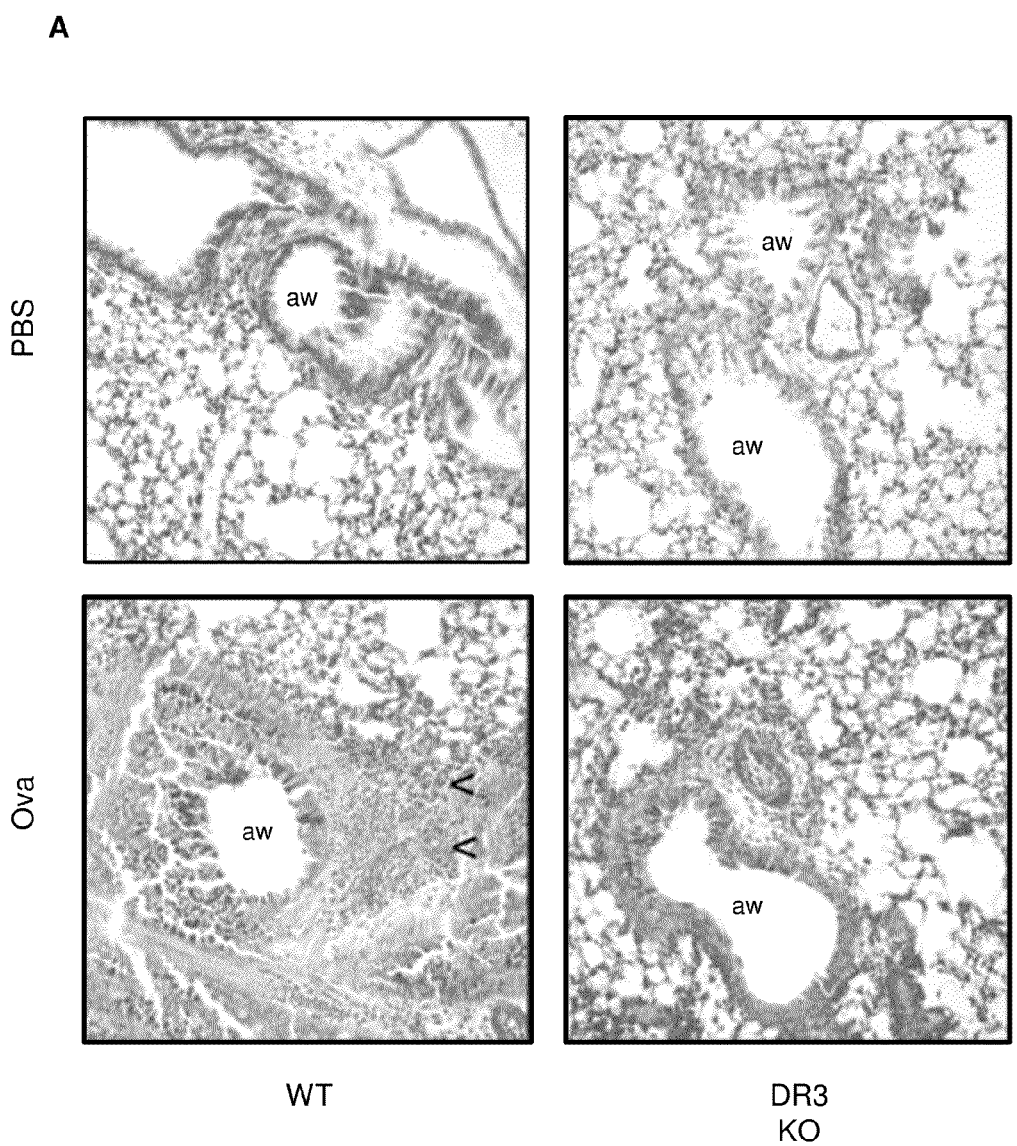
FIGS. 12A-12F show that DR3 is required for Th2-mediated lung inflammation. Mice were sensitized with Alum+PBS (control) or Alum+Ova. Mice were then challenged with PBS (control) or Ova.
Figure 12B:
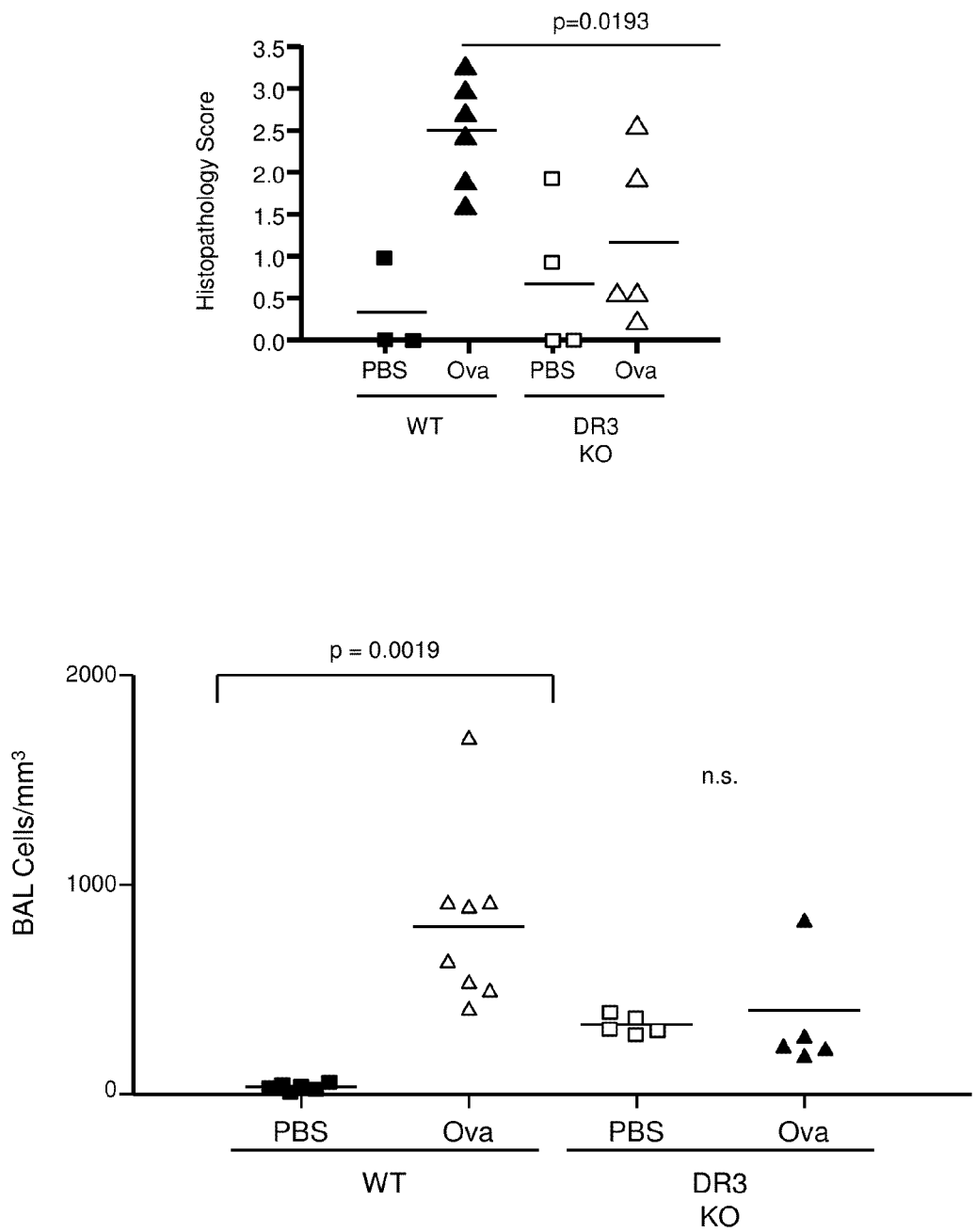
Figure 12C:
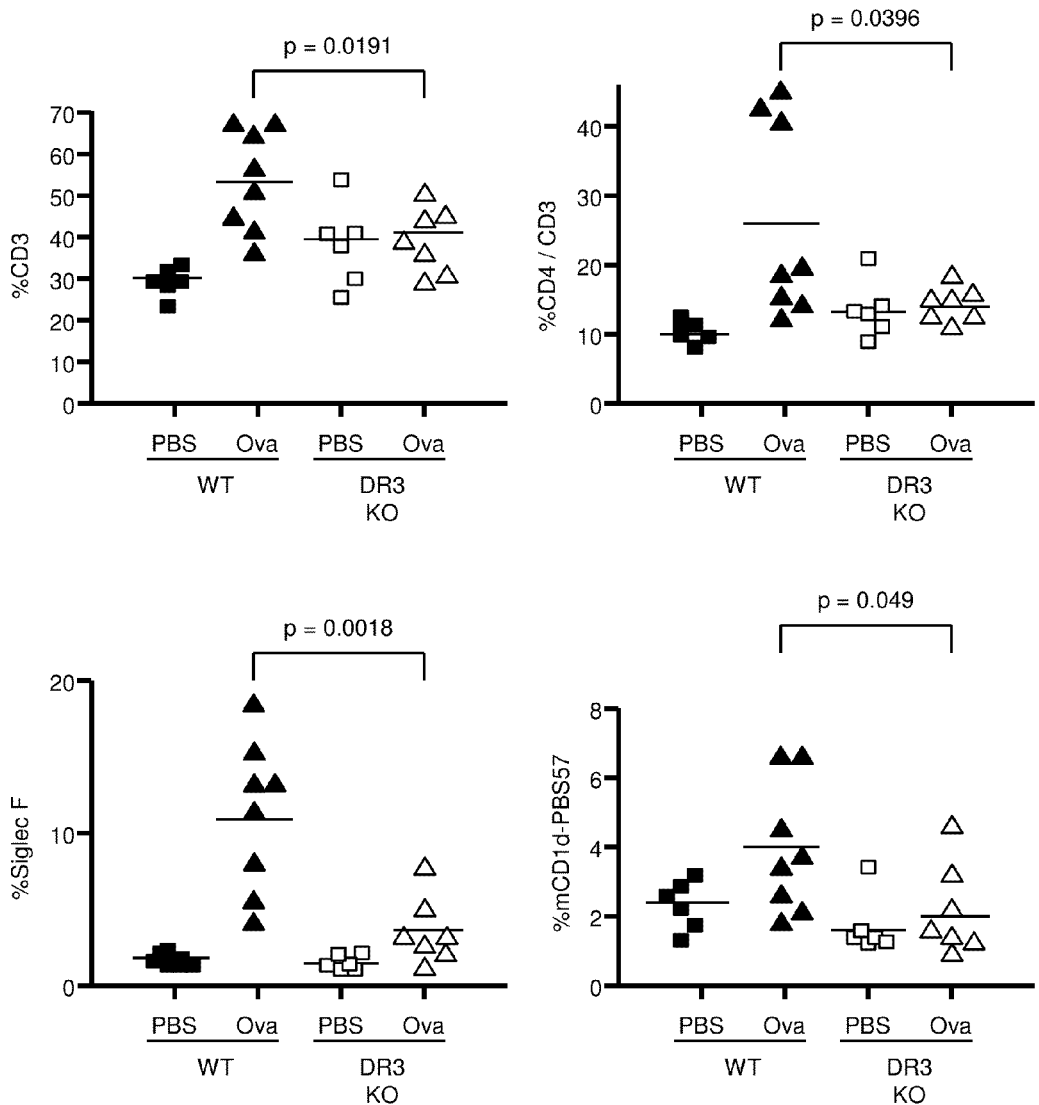
Figure 12D:
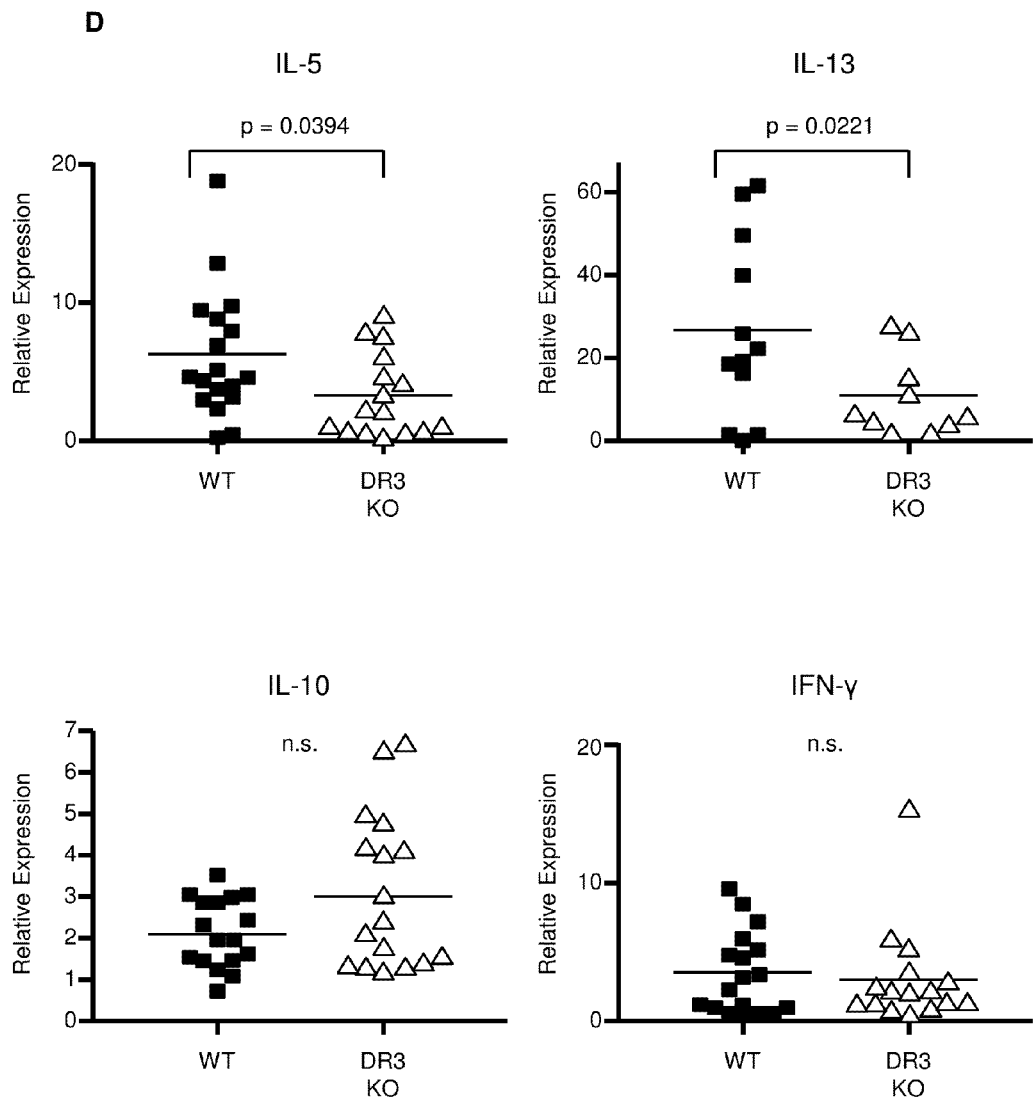
Figure 12E:
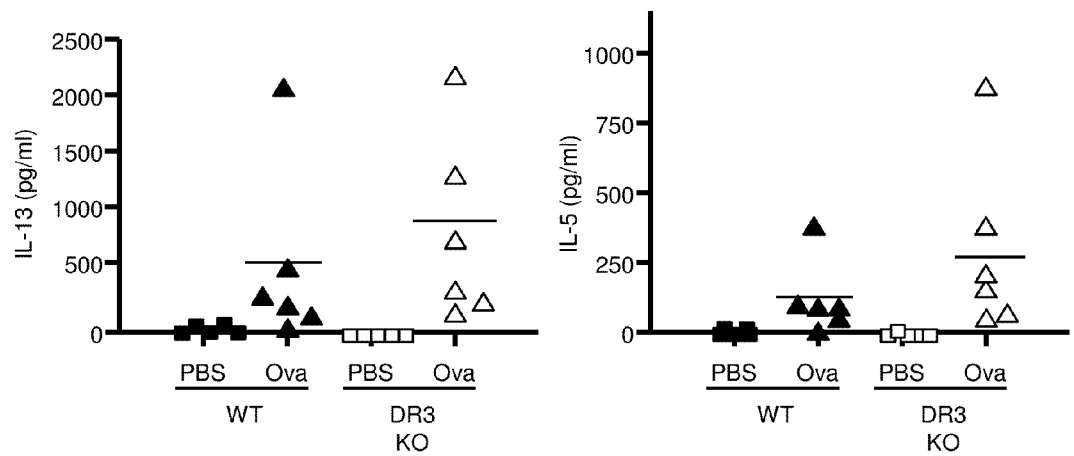
Figure 12F:
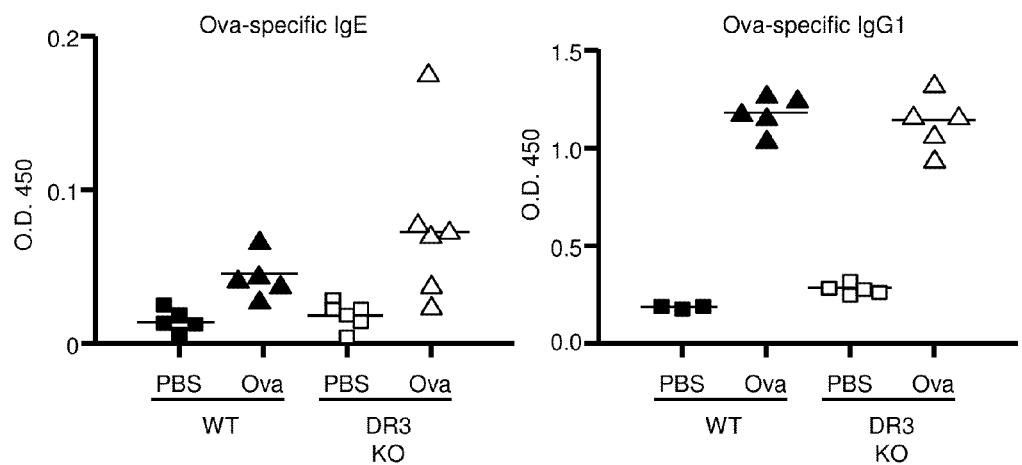
Figure 18:
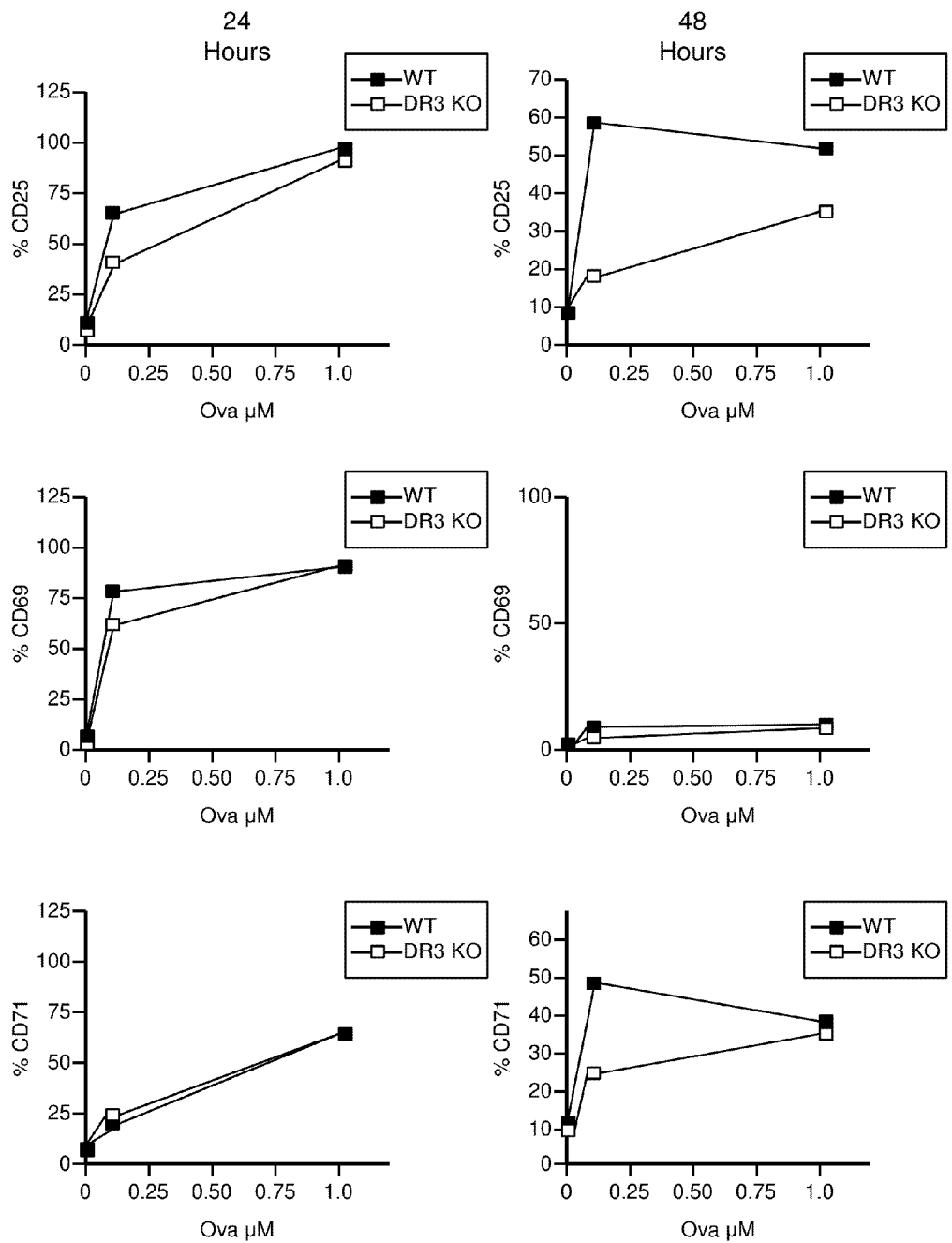
FIG. 18 shows surface marker expression after activation of DR3 KO and WT OT-II T cells with Ova peptide-pulsed DC. Bone marrow-derived DC were cultured with naïve OT-II or DR3 KO OT-II CD4+ T cells in the presence of the indicated concentration of Ova peptide. Cells were stained for CD4 and the indicated surface expression markers after 24 and 48 hours and analyzed by flow cytometry.
Figure 19:
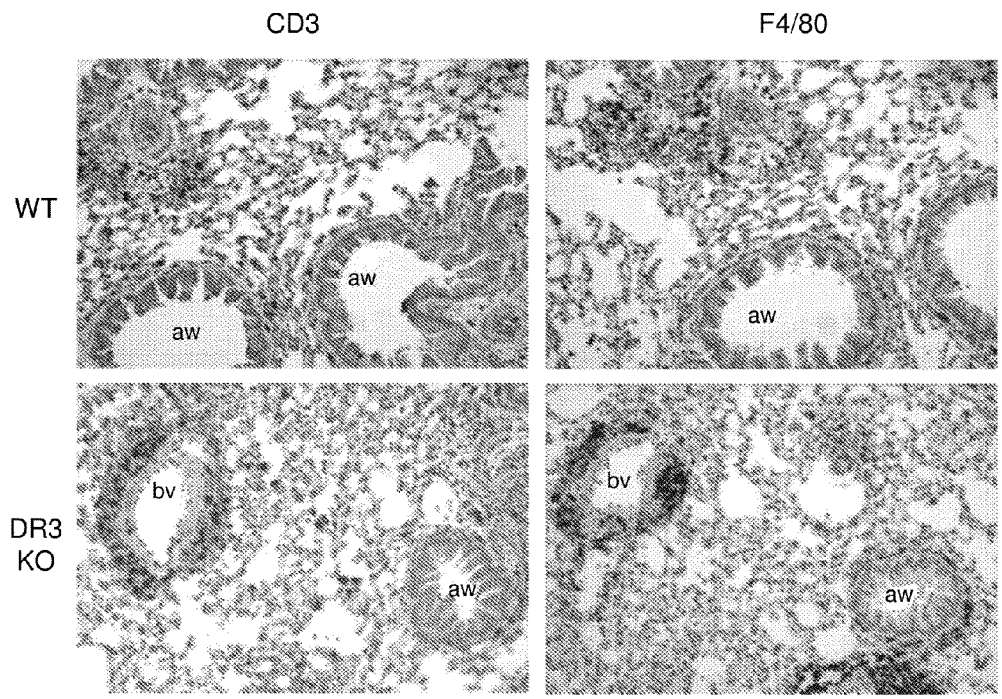
FIG. 19 shows altered localization of T cells and macrophages in Ova-induced lung inflammation. Histological sections of lungs from mice of the indicated genotype, primed and challenged with Ova as described below, were subjected to immunohistochemical labeling with anti-CD3 (T cells) or anti-F4/80 (macrophage) marker antibodies and HRP-conjugated secondary antibodies. Airways (aw) and blood vessels (bv) are indicated.

To study the role of TL1A-DR3 interactions in a more physiological model of T cell activation, DR3-deficient mice were backcrossed to the Ovalbumin (Ova)-specific TCR transgenic line OT-II, and cultured naïve T cells from DR3 KO OT-II and OT-II control mice with Ova peptide and wild-type bone marrow-derived DC. Under these conditions, proliferation of DR3 KO OT-II cells was diminished especially at low concentrations of Ova (FIG. 10A). The cytokine profile of T cells stimulated with Ova peptide and DC is characteristically dependent on the dose of antigen, with higher doses favoring IFN-γ production and lower doses favoring IL-4 production (Tao et al., 1997). DR3 KO OT-II cells produced less IL-2 at lower doses of Ova and lower amounts of IL-4 at all doses of Ova tested. By contrast, production of IFN-γ was higher than controls at all doses tested (FIG. 10B). Analysis of T cell activation marker expression revealed that optimal upregulation of CD25 and CD71 was also DR3 dependent at low doses of Ova peptide (FIG. 18). These data indicate that during interactions between T cells and dendritic cells presenting cognate antigen, TL1A-DR3 interactions function to costimulate T cell proliferation and production of IL-2, IL-4, but not IFN-γ. These alterations in cytokine production and proliferation in the absence of DR3 may influence T cell polarization. To test this, naïve CD4$^+$ T cells from DR3 KO or control mice were activated in the presence of dendritic cells under conditions optimized for differentiation of Th1, Th2, or Th17 effector T cells or under neutral conditions, and was cytokine production measured after restimulation (FIG. 11). In the absence of exogenous polarizing stimuli, DR3 KO T cells exhibited mild skewing towards a Th1-IFN-γ secreting profile expected on the C57BL/6 background. In addition, appropriate cytokines polarized DR3 KO cells normally towards IL-4, IFN-γ, or IL-17 producing cells, cultures of DR3 KO OT-II, and control OT-II T cells stimulated with DC and Ova were then set up and polarized with cytokines or Soluble Tachyzoite Antigen (STAg), which in addition to IL-12, induces TL1A production. These conditions also resulted in normal Th1 skewing by antigen-specific DR3 KO T cells (FIG. 11B). Induction of the transcription factors T-bet, GATA-3, or RORγ by appropriate differentiation stimuli was also unaffected in DR3 KO purified T cells. Thus, DR3 appears to be dispensable for the differentiation of naïve T cells into Th1, Th2, or Th17 effector cell subtypes.

c. DR3 is Dispensable for Primary Systemic T Cell Responses, but Essential for Immunopathology in Animal Models of T Cell-Mediated Disease To determine the role of DR3 in T cell differentiation and effector function in the intact immune system, disease models dependent on distinct T cell subsets were studied in DR3 KO mice. A Th2-dependent model of lung inflammation in which mice are primed systemically with Ova and Alum was first investigated and then locally challenged with Ova (Gavett et al., 1994). In three independent experiments, histological analysis showed that the airways in DR3 KO mice lung had less inflammation, including mucin production and peribronchial inflammation (FIG. 12A). Standardized histopathology scores and cell counts in BAL were reduced in OVA-sensitized and challenged DR3 KO mice compared with DR3 WT mice sensitized and challenged in parallel with OVA (FIG. 12B). Percentages of CD3$^+$ and CD4$^+$ T cells, invariant Va14 positive T cells that recognize glycosphingolipid/CD1d tetramers, and eosinophils were all significantly reduced in lung cell preparations from Ova-sensitized and challenged DR3 KO mice compared with controls (FIG. 12C). Localization of CD3$^+$ cells in lung tissue from Ova-sensitized DR3-deficient mice by immunohistochemistry revealed fewer interstitial and peribronchial T cells compared with controls, and increased perivascular localization, suggesting a migration or survival defect of T cells in the lung. Similar increases in perivascular infiltrates were observed for macrophages (FIG. 19). Levels of mRNA for IL-5 and IL-13, which are critical for Th2-mediated lung pathology, were markedly reduced in DR3 KO Ova-sensitized lungs, while IL-10 and IFN-γ were equally produced (FIG. 12D). By contrast, when DR3 KO spleen cells from these mice were restimulated with Ova, there was normal production of IL-5 and IL-13, indicating that systemic priming of Ova-specific Th2 T cells was independent of DR3 (FIG. 12E). In addition, DR3 KO splenocytes proliferated normally in response to Ova. Systemic Th2 function as assessed by the production of Ova-specific IgG1 and Ova-specific IgE after Ova priming was also normal in DR3 KO mice (FIG. 12F). Thus, in this model of Th2-mediated lung inflammation, DR3 is required for Th2 effector cells to accumulate at the site of inflammation but not for systemic differentiation of Th2 T cells. Decreased T cells in the lung may result in defective recruitment of eosinophils and iNKT cells to the site of inflammation as was observed in the DR3 KO lung.

Figure 13A:
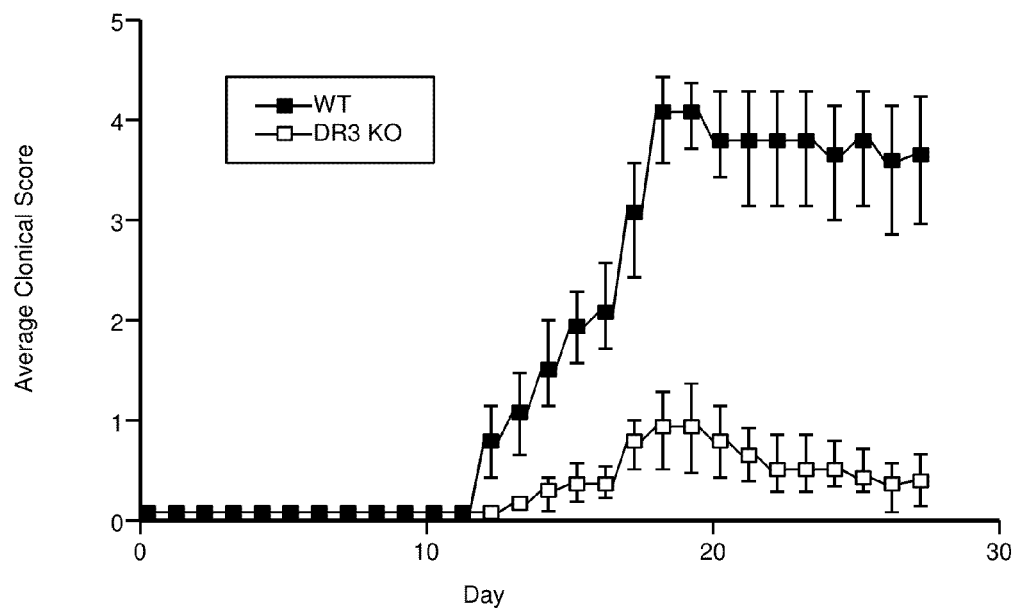
FIGS. 13A-13D show that DR3 KO mice have defective local T cell responses and reduced disease in EAE.
Figure 13B:
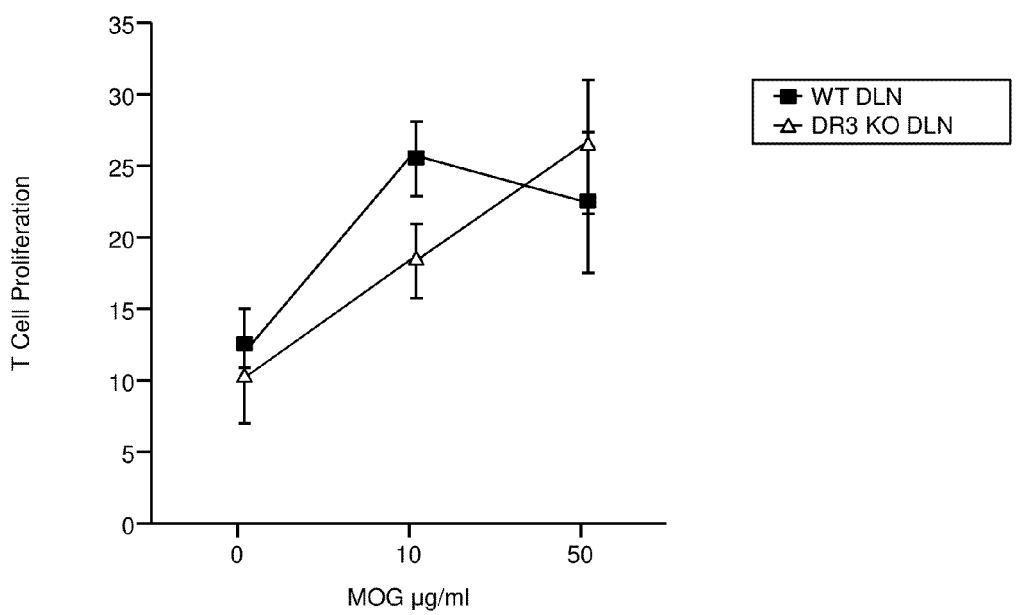
Figure 13C:
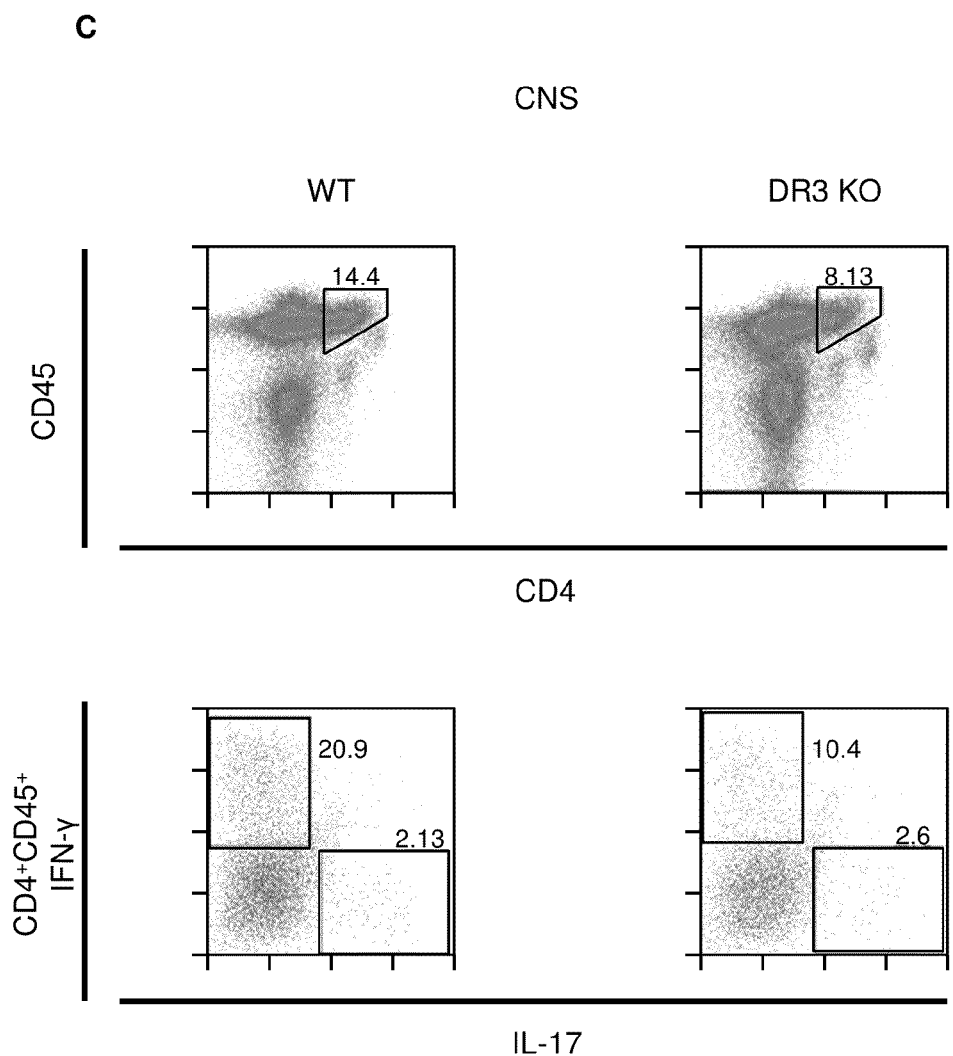
Figure 13D:
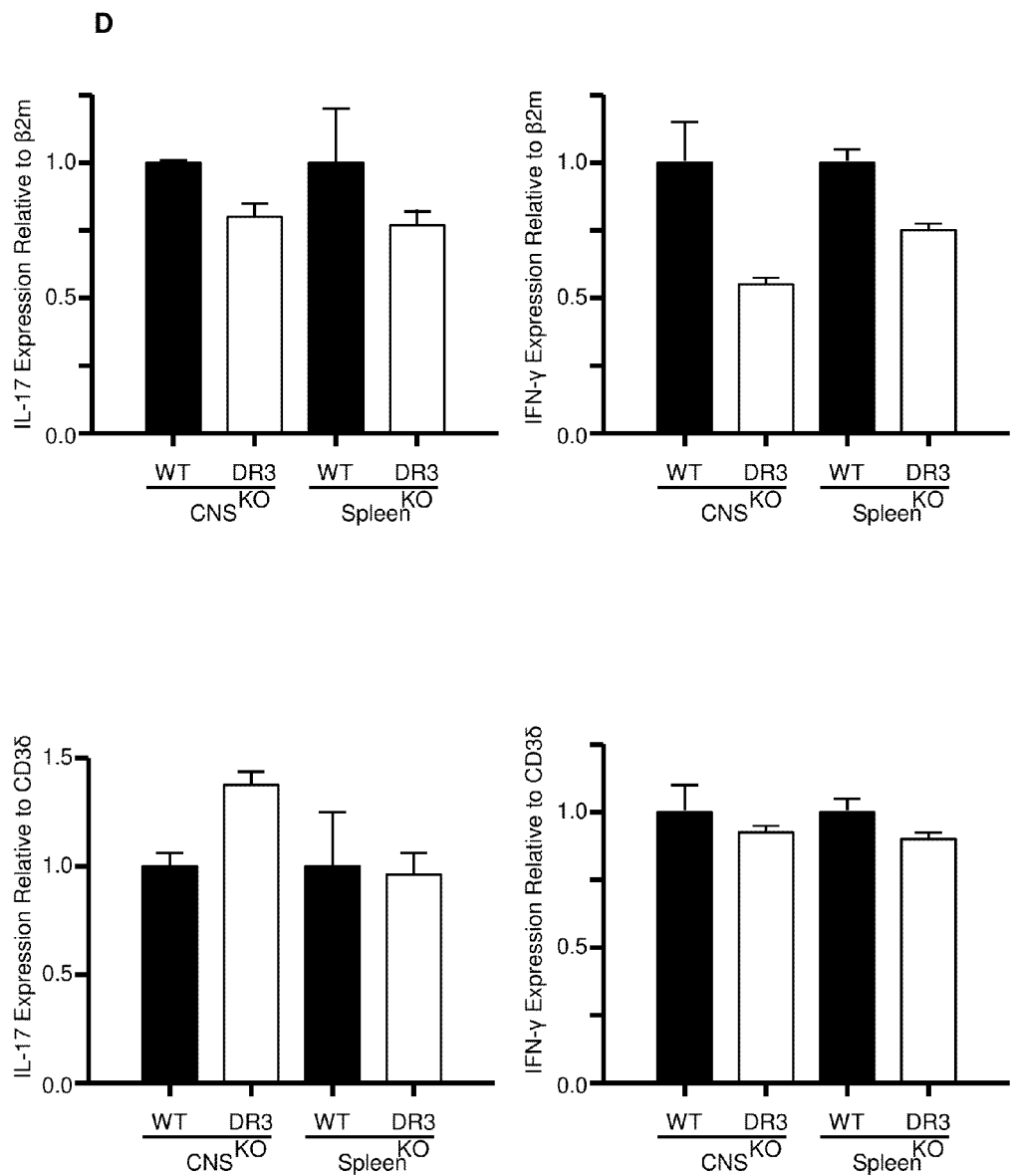

To determine whether DR3 is required for diseases mediated by other T cell subsets, Experimental Autoimmune Encephalomyelitis (EAE), a Th17- and Th1-dependent autoimmune disease, was studied in DR3 KO mice. In four separate experiments, DR3 KO mice exhibited delayed and dramatically reduced paralysis as measured by clinical scores (FIG. 13A). Despite resistance to EAE, T cells from draining lymph nodes of MOG-primed DR3 KO mice proliferated normally in response to MOG (FIG. 13B). The percentage of CD4+ T cells in the spinal cord homogenates was markedly reduced in DR3 KO mice (FIG. 13C). Within the T cell gate, the percentage of IFN-γ-producing cells was also reduced by two-fold in T cells from the spinal cords of DR3 KO mice (FIG. 13C). The percentage of IL-17-producing cells was normal in DR3 KO mice within this gate, but overall was still reduced due to the decreased percentage of CD4+ T cells in the spinal cord. To examine the absolute levels of these cytokines in the inflamed spinal cord, mRNA for IL-17 and IFN-γ was measured by RT-qPCR in spinal cord homogenates. Both cytokines were reduced in spinal cord preparations from MOG-primed DR3 KO mice when normalized to the housekeeping gene β2-microglobulin, with IFN-γ being the most affected. However, when normalized to the expression of the T cell specific gene CD3-6, IL-17 and IFN-γ mRNA expression were not reduced in DR3 KO spinal cord. (FIG. 13D). Thus, DR3 is also critical in this model of autoimmune demyelinating disease associated with a different set of cytokines than the Ova-induced lung inflammation model, and resistance to disease in DR3 KO mice correlated with decreased numbers of effector T cells in the target organ.

Figure 14:
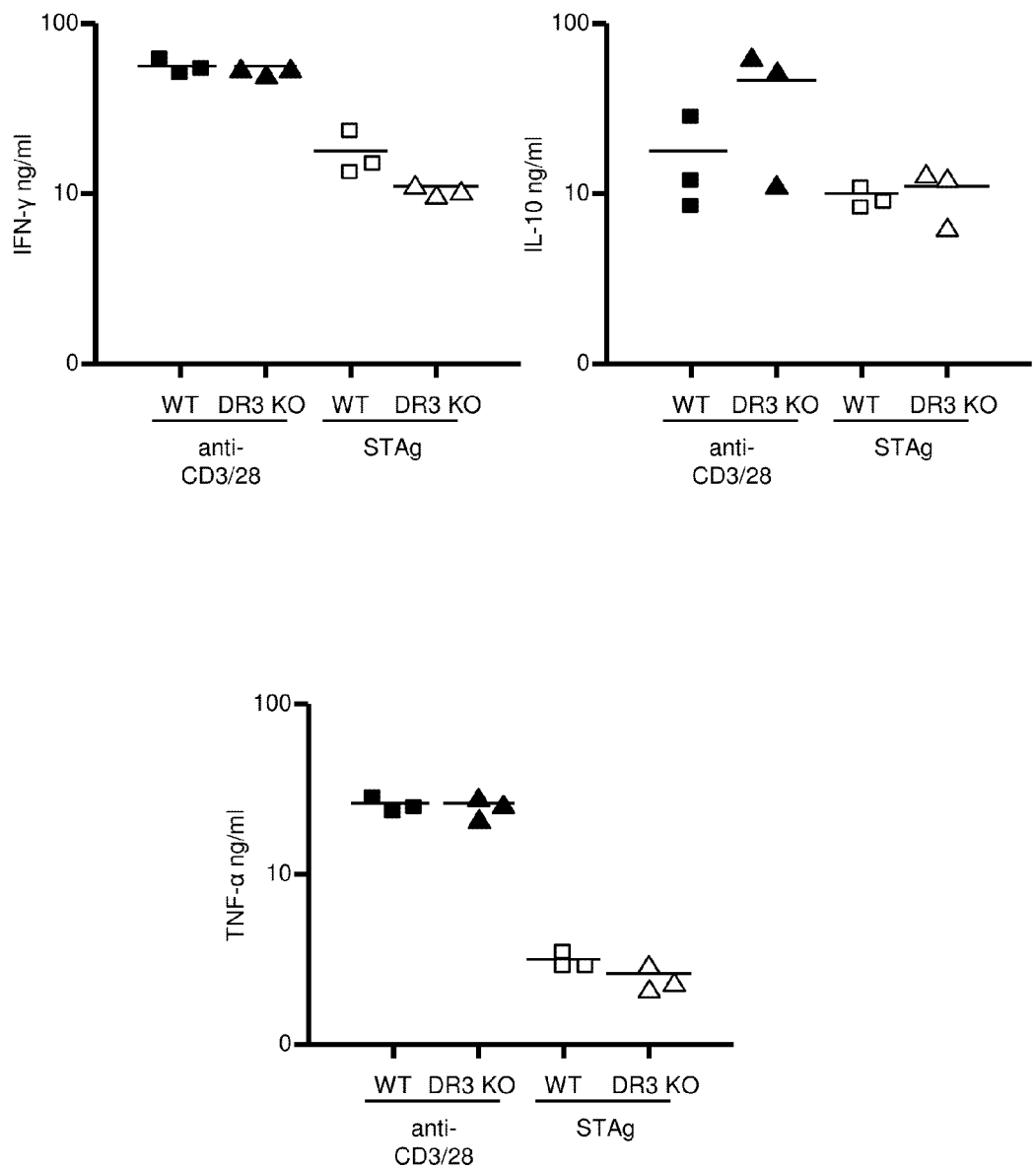
FIG. 14 shows a normal systemic response to *T. gondii*. The indicated mice were inoculated i.p. with an average of 20 cyst/animal. After 7 weeks, spleen cells were harvested, cultured with anti-CD3 and anti-CD28 or with STAg for 48 hours, and supernatants were tested for the production of the indicated cytokines.
Figure 15A:
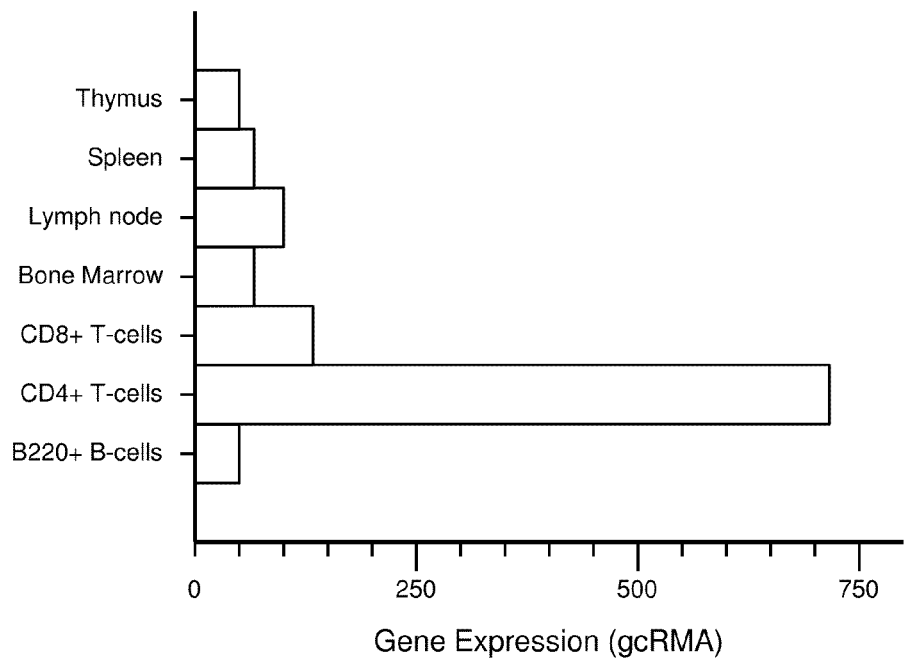
FIGS. 15A-15B show T cell-specific DR3 expression in humans and mice. Microarray-derived gene expression data on DR3 (TNFRSF25) from SymAtlas (symatlas.gnf.org) (Su et al., 2004) are shown for a variety of cell types from mouse (FIG. 15A) and human (FIG. 15B) tissues. Data are normalized by the gcRMA algorithm.
Figure 15A:
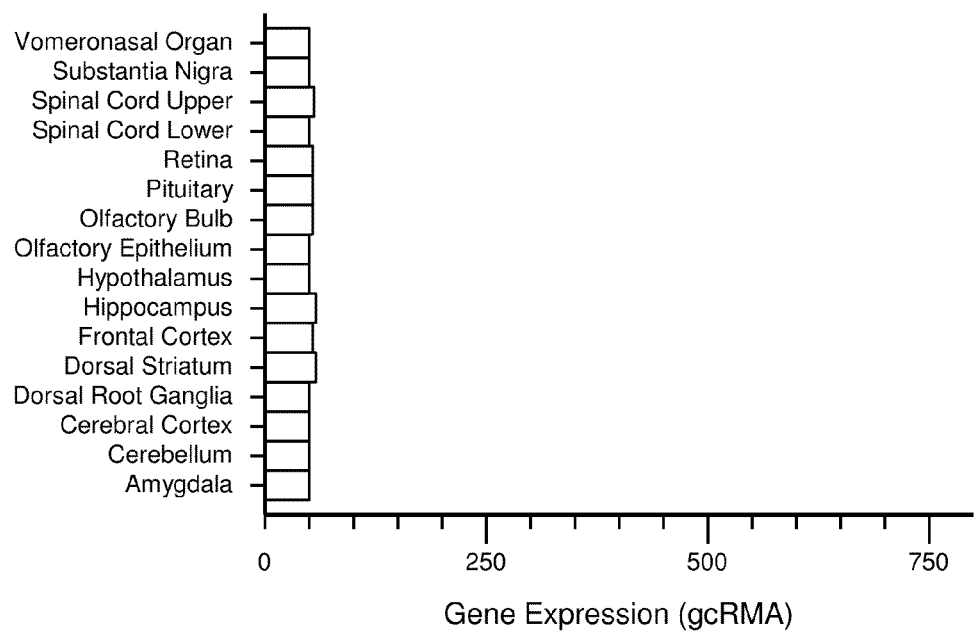
Figure 15A:
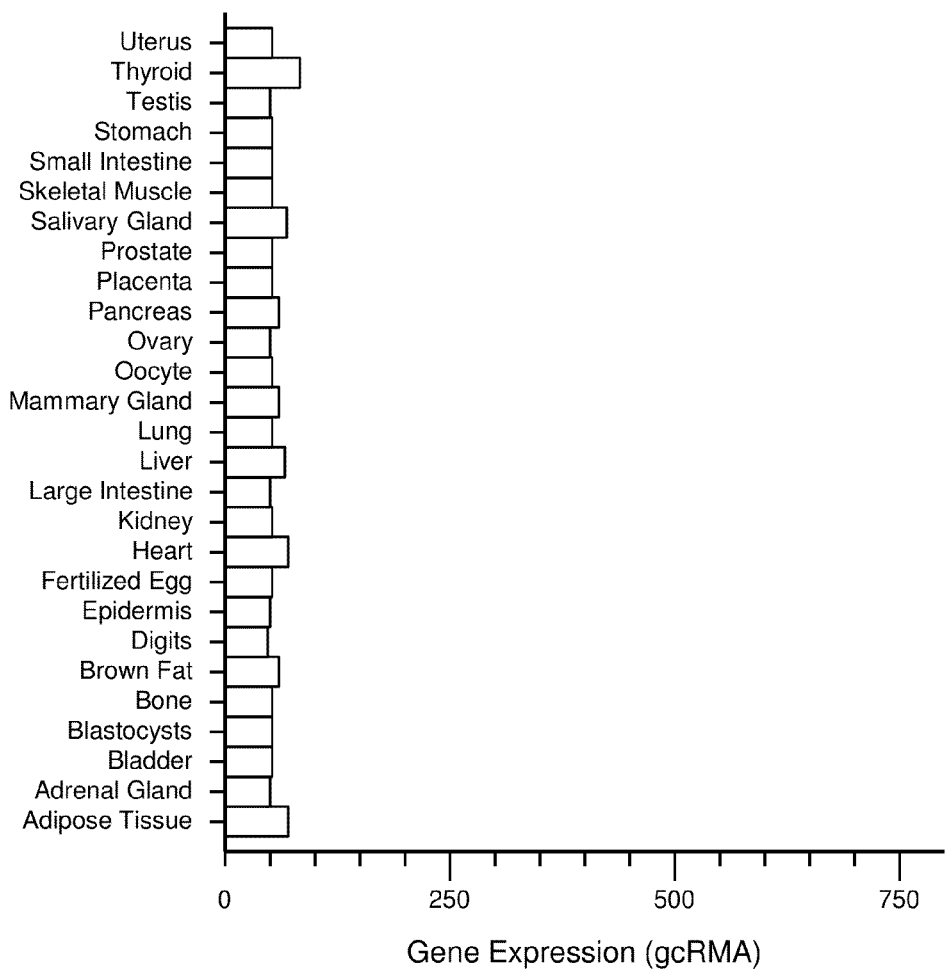
Figure 15B:
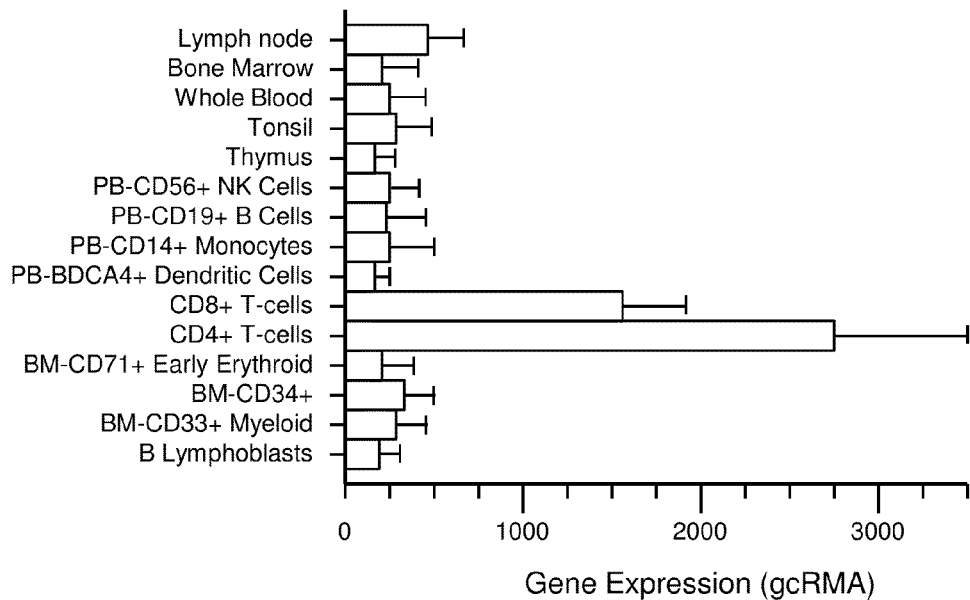
Figure 15B:
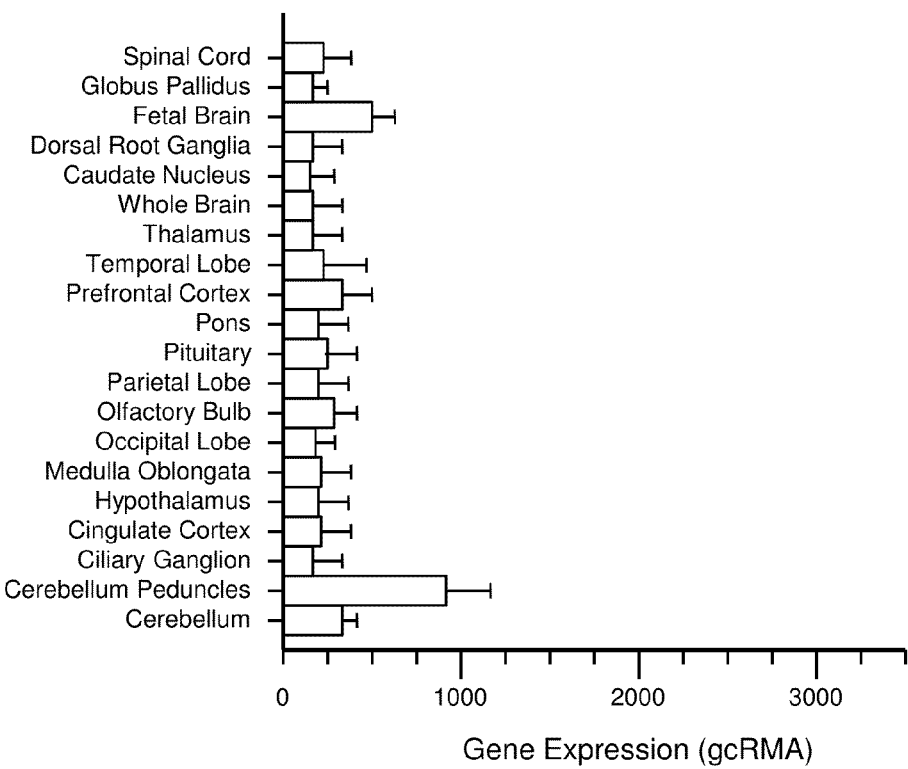
Figure 15B:
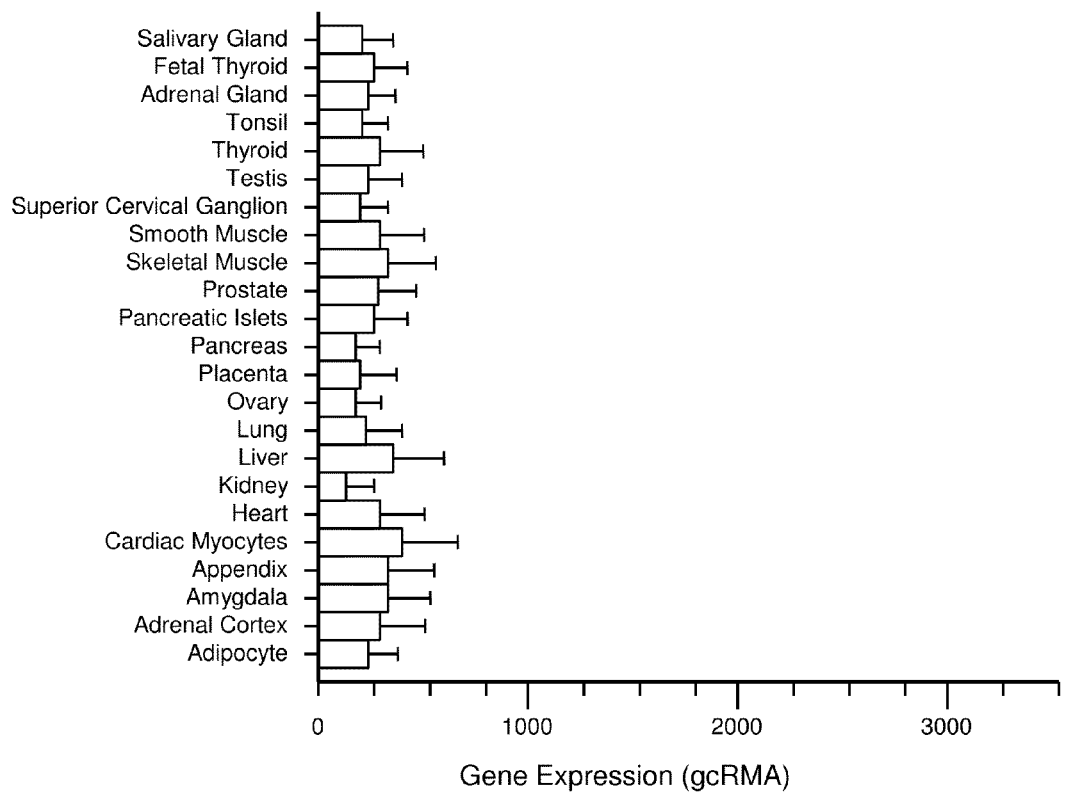

In addition to their role in autoimmune diseases, effector T cells are important in controlling infections. It was decided to further investigate the role of DR3 signaling in toxoplasmosis, an infection in which IFN-γ-secreting Th1 cells are necessary for mice to survive acute infection. After infection with *T. gondii*, DR3 KO as well as control mice had 100% survival for seven weeks. Spleen cells isolated from DR3 KO infected mice at seven weeks post-infection and stimulated with STAg produced comparable amounts of TNF-α, IFN-γ, and IL-10 compared with controls (FIG. 14). These data indicate that the priming and maintenance of effector Th1 cells in response to *T. gondii* is not dependent on DR3.

ii. Experimental Procedures a. Reagents and Mice

LPS from *E. coli* was obtained from Sigma. Soluble Tachyzoite Ag (STAg) was prepared from sonicated *Toxoplasma gondii* tachyzoites, and SEA was prepared from *Schistosoma mansoni* eggs as previously described (Grunvald et al., 1996). C57BL/6 mice were obtained from Jackson Laboratories. DR3 KO mice, generated as previously described (Wang et al., 2001), were back-crossed to the C57BL/6 background for at least eight generations. DR3 KO OT-II mice were generated by crossing DR3 KO mice to OT-II TCR transgenic mice (Taconic farms). IL-2$^{-/-}$ mice were a generous gift from Pushpa Pandiyan, NIAID. All antibodies were purchased from BD Pharmingen unless indicated otherwise. CD1d/PBS57 tetramers that recognize Vα14 iNKT T cells were prepared by the NIH tetramer core facility.

b. Cell Preparation and Purification

Splenic dendritic cells were sorted for high expression of CD11c$^+$ on a MoFlo FACS sorter (Dako Carpenteria, Calif.) from liberase-digested spleens. The purity of CD11c$^+$ DC was at least 97%. T cells were purified from spleen and lymph node cell suspensions by magnetic depletion of CD11b, PanNK, B220, NK1.1, CD24, CD16/32, GR-1, I-Ab using FITC-conjugated mAb to these antigens (BD Pharmigen), and anti-FITC microbeads (Miltenyi). To purify CD4$^+$ T cells, anti-CD8-FITC was added to the above antibodies. For naïve T cells, the CD62L$^+$ CD44$^-$ population of CD4$^+$-purified cells was sorted after staining with PE-Cy5 anti-CD44 and PE anti-CD62L. Bone marrow dendritic cells were generated by culture with RPMI/10% FCS supplemented with 10 ng/ml of murine GM-CSF (PeproTech, Rocky Hill, N.J.). T-depleted APC were obtained by incubating spleen cell suspensions with anti-Thy1.1 for 10 min on ice followed by incubation with low-tox-M rabbit complement (Cedarlane Laboratories) for 30 min at 37° C. Cells were washed and incubated with 25 μg/ml of mitomycin C (Sigma) for 30 min at 37° C.

c. T Cell Activation and Polarization

For costimulation studies, CD4$^+$ or naïve CD4$^+$ cells were stimulated with platebound anti-CD3 mAb (5 μg/ml or at the indicated concentration, 145-2C11; BD Pharmingen) in the presence or absence of plate-bound anti-CD28 mAb (5 μg/ml) (37.51; BD Pharmingen). Recombinant mouse TL1A (R&D systems) was added at 10 ng/ml. For studies with IL2$^{-/-}$ mice, purified T cells were cultured as above, but in the absence or presence of 10 U/ml of IL-2. For DC-T cell co-culture studies, 10$^4$ bone marrow-derived DC were cultured with 10$^5$ OT-II or DR3 KO OT-II naïve CD4$^+$ T cells per well and the indicated concentration of OVA323-339 peptide, with or without 10 μg/ml of mouse CTLA4/Fc (Chimerigen). On day 3, culture supernatants were collected for cytokine measurement, and cells were pulsed with 1 μCi of 3H-thymidine. After an additional 16-20 hours, 3H-thymidine incorporation was measured with a scintillation counter. For polarization studies, 8×10$^5$ T-depleted APC were cultured with 2×10$^5$ naïve CD4$^+$ T cells from C57BL/6 or DR3 KO mice. Th1 polarization was driven with rIL-12 (20 ng/ml) (PeproTech, Rocky Hill, N.J.), and anti-IL-4 (10 μg/ml), Th2 polarization with rIL-4 (20 ng/ml) (PeproTech, Rocky Hill, N.J.), anti-IL-12 (10 μg/ml), and anti IFN-γ (10 μg/ml), Th17 polarization with rhTGFa (5 ng/ml) (eBioscience), IL-6 (20 ng/ml) (eBioscience), anti-IL-12 (10 μg/ml), anti IFN-γ (10 μg/ml) and anti-IL-4 (10 μg/ml), Th0 polarization with anti-IL-12 (10 μg/ml), anti IFN-γ (10 μg/ml) and anti-IL-4 (10 μg/ml). After 4 days of culture, intracellular cytokine staining was performed as described below. For polarization studies with STAg, 5×10$^4$ splenic DC were cultured with 10$^5$ OT-II or DR3 KO OT-II naïve CD4+ T cells per well with 1 μM OVA323-339 peptide. Th1 polarization was driven with rIL-12 (10 ng/ml), Th2 polarization with rIL-4 (10 ng/ml), and STAg polarization with 5 μg/ml STAg. After 72-h culture, supernatants were replaced with fresh medium containing 10 U/ml rIL-2 and, after an additional 2-3 days, intracellular cytokine staining was performed as described below.

d. Induction of Experimental Allergic Encephalomyelitis

Mice were immunized subcutaneously with myelin oligodendrocyte glycoprotein (MOG) 35-55 peptide in CFA with pertussis toxin administrated IP on days 0 and 2 to induce EAE. Five to eight mice were included per group and were scored. Clinical assessment of EAE was performed daily according to the following criteria: (O), no disease; (1), tail paralysis; (2), hind leg weakness; (3), full hind leg paralysis; (4), complete hind limb paralysis plus front limb paraparesis; (5), death. Cells from the CNS were isolated using the Neural Tissue Dissociation Kit from Miltenyi Biotec according to the manufacturer's recommended protocol. Spleen cells from MOG-sensitized animals were isolated using CD4 beads. The cells were restimulated in the presence of irradiated T-depleted splenocytes as APC and the indicated concentrations of MOG peptide in 96-well plates. On day 3, the cells were pulsed with $^3$H-thymidine for 6 h and then harvested and counted on a scintillation counter.

e. Ova-Induced Lung Inflammation

On days 0 and 7, mice were sensitized systemically via a 200-μl intraperitoneal (i.p.) injection containing either 100 μg Chicken Ova (Sigma) or PBS emulsified in an equal volume mixture with alum (Pierce Laboratories, Rockford, Ill.). For assessment of pulmonary inflammation, mice were challenged with 100 μg Ova or PBS/30 μl inoculum intratracheally (i.t.) on day 14 and intranasally (i.n.) on day 15. Mice were euthanized 48-72 h after the final challenge to evaluate cell infiltration, cellular inflammation in the lung, and cytokine levels in the sera and bronchoalveolar lavage fluid (BALF). BAL fluid was obtained by direct cannulation of the lungs with a 20-gauge intravenous catheter and lavage with 500 μl 1% fetal bovine serum (FBS) in PBS (for cytokine analysis) and with 750 μl 1% FBS in PBS (for analysis of cellular infiltration). Samples for cytokine analysis were stored at −80° C. Samples for cellular analysis were prepared as a cytospin (Thermo-Shandon, Pittsburgh, Pa.) for differential cellular analysis after staining with Kwik-diff (Thermo-Shandon), and a portion was used to determine total cell counts. Lung histology was scored by a reader with experimental conditions masked as described previously (McConchie et al., 2006)

f *Toxoplasma* Infection

*T. gondii* cysts from the ME-49 strain were prepared from the brains of infected C57BL/6 mice. For experimental infections, mice were inoculated i.p. with an average of 20 cysts/animal. At 7 weeks post-infection, the number of cysts in the brain of individual infected animals was determined. Spleen cells were harvested, cultured, and stimulated with either anti-CD3 and anti-CD28 or 5 μg/ml STAg. Supernatants were harvested after 72 h and analyzed for cytokine production.

g. Cytokine and Immuno Globulin Measurement

Detection of IFN-γ-, IL-4-, and IL-17-producing cells was determined by intracellular cytokine staining using anti IFN-γ-APC, anti IL-4-PE, anti-IL-17-PE (BD Biosciences). Briefly, cells were stimulated for five hours with anti-CD3 and anti-CD28 or phorbol myristate acetate and ionomycin, with monensin added after two hours. Cells were fixed in 3% paraformaldehyde, permeabilized in 0.1% saponin, and analyzed on a FACS Calibur flow cytometer (Becton Dickinson). Cytokine production in cell culture supernatants was analyzed by Cytometric Bead Array (BD Biosciences). Serum immunoglobulins were measured by ELISA following the manufacturer's instructions (Bethyl Labs), and OVA-specific IgG1 and IgE were measured by IgG1- or IgE-specific ELISA using plates coated with 50 μl OVA (100 μg/ml).

h. TL1A Induction in Dendritic Cells and T Cells

Bone marrow-derived DC, or splenic CD11c$^+$ DC from C57BL/6 mice and the indicated knock-out mice were cultured and stimulated for the indicated time with or without 100 ng/ml LPS, 20 μg/ml SEA or 10 μg/ml STAg. Stimulation with Ig cross-linking was performed by coating plates with 0.5 mg/ml mouse IgG (Jackson Immunoresearch) for 1 h at 37° C., followed by 50 μg/ml sheep anti-mouse IgG (Jackson Immunoresearch) for 1 h at 37° C. Purified T cells were stimulated with 5 μg/ml anti-CD3 and anti-CD28 for the indicated time.

i. Measurement of RNA by Quantitative RT-PCR

Total RNA was isolated from cells using TriZOL and the pure Link™ Micro-to midi kit (Invitrogen). Quantitative RT-PCR was performed using an ABI PRISM 7700 sequence detection system using SuperScript One-Step RT-PCR System (Invitrogen). Pre-designed Primer/probe sets were from Applied Biosystems with the exception of TL1A, which was detected with primers designed to recognize full-length TL1A (forward: CCCCGGAAAAGACTGTATGC; reverse: GGTGAGTAAACTTGCTGTGGTGAA; probe: TCGGGC-CATAACAGAAGAGAGATCTGAGC). Probes specific for β2-microglobulin or CD3-δ were used as internal controls.

3. Example 3

TL1A-Induced Inflammatory Bowel Disease

To evaluate the function of TL1A, transgenic mice were generated in which TL1A is constitutively expressed on dendritic cells and T cells. For T cells, an improved version of the human CD2 enhancer construct (Zhumabekov, T., et al. 1995) was used, and for dendritic cell-specific expression, a CD11c promoter construct was used (Brocker, T., et al. 1997). An Influenza Hemagglutinin (HA) epitope tag was added to the N-terminus of the TL1A cDNA for identification of trans-gene-derived TL1A mRNA and protein. Transgene expression was assessed in each founder line of transgenic mice. For the CD2-TL1A construct, four lines (R1, R6, U8, and Z9) had similar detectable levels of TL1A expression in the spleen and lymph node T cells assayed by intracellular flow cytometry for the HA tag in T cells gated on CD3, with no HA staining detected in other immune cell subsets, and were used in subsequent analysis. For the CD11c-TL1A transgenic mice there was a wider range of expression. Transgene expression relative to endogenous TL1A ranged from 2 to over 500-fold, and founders were divided into high and low expressers based on a cutoff of 8-fold overexpression. Increased numbers of CD69$^+$ T cells were present in spleen and lymph nodes from both CD2 and CD11c TL1A transgenic lines. Spontaneous T cell activation was more prominent in CD4 than CD8 T cell subsets. These results indicate that deregulation of TL1A in either T cells or DC results in spontaneous T cell activation and disruption of T cell homeostasis.

Figure 21A:
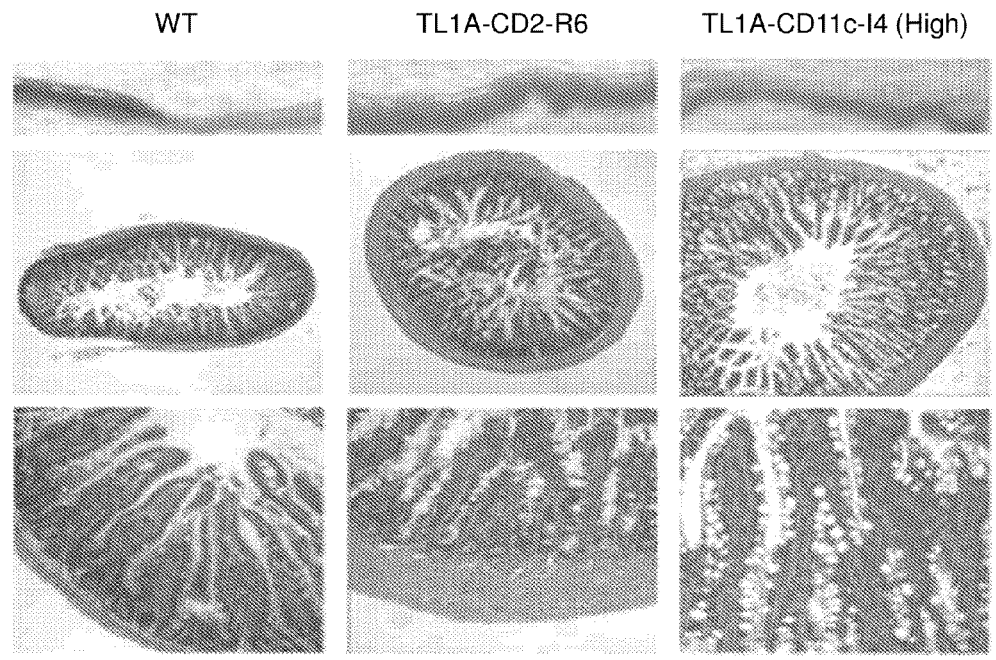
FIGS. 21A-21E show inflammatory bowel disease in TL1A transgenic mice.
Figure 21B:
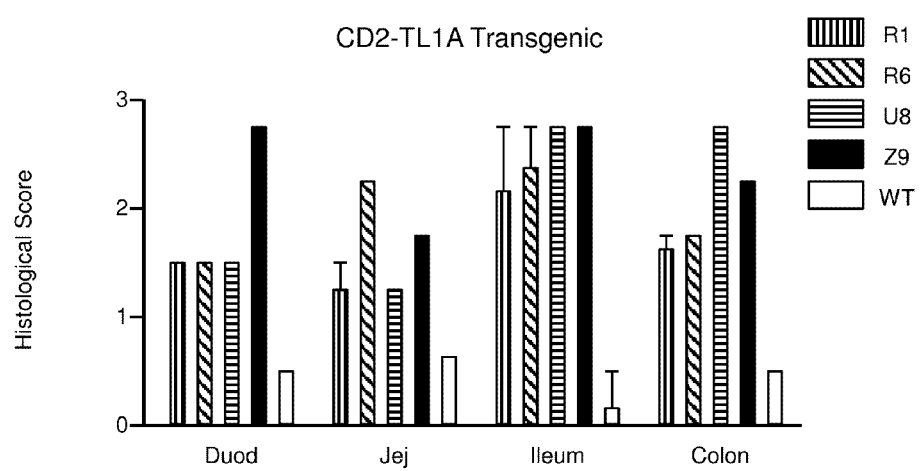
Figure 21C:
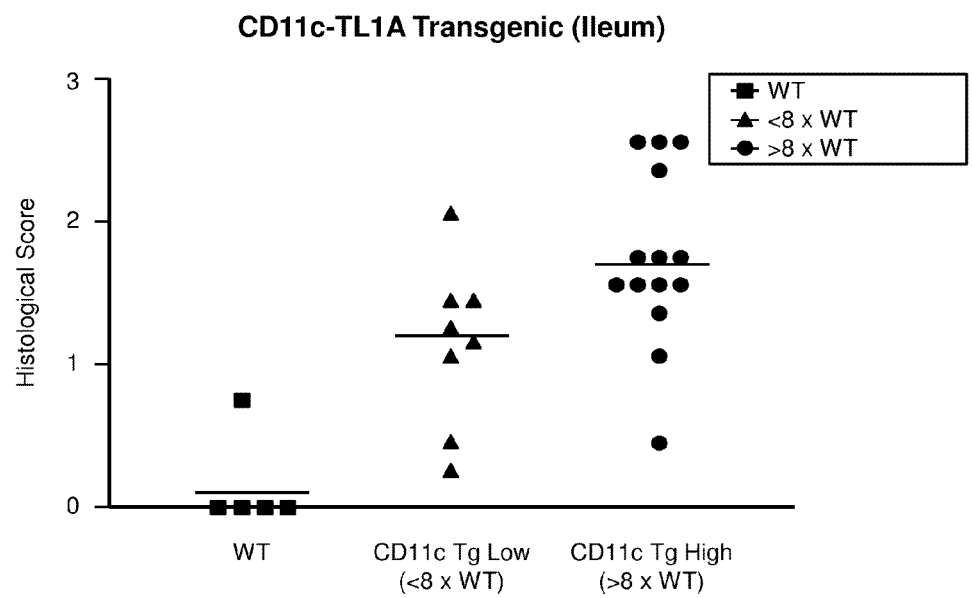
Figure 21D:
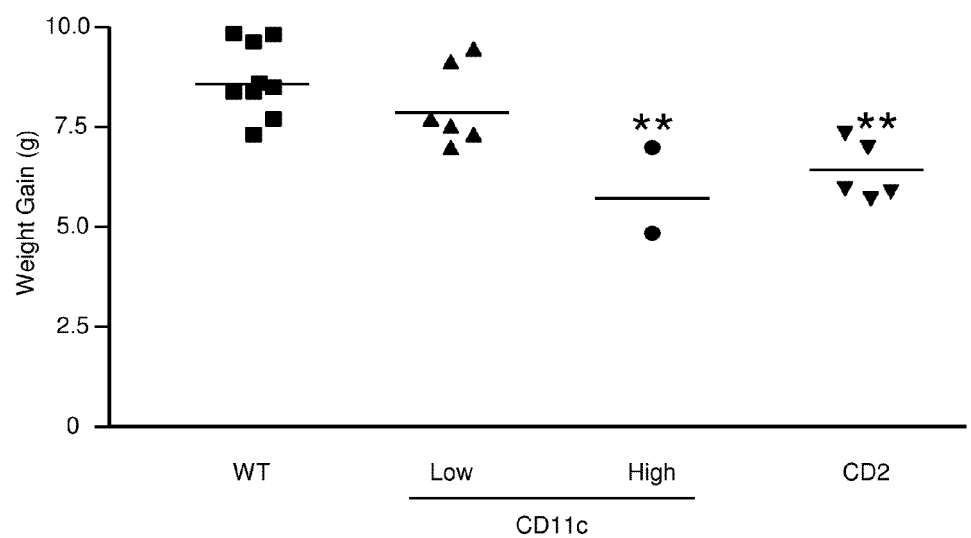

On further inspection of transgenic mice from both CD11c-TL1A and CD2-TL1A lines, frequent bowel edema and evidence of bowel wall thickening throughout the small bowel were observed. Incidence of these features was virtually 100% in the four lines of CD2-TL1A transgenic mice under study and correlated with the level of transgene expression in the CD11c-TL1A lines. Bowel wall thickening, inflammatory infiltrates, goblet cell hyperplasia, enlargement of villi, and distortion of normal architecture can be seen (FIG. 21). These changes were quantitated by an experienced observer blinded to the status of the mice according to a scoring scheme developed for TNBS colitis that encompasses inflammatory cell infiltrates, elongation and destruction of villi, crypt abscesses, and thickening of the muscularis layers (Neurath, M., et al. 2000) (FIG. 21). The terminal ileum was most prominently involved on both gross inspection and histopathology in both CD11c and CD2-TL1A transgenic mice, with the colon relatively spared (FIG. 21B, C). Intestinal inflammation was associated with weight loss in these mice, again dependent on the level of transgene expression (FIG. 21C).

These observations establish TL1A transgenic mice as a new animal model of inflammatory bowel disease, with some features strikingly similar to human Crohn's disease, including transmural inflammation and a predilection for the terminal ileum. Interestingly, a number of recent reports describe increased expression of TL1A and DR3 in the lamina propria of biopsy specimens of patients with ulcerative colitis or Crohn's disease. Increased TL1A and DR3 expression was also noted in two other animal models of IBD, the SAMP1/YitFc and $TNF^{\Delta ARE}$ strains (Bamias, G., et al. 2003; Bamias, G., et al. 2006). Taken together with the discovery that deregulated TL1A expression provokes spontaneous IBD in transgenic mice, TL1A-DR3 interactions can be important in the pathogenesis of IBD and constitute a promising therapeutic target in IBD and related inflammatory diseases with a T cell component, including Rheumatoid Arthritis.

i. Characterization of the Pathogenic Cell Types and Role of Gut Flora in TL1A-Driven IBD.

Immunohistochemical and immunofluorescence studies are carried out on tissue sections from selected CD2-TL1A and CD11c-TL1A transgenic mice. Initial studies localize T cells with anti-CD3 and macrophages with F4-80 by immunostaining frozen sections of intestine from TL1A transgenic mice. FACS analysis is performed on intraepithelial and lamina propria lymphocyte preparations from involved areas of bowel from TL1A transgenic mice. $\alpha\beta$, $\gamma\delta$, and NKT cells are enumerated along with NK cells and B cells, and activation status is examined with CD25, CD69, and CD71 surface markers. FoxP3+CD25+Tregs are also enumerated in these samples to determine whether there is an attempt at immune counter-regulation through Treg, as has been seen in other models of T cell-driven immunopathology (Tang, Q., et al. 2006). Although T cells are the main cell type expressing the TL1A receptor DR3, TL1A expression has been found in NKT cells, NK cells, and B cells. Thus, enforced TL1A can expand other immune cell subsets that could mediate IBD in these mice. To determine which lymphocyte subsets are required for TL1A-driven colitis, TL1A transgenic mice are crossed to various lines of knockout mice which lack different lymphocyte subpopulations. TL1A transgenic mice are first crossed to RAG-deficient mice to determine dependency on T, B, and NKT cells. If these mice lack inflammatory bowel disease, then the dependence of TL1A-driven IBD has been shown on the adaptive immune system. Other crosses are then performed to determine the requirement for $\alpha\beta$ T cells (TCR alpha knockout), NKT cells (CD1d knockout), NK cells (IL-15 knockout), and B cells (IgH knockout) mice. If $\alpha\beta$ T cells are found to be required for IBD in TL1A transgenic mice, then the contribution of different T cell subsets can be examined through crossing CD2-TL1A transgenic mice to Class I or Class II MHC-deficient mice, which lack CD8 and CD4 T cells, respectively. If T cells are implicated, IBD could result from non-antigen-specific costimulation by TL1A or, alternatively, specific T cell reactivates (i.e. to gut-derived antigens) could be required for disease induction. To test this, TL1A mice are crossed with TCR transgenic mice bearing irrelevant specificities such as OT-II ovalbumin-specific TCR transgenic mice. If autoreactive or gut flora-reactive T cells are necessary for TL1A-driven IBD, then these TCR transgenes can ameliorate disease.

ii. Characterization of the Pathogenic Cytokines in TL1A-Driven IBD.

Figure 21E:
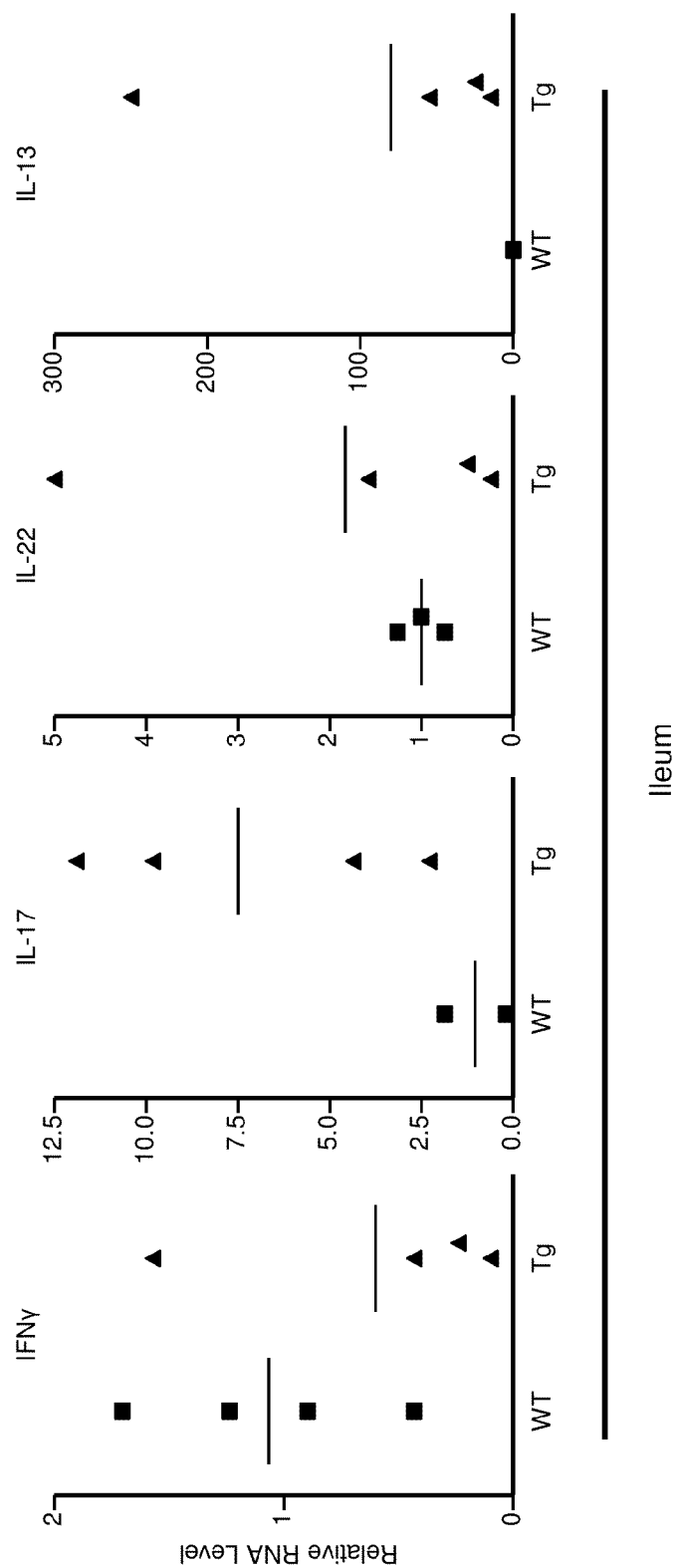
Figure 22:
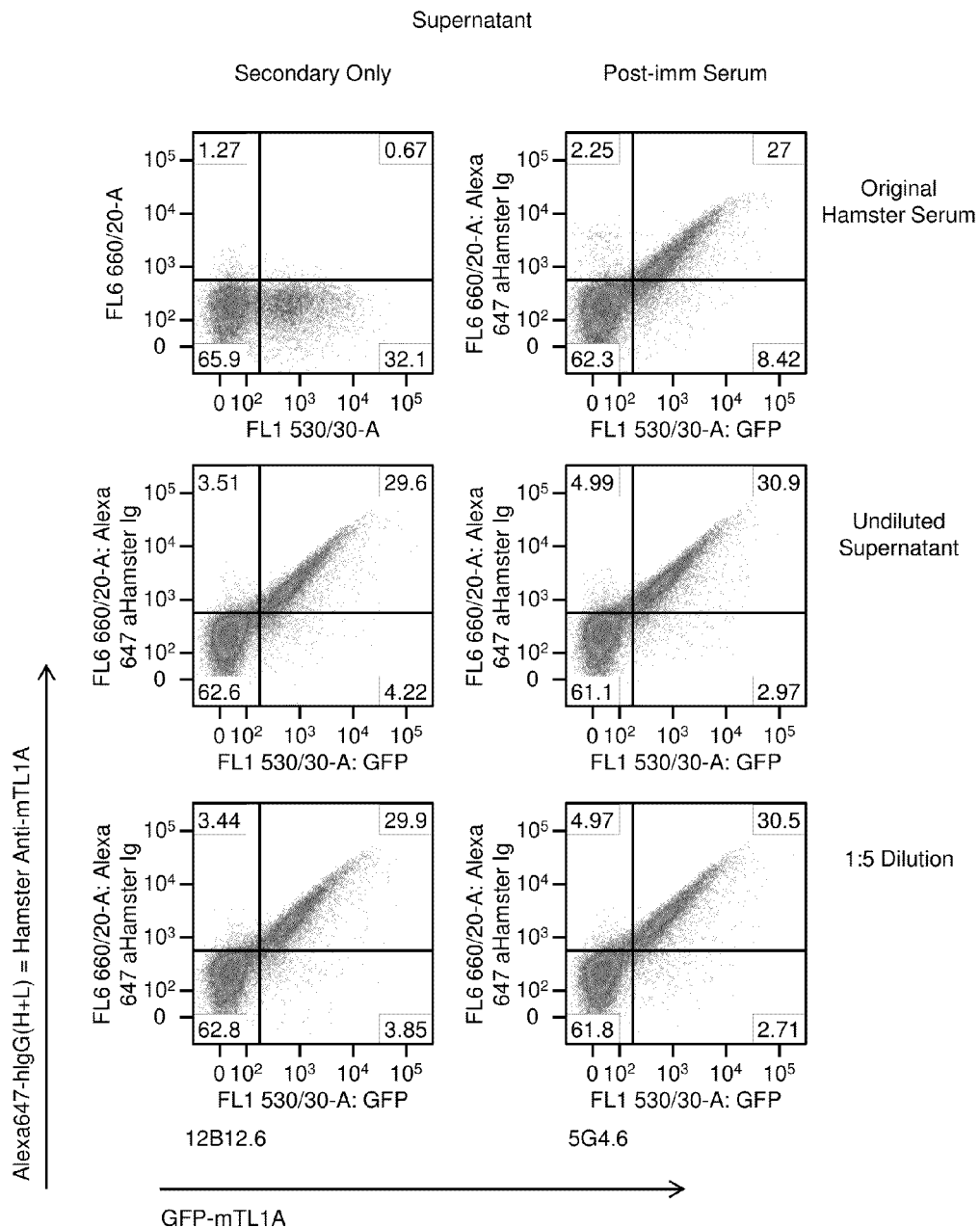
FIG. 22 shows the screening strategy for anti-TL1A antibodies using 293T cells transfected with TL1A fused with Green Fluorescent Protein (GFP). An example is shown from the screening of antibodies against murine TL1A (mTL1A). Armenian Hamsters were immunized with murine recombinant TL1A. Hybridomas were screened by flow cytometry with 293T cells transfected with murine TL1A. An example is shown for a positive clone. Also shown is an example staining of mTL1A by the indicated quantities of the two clones selected for further analysis is shown. The same strategy with 293T cells expressing human TL1A was used for screening hybridomas from mice immunized with human recombinant TL1A to select anti-human TL1A clones 1A9 and 106, which are mIgG2a kappa isotype antibodies.
Figure 22:
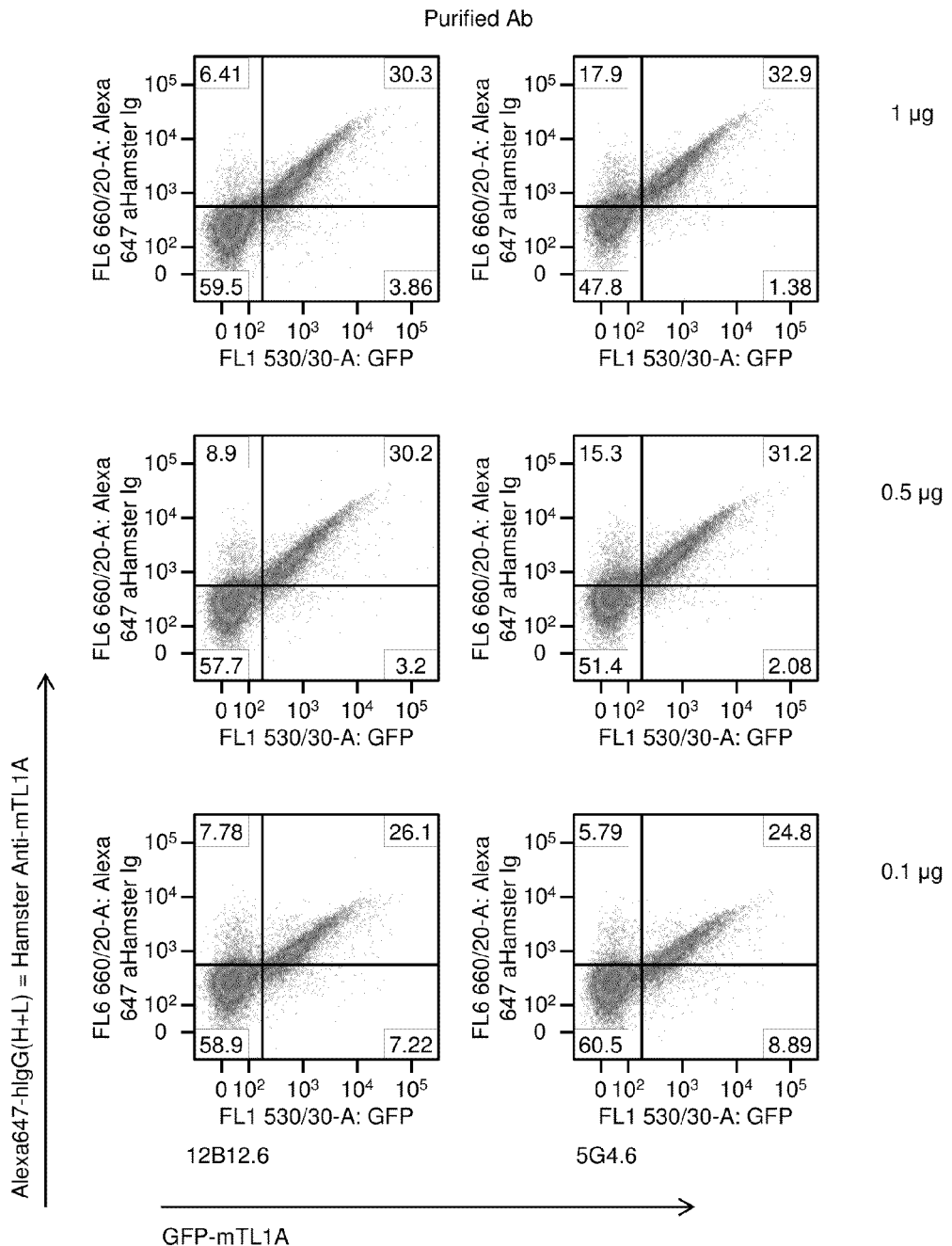
Figure 22:
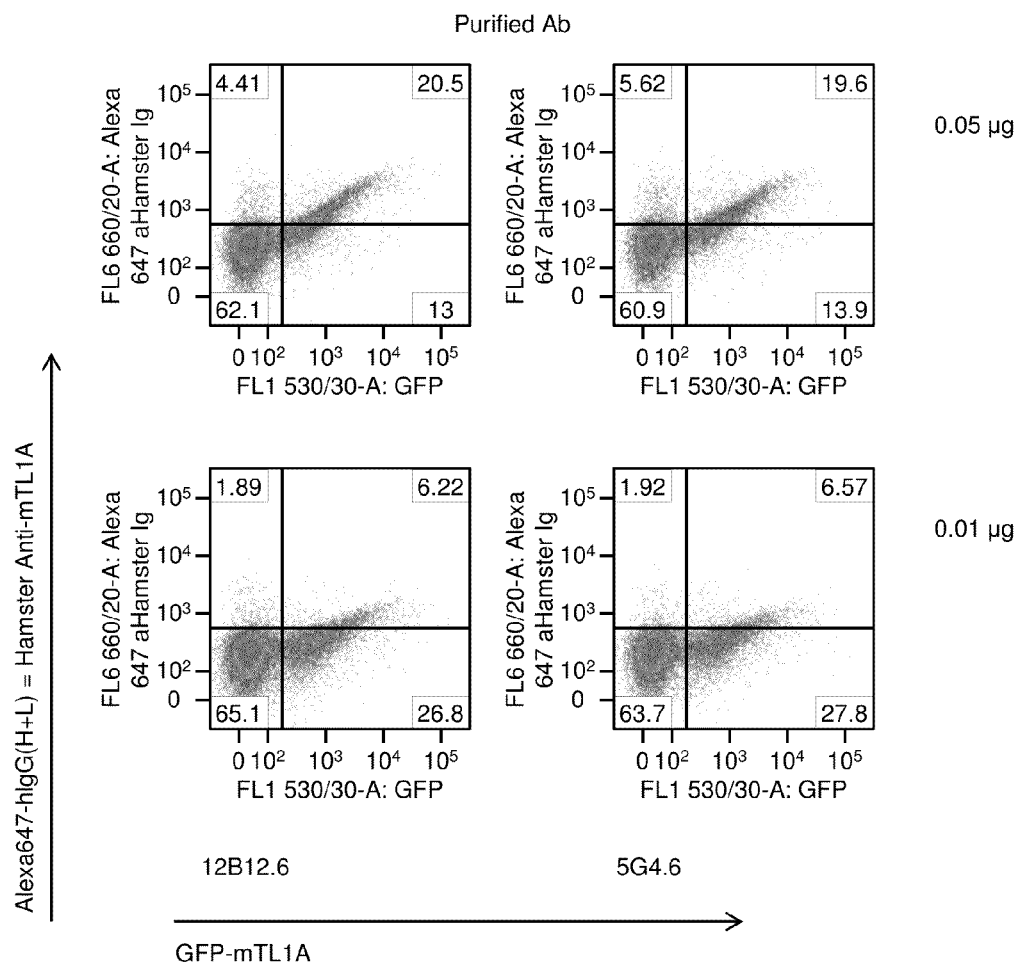
Figure 23:
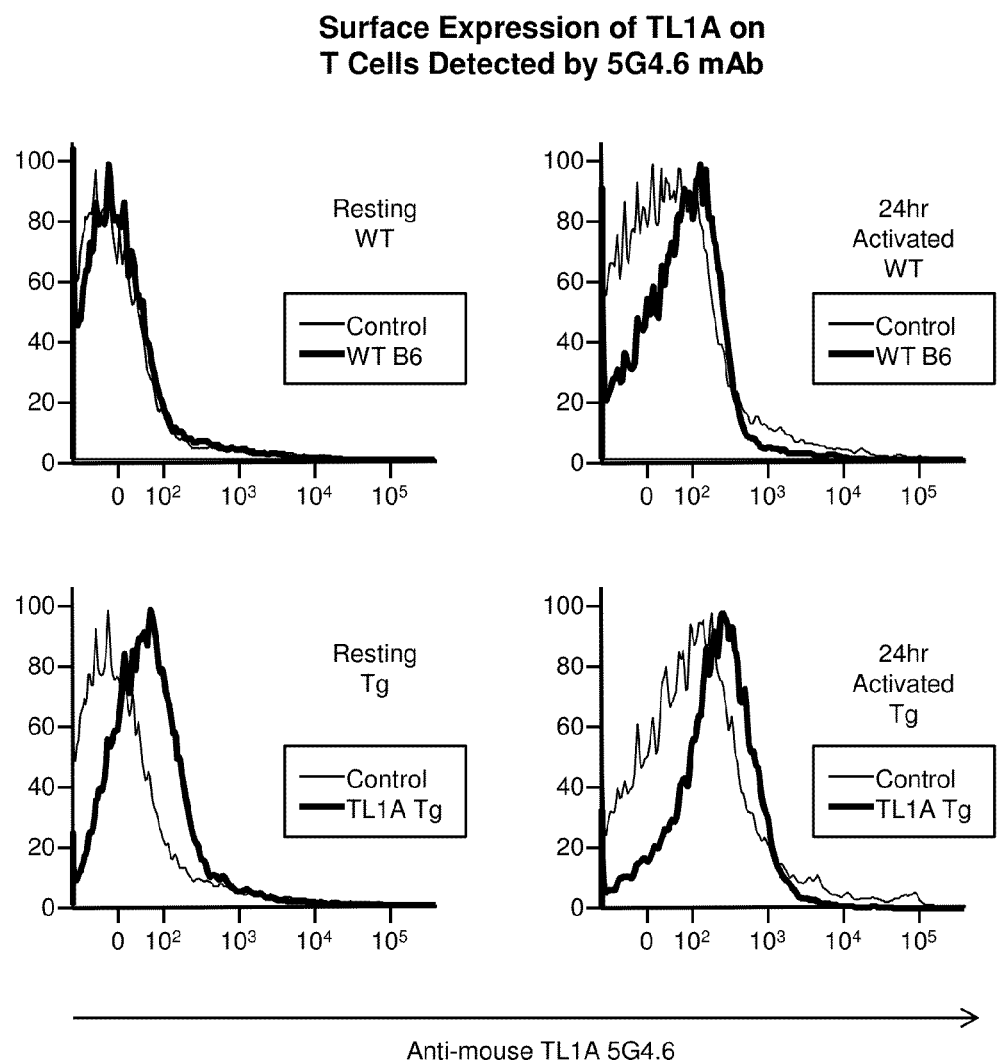
FIG. 23 shows wild-type or TL1A transgenic (Tg) mouse T cells activated with anti-CD3/anti-CD28 for 24 hours and then stained with anti-TL1A mAb 5G4.6 to demonstrate recognition of surface TL1A by this mAb on the indicated cell types (as indicated in the legend). The grey shaded plots represent background levels of fluorescence using hamster Ig as a control staining reagent.
Figure 24:
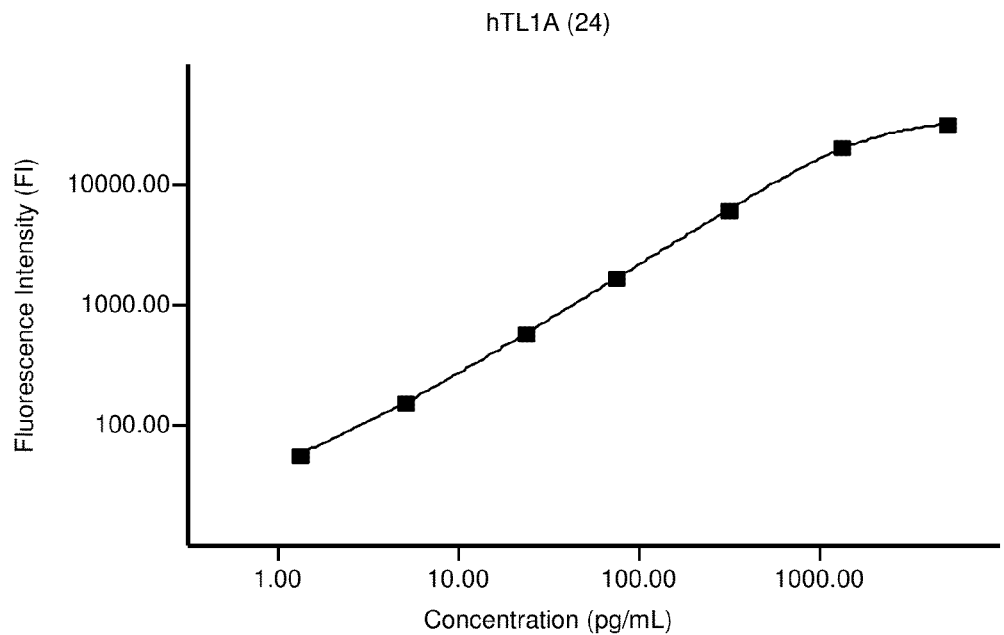
FIG. 24 shows the sensitivity curve for a bead-based assay for detection of human TL1A in body fluids and culture supernatants using anti-human TL1A mAb 1A9.
Figure 25:
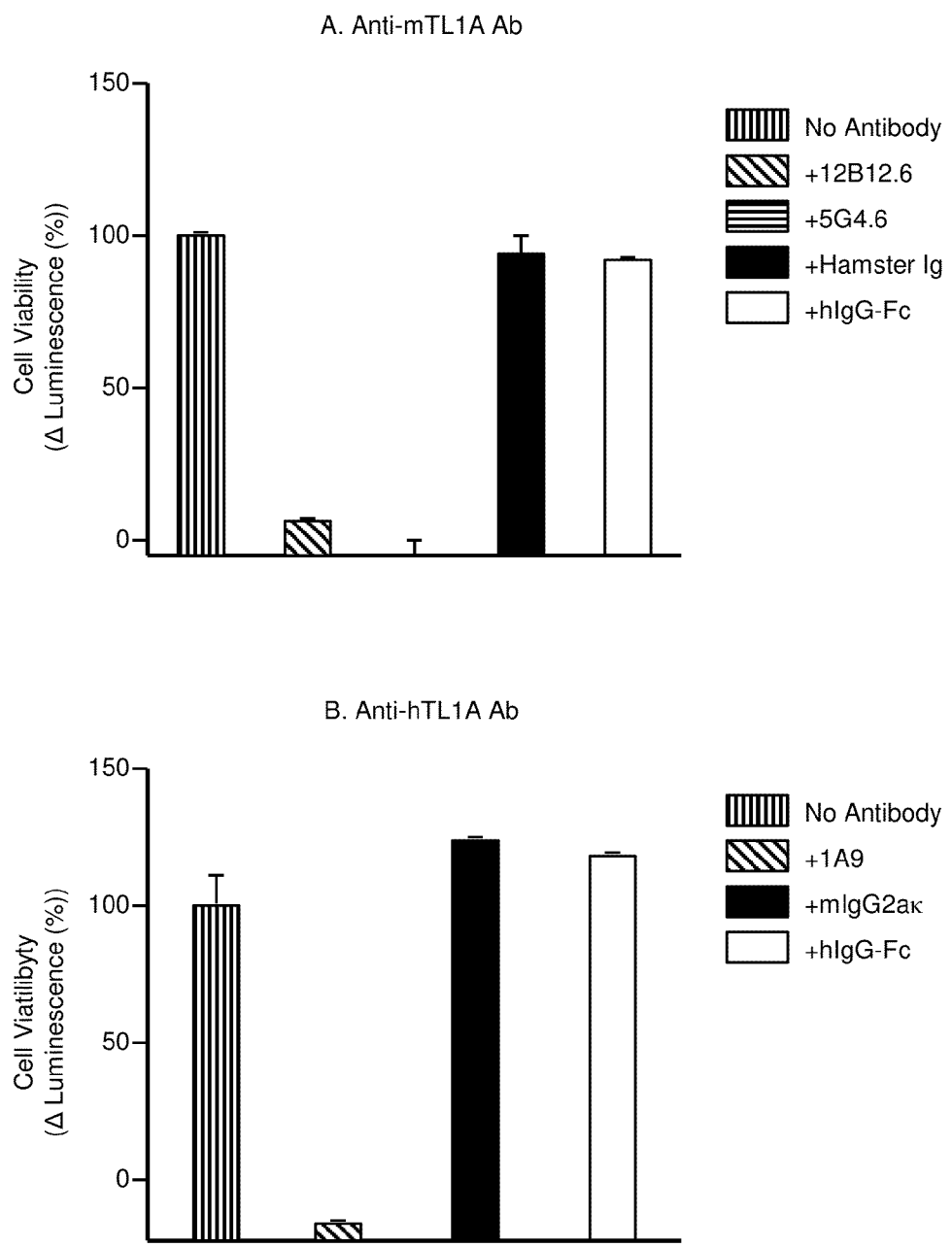
FIG. 25 shows anti-TL1A mAb blocking cell death mediated by mouse and human TL1A in TF-1 cells in a species-specific manner. TF1 erythroleukemia cells treated with murine (A) or Human (B) TL1A+Cycloheximide (CHX) in the presence of the indicated mAb are shown. Cell viability was measured by the Promega CellTiter-Glo® ATP reagent. A change in luminescence indicates cell death, a known response to TL1A+CHX in these cells. Reduction in the change in luminescence indicates blockade of TL1A action by the mAb. These mAb were also shown not to cross-react between human and mouse TL1A.
Figure 26:
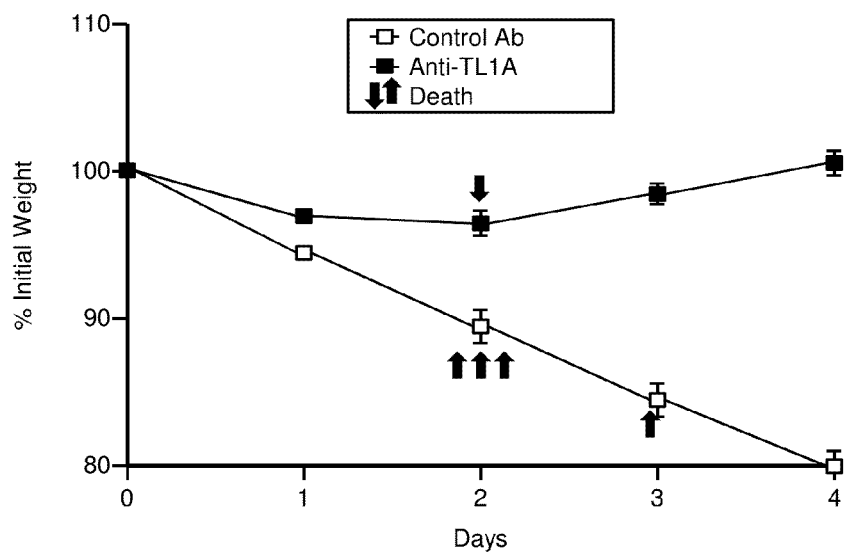
FIG. 26 shows prevention of TNBS colitis with anti-mouse TL1A mAb. Panel A) Weight loss in a cohort of mice induced to develop TNBS colitis with intra-rectal administration of trinitro-benzene sulphonic acid (TNBS) at day 0.10 mg/kg anti-TL1A mAb 5G4.6 or control hamster IgG was injected i.p on days −1 and 0. Each point represents the average weight of the cohort. Mice that died before the end of the experiment are indicated with arrows. Data is representative of two independent experiments with a minimum of 8 mice per group. Panel B) Representative H&E sections of the colon from mice induced to develop TNBS colitis treated with control or anti-TL1A mAb as in (A). The control Ab-treated mouse showed area of severe inflammation. Left panels are 50×, and right panels 200×, enlargements of the same sections. Average pathology scores of the mice in (A) at day 6 after induction of colitis are indicated.
Figure 26:
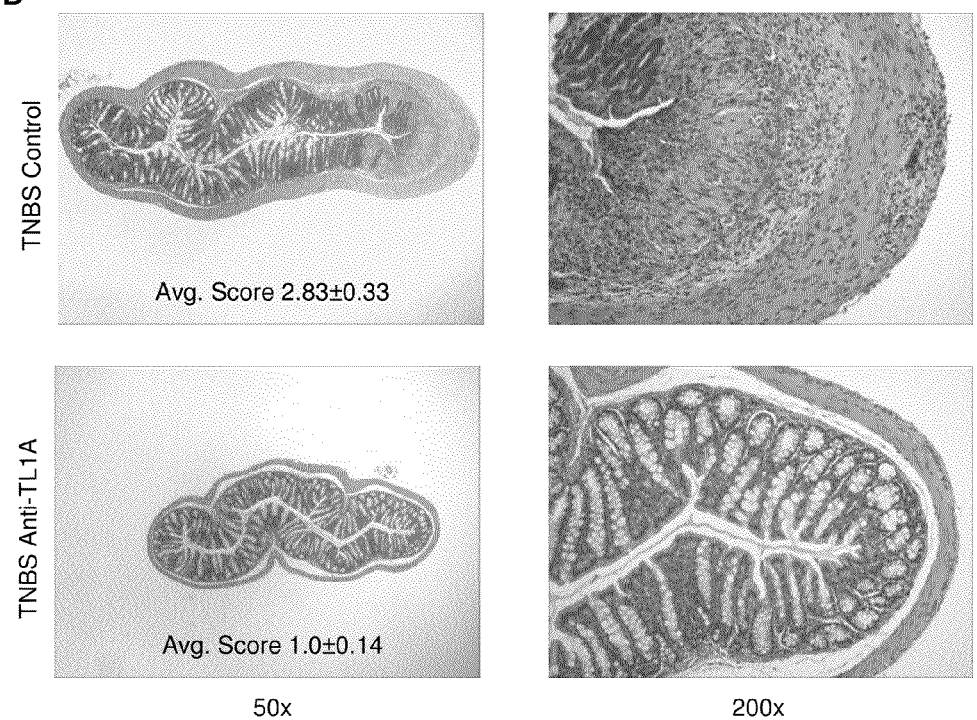
Figure 27:
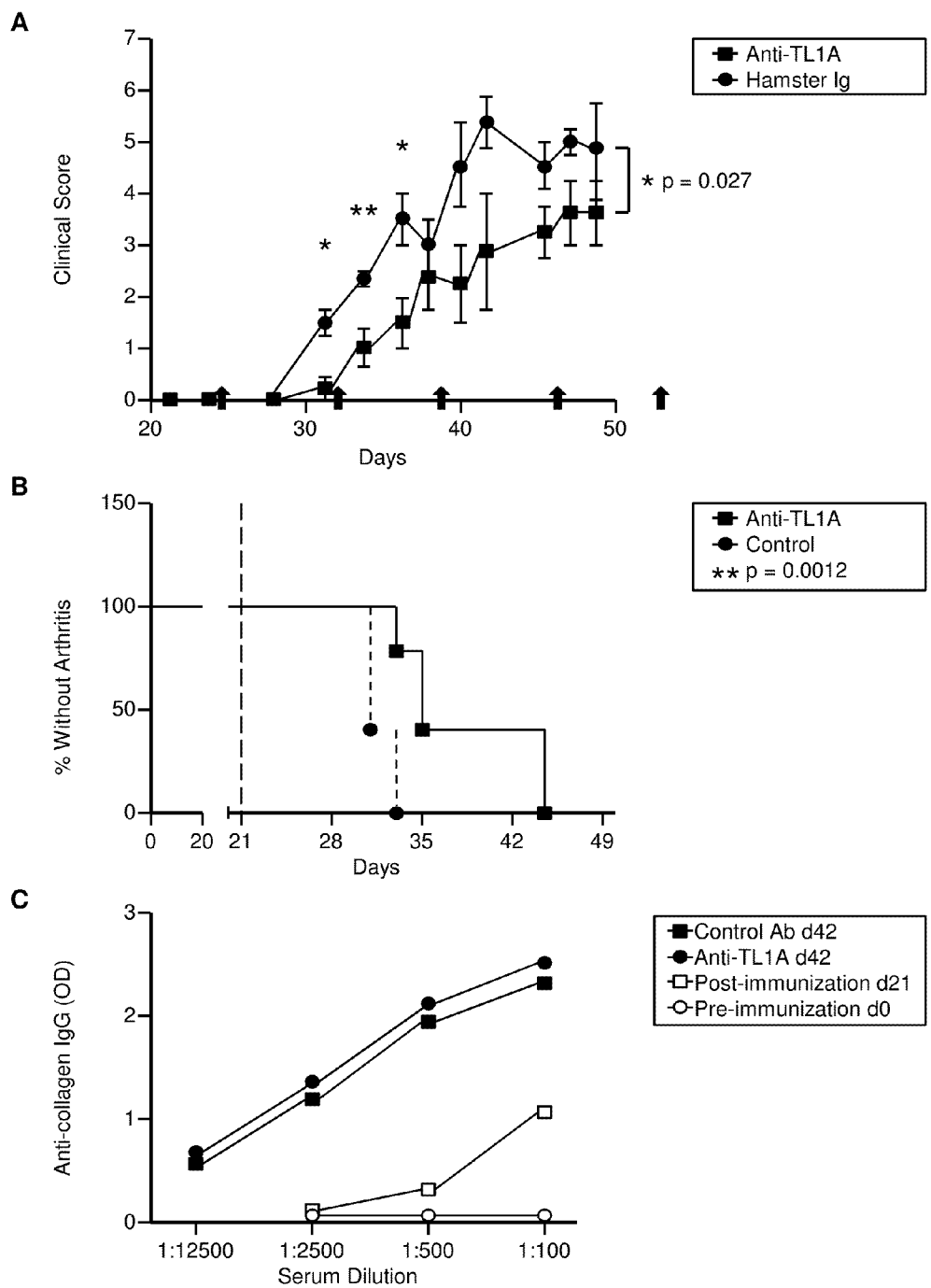
FIG. 27 shows prevention of Collagen-Induced Arthritis (CIA) by anti-mouse TL1A mAb 5G4.6. Panel A. CIA was induced in DBA/1 mice by standard methods. Weekly intra-peritoneal injections of 20 mg/kg of either anti-TL1A mAb 5G4.6 (treatment, n=5) or hamster immunoglobulin (control, n=7) were begun at day 21 after initial immunization with collagen. Representative results of three independent experiments are shown. Clinical scores on each day were compared using an unpaired t-test, and p values for significance are shown above each time-point represented by asterisks (*=p<0.05, **=p<0.005) above each date. 2-way ANOVA was also performed to compare the trend of the two graphs, with p values shown to the right of each experiment. Panel B. Survival analysis of the percentage of mice without arthritis on each day is compared between the anti-TL1A-treated group and the control group. Arthritis was defined by a combined clinical score of two or more. Panel C. Sera from mice from each group induced to develop CIA as in panel A were collected at indicated time points and anti-chicken collagen IgG levels were measured by ELISA.
Figure 28:
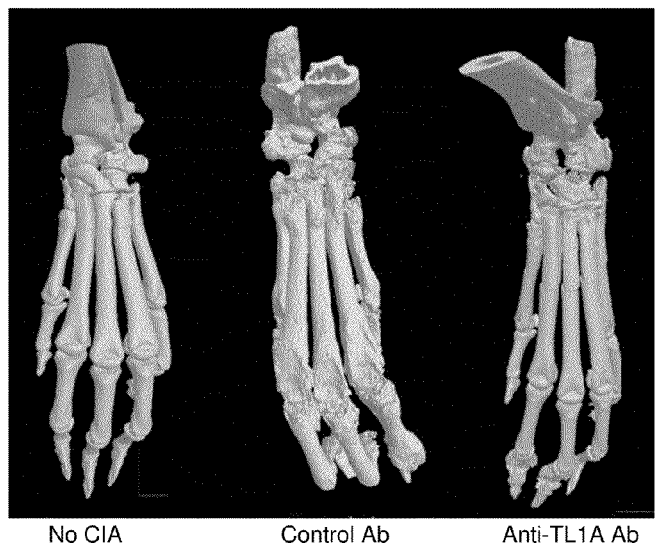
FIG. 28 shows that blocking TL1A with anti-mouse TL1A mAb 5G4.6 reduces bony erosions independently of joint scores in CIA. Panel A) Hind paws from mice induced to develop CIA as described below were harvested and fixed in 10% formaldehyde. Paws were scanned by micro-CT and images reconstructed as described below. Examples are shown from each treatment group, with the maximum clinical scores and the erosion score obtained for that paw by two separate observers blinded to treatment groups. Panel B) Erosion scores obtained by two separate observers blinded to clinical scores were averaged for each sample. Shown here is the composite of the scores from the anti-TL1A mAb 5G4.6-treated group (n=18) and control antibody-treated group (n=20), with the p value from an unpaired t-test with Welch's correlation (*p=0.05). Analysis of individual regions resulted in p values of 0.078 at ankle/tarsus, 0.042 at metatarsophalangeal (MTP) joints, and 0.015 at toes. Panel C) Comparison of the CT scores of the paws from the two groups based on the maximum clinical scores. Anti-TL1A mAb treatment significantly reduced erosions independent of the clinical score. P<0.0001 using 2-way ANOVA (***p<0.0001).
Figure 28:
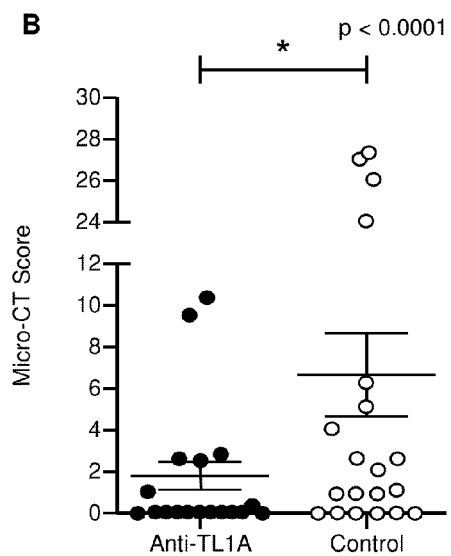
Figure 28:
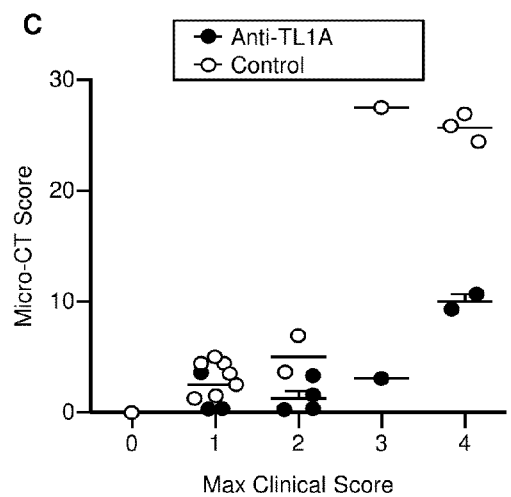

Inflammatory bowel disease models have been found to depend on a wide variety of different cytokines (Strober, W., et al. 2007). Initially, interest focused on interferon-$\gamma$ and IL-12 and, indeed, antibodies against the p40 subunit of IL-12 are effective in human inflammatory bowel disease and mouse IBD models. More recently, it has been discovered that p40 is a component of IL-23, an IL-12 family cytokine that has been shown to be critical in inflammatory bowel disease. IL-23 acts at least in part through enhancing the differentiation and/or survival of T cells producing IL-17, a cytokine that potently attracts and activates neutrophils and monocytes (Fuss, U., et al. 2006; Hue, S., et al. 2006; McKenzie, B. S., et al. 2006). Experiments have been conducted to determine the predominant cytokines expressed in TL1A-induced IBD to determine which effector cell populations are critical in this disease and to better understand the effects of chronic TL1A stimulation. Quantitation of cytokines from RNA extracted from ileum and other regions of the intestines in TL1A transgenic mice revealed consistent elevation of IL-17 and IL-13 (FIG. 21E). Interestingly, IL-22, another cytokine produced by the Th17 subset of T cells, was not detectable, and IFN-$\gamma$, the characteristic product of Th1 cells, was also not elevated over controls. Examination of T cells in the mesenteric lymph nodes revealed that IL-17-producing T cells were the most elevated over controls compared with IFN-$\gamma$ and IL-4. Blocking anti-cytokine antibodies or knockout mice in genes known to be critical for development of particular T cell subset (e.g. IL-17, STAT4, STAT6, ROR-$\gamma$) can then be used to determine which of the cytokines and Th cell subsets are required for the development of TL1A-driven IBD.

iii. Determination of Whether TL1A Blocks Regulatory T Cell Function or Renders T Cells Resistant to Treg.

Whether TL1A affects the generation or function of natural Tregs is not known. In rheumatoid arthritis, the related cytokine TNF was shown to impair the function of FOXP3+ regulatory T cells independent of their numbers (Nadkarni, S., et al. 2007; Valencia, X., et al. 2006). FOXP3-positive Tregs are present in normal numbers in DR3 knockout mice and, interestingly, are present in increased numbers in the mesenteric lymph nodes of TL1A transgenic mice. To aid in the isolation of Tregs from TL1A transgenic mice, which have increased numbers of activated CD25+ T cells, selected lines of TL1A transgenic mice are crossed with FOXP3-GFP reporter mice to make sure that only FOXP3-positive Tregs are studied in these experiments. Tregs isolated from TL1A transgenic mice are assayed for their function, and it also is tested whether TL1A can block the suppressive function of normal Tregs through the use of CD2-TL1A transgenic responder cells (Tresp) and the addition of TL1A to Treg/Tresp cultures. In vivo assays of Treg function are also performed, in which Tregs are transferred with naïve CD45RB-hi cells into immunodeficient hosts (Powrie, F., et al. 1993). Reciprocal experiments are carried out with either Treg or naïve T cells derived from CD2-TL1A transgenic mice to determine whether Treg function or the ability of naïve T cells to cause IBD is influenced by TL1A.

iv. Requirement for TL1A-DR3 Interactions in the Development of IBD.

It is also determined whether DR3 is required for the development of colitis in the absence of transgene-derived TL1A. The colitis induced by intrarectal administration of the hapten TNBS has been extensively characterized. It is known that colitis requires T cells, and is also dependent on TNF and IL-12p40 (Neurath, M., et al. 2000; Neurath, M. F., et al. 1997). Recent evidence has also implicated the IL-23 target cytokine IL-17 in pathogenesis of this experimental disease (Zhang, Z., et al. 2006). Resistance to EAE and Ova-induced asthma indicates that DR3-deficient mice can be resistant to TNBS colitis compared with littermate controls. To do these experiments, DR3 KO mice are backcrossed onto the susceptible C57Bl/10 strain. Alternatively, while backcrossing is in progress, susceptible mice are treated with TL1A blocking antibodies prior to or after induction of TNBS colitis. DR3-deficient T cells are also transferred into immunodeficient hosts in the transfer model of colitis to determine if DR3 on T cells is necessary in this model of colitis.

Example 3

TL1A has been detected in rheumatoid synovium. We used novel monoclonal antibodies against human TL1A to determine the factors that induce TL1A and the specificity of elevated TL1A levels in the synovial fluid (SF) or blood for RA versus other rheumatic diseases. In the mouse collagen-induced arthritis (CIA) model, we blocked TL1A-DR3 interactions with neutralizing antibodies against TL1A and measured the effects of TL1A blockade on anti-collagen antibodies, clinical joint inflammation, and erosions by micro CT. TL1A was induced by Fc receptor crosslinking and, to a lesser extent, by plasma membrane TLR in human monocytes. Significantly higher blood and SF levels of TL1A were seen in patients with RA compared to other rheumatic diseases. Plasma TL1A was predictive of SF TL1A levels. However, SF TL1A was elevated independently of TNF and disease activity in RA patients. TL1A blockade was efficacious in reducing clinical joint scores in CIA and dramatically reduced bone erosions independently of effects on paw swelling. TL1A is important in both human and mouse autoimmune arthritis, especially in the pathogenesis of erosions. We disclose TL1A blockade as a potent disease-modifying treatment for RA that acts independently of TNF.

Monocyte Cell Culture and Stimulation

Elutriated monocytes from normal donors were obtained from the NIH transfusion medicine department under NIH IRB-approved clinical protocols. Monocytes were cultured at $1\times10^6$ cells/ml in RPMI medium with 10% FCS in a 37° C., 5% $CO_2$ incubator. At specified time points, culture supernatant was collected for measurement of TL1A, and cells were harvested for qRT-PCR for measurement of TL1A mRNA. LPS (Ultrapure *Salmonella* Minnesota R595, List Biological Laboratories inc., Campbell, Calif.) was added at the indicated concentrations. Stimulation with immune complexes was performed as previously described. Quantitative RT-PCR was performed with the use of an ABI PRISM 7700 sequence detection system with qScript One-Step qRT-PCR Kit, Low ROX (Quanta BioSciences, Inc.). Predesigned primer/probe sets were from Applied Biosystems, and the sequences designed to detect full-length TL1A are forward: 5'-CCCCG-GAAAAGACTGTATGC-3'; reverse: 5'GGTGAGTAAACT-TGCTGTGGTGAA 3'; probe: 5'-TCGGGCCATAACA-GAAGAGAGATCTGAGC-3'). Each measurement was normalized to expression of β2 microglobulin (delta Ct). $2\text{-}\Delta\Delta CT$ was then used as the level of gene expression. Gene expression levels were normalized to the level present in un-stimulated cells.

Human Samples

Simultaneous synovial fluid and plasma samples were obtained at the Los Angeles County+University of Southern California Medical Center (IRB protocol HS-05-00270). Underlying causes of joint effusions were determined by the medical history, physical examination, and synovial fluid analyses. Treatment data was not available. Synovial fluids from patients with osteoarthritis, rheumatoid arthritis (RA), psoriatic arthritis, gout, and pseudogout were obtained from discarded de-identified, anonymized clinical samples obtained at the Brigham and Women's Hospital Rheumatology clinic. Treatment data was not available. Sera from systemic lupus erythematosus (SLE) patients at HSS had been previously collected for another study. Demographic data and SLE disease activity data (SELENA-SLEDAI) were recorded at the time of their clinical visit. All data were de-identified, and all patients signed an IRB-approved informed consent prior to blood drawing. Sjogren's disease patient serum samples were obtained from Dr. Gabor Illei at National Institute of Health (NIH) under IRB-approved protocol numbers 99-D-0070 and 84-D-0056. Serum samples from RA patients were provided by Dr. Raphaela Goldbach-Mansky at NIH under IRB-approved protocol number 00-AR-0222. Ankylosing spondylitis (AS) patient serum samples were provided by Dr. Michael Ward at NIH under IRB-approved protocol number 03-AR-0131.

Measurement of TL1A by ELISA

A commercially available human TL1A ELISA kit (PeproTech, cat no. 900-K290) was used to measure TL1A in cell culture supernatants. For measuring human TL1A in matching plasma and synovial fluid samples, ELISA was performed as follows: 96-well, flat-bottom plates were coated with 1 μg/mL-mouse anti-human TL1A (clone 1A9) in PBS overnight at 4° C. Plates were blocked with blocking buffer (5% BSA, 0.1% Tween 20 in PBS) for 1 hour. 25 μL of sample diluted 10-fold with 225 μL sample diluent (1% BSA, 0.1% Tween 20 in PBS) were loaded into each well, and the plates were incubated for two hours at 37° C. TL1A was detected by polyclonal biotinylated rabbit anti-human TL1A Ab followed by Steptavidin-Horseradish peroxidase (SA-HRP) 0.5 μg/mL for one hour at 37° C. TMB (3,3',5,5'-tetramethylbenzidine) was used as the substrate. Reactions were stopped with 100 μL 1N sulfuric acid, and OD 450 nm was measured. The Standard curve was generated using recombinant human TL1A (PeproTech) diluted in standard diluent (sample diluent with added 10% pooled normal human sera). An independent bead-based assay system was developed using anti-human TL1A antibody (clone 1A9) conjugated onto Bio-Plex COOH beads (Bio-Rad). 3000 anti-TL1A conjugated beads were added into each well of a 96-well filter plate (MultiScreen HTSTM by Millipore, Cat No. MSBVN1250), followed by 50 μL serum or synovial fluid. Synovial fluid was diluted two-fold using Bio-Plex Human Serum Diluent (Bio-Rad, Cat no. 171-305000). Samples and standards were incubated for 30 minutes, followed by 30 minutes incubation with 25 μL 1 μg/mL biotinylated polyclonal anti-human TL1A (PeproTech, Cat no. 500-P240Bt), and 50 μL of 1:100 diluted SA-PE (Bio-Plex Cytokine Reagent Kit, Bio-Rad, 171-304001). Each well was re-suspended with 125 μL of assay buffer, and cytokine levels were measured with the Bio-Plex 200 System (Bio-Rad). Data was analyzed using Prism (GraphPad Software, Inc.) software. For TNF assay, the Bio-Plex Pro Human Cytokine TNF-α set was used according to the manufacturer's instructions (Bio-Rad, Cat no. 171-B5026M).

Induction of Collagen-Induced Arthritis (CIA) and Administration of Blocking Reagents Male DBA/1J mice (8-10 weeks old) obtained from the Jackson Laboratory (Bar Harbor, Me.) were injected intradermally with 100 μg chicken collagen type II (CII) in complete Freund's adjuvant (1:1, w/v) to the tail base at day 0 and boosted with an intradermal injection of 100 μg CII in incomplete Freund's adjuvant (1:1, w/v) on day 21. The mice were then randomized at day 21 to receive either control or treatment. Mice in the treatment group were injected i.p. with 20 mg/kg hamster anti-mouse TL1A antibody (clone 5G4.6) every seven days starting on day 21. Control group mice received 20 mg/kg hamster immunoglobulin. Mice were euthanized at day 49. Hind legs were cut above the knees and were fixed in 10% formaldehyde. Animals were used under protocols approved by the NIAMS ACUC.

Assessment of Clinical Severity of Arthritis in CIA

The development of arthritis was evaluated by macroscopic scoring of each paw on a 0-4 scale previously described. Scoring was done by two separate investigators blinded to the randomization, and the average score of each mouse was used.

ELISA for Measuring Anti-Chicken Collagen IgG 96-well, flat-bottom plates were coated with 100 µL 50 µg/mL chicken collagen dissolved in 0.05M TRIS-0.2M NaCl overnight at 4° C. Plates were blocked with 200 µL blocking buffer (1% BSA in PBS) for 30 minutes at room temperature. 50 µL of samples of 5-fold serially diluted serum from 1:100 to 1:12500 with sample diluent (1% BSA, 0.05% Tween 20 in PBS) were loaded in duplicate wells, and the plates were incubated for two hours at room temperature. Antibodies were detected with 5 ng/mL goat anti-mouse HRP (Pierce, cat. no. 1858413) for one hour at room temperature and detected with substrate detection kit (R&D, cat. no. DY999), stopped by 50 µL 2M H2SO4, OD 450 measured.

Micro-Computed Tomography (Micro-CT) and Assessment of Erosions

Legs from CIA experiments were stored in 10% formaldehyde until they were scanned. Micro-CT of mouse anatomy was performed with a SkyScan 1172 Micro Xray CT scanner (MicroPhotonics, Inc. Allentown Pa., USA, SkyScan, Kontich, Belgium) with the x-ray source (focal spot size 4 micrometers, energy range 20-100 kV) biased at 44 kV/22 microamps and with a 0.5 mm aluminum filter to reduce beam hardening. The images were acquired with a voxel size of 12.17 micrometers, with the camera to source distance of 220 mm and an object to source distance of 116 mm. 450 projections were acquired with an angular resolution of 0.4 degrees through 180 degrees rotation. 8 frames were averaged for each projection radiograph with an exposure time of 295 ms per frame. The scan duration was approximately 40 minutes. Tomographic images were reconstructed using vendor-supplied software based on the Feldkamp cone beam algorithm. Reconstructed images were then made into three-dimensional image using CTAn (v.1.10), then visualized using CTVol (v.2.1) (SkyScan). Three-dimensional images were scored on de-identified 3-D reconstructions by two separate investigators based on the scoring system described.

Fc receptor (FcR) cross-linking and TLR ligands induce TL1A expression in human monocytes. In RA, FcR cross-linking by immune complexes and stimulation of TLRs by endogenous ligands may sustain inflammation by stimulating monocytes and other innate immune cells in the joint. Accordingly, we tested the ability of immune complexes and TLR ligands to induce expression of TL1A by human monocytes. Both FcR cross-linking and LPS induced TL1A at the mRNA level, with levels peaking at 18 hours and then rapidly declining, consistent with degradation of TL1A RNA governed by AU-rich elements present in the 3' untranslated region of the TL1A mRNA. The peak of TL1A induction was ~6-fold higher following FcR cross-linking than following optimal concentrations of LPS. At the protein level, FcR cross-linking induced higher levels of TL1A that were detectable at 18 hours, whereas LPS-induced TL1A was only detectable at 48 hours, with TL1A production approximately 10-fold lower with optimal doses of LPS than with FcR cross-linking. TLRs can be divided into subclasses depending on whether they activate signaling pathways linked to the adaptor protein MyD88, TRIF, or both. To determine which of these signaling pathways are important in induction of TL1A expression, we stimulated human monocytes with a panel of TLR ligands specific for each receptor. Stimulation through TLR1, 2, 4, and 6 was the most efficient at inducing TL1A; TLR 5 and 9 were intermediate; and stimulation through TLR 3, 7, and 8 had no effect on TL1A production. These results are consistent with MyD88-dependent rapid NF-kB upregulation being important in TL1A induction, since TLR 3, 7, and 8 poorly activate MyD88. These results are also consistent with those obtained with murine DC, in which TL1A production in response to LPS is primarily dependent on MyD88.

TL1A is a Biomarker for Rheumatoid Arthritis in Synovial Fluid and Blood

Given the potent ability of immune complexes to promote TL1A production in vitro, we reasoned that this cytokine may be preferentially elevated in RA, in which rheumatoid factor (RF) and other immune complexes stimulate innate immune cells. To that end, we measured TL1A levels in matched samples of plasma and SF from a cohort of patients with RA (39 samples from 31 patients) or other types of arthritis (37 samples from 31 patients), including psoriatic arthritis, crystal-induced arthritis, reactive arthritis, osteoarthritis, non-specific inflammatory arthritis, juvenile inflammatory arthritis, or infectious arthritis. The majority (27 of 39) of SF samples from RA patients had TL1A levels above 0.1 ng/mL, with a mean of 0.59 ng/mL and up to 3.25 ng/mL detected. By contrast, only 2 of 37 non-RA samples (one each from a patient with reactive arthritis and a patient with psoriatic arthritis) contained more than 0.1 ng/mL TL1A. In plasma, a smaller but still significant percentage of RA patients had elevated TL1A levels, while no samples from patients with other arthritides had detectable TL1A levels. Five RA and five non-RA patients contributed more than one sample to this cohort. In SF, TL1A levels fluctuated depending on the day of SF collection. In plasma, however, TL1A levels of patients with repeated measurements remained fairly constant, either highly elevated (>2 ng/mL) or below 0.1 ng/ml. This likely reflects the variability in inflammation between involved joints among patients subjected to repeated synovial aspirations. Elevated TL1A correlated more with markers such as anti-CCP that predict more severe disease and erosions than with disease activity at the time of sample collection. Among RA patients tested for anti-CCP antibodies, those with a positive anti-CCP (n=15) had significantly higher level of TL1A in SF (p=0.039) and a trend toward higher TL1A in plasma (p=0.129) than in those without (n=4). Comparing TL1A level in SF and plasma between RA patients with or without RF was not feasible because most of the patients in this cohort were sero-positive. Still, sero-negative patients (n=2) had mostly undetectable TL1A in both SF and plasma, suggesting that TL1A may be preferentially elevated in patients with RF. However, the quantitative level of RF or anti-CCP did not correlate with TL1A levels in plasma or SF. In addition, TL1A levels in SF or plasma did not correlate with measures of clinical severity including DAS-28 score, ESR, CRP, or tender/swollen joint counts, nor did SF TL1A levels correlate with SF WBC counts. There was a trend toward higher TL1A (n=9) in both SF (mean 0.68 ng/mL in erosive vs 0.55 ng/mL in non-erosive) and in plasma (mean 1.09 ng/mL in erosive vs 0.25 ng/mL in non-erosive). Of note, there was a linear correlation between plasma and SF TL1A levels in 39 matched RA plasma and SF samples ($R^2=0.52$, $p<0.0001$), indicating that serum TL1A may be a surrogate for TL1A in the joint. To determine the generalizability of these findings, we measured TL1A with a bead-based fluorescent TL1A assay in SF samples from an independent cohort of patients with RA or other arthritides. Inter-assay variability between this assay and the one used was less than 10% for samples with values above 100 pg/ml, and this bead-based assay had the additional capability of detecting TL1A levels as low as 10 pg/ml. In this second cohort, SF TL1A levels were significantly higher in RA than in patients with osteoarthritis (OA), gout or pseudogout, or psoriatic arthritis (PsA), although SF TL1A levels in the other inflammatory arthritides were also significantly higher than in OA. Although TNF, a key pathogenic cytokine in RA, can induce TL1A expression in endothelial cells, chondrocytes, and synovial fibroblasts, SF levels of TNF and TL1A did not correlate in 17 RA samples tested. Thus, there appears to be a TNF-independent component to TL1A expression in SF. RA is not the only rheumatic disorder associated with circulating immune complexes. Anti-nuclear antibodies (ANA) complexed with components of chromatin are associated with SLE and Sjogren's syndrome. To determine whether serum TL1A levels are also elevated in these disorders, we tested sera from patients with Sjogren's syndrome and SLE over a wide range of disease activity and compared these to sera from an independent cohort of RA patients to sera from healthy volunteers. Serum TL1A levels were significantly elevated in patients with RA compared to normal controls, none of whom had detectable serum TL1A. In this cohort of RA patients, anti-TNF treatment status did not correlate with TL1A values. Serum TL1A levels were elevated in Sjogren's syndrome, but not to the extent seen in RA (RA versus Sjogren's, p=0.0006). Moreover, TL1A was undetectable in the serum of all but three SLE patients. Each of these 3 SLE patients had high SLEDAI levels (8-12), and two of them had arthritic flares at the time of sample collection. As an additional control, we measured the level of TL1A in the serum of patients with ankylosing spondylitis (AS), which is not associated with circulating immune complexes. Only a minority of AS serum contained TL1A at levels higher than 100 pg/ml. TL1A was significantly less elevated than in RA (t test of RA versus AS, p=0.0003). However, as in Sjogren's syndrome, TL1A was still significantly elevated in the serum of AS patients compared to healthy controls. There was no correlation of TL1A levels with number of affected peripheral joints, degree of spine ankylosis, anti-TNF treatment, or overall disease activity in AS. Taken together, these results indicate that RA is more strongly associated with increased TL1A levels than are other rheumatic diseases, and elevated serum TL1A can be considered a biomarker for seropositive RA in the setting of inflammatory arthritis.

Blocking TL1A-DR3 interactions improves clinical outcome and bony erosions in CIA. Previous studies have found a beneficial effect of TL1A in murine CIA, but the effects of TL1A blockade on bony erosions have not been quantitated. To these ends, we administered an antagonistic anti-TL1A monoclonal antibody to DBA/1 mice at the time of boosting with antigen in CIA. Significant reductions in total joint scores were observed for the ensuing 28 days, particularly at earlier time-points. The onset of measurable clinical signs of arthritis was significantly delayed by anti-TL1A mAb. Interestingly, the decrease in the clinical severity in mice treated with anti-TL1A was not associated with decreases in titers of anti-collagen antibodies. Taken together, these data show that blocking TL1A-DR3 interactions potently reduces the clinical inflammatory signs of CIA without affecting systemic immune responses against the collagen immunogen. Since blocking TL1A-DR3 interactions clearly improved the clinical severity of CIA, we assessed whether these treatments also prevented bone erosions. We used micro-computed tomography (micro-CT) to provide a quantitative and global assessment of erosions. Anti-TL1A treatment dramatically reduced erosions in the hind-paws of mice induced to develop CIA. Quantitation of erosions in hind-paws according to a scoring system that takes account of peri-articular erosions and deformities in each joint in the hind-paws showed a significant reduction in average and maximum erosion scores in TL1A-treated mice. The reduction was especially pronounced in the MTP joints (*p=0.042) and in toes (*p=0.015). Also, generalized deformity occurred in only the control group (20%, versus 0% in the treatment group). Strikingly, erosions in anti-TL1A-treated mice were significantly reduced in paws with similar maximum clinical scores (2-way ANOVA p<0.0001 for treatment effect independent of maximum clinical score, p<0.0001 for treatment and p<0.0001 for maximum clinical score). This indicates that anti-TL1A antibody treatment not only diminished the erosions by inhibiting clinical arthritis, but also provided protection against erosions independent of inflammation as measured by the clinical joint score.

H. REFERENCES

Adams D J, Biggs P J, Cox T, et al. Mutagenic insertion and chromosome engineering resource (MICER). Nat Genet 2004; 36(8):867-71.

Adler B, Ashkar S, Cantor H, Weber G F. Costimulation by extracellular matrix proteins determines the response to TCR ligation. Cell Immunol 2001; 210(1):30-40.

Adriani M, Aoki J, Horai R, et al. Impaired in vitro regulatory T cell function associated with Wiskott-Aldrich syndrome. Clin Immunol 2007; 124(1):41-8.

Arestides, R. S., He, H., Westlake, R. M., Chen, A. I., Sharpe, A. H., Perkins, D. L., and Finn, P. W. (2002). Costimulatory molecule OX40L is critical for both Th1 and Th2 responses in allergic inflammation. Eur J Immunol 32, 2874-2880.

Badour K, Zhang J, Shi F, Leng Y, Collins M, Siminovitch K A. Fyn and PTP-PEST-mediated regulation of Wiskott-Aldrich syndrome protein (WASp) tyrosine phosphorylation is required for coupling T cell antigen receptor engagement to WASp effector function and T cell activation. J Exp Med 2004; 199(1):99-112.

Bamias, G., Martin, C., 3rd, Marini, M., Hoang, S., Mishina, M., Ross, W. G., Sachedina, M. A., Friel, C. M., Mize, J., Bickston, S. J., et al. (2003). Expression, localization, and functional activity of TL1A, a novel Th1-polarizing cytokine in inflammatory bowel disease. J Immunol 171, 4868-4874.

Bamias, G., Mishina, M., Nyce, M., Ross, W. G., Kollias, G., Rivera-Nieves, J., Pizarro, T. T., and Cominelli, F. (2006). Role of TL1A and its receptor DR3 in two models of chronic murine ileitis. Proc Natl Acad Sci USA.

Baum W, Kirkin V, Fernandez S B, et al. Binding of the intracellular Fas ligand (FasL) domain to the adaptor protein PSTPIP results in a cytoplasmic localization of FasL. J Biol Chem 2005; 280(48):40012-24.

Blott E J, Bossi G, Clark R, Zvelebil M, Griffiths G M. Fas ligand is targeted to secretory lysosomes via a proline-rich domain in its cytoplasmic tail. J Cell Sci 2001; 114(Pt 13):2405-16.

Brocker T, Riedinger M, Karjalainen K. Targeted expression of major histocompatibility complex (MHC) class II molecules demonstrates that dendritic cells can induce negative but not positive selection of thymocytes in vivo. J Exp Med 1997; 185(3):541-50.

Bruijn L I, Becher M W, Lee M K, et al. ALS-linked SOD1 mutant G85R mediates damage to astrocytes and promotes rapidly progressive disease with SOD1-containing inclusions. Neuron 1997; 18(2):327-38.

Cassatella, M. A., da Silva, G. P., Tinazzi, I., Facchetti, F., Scapini, P., Calzetti, F., Tamassia, N., Wei, P., Nardelli, B., Roschke, V., et al. (2007). Soluble TNF-like cytokine (TL1A) production by immune complexes stimulated monocytes in rheumatoid arthritis. J Immunol 178, 7325-7333.

Chakrabandhu K, Herincs Z, Huault S, et al. Palmitoylation is required for efficient Fas cell death signaling. Embo J 2007; 26(1):209-20.

Chinnaiyan, A. M., O'Rourke, K., Yu, G. L., Lyons, R. H., Garg, M., Duan, D. R., Xing, L., Gentz, R., Ni, J., and Dixit, V. M. (1996). Signal transduction by DR3, a death domaincontaining receptor related to TNFR-1 and CD95. Science 274, 990-992.

Croft, M. (2003). Co-stimulatory members of the TNFR family: keys to effective T-cell immunity. Nat Rev Immunol 3, 609-620.

Dagnaes-Hansen, F., Holst, H. U., Sondergaard, M., Vorup-Jensen, T., Flyvbjerg, A., Jensen, U. B., and Jensen, T. G. (2002). Physiological effects of human growth hormone produced after hydrodynamic gene transfer of a plasmid vector containing the human ubiquitin promotor. Journal of molecular medicine (Berlin, Germany) 80, 665-670.

Derry J M, Ochs H D, Francke U. Isolation of a novel gene mutated in Wiskott-Aldrich syndrome. Cell 1994; 79(5): following 922.

Deshpande P, King I L, Segal B M. IL-12 driven upregulation of P-selectin ligand on myelin-specific T cells is a critical step in an animal model of autoimmune demyelination. Journal of neuroimmunology 2006; 173(1-2):35-44.

Deshpande S S, Angkeow P, Huang J, Ozaki M, Irani K. Rac1 inhibits TNF-alpha-induced endothelial cell apoptosis: dual regulation by reactive oxygen species. Faseb J 2000; 14(12):1705-14.

Devadas S, Das J, Liu C, et al. Granzyme B is critical for T cell receptor-induced cell death of type 2 helper T cells. Immunity 2006; 25(2):237-47.

Di Prospero N A, Baker A, Jeffries N, Fischbeck K H. Neurological effects of high-dose idebenone in patients with Friedreich's ataxia: a randomised, placebo-controlled trial. Lancet neurology 2007; 6(10):878-86.

Dupuis-Girod S, Medioni J, Haddad E, et al. Autoimmunity in Wiskott-Aldrich syndrome: risk factors, clinical features, and outcome in a single-center cohort of 55 patients. Pediatrics 2003; 111(5 Pt 1):e622-7.

Faure S, Salazar-Fontana L I, Semichon M, et al. ERM proteins regulate cytoskeleton relaxation promoting T cell-APC conjugation. Nat Immunol 2004; 5(3):272-9.

Feig C, Tchikov V, Schutze S, Peter M E. Palmitoylation of CD95 facilitates formation of SDS-stable receptor aggregates that initiate apoptosis signaling. Embo J 2007; 26(1): 221-31.

Fritsch R D, Shen X, Illei G G, et al. Abnormal differentiation of memory T cells in systemic lupus erythematosus. Arthritis Rheum 2006; 54(7):2184-97.

Fritzsching B, Oberle N, Eberhardt N, et al. In contrast to effector T cells, CD4+CD25+FoxP3+ regulatory T cells are highly susceptible to CD95 ligand- but not to TCR-mediated cell death. J Immunol 2005; 175(1):32-6.

Fuss I J, Becker C, Yang Z, et al. Both IL-12p70 and IL-23 are synthesized during active Crohn's disease and are downregulated by treatment with anti-IL-12 p40 monoclonal antibody. Inflammatory bowel diseases 2006; 12(1):9-15.

Gaudet S, Janes K A, Albeck J G, Pace E A, Lauffenburger D A, Sorger P K. A compendium of signals and responses triggered by prodeath and prosurvival cytokines. Mol Cell Proteomics 2005; 4(10):1569-90.

Gavett, S. H., Chen, X., Finkelman, F., and Wills-Karp, M. (1994). Depletion of murine CD4+ T lymphocytes prevents antigen-induced airway hyperreactivity and pulmonary eosinophilia. American journal of respiratory cell and molecular biology 10, 587-593.

Gout S, Morin C, Houle F, Huot J. Death receptor-3, a new E-Selectin counter-receptor that confers migration and survival advantages to colon carcinoma cells by triggering p38 and ERK MAPK activation. Cancer Res 2006; 66(18): 9117-24.

Grunvald, E., Chiaramonte, M., Hieny, S., Wysocka, M., Trinchieri, G., Vogel, S. N., Gazzinelli, R. T., and Sher, A. (1996). Biochemical characterization and protein kinase C dependency of monokine-inducing activities of *Toxoplasma gondii*. Infect Immun 64, 2010-2018.

Hao, Z., Hampel, B., Yagita, H., and Rajewsky, K. (2004). T cell-specific ablation of Fas leads to Fas ligand-mediated lymphocyte depletion and inflammatory pulmonary fibrosis. J Exp Med 199, 1355-1365.

He L, Wu X, Meylan F, et al. Monitoring caspase activity in living cells using fluorescent proteins and flow cytometry. Am J Pathol 2004; 164(6):1901-13.

Hodges, B. L., and Scheule, R. K. (2003). Hydrodynamic delivery of DNA. Expert opinion on biological therapy 3, 911-918.

Hue S, Ahern P, Buonocore S, et al. Interleukin-23 drives innate and T cell-mediated intestinal inflammation. J Exp Med 2006; 203(11):2473-83.

Humblet-Baron S, Sather B, Anover S, et al. Wiskott-Aldrich syndrome protein is required for regulatory T cell homeostasis. J Clin Invest 2007; 117(2):407-18.

Jones R G, Elford A R, Parsons M J, et al. CD28-dependent activation of protein kinase B/Akt blocks Fas-mediated apoptosis by preventing death-inducing signaling complex assembly. J Exp Med 2002; 196(3):335-48.

Kamata H, Honda S, Maeda S, Chang L, Hirata H, Karin M. Reactive oxygen species promote TNFalpha-induced death and sustained JNK activation by inhibiting MAP kinase phosphatases. Cell 2005; 120(5):649-61.

Kim Y S, Morgan M J, Choksi S, Liu Z G. TNF-induced activation of the Nox1 NADPH oxidase and its role in the induction of necrotic cell death. Mol Cell 2007; 26(5):675-87.

Kim, S., and Zhang, L. (2005). Identification of naturally secreted soluble form of TL1A, a TNF-like cytokine. J Immunol Methods 298, 1-8.

Kimberley F C, Lobito A A, Siegel R M, Screaton G R. Falling into TRAPS-receptor misfolding in the TNF receptor 1-associated periodic fever syndrome. Arthritis research & therapy 2007; 9(4):217.

Lambeth J D. NOX enzymes and the biology of reactive oxygen. Nat Rev Immunol 2004; 4(3):181-9.

Lecocq, M., Andrianaivo, F., Warnier, M. T., Wattiaux-De Coninck, S., Wattiaux, R., and Jadot, M. (2003). Uptake by mouse liver and intracellular fate of plasmid DNA after a rapid tail vein injection of a small or a large volume. The journal of gene medicine 5, 142-156.

Li Q J, Chau J, Ebert P J, et al. miR-181a is an intrinsic modulator of T cell sensitivity and selection. Cell 2007; 129(1):147-61.

Lobito A A, Kimberley F C, Muppidi J R, et al. Abnormal disulfide-linked oligomerization results in ER retention and altered signaling by TNFR1 mutants in TNFR1-associated periodic fever syndrome (TRAPS). Blood 2006; 108(4):1320-7.

Maillard M H, Cotta-de-Almeida V, Takeshima F, et al. The Wiskott-Aldrich syndrome protein is required for the function of CD4(+)CD25(+)Foxp3(+) regulatory T cells. Exp Med 2007; 204(2):381-91.

Man S, Ubogu E E, Ransohoff R M. Inflammatory cell migration into the central nervous system: a few new twists on an old tale. Brain Pathol 2007; 17(2):243-50.

Marsters S A, Sheridan J P, Donahue C J, et al. Apo-3, a new member of the tumor necrosis factor receptor family, contains a death domain and activates apoptosis and NF-kappa B. Curr Biol 1996; 6(12):1669-76.

Martinez-Lorenzo M J, Anel A, Gamen S, et al. Activated human T cells release bioactive Fas ligand and APO2 ligand in microvesicles. J Immunol 1999; 163(3):1274-81.

McConchie, B. W., Norris, H. H., Bundoc, V. G., Trivedi, S., Boesen, A., Urban, J. F., Jr., and Keane-Myers, A. M. (2006). *Ascaris suum*-derived products suppress mucosal allergic inflammation in an interleukin-10-independent manner via interference with dendritic cell function. Infect Immun 74, 6632-6641.

McDermott M F, Aksentijevich I, Galon J, et al. Germline mutations in the extracellular domains of the 55 kDa TNF receptor, TNFR1, define a family of dominantly inherited autoinflammatory syndromes. Cell 1999; 97(1):133-44.

McKenzie B S, Kastelein R A, Cua D J. Understanding the IL-23-IL-17 immune pathway. Trends Immunol 2006; 27(1):17-23.

Micheau O, Tschopp J. Induction of TNF receptor I-mediated apoptosis via two sequential signaling complexes. Cell 2003; 114(2):181-90.

Migone, T. S., Zhang, J., Luo, X., Zhuang, L., Chen, C., Hu, B., Hong, J. S., Perry, J. W., Chen, S. F., Zhou, J. X., et al. (2002). TL1A is a TNF-like ligand for DR3 and TR6/DcR3 and functions as a T cell costimulator. Immunity 16, 479-492.

Misulovin Z, Yang X W, Yu W, Heintz N, Meffre E. A rapid method for targeted modification and screening of recombinant bacterial artificial chromosome. Journal of immunological methods 2001; 257 (1-2): 99-105 .

Morales-Tirado V, Johannson S, Hanson E, et al. Cutting edge: selective requirement for the Wiskott-Aldrich syndrome protein in cytokine, but not chemokine, secretion by CD4+ T cells. J Immunol 2004; 173(2):726-30.

Muppidi J R, Lobito A A, Ramaswamy M, et al. Homotypic FADD interactions through a conserved RXDLL motif are required for death receptor-induced apoptosis. Cell Death Differ 2006; 13(10):1641-50.

Muppidi J R, Siegel R M. Ligand-independent redistribution of Fas (CD95) into lipid rafts mediates clonotypic T cell death. Nat Immunol 2004; 5(2):182-9.

Nadkarni S, Mauri C, Ehrenstein M R. Anti-TNF-{alpha} therapy induces a distinct regulatory T cell population in patients with rheumatoid arthritis via TGF-{beta}. J Exp Med 2007.

Nakajima, A., Oshima, H., Nohara, C., Morimoto, S., Yoshino, S., Kobata, T., Yagita, H., and Okumura, K. (2000). Involvement of CD70-CD27 interactions in the induction of experimental autoimmune encephalomyelitis. Journal of neuroimmunology 109, 188-196.

Neurath M, Fuss I, Strober W. TNBS-colitis. International reviews of immunology 2000; 19(1):51-62.

Neurath M F, Fuss I, Pasparakis M, et al. Predominant pathogenic role of tumor necrosis factor in experimental colitis in mice. Eur J Immunol 1997; 27(7):1743-50.

Nohara, C., Akiba, H., Nakajima, A., Inoue, A., Koh, C. S., Ohshima, H., Yagita, H., Mizuno, Y., and Okumura, K. (2001). Amelioration of experimental autoimmune encephalomyelitis with anti-OX40 ligand monoclonal antibody: a critical role for OX40 ligand in migration, but not development, of pathogenic T cells. J Immunol 166, 2108-2115.

Osawa, K., Takami, N., Shiozawa, K., Hashiramoto, A., and Shiozawa, S. (2004). Death receptor 3 (DR3) gene duplication in a chromosome region 1p36.3: gene duplication is more prevalent in rheumatoid arthritis. Genes and immunity 5, 439-443.

Papadakis, K. A., Prehn, J. L., Landers, C., Han, Q., Luo, X., Cha, S. C., Wei, P., and Targan, S. R. (2004). TL1A synergizes with IL-12 and IL-18 to enhance IFN-gamma production in human T cells and NK cells. J Immunol 172, 7002-7007.

Papadakis, K. A., Zhu, D., Prehn, J. L., Landers, C., Avanesyan, A., Lafkas, G., and Targan, S. R. (2005). Dominant role for TL1A/DR3 pathway in IL-12 plus IL-18-induced IFN-gamma production by peripheral blood and mucosal CCR9+ T lymphocytes. J Immunol 174, 4985-4990.

Parlato S, Giammarioli A M, Logozzi M, et al. CD95 (APO-1/Fas) linkage to the actin cytoskeleton through ezrin in human T lymphocytes: a novel regulatory mechanism of the CD95 apoptotic pathway. Embo J 2000; 19(19):5123-34.

Pivniouk V I, Snapper S B, Kettner A, et al. Impaired signaling via the high-affinity IgE receptor in Wiskott-Aldrich syndrome protein-deficient mast cells. Int Immunol 2003; 15(12):1431-40.

Powrie F, Leach M W, Mauze S, Caddle L B, Coffman R L. Phenotypically distinct subsets of CD4+ T cells induce or protect from chronic intestinal inflammation in C. B-17 scid mice. Int Immunol 1993; 5(11):1461-71.

Prehn, J. L., Thomas, L. S., Landers, C. J., Yu, Q. T., Michelsen, K. S., and Targan, S. R. (2007). The T cell costimulator TL1A is induced by FcgammaR signaling in human monocytes and dendritic cells. J Immunol 178, 4033-4038.

Ramaswamy M, Dumont C, Cruz A C, et al. Cutting Edge: Rac GTPases Sensitize Activated T Cells to Die via Fas. J Immunol 2007; 179(10):6384-8.

Reinhardt R L, Khoruts A, Merica R, Zell T, Jenkins M K. Visualizing the generation of memory CD4 T cells in the whole body. Nature 2001; 410(6824):101-5.

Riou C, Yassine-Diab B, Van grevenynghe J, et al. Convergence of TCR and cytokine signaling leads to FOXO3a phosphorylation and drives the survival of CD4+ central memory T cells. J Exp Med 2007; 204(1):79-91.

Salek-Ardakani, S., Song, J., Halteman, B. S., Jember, A. G., Akiba, H., Yagita, H., and Croft, M. (2003). OX40 (CD134) controls memory T helper 2 cells that drive lung inflammation. J Exp Med 198, 315-324.

Schwartz M. Rho signalling at a glance. J Cell Sci 2004; 117(Pt 23):5457-8.

Screaton, G. R., Xu, X. N., Olsen, A. L., Cowper, A. E., Tan, R., McMichael, A. J., and Bell, J. I. (1997). LARD: a new lymphoid-specific death domain containing receptor regulated by alternative pre-mRNA splicing. Proc Natl Acad Sci USA 94, 4615-4619.

Shaner N C, Campbell R E, Steinbach P A, Giepmans B N, Palmer A E, Tsien R Y. Improved monomeric red, orange and yellow fluorescent proteins derived from *Discosoma* sp. red fluorescent protein. Nat Biotechnol 2004; 22(12):1567-72.

Shell S, Park S M, Radjabi A R, et al. Let-7 expression defines two differentiation stages of cancer. Proc Natl Acad Sci USA 2007; 104(27):11400-5.

Siegel R M, Chan F K, Chun H J, Lenardo M J. The multifaceted role of Fas signaling in immune cell homeostasis and autoimmunity. Nat Immunol 2000; 1(6):469-74.

Siegel R M, Frederiksen J K, Zacharias D A, et al. Fas preassociation required for apoptosis signaling and dominant inhibition by pathogenic mutations. Science 2000; 288 (5475):2354-7.

Siegel R M, Muppidi J R, Sarker M, et al. SPOTS: signaling protein oligomeric transduction structures are early mediators of death receptor-induced apoptosis at the plasma membrane. J Cell Biol 2004; 167(4):735-44.

Soroosh, P., Ine, S., Sugamura, K., and Ishii, N. (2006). OX40-OX40 ligand interaction through T cell-T cell contact contributes to CD4 T cell longevity. J Immunol 176, 5975-5987.

Steed, P. M., Tansey, M. G., Zalevsky, J., Zhukovsky, E. A., Desjarlais, J. R., Szymkowski, D. E., Abbott, C., Carmichael, D., Chan, C., Cherry, L., et al. (2003). Inactivation of TNF signaling by rationally designed dominant-negative TNF variants. Science 301, 1895-1898.

Storey H, Stewart A, Vandenabeele P, Luzio J P. The p55 tumour necrosis factor receptor TNFR1 contains a trans-Golgi network localization signal in the C-terminal region of its cytoplasmic tail. The Biochemical journal 2002; 366 (Pt 1):15-22.

Stranges P B, Watson J, Cooper C J, et al. Elimination of antigen-presenting cells and autoreactive T cells by fas contributes to prevention of autoimmunity. Immunity 2007; 26(5):629-41.

Strober W, Fuss I, Mannon P. The fundamental basis of inflammatory bowel disease. Clin Invest 2007; 117(3):514-21.

Su, A. I., Wiltshire, T., Batalov, S., Lapp, H., Ching, K. A., Block, D., Zhang, J., Soden, R., Hayakawa, M., Kreiman, G., et al. (2004). A gene atlas of the mouse and human protein-encoding transcriptomes. Proc Natl Acad Sci USA 101, 6062-6067.

Sukits S F, Lin L L, Hsu S, Malakian K, Powers R, Xu G Y. Solution structure of the tumor necrosis factor receptor-1 death domain. Journal of molecular biology 2001; 310(4): 895-906.

Sullivan K E, Mullen C A, Blaese R M, Winkelstein J A. A multiinstitutional survey of the Wiskott-Aldrich syndrome. J Pediatr 1994; 125(6 Pt 1):876-85.

Suzuki A, Yamaguchi M T, Ohteki T, et al. T cell-specific loss of Pten leads to defects in central and peripheral tolerance. Immunity 2001; 14(5):523-34.

Tang Q, Adams J Y, Tooley A J, et al. Visualizing regulatory T cell control of autoimmune responses in nonobese diabetic mice. Nat Immunol 2006; 7(1):83-92.

Tao, X., Constant, S., Jorritsma, P., and Bottomly, K. (1997). Strength of TCR signal determines the costimulatory requirements for Th1 and Th2 CD4+ T cell differentiation. J Immunol 159, 5956-5963.

Touitou I, Lesage S, McDermott M, et al. Infevers: an evolving mutation database for auto-inflammatory syndromes. Human mutation 2004; 24(3):194-8.

Valencia X, Stephens G, Goldbach-Mansky R, Wilson M, Shevach E M, Lipsky P E. TNF downmodulates the function of human CD4+CD25hi T-regulatory cells. Blood 2006; 108(1):253-61.

von Andrian U H, Mackay C R. T-cell function and migration. Two sides of the same coin. N Engl J Med 2000; 343(14): 1020-34.

Wang, E. C., Them, A., Denzel, A., Kitson, J., Farrow, S. N., and Owen, M. J. (2001). DR3 regulates negative selection during thymocyte development. Mol Cell Biol 21, 3451-3461.

Watts, T. H. (2005). TNF/TNFR family members in costimulation of T cell responses. Annu Rev Immunol 23, 23-68.

Wen, L., Zhuang, L., Luo, X., and Wei, P. (2003). TL1A-induced NF-kappaB activation and c-IAP2 production prevent DR3-mediated apoptosis in TF-1 cells. J Biol Chem 278, 39251-39258.

Wise C A, Gillum J D, Seidman C E, et al. Mutations in CD2BP1 disrupt binding to PTP PEST and are responsible for PAPA syndrome, an autoinflammatory disorder. Human molecular genetics 2002; 11(8):961-9.

Xiao, Q., Hsu, C. Y., Chen, H., Ma, X., Xu, J., and Lee, J. M. (2005). Characterization of cis-regulatory elements of the vascular endothelial growth inhibitor gene promoter. Biochem J 388, 913-920.

Yamazaki, K., McGovern, D., Ragoussis, J., Paolucci, M., Butler, H., Jewell, D., Cardon, L., Takazoe, M., Tanaka, T., Ichimori, T., et al. (2005). Single nucleotide polymorphisms in TNFSF15 confer susceptibility to Crohn's disease. Human molecular genetics 14, 3499-3506.

Zhang Z, Zheng M, Bindas J, Schwarzenberger P, Kolls J K. Critical role of IL-17 receptor signaling in acute TNBS-induced colitis. Inflammatory bowel diseases 2006; 12(5): 382-8.

Zhang, J., Salcedo, T. W., Wan, X., Ullrich, S., Hu, B., Gregorio, T., Feng, P., Qi, S., Chen, H., Cho, Y. H., et al. (2001). Modulation of T-cell responses to alloantigens by TR6/DcR3. J Clin Invest 107, 1459-1468.

Zhumabekov T, Corbella P, Tolaini M, Kioussis D. Improved version of a human CD2 minigene based vector for T cell-specific expression in transgenic mice. Journal of immunological methods 1995; 185(1):133-40.

---

I. Sequences

1. SEQ ID NO: 1 (Human DR3 nucleic acid sequence)

```
  1 ctgaaggcgg aaccacgacg ggcagagagc acggagccgg gaagccctg  ggcgccgtc
 61 ggagggctat ggagcagcgg ccgcggggct gcgcggcggt ggcggcggcg ctcctcctgg
121 tgctgctggg ggcccgggcc cagggcggca ctcgtagccc caggtgtgac tgtgccggtg
181 acttccacaa gaagattggt ctgttttgtt gcagaggctg cccagcgggg cactacctga
241 aggcccttg cacggagccc tgcggcaact ccacctgcct tgtgtgtccc caagacacct
301 tcttggcctg ggagaaccac cataattctg aatgtgcccg ctgccaggcc tgtgatgagc
361 aggcctccca ggtggcgctg gagaactgtt cagcagtggc cgacacccgc tgtggctgta
421 agccaggctg gtttgtggag tgccaggtca gccaatgtgt cagcagttca cccttctact
481 gccaaccatg cctagactgc ggggccctgc accgccacac acggctactc tgttcccgca
541 gagatactga ctgtggggacc tgcctgcctg gcttctatga acatgcgat ggctgcgtgt
601 cctgccccac gagcaccctg gggagctgtc cagagcgctg tgccgctgtc tgtggctgga
661 ggcagagtag gtgtgtgct gggaatgcgc gtgggagaac tgggatggac cgagggagg
721 cgggtgagga gggggcaac cacccaacac ccaccagctg ctttcagtgt tctgggtcca
781 ggtgctcctg gctggccttg tggtccccct cctgcttggg gccaccctga cctacacata
841 ccgccactgc tggcctcaca agcccctggt tactgcagat gaagctggga tggaggctct
```

| I. Sequences |
|---|
| 901  gaccccacca ccggccaccc atctgtcacc cttggacagc gcccacaccc ttctagcacc
 961  tcctgacagc agtgagaaga tctgcaccgt ccagttggtg ggtaacagct ggacccctgg
1021  ctaccccgag acccaggagg cgctctgccc gcaggtgaca tggtcctggg accagttgcc
1081  cagcagagct cttggcccc ctcgtgcgcc cacactctcg ccagagtccc cagccggctc
1141  gccagccatg atgctgcagc cgggcccgca gctctacgac gtgatggacg cggtcccagc
1201  gcggcgctgg aaggagttcg tgcgcacgct ggggctgcgc gaggcagaga tcgaagccgt
1261  ggaggtggag atcggtctct tccgagacca gcagtacgag atgctcaagc actggcgcca
1321  gcagcagccc gcgggcctcg gagccgttta cgcggccctg gagcgcatgg ggctggacgg
1381  ctgcgtggaa gacttgcgca gccgcctgca gcgtggcccg tgacacgcag cccacttgcc
1441  acctaggcgc tctggtggcc cttgcagaag ccctaagtac ggttacttat gcgtgtagac
1501  attttatgtc acttattaag ccgctggcac ggccctgcgt aggcacacca gccggcccca
1561  cccctgctcg cccctatcgc tccagccaag gcgaagaagc acgaacgaat gtcgagaggg
1621  ggtgaagaca tttctcaact tctcggccgg agtttggctg agatcgcggt attaaatctg
1681  tgaaagaaat aaagaaaaaa acaaaacaaa acaaaaaaaa aaaaaaaaa aaaaaaaaa
1741  aaa |

2. SEQ ID NO: 2 (Human DR3 amino acid sequence)
```
MEQRPRGCAA VAAALLLVLL GARAQGGTRS PRCDCAGDFH KKIGLFCCRG  50
CPAGHYLKAP CTEPCGNSTC LVCPQDTFLA WENHHNSECA RCQACDEQAS 100
QVALENCSAV ADTRCGCKPG WFVECQVSQC VSSSPFYCQP CLDCGALHRH 150
TRLLCSRRDT DCGTCLPGFY EHGDGCVSCP TSTLGSCPER CAAVCGWRQM 200
FWVQVLLAGL VVPLLLGATL TYTYRHCWPH KPLVTADEAG MEALTPPPAT 250
HLSPLDSAHT LLAPPDSSEK ICTVQLVGNS WTPGYPETQE ALCPQVTWSW 300
DQLPSRALGP AAAPTLSPES PAGSPAMMLQ PGPQLYDVMD AVPARRWKEF 350
VRTLGLREAE IEAVEVEIGR FRDQQYEMLK RWRQQQPAGL GAVYAALERM 400
GLDGCVEDLR SRLQRGP                                    417
```

3. SEQ ID NO: 3 (Human TL1A nucleic acid sequence)
```
   1 gagagggaaa agggaaggag gagactgagt gattaagtca cccactgtga agagctggtc
  61 ttctatttaa tgggggctct ctctgcccag gagtcagagg tgcctccagg agcagcagga
 121 gcatggccga ggatctggga ctgagctttg gggaaacagc cagtgtggaa atgctgccag
 181 agcacggcag ctgcaggccc aaggccagga gcagcagcac acgctgggct ctcacctgct
 241 gcctggtgtt gctcccttc cttgcaggac tcaccacata cctgcttgtc agccagctcc
 301 gggcccaggg agaggcctgt gtgcagttcc aggctctaaa aggacaggag tttgcacctt
 361 cacatcagca agtttatgca cctcttagag cagacggaga taagccaagg gcacacctga
 421 cagttgtgag acaaactccc acacagcact ttaaaaatca gttcccagct ctgcactggg
 481 aacatgaact aggcctggcc ttcaccaaga accgaatgaa ctataccaac aaattcctgc
 541 tgatcccaga gtcgggagac tacttcattt actcccaggt cacattccgt gggatgacct
 601 ctgagtgcag tgaaatcaga caagcaggcc gaccaaacaa gccagactcc atcactgtgg
 661 tcatccaccaa ggtaacagac agctaccctg agccaaccca gctcctcatg ggaccaagt
 721 ctgtatgcga gtaggtagc aactggttcc agccccatct cctcggagcc atgttctcct
 781 tgcaagaagg ggacaagcta atggtgaacg tcagtgacat ctctttggtg gattacacaa
 841 aagaagataa aaccttcttt ggagccttct tactatagga ggagagcaaa tatcattata
 901 tgaaagtcct ctgccaccga gttcctaatt ttctttgttc aaatgtaatt ataaccaggg
 961 gttttcttgg ggccgggagt agggggcatt ccacagggac aacggtttag ctatgaaatt
1021 tggggcccaa aatttcacac ttcatgtgcc ttactgatga gagtactaac tggaaaaggc
1081 tgaagagagc aaatatatta ttaagatggg ttggaggatt ggcgagtttc taaatattaa
1141 gacactgatc actaaatgaa tggatgatct actcgggtca ggattgaaag agaaatattt
1201 caacacctcc ctgctataca atggtcacca gtggtccagt tattgttcaa tttgatcata
1261 aatttgcttc aattcaggag cttttgaagga agtccaagga aagctctaga aaacagtata
1321 aactttcaga ggcaaaatcc ttcaccaatt tttccacata ctttcatgcc ttgcctaaaa
1381 aaaatgaaaa gagagttggt atgtctcatg aatgttcaca cagaaggagt tggttttcat
1441 gtcatctaca gcatatgaga aaagctacct ttcttttgat tatgtacaca gatatctaaa
1501 taaggaagta tgagtttcac atgtatatca aaaatacaac agttgcttgt attcagtaga
1561 gttttcttgc ccacctattt tgtgctgggt tctaccttaa cccagaagac actatgaaaa
1621 acaagacaga ctccactcaa aatttatatg aacaccacta gatacttcct gatcaaacat
1681 cagtcaacat actctaaaga ataactccaa gtcttggcca ggcgcagtgg ctcacacctg
1741 taatcccaac actttgggag gccaaggtgg gtggatcatc taaggccggg agttcaagac
1801 cagcctgacc aacgtggaga aacccatct ctactaaaaa tacaaaatta gccggcgtg
1861 gtagcgcatg gctgtaatcc tggctactca ggaggccgag gcagaagaat tgcttgaact
1921 ggggaggcag aggttgcggt gagcccagat cgcgccattg cactccagcc tgggtaacaa
1981 gagcaaaact ctgtccaaaa aaaaaaaaaa aaaaaa
```

4. SEQ ID NO: 4 (Human TL1A amino acid sequence)
```
   1 maedlglsfg etasvemlpe hgscrpkars ssarwaltcc lvllpflagl ttyllvsqlr
  61 aqgeacvqfq alkgqefaps hqqvyaplra dgdkprahlt vvrqtptqhf knqfpalhwe
 121 helglaftkn rmnytnkfll ipesgdyfiy sqvtfrgmts ecseirqagr pnkpdsitvv
 181 itkvtdsype ptqllmgtks vcevgsnwfq piylgamfsl qegdklmvnv sdislvdytk
 241 edktffgafl l
```

5. SEQ ID NO: 5 (NP_683866.1)
meqrprgcaa vaaalllvll garaqggtrs prcdcagdfh kkiglfccrg cpaghylkap
ctepcgnstc lvcpqdtfla wenhhnseca rcqacdeqas qvalencsav adtrcgckpg
wfvecqvsqc vssspfycqp c 6. SEQ ID NO: 6 (1-159 of NP_149031.2)
meelprrers ppgaatpgst arvlqplflp llllllllg gqgqggmsgr cdcasesqkr -continued I. Sequences ygpfccrgcp kghymkapca epcgnstclp cpsdtfltrd nhfktdctrc qvcdeeealqv
tlencsaksd thcgcqsgwc vdcstepcgk sspfscvpc 7. SEQ ID NO: 7 (NP_005109.2)
qqvyaplra dgdkprahlt vvrqtptqhf knqfpalhwe helglaftkn rmnytnkfll
ipesgdyfiy sqvtfrgmts ecseirqagr pnkpdsitvv itkvtdsype ptqllmgtks
vcevgsnwfq piylgamfsl qegdklmvnv sdislvdytk edktffgafl l 8. SEQ ID NO: 8 (72-251 from NP_796345)
mlraiteer sepspqqvys pprgkprahl tikkqtpaph lknqlsalhwehdlgmaftk
ngmkyinksl vipesgdyfi ysqitfrgtt svcgdisrgr rpnkpdsit vitkvadsyp
eparlltgsk svceisnnwf qslylgatfs leegdrlmvn vsdislvdyt kedktffgaf ll
(SEQ ID NO: 8).

9. SEQ ID NO: 9
GARAQGGTRSPRCDCAGDFHKKIGLFCCRGCPAGHYLKAPCTEPCGNSTCLVCPQDTFLA

10. SEQ ID NO: 10
GARAQGGTRSPRCDCAGDFHKKIGLFCCRGCPAGHYLKAPCTEPCGNSTC

11. SEQ ID NO: 11
GARAQGGTRSPRCDCAGDFHKKIGLFCCRGCPAGHYLKAP

12. SEQ ID NO: 12
GARAQGGTRSPRCDCAGDFHKKIGLFCCRGCPAGHYLK

13. SEQ ID NO: 13
PRCDCAGDFHKKIGLFCCRGCPAGHYLKAPCTEPCGNSTCLVCPQDTFLA

14. SEQ ID NO: 14
KKIGLFCCRGCPAGHYLKAPCTEPCGNSTCLVCPQDTFLA

15. SEQ ID NO: 15
IGLFCCRGCPAGHYLKAPCTEPCGNSTCLVCPQDTFLA

16. SEQ ID NO: 16
RRRRRRRR

17. SEQ ID NO: 17
RQPKIWFPNRRKPWKK

18. SEQ ID NO: 18
GRKKRRQRPPQ

19. SEQ ID NO: 19
RQIKIWFQNRRMKWKK

20. SEQ ID NO: 20
RQIAIWFQNRRMKWAA

21. SEQ ID NO: 21
RKKRRQRRR

22. SEQ ID NO: 22
TRSSRAGLQFPVGRVHRLLRK

23. SEQ ID NO: 23
GWTLNSAGYLLGKINKALAALAKKIL

24. SEQ ID NO: 24
KLALKLALKALKAALKLA

25. SEQ ID NO: 25
AAVALLPAVLLALLAP

26. SEQ ID NO: 26
VPMLK- PMLKE

27. SEQ ID NO: 27
MANLGYWLLALFVTMWTDVGLCKKRPKP

28. SEQ ID NO: 28
LLIILRRRIRKQAHAHSK

29. SEQ ID NO: 29
KETWWETWWTEWSQPKKKRKV

I. Sequences

30. SEQ ID NO: 30
RGGRLSYSRRRFSTSTGR

31. SEQ ID NO: 31
SDLWEMMMVSLACQY

32. SEQ ID NO: 32
TSPLNIHNGQKL

What is claimed is:

1. A monoclonal antibody produced by a murine hybridoma clone selected from the group consisting of the anti-human TL1A clone 1A9 and the anti-human TL1A clone 1C6, that binds specifically to TL1A and blocks the interaction between DR3 and TL1A.

2. A monoclonal antibody produced by a murine hybridoma clone selected from the group consisting of the anti-human TL1A clone 1A9 and the anti-human TL1A clone 1C6, that binds specifically to TL1A and blocks the interaction between DR3 and TL1A, wherein the monoclonal antibody is humanized.

3. A monoclonal antibody produced by a murine hybridoma clone selected from the group consisting of the anti-human TL1A clone 1A9 and the anti-human TL1A clone 1C6, that binds specifically to TL1A and blocks the interaction between DR3 and TL1A, wherein the monoclonal antibody is humanized, wherein the antibody comprises a humanized heavy chain variable region and a humanized light chain variable region.

4. A monoclonal antibody produced by a murine hybridoma clone selected from the group consisting of the anti-human TL1A clone 1A9 and the anti-human TL1A clone 1C6, that: i) binds specifically to TL1A; ii) blocks the interaction between DR3 and TL1A; and iii) blocks TL1A's ability to stimulate T cell proliferation.

5. A monoclonal antibody produced by a murine hybridoma clone selected from the group consisting of the anti-human TL1A clone 1A9 and the anti-human TL1A clone 1C6.

6. A composition comprising a monoclonal antibody produced by a murine hybridoma clone selected from the group consisting of the anti-human TL1A clone 1A9 and the anti-human TL1A clone 1C6, that binds specifically to TL1A and blocks the interaction between DR3 and TL1A, for the treatment of inflammatory or autoimmune disease.

7. A composition comprising a monoclonal antibody produced by a murine hybridoma clone selected from the group consisting of the anti-human TL1A clone 1A9 and the anti-human TL1A clone 1C6, that binds specifically to TL1A and blocks the interaction between DR3 and TL1A, for the detection of cell surface expression of TL1A.

8. A composition comprising a monoclonal antibody produced by a murine hybridoma clone selected from the group consisting of the anti-human TL1A clone 1A9 and the anti-human TL1A clone 1C6, that binds specifically to TL1A and blocks the interaction between DR3 and TL1A, for the detection of soluble TL1A.

9. A method of treating an inflammatory or autoimmune disease in a subject, comprising administering to the subject an effective amount of anti-TL1A antibodies produced by a murine hybridoma clone selected from the group consisting of the anti-human TL1A clone 1A9 and the anti-human TL1A clone 1C6, which antibodies bind specifically to TL1A and block the interaction between DR3 and TL1A.

10. The method of claim 9, wherein the inflammatory or autoimmune disease is asthma.

11. The method of claim 9, wherein the inflammatory or autoimmune disease is multiple sclerosis.

12. The method of claim 9, wherein the inflammatory or autoimmune disease is rheumatoid arthritis.

13. The method of claim 9, wherein the inflammatory or autoimmune disease is selected from the group consisting of inflammatory bowel disease, type 1 diabetes, graft versus host disease, and autoimmune disease with a T cell component.

* * * * *